(12) United States Patent
Tellio et al.

(10) Patent No.: US 9,545,290 B2
(45) Date of Patent: Jan. 17, 2017

(54) NEEDLE PROBE GUIDE

(75) Inventors: Karalyn R. Tellio, Cincinnati, OH (US); Mark S. Zeiner, Mason, OH (US); David N. Plescia, Mentor, OH (US); Gary L. Long, Cincinnati, OH (US); Peter K. Shires, Hamilton, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 429 days.

(21) Appl. No.: 13/561,945

(22) Filed: Jul. 30, 2012

(65) Prior Publication Data

US 2014/0031813 A1  Jan. 30, 2014

(51) Int. Cl.
| | | |
|---|---|---|
| *A61B 90/11* | (2016.01) | |
| *A61B 18/00* | (2006.01) | |
| *A61B 18/14* | (2006.01) | |

(52) U.S. Cl.
CPC ...... *A61B 90/11* (2016.02); *A61B 2018/00577* (2013.01); *A61B 2018/143* (2013.01); *A61B 2018/1475* (2013.01)

(58) Field of Classification Search
CPC .................. A61B 19/201; A61B 2018/00577; A61B 2018/143; A61B 2018/1475
USPC .......................................... 606/34, 41; 607/2
See application file for complete search history.

(56) References Cited

U.S. PATENT DOCUMENTS

| | | |
|---|---|---|
| 645,576 A | 3/1900 | Tesla |
| 649,621 A | 5/1900 | Tesla |
| 787,412 A | 4/1905 | Tesla |
| 1,039,354 A | 9/1912 | Bonadio |
| 1,127,948 A | 2/1915 | Wappler |
| 1,482,653 A | 2/1924 | Lilly |
| 1,581,706 A * | 4/1926 | White .......................... 24/114.7 |
| 1,581,707 A * | 4/1926 | White .......................... 24/114.7 |
| 1,581,708 A * | 4/1926 | White .......................... 24/114.7 |
| 1,581,709 A * | 4/1926 | White .......................... 24/114.7 |
| 1,581,710 A * | 4/1926 | White .......................... 24/114.7 |
| 1,625,602 A | 4/1927 | Gould et al. |

(Continued)

FOREIGN PATENT DOCUMENTS

| | | |
|---|---|---|
| AU | 666310 B2 | 2/1996 |
| DE | 3008120 A1 | 9/1980 |

(Continued)

OTHER PUBLICATIONS

Michael S. Kavic, M.D., "Natural Orifice Translumenal Endoscopic Surgery: "NOTES"", JSLS, vol. 10, pp. 133-134 (2006).

(Continued)

*Primary Examiner* — Christopher A Flory

(57) ABSTRACT

A device for guiding electrodes relative to a tissue treatment region. The device can comprise a body have a plurality of passages therethrough. Each passage can axially restrain an electrode positioned therein. When each electrode is axially restrained in a passage, the distal ends of the electrodes can be spaced a predetermined distance apart. Further, the electrodes can be held in a parallel or substantially parallel alignment when axially retained in the passages. The predetermined distance between the electrodes can correspond to a treatment distance in a tissue treatment region and the distal ends of the electrodes can be operably structured to conduct current therebetween when at least one of electrodes is energized by an energy source.

11 Claims, 56 Drawing Sheets

(56) References Cited

U.S. PATENT DOCUMENTS

| | | |
|---|---|---|
| 1,916,722 A | 7/1933 | Ende |
| 2,028,635 A | 1/1936 | Wappler |
| 2,031,682 A | 2/1936 | Wappler et al. |
| 2,113,246 A | 4/1938 | Wappler |
| 2,137,710 A | 11/1938 | Anderson |
| 2,155,365 A | 4/1939 | Rankin |
| 2,191,858 A | 2/1940 | Moore |
| 2,196,620 A | 4/1940 | Attarian |
| 2,388,137 A | 10/1945 | Graumlich |
| 2,451,077 A * | 10/1948 | Emsig .................... 24/114.7 |
| 2,493,108 A | 1/1950 | Casey, Jr. |
| 2,504,152 A | 4/1950 | Riker et al. |
| 2,938,382 A | 5/1960 | De Graaf |
| 2,952,206 A | 9/1960 | Becksted |
| 3,044,461 A | 7/1962 | Murdock |
| 3,069,195 A | 12/1962 | Buck |
| 3,070,088 A | 12/1962 | Brahos |
| 3,110,956 A * | 11/1963 | Fischer, Jr. .............. B23K 3/08 414/626 |
| 3,170,471 A | 2/1965 | Schnitzer |
| 3,435,824 A | 4/1969 | Gamponia |
| 3,470,876 A | 10/1969 | Barchilon |
| 3,481,325 A | 12/1969 | Glassman |
| 3,595,239 A | 7/1971 | Petersen |
| 3,669,487 A | 6/1972 | Roberts et al. |
| 3,746,881 A | 7/1973 | Fitch et al. |
| 3,799,672 A | 3/1974 | Vurek |
| 3,854,473 A | 12/1974 | Matsuo |
| 3,946,740 A | 3/1976 | Bassett |
| 3,948,251 A | 4/1976 | Hosono |
| 3,961,632 A | 6/1976 | Moossun |
| 3,965,890 A | 6/1976 | Gauthier |
| 3,994,301 A | 11/1976 | Agris |
| 4,011,872 A | 3/1977 | Komiya |
| 4,012,812 A | 3/1977 | Black |
| 4,085,743 A | 4/1978 | Yoon |
| 4,164,225 A | 8/1979 | Johnson et al. |
| 4,170,997 A | 10/1979 | Pinnow et al. |
| 4,174,715 A | 11/1979 | Hasson |
| 4,178,920 A | 12/1979 | Cawood, Jr. et al. |
| 4,207,873 A | 6/1980 | Kruy |
| 4,235,238 A | 11/1980 | Ogiu et al. |
| 4,258,716 A | 3/1981 | Sutherland |
| 4,269,174 A | 5/1981 | Adair |
| 4,278,077 A | 7/1981 | Mizumoto |
| 4,281,646 A | 8/1981 | Kinoshita |
| 4,285,344 A | 8/1981 | Marshall |
| 4,311,143 A | 1/1982 | Komiya |
| 4,329,980 A | 5/1982 | Terada |
| 4,393,872 A | 7/1983 | Reznik et al. |
| 4,396,021 A | 8/1983 | Baumgartner |
| 4,406,656 A | 9/1983 | Hattler et al. |
| 4,452,246 A | 6/1984 | Bader et al. |
| 4,461,281 A | 7/1984 | Carson |
| 4,491,132 A | 1/1985 | Aikins |
| 4,492,232 A | 1/1985 | Green |
| 4,527,331 A | 7/1985 | Lasner et al. |
| 4,527,564 A | 7/1985 | Eguchi et al. |
| 4,538,594 A | 9/1985 | Boebel et al. |
| D281,104 S | 10/1985 | Davison |
| 4,569,347 A | 2/1986 | Frisbie |
| 4,580,551 A | 4/1986 | Siegmund et al. |
| 4,646,722 A | 3/1987 | Silverstein et al. |
| 4,653,476 A | 3/1987 | Bonnet |
| 4,655,219 A | 4/1987 | Petruzzi |
| 4,657,018 A | 4/1987 | Hakky |
| 4,669,470 A | 6/1987 | Brandfield |
| 4,671,477 A | 6/1987 | Cullen |
| 4,677,982 A | 7/1987 | Llinas et al. |
| 4,685,447 A | 8/1987 | Iversen et al. |
| 4,711,240 A | 12/1987 | Goldwasser et al. |
| 4,712,545 A | 12/1987 | Honkanen |
| 4,721,116 A | 1/1988 | Schintgen et al. |
| 4,727,600 A | 2/1988 | Avakian |
| 4,733,662 A | 3/1988 | DeSatnick et al. |
| D295,894 S | 5/1988 | Sharkany et al. |
| 4,742,817 A | 5/1988 | Kawashima et al. |
| 4,753,223 A | 6/1988 | Bremer |
| 4,763,669 A | 8/1988 | Jaeger |
| 4,770,188 A | 9/1988 | Chikama |
| 4,790,624 A | 12/1988 | Van Hoye et al. |
| 4,791,707 A | 12/1988 | Tucker |
| 4,796,627 A | 1/1989 | Tucker |
| 4,815,450 A | 3/1989 | Patel |
| 4,823,794 A | 4/1989 | Pierce |
| 4,829,999 A | 5/1989 | Auth |
| 4,836,188 A | 6/1989 | Berry |
| 4,846,573 A | 7/1989 | Taylor et al. |
| 4,867,140 A | 9/1989 | Hovis et al. |
| 4,869,238 A | 9/1989 | Opie et al. |
| 4,869,459 A | 9/1989 | Bourne |
| 4,873,979 A | 10/1989 | Hanna |
| 4,880,015 A | 11/1989 | Nierman |
| 4,904,048 A | 2/1990 | Sogawa et al. |
| 4,911,148 A | 3/1990 | Sosnowski et al. |
| 4,926,860 A | 5/1990 | Stice et al. |
| 4,934,364 A | 6/1990 | Green |
| 4,938,214 A | 7/1990 | Specht et al. |
| 4,950,273 A | 8/1990 | Briggs |
| 4,950,285 A | 8/1990 | Wilk |
| 4,953,539 A | 9/1990 | Nakamura et al. |
| 4,960,133 A | 10/1990 | Hewson |
| 4,977,887 A | 12/1990 | Gouda |
| 4,979,496 A | 12/1990 | Komi |
| 4,979,950 A | 12/1990 | Transue et al. |
| 4,984,581 A | 1/1991 | Stice |
| 4,990,152 A | 2/1991 | Yoon |
| 4,991,565 A | 2/1991 | Takahashi et al. |
| 4,994,079 A | 2/1991 | Genese et al. |
| 5,007,917 A | 4/1991 | Evans |
| 5,010,876 A | 4/1991 | Henley et al. |
| 5,020,514 A | 6/1991 | Heckele |
| 5,020,535 A | 6/1991 | Parker et al. |
| 5,025,778 A | 6/1991 | Silverstein et al. |
| 5,026,379 A | 6/1991 | Yoon |
| 5,033,169 A | 7/1991 | Bindon |
| 5,037,433 A | 8/1991 | Wilk et al. |
| 5,041,129 A | 8/1991 | Hayhurst et al. |
| 5,046,513 A | 9/1991 | Gatturna et al. |
| 5,050,585 A | 9/1991 | Takahashi |
| 5,052,372 A | 10/1991 | Shapiro |
| 5,065,516 A | 11/1991 | Dulebohn |
| 5,066,295 A | 11/1991 | Kozak et al. |
| 5,098,378 A | 3/1992 | Piontek et al. |
| 5,108,421 A | 4/1992 | Fowler |
| 5,123,913 A | 6/1992 | Wilk et al. |
| 5,123,914 A | 6/1992 | Cope |
| 5,133,727 A | 7/1992 | Bales et al. |
| 5,147,374 A | 9/1992 | Fernandez |
| 5,174,300 A | 12/1992 | Bales et al. |
| 5,176,126 A | 1/1993 | Chikama |
| 5,190,050 A | 3/1993 | Nitzsche |
| 5,190,555 A | 3/1993 | Wetter et al. |
| 5,192,284 A | 3/1993 | Pleatman |
| 5,192,300 A | 3/1993 | Fowler |
| 5,197,963 A | 3/1993 | Parins |
| 5,201,752 A | 4/1993 | Brown et al. |
| 5,201,908 A | 4/1993 | Jones |
| 5,203,785 A | 4/1993 | Slater |
| 5,203,787 A | 4/1993 | Noblitt et al. |
| 5,209,747 A | 5/1993 | Knoepfler |
| 5,217,003 A | 6/1993 | Wilk |
| 5,217,453 A | 6/1993 | Wilk |
| 5,219,357 A | 6/1993 | Honkanen et al. |
| 5,219,358 A | 6/1993 | Bendel et al. |
| 5,222,362 A | 6/1993 | Maus et al. |
| 5,222,965 A | 6/1993 | Haughton |
| 5,234,437 A | 8/1993 | Sepetka |
| 5,234,453 A | 8/1993 | Smith et al. |
| 5,235,964 A | 8/1993 | Abenaim |
| 5,242,456 A | 9/1993 | Nash et al. |
| 5,245,460 A | 9/1993 | Allen et al. |
| 5,246,424 A | 9/1993 | Wilk |
| 5,257,999 A | 11/1993 | Slanetz, Jr. |

(56) References Cited

U.S. PATENT DOCUMENTS

| | | |
|---|---|---|
| 5,259,366 A | 11/1993 | Reydel et al. |
| 5,263,958 A | 11/1993 | deGuillebon et al. |
| 5,273,524 A | 12/1993 | Fox et al. |
| 5,275,607 A | 1/1994 | Lo et al. |
| 5,275,614 A | 1/1994 | Haber et al. |
| 5,275,616 A | 1/1994 | Fowler |
| 5,284,128 A | 2/1994 | Hart |
| 5,284,162 A | 2/1994 | Wilk |
| 5,287,845 A | 2/1994 | Faul et al. |
| 5,287,852 A | 2/1994 | Arkinstall |
| 5,290,299 A | 3/1994 | Fain et al. |
| 5,290,302 A | 3/1994 | Pericic |
| 5,295,977 A | 3/1994 | Cohen et al. |
| 5,297,536 A | 3/1994 | Wilk |
| 5,297,687 A | 3/1994 | Freed |
| 5,301,061 A | 4/1994 | Nakada et al. |
| 5,312,023 A | 5/1994 | Green et al. |
| 5,312,333 A | 5/1994 | Churinetz et al. |
| 5,312,351 A | 5/1994 | Gerrone |
| 5,312,416 A | 5/1994 | Spaeth et al. |
| 5,312,423 A | 5/1994 | Rosenbluth et al. |
| 5,318,589 A | 6/1994 | Lichtman |
| 5,320,636 A | 6/1994 | Slater |
| 5,324,261 A | 6/1994 | Amundson et al. |
| 5,325,845 A | 7/1994 | Adair |
| 5,330,471 A | 7/1994 | Eggers |
| 5,330,486 A | 7/1994 | Wilk |
| 5,330,488 A | 7/1994 | Goldrath |
| 5,330,496 A | 7/1994 | Alferness |
| 5,330,502 A | 7/1994 | Hassler et al. |
| 5,331,971 A | 7/1994 | Bales et al. |
| 5,334,168 A | 8/1994 | Hemmer |
| 5,334,198 A | 8/1994 | Hart et al. |
| 5,336,192 A | 8/1994 | Palestrant |
| 5,339,805 A | 8/1994 | Parker |
| 5,341,815 A | 8/1994 | Cofone et al. |
| 5,342,396 A | 8/1994 | Cook |
| 5,344,428 A | 9/1994 | Griffiths |
| 5,345,927 A | 9/1994 | Bonutti |
| 5,348,259 A | 9/1994 | Blanco et al. |
| 5,350,391 A | 9/1994 | Iacovelli |
| 5,352,184 A | 10/1994 | Goldberg et al. |
| 5,352,222 A | 10/1994 | Rydell |
| 5,354,302 A | 10/1994 | Ko |
| 5,354,311 A | 10/1994 | Kambin et al. |
| 5,356,381 A | 10/1994 | Ensminger et al. |
| 5,356,408 A | 10/1994 | Rydell |
| 5,360,428 A | 11/1994 | Hutchinson, Jr. |
| 5,364,408 A | 11/1994 | Gordon |
| 5,364,410 A | 11/1994 | Failla et al. |
| 5,366,466 A | 11/1994 | Christian et al. |
| 5,366,467 A | 11/1994 | Lynch et al. |
| 5,368,605 A | 11/1994 | Miller, Jr. |
| 5,370,647 A | 12/1994 | Graber et al. |
| 5,370,679 A | 12/1994 | Atlee, III |
| 5,374,273 A | 12/1994 | Nakao et al. |
| 5,374,275 A | 12/1994 | Bradley et al. |
| 5,374,277 A | 12/1994 | Hassler |
| 5,374,953 A | 12/1994 | Sasaki et al. |
| 5,376,077 A | 12/1994 | Gomringer |
| 5,377,695 A | 1/1995 | An Haack |
| 5,383,877 A | 1/1995 | Clarke |
| 5,383,888 A | 1/1995 | Zvenyatsky et al. |
| 5,386,817 A | 2/1995 | Jones |
| 5,387,259 A | 2/1995 | Davidson |
| 5,391,174 A | 2/1995 | Weston |
| 5,392,789 A | 2/1995 | Slater et al. |
| 5,395,386 A | 3/1995 | Slater |
| 5,397,332 A | 3/1995 | Kammerer et al. |
| 5,401,248 A | 3/1995 | Bencini |
| 5,403,311 A | 4/1995 | Abele et al. |
| 5,403,328 A | 4/1995 | Shallman |
| 5,403,342 A | 4/1995 | Tovey et al. |
| 5,403,348 A | 4/1995 | Bonutti |
| 5,405,073 A | 4/1995 | Porter |
| 5,405,359 A | 4/1995 | Pierce |
| 5,409,478 A | 4/1995 | Gerry et al. |
| 5,417,699 A | 5/1995 | Klein et al. |
| 5,423,821 A | 6/1995 | Pasque |
| 5,431,635 A | 7/1995 | Yoon |
| 5,433,721 A | 7/1995 | Hooven et al. |
| 5,433,735 A | 7/1995 | Zanakis et al. |
| 5,439,471 A | 8/1995 | Kerr |
| 5,439,478 A | 8/1995 | Palmer |
| 5,441,059 A | 8/1995 | Dannan |
| 5,441,494 A | 8/1995 | Ortiz |
| 5,441,498 A | 8/1995 | Perkins |
| 5,441,499 A | 8/1995 | Fritzsch |
| 5,443,463 A | 8/1995 | Stern et al. |
| 5,445,638 A | 8/1995 | Rydell et al. |
| 5,445,648 A | 8/1995 | Cook |
| 5,449,021 A | 9/1995 | Chikama |
| 5,454,827 A | 10/1995 | Aust et al. |
| 5,456,667 A | 10/1995 | Ham et al. |
| 5,456,684 A | 10/1995 | Schmidt et al. |
| 5,458,131 A | 10/1995 | Wilk |
| 5,458,583 A | 10/1995 | McNeely et al. |
| 5,460,168 A | 10/1995 | Masubuchi et al. |
| 5,460,629 A | 10/1995 | Shlain et al. |
| 5,462,561 A | 10/1995 | Voda |
| 5,465,731 A | 11/1995 | Bell et al. |
| 5,467,763 A | 11/1995 | McMahon et al. |
| 5,468,250 A | 11/1995 | Paraschac et al. |
| 5,470,308 A | 11/1995 | Edwards et al. |
| 5,470,320 A | 11/1995 | Tiefenbrun et al. |
| 5,478,347 A | 12/1995 | Aranyi |
| 5,478,352 A | 12/1995 | Fowler |
| 5,480,404 A | 1/1996 | Kammerer et al. |
| 5,482,029 A | 1/1996 | Sekiguchi et al. |
| 5,482,054 A | 1/1996 | Slater et al. |
| 5,484,451 A | 1/1996 | Akopov et al. |
| 5,489,256 A | 2/1996 | Adair |
| 5,496,347 A | 3/1996 | Hashiguchi et al. |
| 5,499,990 A | 3/1996 | Schulken et al. |
| 5,499,992 A | 3/1996 | Meade et al. |
| 5,499,997 A | 3/1996 | Sharpe et al. |
| 5,501,692 A | 3/1996 | Riza |
| 5,503,616 A | 4/1996 | Jones |
| 5,505,686 A | 4/1996 | Willis et al. |
| 5,507,755 A | 4/1996 | Gresl et al. |
| 5,511,564 A | 4/1996 | Wilk |
| 5,514,157 A | 5/1996 | Nicholas et al. |
| 5,518,501 A | 5/1996 | Oneda et al. |
| 5,522,829 A | 6/1996 | Michalos |
| 5,522,830 A | 6/1996 | Aranyi |
| 5,527,321 A | 6/1996 | Hinchliffe |
| 5,533,418 A | 7/1996 | Wu et al. |
| 5,536,248 A | 7/1996 | Weaver et al. |
| 5,538,509 A | 7/1996 | Dunlap et al. |
| 5,540,648 A | 7/1996 | Yoon |
| 5,549,637 A | 8/1996 | Crainich |
| 5,554,151 A | 9/1996 | Hinchliffe |
| 5,555,883 A | 9/1996 | Avitall |
| 5,558,133 A | 9/1996 | Bortoli et al. |
| 5,562,693 A | 10/1996 | Devlin et al. |
| 5,569,243 A | 10/1996 | Kortenbach et al. |
| 5,569,298 A | 10/1996 | Schnell |
| 5,571,090 A | 11/1996 | Sherts |
| 5,573,540 A | 11/1996 | Yoon |
| 5,578,030 A | 11/1996 | Levin |
| 5,582,611 A | 12/1996 | Tsuruta et al. |
| 5,582,617 A | 12/1996 | Klieman et al. |
| 5,584,845 A | 12/1996 | Hart |
| 5,590,660 A | 1/1997 | MacAulay et al. |
| 5,591,179 A | 1/1997 | Edelstein |
| 5,591,205 A | 1/1997 | Fowler |
| 5,593,420 A | 1/1997 | Eubanks, Jr et al. |
| 5,595,562 A | 1/1997 | Grier |
| 5,597,378 A | 1/1997 | Jervis |
| 5,601,573 A | 2/1997 | Fogelberg et al. |
| 5,601,574 A | 2/1997 | Stefanchik et al. |
| 5,601,588 A | 2/1997 | Tonomura et al. |
| 5,601,602 A | 2/1997 | Fowler |
| 5,604,531 A | 2/1997 | Iddan et al. |

(56) References Cited

U.S. PATENT DOCUMENTS

| | | |
|---|---|---|
| 5,607,389 A | 3/1997 | Edwards et al. |
| 5,607,406 A | 3/1997 | Hernandez et al. |
| 5,607,450 A | 3/1997 | Zvenyatsky et al. |
| 5,609,601 A | 3/1997 | Kolesa et al. |
| 5,613,975 A | 3/1997 | Christy |
| 5,613,977 A | 3/1997 | Weber et al. |
| 5,614,943 A | 3/1997 | Nakamura et al. |
| 5,616,117 A | 4/1997 | Dinkler et al. |
| 5,618,303 A | 4/1997 | Marlow et al. |
| 5,620,415 A | 4/1997 | Lucey et al. |
| 5,624,399 A | 4/1997 | Ackerman |
| 5,624,431 A | 4/1997 | Gerry et al. |
| 5,626,578 A | 5/1997 | Tihon |
| 5,626,587 A | 5/1997 | Bishop et al. |
| 5,628,732 A | 5/1997 | Antoon, Jr. et al. |
| 5,630,782 A | 5/1997 | Adair |
| 5,630,795 A | 5/1997 | Kuramoto et al. |
| 5,643,283 A | 7/1997 | Younker |
| 5,643,292 A | 7/1997 | Hart |
| 5,643,294 A | 7/1997 | Tovey et al. |
| 5,644,798 A | 7/1997 | Shah |
| 5,645,083 A | 7/1997 | Essig et al. |
| 5,645,565 A | 7/1997 | Rudd et al. |
| 5,649,372 A | 7/1997 | Souza |
| 5,653,677 A | 8/1997 | Okada et al. |
| 5,653,690 A | 8/1997 | Booth et al. |
| 5,653,722 A | 8/1997 | Kieturakis |
| 5,657,755 A | 8/1997 | Desai |
| 5,662,621 A | 9/1997 | Lafontaine |
| 5,662,663 A | 9/1997 | Shallman |
| 5,667,527 A | 9/1997 | Cook |
| 5,669,875 A | 9/1997 | van Eerdenburg |
| 5,681,276 A | 10/1997 | Lundquist |
| 5,681,324 A | 10/1997 | Kammerer et al. |
| 5,681,330 A | 10/1997 | Hughett et al. |
| 5,685,820 A | 11/1997 | Riek et al. |
| 5,690,606 A | 11/1997 | Slotman |
| 5,690,656 A | 11/1997 | Cope et al. |
| 5,690,660 A | 11/1997 | Kauker et al. |
| 5,695,448 A | 12/1997 | Kimura et al. |
| 5,695,505 A | 12/1997 | Yoon |
| 5,695,511 A | 12/1997 | Cano et al. |
| 5,700,275 A | 12/1997 | Bell et al. |
| 5,702,438 A | 12/1997 | Avitall |
| 5,704,892 A | 1/1998 | Adair |
| 5,709,708 A | 1/1998 | Thal |
| 5,711,921 A | 1/1998 | Langford |
| 5,716,326 A | 2/1998 | Dannan |
| 5,716,375 A | 2/1998 | Fowler |
| 5,725,542 A | 3/1998 | Yoon |
| 5,728,094 A | 3/1998 | Edwards |
| 5,730,740 A | 3/1998 | Wales et al. |
| 5,735,849 A | 4/1998 | Baden et al. |
| 5,741,234 A | 4/1998 | Aboul-Hosn |
| 5,741,278 A | 4/1998 | Stevens |
| 5,741,285 A | 4/1998 | McBrayer et al. |
| 5,741,429 A | 4/1998 | Donadio, III et al. |
| 5,743,456 A | 4/1998 | Jones et al. |
| 5,746,759 A | 5/1998 | Meade et al. |
| 5,749,826 A | 5/1998 | Faulkner |
| 5,749,881 A | 5/1998 | Sackier et al. |
| 5,749,889 A | 5/1998 | Bacich et al. |
| 5,752,951 A | 5/1998 | Yanik |
| 5,755,731 A | 5/1998 | Grinberg |
| 5,759,151 A | 6/1998 | Sturges |
| 5,762,604 A | 6/1998 | Kieturakis |
| 5,766,167 A | 6/1998 | Eggers et al. |
| 5,766,170 A | 6/1998 | Eggers |
| 5,766,205 A | 6/1998 | Zvenyatsky et al. |
| 5,769,849 A | 6/1998 | Eggers |
| 5,776,188 A | 7/1998 | Shepherd et al. |
| 5,779,701 A | 7/1998 | McBrayer et al. |
| 5,779,716 A | 7/1998 | Cano et al. |
| 5,779,720 A | 7/1998 | Walder-Utz et al. |
| 5,779,727 A | 7/1998 | Orejola |
| 5,782,859 A | 7/1998 | Nicholas et al. |
| 5,782,861 A | 7/1998 | Cragg et al. |
| 5,782,866 A | 7/1998 | Wenstrom, Jr. |
| 5,791,022 A | 8/1998 | Bohman |
| 5,792,113 A | 8/1998 | Kramer et al. |
| 5,792,153 A | 8/1998 | Swain et al. |
| 5,792,165 A | 8/1998 | Klieman et al. |
| 5,797,835 A | 8/1998 | Green |
| 5,797,928 A | 8/1998 | Kogasaka |
| 5,797,939 A | 8/1998 | Yoon |
| 5,797,941 A | 8/1998 | Schulze et al. |
| 5,797,959 A | 8/1998 | Castro et al. |
| 5,797,960 A | 8/1998 | Stevens et al. |
| 5,800,451 A | 9/1998 | Buess et al. |
| 5,803,903 A | 9/1998 | Athas et al. |
| 5,808,665 A | 9/1998 | Green |
| 5,810,806 A | 9/1998 | Ritchart et al. |
| 5,810,849 A | 9/1998 | Kontos |
| 5,810,865 A | 9/1998 | Koscher et al. |
| 5,810,876 A | 9/1998 | Kelleher |
| 5,810,877 A | 9/1998 | Roth et al. |
| 5,813,976 A | 9/1998 | Filipi et al. |
| 5,814,026 A | 9/1998 | Yoon |
| 5,814,058 A | 9/1998 | Carlson et al. |
| 5,817,061 A | 10/1998 | Goodwin et al. |
| 5,817,107 A | 10/1998 | Schaller |
| 5,817,119 A | 10/1998 | Klieman et al. |
| 5,818,527 A | 10/1998 | Yamaguchi et al. |
| 5,819,736 A | 10/1998 | Avny et al. |
| 5,823,947 A | 10/1998 | Yoon et al. |
| 5,824,071 A | 10/1998 | Nelson et al. |
| 5,827,190 A | 10/1998 | Palcic et al. |
| 5,827,276 A | 10/1998 | LeVeen et al. |
| 5,827,281 A | 10/1998 | Levin |
| 5,827,299 A | 10/1998 | Thomason et al. |
| 5,827,323 A | 10/1998 | Klieman et al. |
| 5,830,221 A | 11/1998 | Stein et al. |
| 5,830,231 A | 11/1998 | Geiges, Jr. |
| 5,833,603 A | 11/1998 | Kovacs et al. |
| 5,833,700 A | 11/1998 | Fogelberg et al. |
| 5,833,703 A | 11/1998 | Manushakian |
| 5,833,715 A | 11/1998 | Vachon et al. |
| 5,836,960 A | 11/1998 | Kolesa et al. |
| 5,843,017 A | 12/1998 | Yoon |
| 5,843,121 A | 12/1998 | Yoon |
| 5,849,022 A | 12/1998 | Sakashita et al. |
| 5,853,374 A | 12/1998 | Hart et al. |
| 5,855,569 A | 1/1999 | Komi |
| 5,855,585 A | 1/1999 | Kontos |
| 5,860,913 A | 1/1999 | Yamaya et al. |
| 5,860,995 A | 1/1999 | Berkelaar |
| 5,868,762 A | 2/1999 | Cragg et al. |
| 5,876,411 A | 3/1999 | Kontos |
| 5,882,331 A | 3/1999 | Sasaki |
| 5,882,344 A | 3/1999 | Stouder, Jr. |
| 5,893,846 A | 4/1999 | Bales et al. |
| 5,893,874 A | 4/1999 | Bourque et al. |
| 5,893,875 A | 4/1999 | O'Connor et al. |
| 5,897,487 A | 4/1999 | Ouchi |
| 5,899,919 A | 5/1999 | Eubanks, Jr. et al. |
| 5,902,238 A | 5/1999 | Golden et al. |
| 5,902,254 A | 5/1999 | Magram |
| 5,904,702 A | 5/1999 | Ek et al. |
| 5,906,625 A | 5/1999 | Bito et al. |
| 5,908,420 A | 6/1999 | Parins et al. |
| 5,908,429 A | 6/1999 | Yoon |
| 5,911,737 A | 6/1999 | Lee et al. |
| 5,916,146 A | 6/1999 | Allotta et al. |
| 5,916,147 A | 6/1999 | Boury |
| 5,921,993 A | 7/1999 | Yoon |
| 5,921,997 A | 7/1999 | Fogelberg et al. |
| 5,922,008 A | 7/1999 | Gimpelson |
| 5,925,052 A | 7/1999 | Simmons |
| 5,928,255 A | 7/1999 | Meade et al. |
| 5,928,266 A | 7/1999 | Kontos |
| 5,936,536 A | 8/1999 | Morris |
| 5,938,661 A * | 8/1999 | Hahnen .............. 606/46 |
| 5,941,815 A | 8/1999 | Chang |
| 5,944,718 A | 8/1999 | Austin et al. |

(56) References Cited

U.S. PATENT DOCUMENTS

| | | |
|---|---|---|
| 5,951,547 A | 9/1999 | Gough et al. |
| 5,951,549 A | 9/1999 | Richardson et al. |
| 5,954,720 A | 9/1999 | Wilson et al. |
| 5,954,731 A | 9/1999 | Yoon |
| 5,957,936 A | 9/1999 | Yoon et al. |
| 5,957,943 A | 9/1999 | Vaitekunas |
| 5,957,953 A | 9/1999 | DiPoto et al. |
| 5,964,782 A | 10/1999 | Lafontaine et al. |
| 5,970,581 A | 10/1999 | Chadwick et al. |
| 5,971,995 A | 10/1999 | Rousseau |
| 5,972,002 A | 10/1999 | Bark et al. |
| 5,976,074 A | 11/1999 | Moriyama |
| 5,976,075 A | 11/1999 | Beane et al. |
| 5,976,130 A | 11/1999 | McBrayer et al. |
| 5,976,131 A | 11/1999 | Guglielmi et al. |
| 5,980,539 A | 11/1999 | Kontos |
| 5,980,556 A | 11/1999 | Giordano et al. |
| 5,984,938 A | 11/1999 | Yoon |
| 5,984,939 A | 11/1999 | Yoon |
| 5,984,950 A | 11/1999 | Cragg et al. |
| 5,989,182 A | 11/1999 | Hori et al. |
| 5,993,447 A | 11/1999 | Blewett et al. |
| 5,993,474 A | 11/1999 | Ouchi |
| 5,995,875 A | 11/1999 | Blewett et al. |
| 5,997,555 A | 12/1999 | Kontos |
| 6,001,120 A | 12/1999 | Levin |
| 6,004,269 A | 12/1999 | Crowley et al. |
| 6,004,330 A | 12/1999 | Middleman et al. |
| 6,007,566 A | 12/1999 | Wenstrom, Jr. |
| 6,010,515 A | 1/2000 | Swain et al. |
| 6,012,494 A | 1/2000 | Balazs |
| 6,016,452 A | 1/2000 | Kasevich |
| 6,017,356 A | 1/2000 | Frederick et al. |
| 6,019,770 A | 2/2000 | Christoudias |
| 6,024,708 A | 2/2000 | Bales et al. |
| 6,024,747 A | 2/2000 | Kontos |
| 6,027,522 A | 2/2000 | Palmer |
| 6,030,365 A | 2/2000 | Laufer |
| 6,030,384 A | 2/2000 | Nezhat |
| 6,030,634 A | 2/2000 | Wu et al. |
| 6,033,399 A | 3/2000 | Gines |
| 6,036,640 A | 3/2000 | Corace et al. |
| 6,036,685 A | 3/2000 | Mueller |
| 6,053,927 A | 4/2000 | Hamas |
| 6,053,937 A | 4/2000 | Edwards et al. |
| 6,059,719 A | 5/2000 | Yamamoto et al. |
| 6,066,160 A | 5/2000 | Colvin et al. |
| 6,068,603 A | 5/2000 | Suzuki |
| 6,068,629 A | 5/2000 | Haissaguerre et al. |
| 6,071,233 A | 6/2000 | Ishikawa et al. |
| 6,074,408 A | 6/2000 | Freeman |
| 6,086,530 A | 7/2000 | Mack |
| 6,090,105 A | 7/2000 | Zepeda et al. |
| 6,090,108 A | 7/2000 | McBrayer et al. |
| 6,090,129 A | 7/2000 | Ouchi |
| 6,096,046 A | 8/2000 | Weiss |
| 6,102,909 A | 8/2000 | Chen et al. |
| 6,102,926 A | 8/2000 | Tartaglia et al. |
| 6,106,473 A | 8/2000 | Violante et al. |
| 6,106,521 A | 8/2000 | Blewett et al. |
| 6,109,852 A | 8/2000 | Shahinpoor et al. |
| 6,110,154 A | 8/2000 | Shimomura et al. |
| 6,110,183 A | 8/2000 | Cope |
| 6,113,593 A | 9/2000 | Tu et al. |
| 6,117,144 A | 9/2000 | Nobles et al. |
| 6,117,158 A | 9/2000 | Measamer et al. |
| 6,123,718 A | 9/2000 | Tu et al. |
| 6,131,790 A | 10/2000 | Piraka |
| 6,139,555 A | 10/2000 | Hart et al. |
| 6,141,037 A | 10/2000 | Upton et al. |
| 6,146,391 A | 11/2000 | Cigaina |
| 6,148,222 A | 11/2000 | Ramsey, III |
| 6,149,653 A | 11/2000 | Deslauriers |
| 6,149,662 A | 11/2000 | Pugliesi et al. |
| 6,152,920 A | 11/2000 | Thompson et al. |
| 6,156,006 A | 12/2000 | Brosens et al. |
| 6,159,200 A | 12/2000 | Verdura et al. |
| 6,165,175 A | 12/2000 | Wampler et al. |
| 6,165,184 A | 12/2000 | Verdura et al. |
| 6,168,570 B1 | 1/2001 | Ferrera |
| 6,168,605 B1 | 1/2001 | Measamer et al. |
| 6,169,269 B1 | 1/2001 | Maynard |
| 6,170,130 B1 | 1/2001 | Hamilton et al. |
| 6,173,872 B1 | 1/2001 | Cohen |
| 6,179,776 B1 | 1/2001 | Adams et al. |
| 6,179,832 B1 | 1/2001 | Jones et al. |
| 6,179,837 B1 | 1/2001 | Hooven |
| 6,183,420 B1 | 2/2001 | Douk et al. |
| 6,190,353 B1 | 2/2001 | Makower et al. |
| 6,190,383 B1 | 2/2001 | Schmaltz et al. |
| 6,190,384 B1 | 2/2001 | Ouchi |
| 6,190,399 B1 | 2/2001 | Palmer et al. |
| 6,203,533 B1 | 3/2001 | Ouchi |
| 6,206,872 B1 | 3/2001 | Lafond et al. |
| 6,206,877 B1 | 3/2001 | Kese et al. |
| 6,206,904 B1 | 3/2001 | Ouchi |
| 6,210,409 B1 | 4/2001 | Ellman et al. |
| 6,214,007 B1 | 4/2001 | Anderson |
| 6,214,028 B1 | 4/2001 | Yoon et al. |
| 6,216,043 B1 | 4/2001 | Swanson et al. |
| 6,228,096 B1 | 5/2001 | Marchand |
| 6,231,506 B1 | 5/2001 | Hu et al. |
| 6,234,958 B1 | 5/2001 | Snoke et al. |
| 6,240,312 B1 | 5/2001 | Alfano et al. |
| 6,245,079 B1 | 6/2001 | Nobles et al. |
| 6,246,914 B1 | 6/2001 | de la Rama et al. |
| 6,258,064 B1 | 7/2001 | Smith et al. |
| 6,261,242 B1 | 7/2001 | Roberts et al. |
| 6,264,664 B1 | 7/2001 | Avellanet |
| 6,270,497 B1 | 8/2001 | Sekino et al. |
| 6,270,505 B1 | 8/2001 | Yoshida et al. |
| 6,277,136 B1 | 8/2001 | Bonutti |
| 6,283,963 B1 | 9/2001 | Regula |
| 6,293,909 B1 | 9/2001 | Chu et al. |
| 6,293,952 B1 | 9/2001 | Brosens et al. |
| 6,296,630 B1 | 10/2001 | Altman et al. |
| 6,314,963 B1 | 11/2001 | Vaska et al. |
| 6,322,578 B1 | 11/2001 | Houle et al. |
| 6,325,534 B1 | 12/2001 | Hawley et al. |
| 6,326,177 B1 | 12/2001 | Schoenbach et al. |
| 6,328,730 B1 | 12/2001 | Harkrider, Jr. |
| 6,350,267 B1 | 2/2002 | Stefanchik |
| 6,350,278 B1 | 2/2002 | Lenker et al. |
| 6,352,503 B1 | 3/2002 | Matsui et al. |
| 6,352,541 B1 | 3/2002 | Kienzle et al. |
| 6,352,543 B1 | 3/2002 | Cole |
| 6,355,013 B1 | 3/2002 | van Muiden |
| 6,355,035 B1 | 3/2002 | Manushakian |
| 6,361,534 B1 | 3/2002 | Chen et al. |
| 6,364,879 B1 | 4/2002 | Chen et al. |
| 6,368,340 B2 | 4/2002 | Malecki et al. |
| 6,371,956 B1 | 4/2002 | Wilson et al. |
| 6,379,366 B1 | 4/2002 | Fleischman et al. |
| 6,383,195 B1 | 5/2002 | Richard |
| 6,383,197 B1 | 5/2002 | Conlon et al. |
| 6,387,671 B1 | 5/2002 | Rubinsky et al. |
| 6,391,029 B1 | 5/2002 | Hooven et al. |
| 6,398,708 B1 | 6/2002 | Hastings et al. |
| 6,402,735 B1 | 6/2002 | Langevin |
| 6,402,746 B1 | 6/2002 | Whayne et al. |
| 6,406,440 B1 | 6/2002 | Stefanchik |
| 6,409,727 B1 | 6/2002 | Bales et al. |
| 6,409,733 B1 | 6/2002 | Conlon et al. |
| 6,419,639 B2 | 7/2002 | Walther et al. |
| 6,419,641 B1 | 7/2002 | Mark et al. |
| 6,427,089 B1 | 7/2002 | Knowlton |
| 6,431,500 B1 | 8/2002 | Jacobs et al. |
| 6,436,107 B1 | 8/2002 | Wang et al. |
| 6,443,970 B1 | 9/2002 | Schulze et al. |
| 6,443,988 B2 | 9/2002 | Felt et al. |
| 6,447,511 B1 | 9/2002 | Slater |
| 6,447,523 B1 | 9/2002 | Middleman et al. |
| 6,454,783 B1 | 9/2002 | Piskun |
| 6,454,785 B2 | 9/2002 | De Hoyos Garza |

(56) References Cited

U.S. PATENT DOCUMENTS

| | | |
|---|---|---|
| 6,458,076 B1 | 10/2002 | Pruitt |
| 6,464,701 B1 | 10/2002 | Hooven et al. |
| 6,464,702 B2 | 10/2002 | Schulze et al. |
| 6,470,218 B1 | 10/2002 | Behl |
| 6,475,104 B1 | 11/2002 | Lutz et al. |
| 6,485,411 B1 | 11/2002 | Konstorum et al. |
| 6,489,745 B1 | 12/2002 | Koreis |
| 6,491,626 B1 | 12/2002 | Stone et al. |
| 6,491,627 B1 | 12/2002 | Komi |
| 6,491,691 B1 | 12/2002 | Morley et al. |
| 6,493,590 B1 | 12/2002 | Wessman et al. |
| 6,494,893 B2 | 12/2002 | Dubrul et al. |
| 6,500,176 B1 | 12/2002 | Truckai et al. |
| 6,503,192 B1 | 1/2003 | Ouchi |
| 6,506,190 B1 | 1/2003 | Walshe |
| 6,508,827 B1 | 1/2003 | Manhes |
| 6,514,239 B2 | 2/2003 | Shimmura et al. |
| 6,520,954 B2 | 2/2003 | Ouchi |
| 6,526,320 B2 | 2/2003 | Mitchell |
| 6,527,782 B2 | 3/2003 | Hogg et al. |
| 6,530,922 B2 | 3/2003 | Cosman et al. |
| 6,535,764 B2 | 3/2003 | Imran et al. |
| 6,537,200 B2 | 3/2003 | Leysieffer et al. |
| 6,543,456 B1 | 4/2003 | Freeman |
| 6,551,270 B1 | 4/2003 | Bimbo et al. |
| 6,551,356 B2 | 4/2003 | Rousseau |
| 6,554,766 B2 | 4/2003 | Maeda et al. |
| 6,554,823 B2 | 4/2003 | Palmer et al. |
| 6,554,829 B2 | 4/2003 | Schulze et al. |
| 6,558,384 B2 | 5/2003 | Mayenberger |
| 6,562,034 B2 | 5/2003 | Edwards et al. |
| 6,562,035 B1 | 5/2003 | Levin |
| 6,562,052 B2 | 5/2003 | Nobles et al. |
| 6,569,120 B1 | 5/2003 | Green et al. |
| 6,569,159 B1 | 5/2003 | Edwards et al. |
| 6,572,629 B2 | 6/2003 | Kalloo et al. |
| 6,572,635 B1 | 6/2003 | Bonutti |
| 6,575,988 B2 | 6/2003 | Rousseau |
| 6,579,311 B1 | 6/2003 | Makower |
| 6,581,889 B2 | 6/2003 | Carpenter et al. |
| 6,585,642 B2 | 7/2003 | Christopher |
| 6,585,717 B1 | 7/2003 | Wittenberger et al. |
| 6,587,750 B2 | 7/2003 | Gerbi et al. |
| 6,592,559 B1 | 7/2003 | Pakter et al. |
| 6,592,603 B2 | 7/2003 | Lasner |
| 6,594,971 B1 | 7/2003 | Addy et al. |
| 6,602,262 B2 | 8/2003 | Griego et al. |
| 6,605,105 B1 | 8/2003 | Cuschieri et al. |
| 6,610,072 B1 | 8/2003 | Christy et al. |
| 6,610,074 B2 | 8/2003 | Santilli |
| 6,613,038 B2 | 9/2003 | Bonutti et al. |
| 6,613,068 B2 | 9/2003 | Ouchi |
| 6,616,632 B2 | 9/2003 | Sharp et al. |
| 6,620,193 B1 | 9/2003 | Lau et al. |
| 6,623,448 B2 | 9/2003 | Slater |
| 6,626,919 B1 | 9/2003 | Swanstrom |
| 6,632,229 B1 | 10/2003 | Yamanouchi |
| 6,632,234 B2 | 10/2003 | Kieturakis et al. |
| 6,638,275 B1 | 10/2003 | McGaffigan et al. |
| 6,638,286 B1 | 10/2003 | Burbank et al. |
| 6,645,225 B1 | 11/2003 | Atkinson |
| 6,652,518 B2 | 11/2003 | Pendekanti et al. |
| 6,652,521 B2 | 11/2003 | Schulze |
| 6,652,545 B2 | 11/2003 | Shipp et al. |
| 6,652,551 B1 | 11/2003 | Heiss |
| 6,656,194 B1 | 12/2003 | Gannoe et al. |
| 6,663,641 B1 | 12/2003 | Kovac et al. |
| 6,663,655 B2 | 12/2003 | Ginn et al. |
| 6,666,854 B1 | 12/2003 | Lange |
| 6,672,338 B1 | 1/2004 | Esashi et al. |
| 6,673,058 B2 | 1/2004 | Snow |
| 6,673,087 B1 | 1/2004 | Chang et al. |
| 6,673,092 B1 | 1/2004 | Bacher |
| 6,676,685 B2 | 1/2004 | Pedros et al. |
| 6,679,882 B1 | 1/2004 | Kornerup |
| 6,685,628 B2 | 2/2004 | Vu |
| 6,685,724 B1 | 2/2004 | Haluck |
| 6,692,445 B2 | 2/2004 | Roberts et al. |
| 6,692,462 B2 | 2/2004 | Mackenzie et al. |
| 6,692,493 B2 | 2/2004 | McGovern et al. |
| 6,699,180 B2 | 3/2004 | Kobayashi |
| 6,699,256 B1 | 3/2004 | Logan et al. |
| 6,699,263 B2 | 3/2004 | Cope |
| 6,706,018 B2 | 3/2004 | Westlund et al. |
| 6,708,066 B2 | 3/2004 | Herbst et al. |
| 6,709,188 B2 | 3/2004 | Ushimaru |
| 6,709,445 B2 | 3/2004 | Boebel et al. |
| 6,716,226 B2 | 4/2004 | Sixto, Jr. et al. |
| 6,731,875 B1 | 5/2004 | Kartalopoulos |
| 6,736,822 B2 | 5/2004 | McClellan et al. |
| 6,740,030 B2 | 5/2004 | Martone et al. |
| 6,740,082 B2 | 5/2004 | Shadduck |
| 6,743,166 B2 | 6/2004 | Berci et al. |
| 6,743,226 B2 | 6/2004 | Cosman et al. |
| 6,743,239 B1 | 6/2004 | Kuehn et al. |
| 6,743,240 B2 | 6/2004 | Smith et al. |
| 6,749,560 B1 | 6/2004 | Konstorum et al. |
| 6,749,609 B1 | 6/2004 | Lunsford et al. |
| 6,752,768 B2 | 6/2004 | Burdorff et al. |
| 6,752,811 B2 | 6/2004 | Chu et al. |
| 6,752,822 B2 | 6/2004 | Jespersen |
| 6,758,857 B2 | 7/2004 | Cioanta et al. |
| 6,761,685 B2 | 7/2004 | Adams et al. |
| 6,761,718 B2 | 7/2004 | Madsen |
| 6,761,722 B2 | 7/2004 | Cole et al. |
| 6,767,356 B2 | 7/2004 | Kanner et al. |
| 6,773,434 B2 | 8/2004 | Ciarrocca |
| 6,776,165 B2 | 8/2004 | Jin |
| 6,776,787 B2 | 8/2004 | Phung et al. |
| 6,780,151 B2 | 8/2004 | Grabover et al. |
| 6,780,352 B2 | 8/2004 | Jacobson |
| 6,783,491 B2 | 8/2004 | Saadat et al. |
| 6,786,382 B1 | 9/2004 | Hoffman |
| 6,786,864 B2 | 9/2004 | Matsuura et al. |
| 6,786,905 B2 | 9/2004 | Swanson et al. |
| 6,788,977 B2 | 9/2004 | Fenn et al. |
| 6,790,173 B2 | 9/2004 | Saadat et al. |
| 6,790,217 B2 | 9/2004 | Schulze et al. |
| 6,795,728 B2 | 9/2004 | Chornenky et al. |
| 6,800,056 B2 | 10/2004 | Tartaglia et al. |
| 6,808,491 B2 | 10/2004 | Kortenbach et al. |
| 6,817,974 B2 | 11/2004 | Cooper et al. |
| 6,818,007 B1 | 11/2004 | Dampney et al. |
| 6,824,548 B2 | 11/2004 | Smith et al. |
| 6,830,545 B2 | 12/2004 | Bendall |
| 6,836,688 B2 | 12/2004 | Ingle et al. |
| 6,837,847 B2 | 1/2005 | Ewers et al. |
| 6,840,246 B2 | 1/2005 | Downing |
| 6,840,938 B1 | 1/2005 | Morley et al. |
| 6,843,794 B2 | 1/2005 | Sixto, Jr. et al. |
| 6,861,250 B1 | 3/2005 | Cole et al. |
| 6,866,627 B2 | 3/2005 | Nozue |
| 6,866,628 B2 | 3/2005 | Goodman et al. |
| 6,869,394 B2 | 3/2005 | Ishibiki |
| 6,878,106 B1 | 4/2005 | Herrmann |
| 6,878,110 B2 | 4/2005 | Yang et al. |
| 6,881,213 B2 | 4/2005 | Ryan et al. |
| 6,881,216 B2 | 4/2005 | Di Caprio et al. |
| 6,884,213 B2 | 4/2005 | Raz et al. |
| 6,887,255 B2 | 5/2005 | Shimm |
| 6,889,089 B2 | 5/2005 | Behl et al. |
| 6,890,295 B2 | 5/2005 | Michels et al. |
| 6,896,683 B1 | 5/2005 | Gadberry et al. |
| 6,896,692 B2 | 5/2005 | Ginn et al. |
| 6,899,710 B2 | 5/2005 | Hooven |
| 6,908,427 B2 | 6/2005 | Fleener et al. |
| 6,908,476 B2 | 6/2005 | Jud et al. |
| 6,913,613 B2 | 7/2005 | Schwarz et al. |
| 6,916,284 B2 | 7/2005 | Moriyama |
| 6,918,871 B2 | 7/2005 | Schulze |
| 6,918,906 B2 | 7/2005 | Long |
| 6,918,908 B2 | 7/2005 | Bonner et al. |
| 6,926,723 B1 | 8/2005 | Mulhauser et al. |
| 6,926,725 B2 | 8/2005 | Cooke et al. |

(56) References Cited

U.S. PATENT DOCUMENTS

| | | |
|---|---|---|
| 6,932,810 B2 | 8/2005 | Ryan |
| 6,932,824 B1 | 8/2005 | Roop et al. |
| 6,932,827 B2 | 8/2005 | Cole |
| 6,932,834 B2 | 8/2005 | Lizardi et al. |
| 6,936,003 B2 | 8/2005 | Iddan |
| 6,939,290 B2 | 9/2005 | Iddan |
| 6,939,292 B2 | 9/2005 | Mizuno |
| 6,939,327 B2 | 9/2005 | Hall et al. |
| 6,942,613 B2 | 9/2005 | Ewers et al. |
| 6,944,490 B1 | 9/2005 | Chow |
| 6,945,472 B2 | 9/2005 | Wuttke et al. |
| 6,945,979 B2 | 9/2005 | Kortenbach et al. |
| 6,949,096 B2 | 9/2005 | Davison et al. |
| 6,955,683 B2 | 10/2005 | Bonutti |
| 6,958,035 B2 | 10/2005 | Friedman et al. |
| 6,960,162 B2 | 11/2005 | Saadat et al. |
| 6,960,163 B2 | 11/2005 | Ewers et al. |
| 6,962,587 B2 | 11/2005 | Johnson et al. |
| 6,964,662 B2 | 11/2005 | Kidooka |
| 6,966,909 B2 | 11/2005 | Marshall et al. |
| 6,966,919 B2 | 11/2005 | Sixto, Jr. et al. |
| 6,967,462 B1 | 11/2005 | Landis |
| 6,971,988 B2 | 12/2005 | Orban, III |
| 6,972,017 B2 | 12/2005 | Smith et al. |
| 6,974,411 B2 | 12/2005 | Belson |
| 6,976,992 B2 | 12/2005 | Sachatello et al. |
| 6,984,203 B2 | 1/2006 | Tartaglia et al. |
| 6,984,205 B2 | 1/2006 | Gazdzinski |
| 6,986,774 B2 | 1/2006 | Middleman et al. |
| 6,988,987 B2 | 1/2006 | Ishikawa et al. |
| 6,989,028 B2 | 1/2006 | Lashinski et al. |
| 6,991,627 B2 | 1/2006 | Madhani et al. |
| 6,991,631 B2 | 1/2006 | Woloszko et al. |
| 6,994,706 B2 | 2/2006 | Chornenky et al. |
| 6,994,708 B2 | 2/2006 | Manzo |
| 6,997,870 B2 | 2/2006 | Couvillon, Jr. |
| 6,997,931 B2 | 2/2006 | Sauer et al. |
| 7,000,818 B2 | 2/2006 | Shelton, IV et al. |
| 7,001,329 B2 | 2/2006 | Kobayashi et al. |
| 7,001,341 B2 | 2/2006 | Gellman et al. |
| 7,008,375 B2 | 3/2006 | Weisel |
| 7,008,419 B2 | 3/2006 | Shadduck |
| 7,009,634 B2 | 3/2006 | Iddan et al. |
| 7,010,340 B2 | 3/2006 | Scarantino et al. |
| 7,011,669 B2 | 3/2006 | Kimblad |
| 7,020,531 B1 | 3/2006 | Colliou et al. |
| 7,025,580 B2 | 4/2006 | Heagy et al. |
| 7,025,721 B2 | 4/2006 | Cohen et al. |
| 7,029,435 B2 | 4/2006 | Nakao |
| 7,029,438 B2 | 4/2006 | Morin et al. |
| 7,029,450 B2 | 4/2006 | Gellman |
| 7,032,600 B2 | 4/2006 | Fukuda et al. |
| 7,035,680 B2 | 4/2006 | Partridge et al. |
| 7,037,290 B2 | 5/2006 | Gardeski et al. |
| 7,041,052 B2 | 5/2006 | Saadat et al. |
| 7,052,454 B2 | 5/2006 | Taylor |
| 7,052,489 B2 | 5/2006 | Griego et al. |
| 7,056,330 B2 | 6/2006 | Gayton |
| 7,060,024 B2 | 6/2006 | Long et al. |
| 7,060,025 B2 | 6/2006 | Long et al. |
| 7,063,697 B2 | 6/2006 | Slater |
| 7,063,715 B2 | 6/2006 | Onuki et al. |
| 7,066,879 B2 | 6/2006 | Fowler et al. |
| 7,066,936 B2 | 6/2006 | Ryan |
| 7,070,602 B2 | 7/2006 | Smith et al. |
| 7,076,305 B2 | 7/2006 | Imran et al. |
| 7,083,618 B2 | 8/2006 | Couture et al. |
| 7,083,620 B2 | 8/2006 | Jahns et al. |
| 7,083,629 B2 | 8/2006 | Weller et al. |
| 7,083,635 B2 | 8/2006 | Ginn |
| 7,087,071 B2 | 8/2006 | Nicholas et al. |
| 7,088,923 B2 | 8/2006 | Haruyama |
| 7,090,673 B2 | 8/2006 | Dycus et al. |
| 7,090,683 B2 | 8/2006 | Brock et al. |
| 7,090,685 B2 | 8/2006 | Kortenbach et al. |
| 7,093,518 B2 | 8/2006 | Gmeilbauer |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,105,000 B2 | 9/2006 | McBrayer |
| 7,105,005 B2 | 9/2006 | Blake |
| 7,108,696 B2 | 9/2006 | Daniel et al. |
| 7,108,703 B2 | 9/2006 | Danitz et al. |
| 7,112,208 B2 | 9/2006 | Morris et al. |
| 7,115,092 B2 | 10/2006 | Park et al. |
| 7,115,124 B1 | 10/2006 | Xiao |
| 7,117,703 B2 | 10/2006 | Kato et al. |
| 7,118,531 B2 | 10/2006 | Krill |
| 7,118,578 B2 | 10/2006 | West, Jr. et al. |
| 7,118,587 B2 | 10/2006 | Dycus et al. |
| 7,128,708 B2 | 10/2006 | Saadat et al. |
| 7,130,697 B2 | 10/2006 | Chornenky et al. |
| RE39,415 E | 11/2006 | Bales et al. |
| 7,131,978 B2 | 11/2006 | Sancoff et al. |
| 7,131,979 B2 | 11/2006 | DiCarlo et al. |
| 7,131,980 B1 | 11/2006 | Field et al. |
| 7,137,980 B2 | 11/2006 | Buysse et al. |
| 7,137,981 B2 | 11/2006 | Long |
| 7,146,984 B2 | 12/2006 | Stack et al. |
| 7,147,650 B2 | 12/2006 | Lee |
| 7,150,097 B2 | 12/2006 | Sremcich et al. |
| 7,150,655 B2 | 12/2006 | Mastrototaro et al. |
| 7,150,750 B2 | 12/2006 | Damarati |
| 7,152,488 B2 | 12/2006 | Hedrich et al. |
| 7,153,321 B2 | 12/2006 | Andrews |
| 7,160,296 B2 | 1/2007 | Pearson et al. |
| 7,163,525 B2 | 1/2007 | Franer |
| 7,172,714 B2 | 2/2007 | Jacobson |
| 7,175,591 B2 | 2/2007 | Kaladelfos |
| 7,179,254 B2 | 2/2007 | Pendekanti et al. |
| 7,186,265 B2 | 3/2007 | Sharkawy et al. |
| 7,188,627 B2 | 3/2007 | Nelson et al. |
| 7,195,612 B2 | 3/2007 | Van Sloten et al. |
| 7,195,631 B2 | 3/2007 | Dumbauld |
| 7,204,820 B2 | 4/2007 | Akahoshi |
| 7,207,997 B2 | 4/2007 | Shipp et al. |
| 7,208,005 B2 | 4/2007 | Frecker et al. |
| 7,211,089 B2 | 5/2007 | Kear et al |
| 7,211,092 B2 | 5/2007 | Hughett |
| 7,220,227 B2 | 5/2007 | Sasaki et al. |
| 7,223,271 B2 | 5/2007 | Muramatsu et al. |
| 7,223,272 B2 | 5/2007 | Francese et al. |
| 7,229,438 B2 | 6/2007 | Young |
| 7,232,414 B2 | 6/2007 | Gonzalez |
| 7,232,445 B2 | 6/2007 | Kortenbach et al. |
| 7,235,089 B1 | 6/2007 | McGuckin, Jr. |
| 7,241,290 B2 | 7/2007 | Doyle et al. |
| 7,244,228 B2 | 7/2007 | Lubowski |
| 7,250,027 B2 | 7/2007 | Barry |
| 7,252,660 B2 | 8/2007 | Kunz |
| 7,255,675 B2 | 8/2007 | Gertner et al. |
| 7,261,725 B2 | 8/2007 | Binmoeller |
| 7,270,663 B2 | 9/2007 | Nakao |
| 7,288,075 B2 | 10/2007 | Parihar et al. |
| 7,291,127 B2 | 11/2007 | Eidenschink |
| 7,294,139 B1 | 11/2007 | Gengler |
| 7,301,250 B2 | 11/2007 | Cassel |
| 7,306,597 B2 | 12/2007 | Manzo |
| 7,308,828 B2 | 12/2007 | Hashimoto |
| 7,311,107 B2 | 12/2007 | Harel et al. |
| 7,318,802 B2 | 1/2008 | Suzuki et al. |
| 7,320,695 B2 | 1/2008 | Carroll |
| 7,322,934 B2 | 1/2008 | Miyake et al. |
| 7,323,006 B2 | 1/2008 | Andreas et al. |
| 7,329,256 B2 | 2/2008 | Johnson et al. |
| 7,329,257 B2 | 2/2008 | Kanehira et al. |
| 7,329,383 B2 | 2/2008 | Stinson |
| 7,335,220 B2 | 2/2008 | Khosravi et al. |
| 7,344,536 B1 | 3/2008 | Lunsford et al. |
| 7,352,387 B2 | 4/2008 | Yamamoto |
| 7,364,582 B2 | 4/2008 | Lee |
| 7,371,215 B2 | 5/2008 | Colliou et al. |
| 7,381,216 B2 | 6/2008 | Buzzard et al. |
| 7,390,324 B2 | 6/2008 | Whalen et al. |

(56) References Cited

U.S. PATENT DOCUMENTS

| | | |
|---|---|---|
| 7,393,222 B2 | 7/2008 | Asakura |
| 7,402,162 B2 | 7/2008 | Ouchi |
| 7,404,791 B2 | 7/2008 | Linares et al. |
| 7,410,483 B2 | 8/2008 | Danitz et al. |
| 7,413,563 B2 | 8/2008 | Corcoran et al. |
| 7,416,554 B2 | 8/2008 | Lam et al. |
| 7,422,590 B2 | 9/2008 | Kupferschmid et al. |
| 7,435,229 B2 | 10/2008 | Wolf |
| 7,435,257 B2 | 10/2008 | Lashinski et al. |
| 7,441,507 B2 | 10/2008 | Teraura et al. |
| 7,452,327 B2 | 11/2008 | Durgin et al. |
| 7,455,208 B2 | 11/2008 | Wales et al. |
| 7,455,675 B2 | 11/2008 | Schur et al. |
| 7,468,066 B2 | 12/2008 | Vargas et al. |
| 7,476,237 B2 | 1/2009 | Taniguchi et al. |
| 7,479,104 B2 | 1/2009 | Lau et al. |
| 7,485,093 B2 | 2/2009 | Glukhovsky |
| 7,488,295 B2 | 2/2009 | Burbank et al. |
| 7,494,499 B2 | 2/2009 | Nagase et al. |
| 7,497,867 B2 | 3/2009 | Lasner et al. |
| 7,498,950 B1 | 3/2009 | Ertas et al. |
| 7,507,200 B2 | 3/2009 | Okada |
| 7,507,239 B2 | 3/2009 | Shadduck |
| 7,510,107 B2 | 3/2009 | Timm et al. |
| 7,511,733 B2 | 3/2009 | Takizawa et al. |
| 7,515,953 B2 | 4/2009 | Madar et al. |
| 7,520,876 B2 | 4/2009 | Ressemann et al. |
| 7,524,281 B2 | 4/2009 | Chu et al. |
| 7,524,302 B2 | 4/2009 | Tower |
| 7,534,228 B2 | 5/2009 | Williams |
| 7,540,872 B2 | 6/2009 | Schechter et al. |
| 7,542,807 B2 | 6/2009 | Bertolero et al. |
| 7,544,203 B2 | 6/2009 | Chin et al. |
| 7,548,040 B2 | 6/2009 | Lee et al. |
| 7,549,564 B2 | 6/2009 | Boudreaux |
| 7,549,991 B2 | 6/2009 | Lu et al. |
| 7,549,998 B2 | 6/2009 | Braun |
| 7,553,278 B2 | 6/2009 | Kucklick |
| 7,553,298 B2 | 6/2009 | Hunt et al. |
| 7,559,452 B2 | 7/2009 | Wales et al. |
| 7,559,887 B2 | 7/2009 | Dannan |
| 7,559,916 B2 | 7/2009 | Smith et al. |
| 7,560,006 B2 | 7/2009 | Rakos et al. |
| 7,561,907 B2 | 7/2009 | Fuimaono et al. |
| 7,561,916 B2 | 7/2009 | Hunt et al. |
| 7,565,201 B2 | 7/2009 | Blackmore et al. |
| 7,566,334 B2 | 7/2009 | Christian et al. |
| 7,575,144 B2 | 8/2009 | Ortiz et al. |
| 7,575,548 B2 | 8/2009 | Takemoto et al. |
| 7,579,550 B2 | 8/2009 | Dayton et al. |
| 7,582,096 B2 | 9/2009 | Gellman et al. |
| 7,588,177 B2 | 9/2009 | Racenet |
| 7,588,557 B2 | 9/2009 | Nakao |
| 7,597,229 B2 | 10/2009 | Boudreaux et al. |
| 7,604,150 B2 | 10/2009 | Boudreaux |
| 7,608,083 B2 | 10/2009 | Lee et al. |
| 7,611,479 B2 | 11/2009 | Cragg et al. |
| 7,618,398 B2 | 11/2009 | Holman et al. |
| 7,621,936 B2 | 11/2009 | Cragg et al. |
| 7,632,250 B2 | 12/2009 | Smith et al. |
| 7,635,373 B2 | 12/2009 | Ortiz |
| 7,637,903 B2 | 12/2009 | Lentz et al. |
| 7,648,519 B2 | 1/2010 | Lee et al. |
| 7,650,742 B2 | 1/2010 | Ushijima |
| 7,651,483 B2 | 1/2010 | Byrum et al. |
| 7,651,509 B2 | 1/2010 | Bojarski et al. |
| 7,653,438 B2 | 1/2010 | Deem et al. |
| 7,654,431 B2 | 2/2010 | Hueil et al. |
| 7,655,004 B2 | 2/2010 | Long |
| 7,662,089 B2 | 2/2010 | Okada et al. |
| 7,666,180 B2 | 2/2010 | Holsten et al. |
| 7,666,203 B2 | 2/2010 | Chanduszko et al. |
| 7,670,336 B2 | 3/2010 | Young et al. |
| 7,674,259 B2 | 3/2010 | Shadduck |
| 7,678,043 B2 | 3/2010 | Gilad |
| 7,680,543 B2 | 3/2010 | Azure |
| 7,684,599 B2 | 3/2010 | Horn et al. |
| 7,686,826 B2 | 3/2010 | Lee et al. |
| 7,697,970 B2 | 4/2010 | Uchiyama et al. |
| 7,699,835 B2 | 4/2010 | Lee et al. |
| 7,699,864 B2 | 4/2010 | Kick et al. |
| 7,713,189 B2 | 5/2010 | Hanke |
| 7,713,270 B2 | 5/2010 | Suzuki |
| 7,721,742 B2 | 5/2010 | Kalloo et al. |
| 7,736,374 B2 | 6/2010 | Vaughan et al. |
| 7,744,615 B2 | 6/2010 | Couture |
| 7,749,161 B2 | 7/2010 | Beckman et al. |
| 7,751,866 B2 | 7/2010 | Aoki et al. |
| 7,753,901 B2 | 7/2010 | Piskun et al. |
| 7,753,933 B2 | 7/2010 | Ginn et al. |
| 7,758,577 B2 | 7/2010 | Nobis et al. |
| 7,762,949 B2 | 7/2010 | Nakao |
| 7,762,998 B2 | 7/2010 | Birk et al. |
| 7,763,012 B2 | 7/2010 | Petrick et al. |
| 7,765,010 B2 | 7/2010 | Chornenky et al. |
| 7,766,896 B2 | 8/2010 | Kornkven Volk et al. |
| 7,770,584 B2 | 8/2010 | Danek et al. |
| 7,771,416 B2 | 8/2010 | Spivey et al. |
| 7,771,437 B2 | 8/2010 | Hogg et al. |
| 7,780,683 B2 | 8/2010 | Roue et al. |
| 7,780,691 B2 | 8/2010 | Stefanchik |
| 7,784,663 B2 | 8/2010 | Shelton, IV |
| 7,794,409 B2 | 9/2010 | Damarati |
| 7,794,447 B2 | 9/2010 | Dann et al. |
| 7,794,458 B2 | 9/2010 | McIntyre et al. |
| 7,794,475 B2 | 9/2010 | Hess et al. |
| 7,798,386 B2 | 9/2010 | Schall et al. |
| 7,815,565 B2 | 10/2010 | Stefanchik et al. |
| 7,815,566 B2 | 10/2010 | Stefanchik et al. |
| 7,815,659 B2 | 10/2010 | Conlon et al. |
| 7,815,662 B2 | 10/2010 | Spivey et al. |
| 7,819,836 B2 | 10/2010 | Levine et al. |
| 7,828,186 B2 | 11/2010 | Wales |
| 7,833,156 B2 | 11/2010 | Williams et al. |
| 7,833,238 B2 | 11/2010 | Nakao |
| 7,837,615 B2 | 11/2010 | Le et al. |
| 7,842,028 B2 | 11/2010 | Lee |
| 7,842,068 B2 | 11/2010 | Ginn |
| 7,846,171 B2 | 12/2010 | Kullas et al. |
| 7,850,660 B2 | 12/2010 | Uth et al. |
| 7,857,183 B2 | 12/2010 | Shelton, IV |
| 7,862,546 B2 | 1/2011 | Conlon et al. |
| 7,862,553 B2 | 1/2011 | Ewaschuk |
| 7,867,216 B2 | 1/2011 | Wahr et al. |
| 7,879,004 B2 | 2/2011 | Seibel et al. |
| 7,883,458 B2 | 2/2011 | Hamel |
| 7,887,530 B2 | 2/2011 | Zemlok et al. |
| 7,887,558 B2 | 2/2011 | Lin et al. |
| 7,892,220 B2 | 2/2011 | Faller et al. |
| 7,896,804 B2 | 3/2011 | Uchimura et al. |
| 7,896,887 B2 | 3/2011 | Rimbaugh et al. |
| 7,905,828 B2 | 3/2011 | Brock et al. |
| 7,909,809 B2 | 3/2011 | Scopton et al. |
| 7,914,513 B2 | 3/2011 | Voorhees, Jr. |
| 7,918,785 B2 | 4/2011 | Okada et al. |
| 7,918,869 B2 | 4/2011 | Saadat et al. |
| 7,922,743 B2 | 4/2011 | Heinrich et al. |
| 7,927,271 B2 | 4/2011 | Dimitriou et al. |
| 7,931,624 B2 | 4/2011 | Smith et al. |
| 7,945,332 B2 | 5/2011 | Schechter |
| 7,947,000 B2 | 5/2011 | Vargas et al. |
| 7,953,326 B2 | 5/2011 | Farr et al. |
| 7,955,298 B2 | 6/2011 | Carroll et al. |
| 7,959,629 B2 | 6/2011 | Young et al. |
| 7,963,975 B2 | 6/2011 | Criscuolo |
| 7,965,180 B2 | 6/2011 | Koyama |
| 7,967,808 B2 | 6/2011 | Fitzgerald et al. |
| 7,969,473 B2 | 6/2011 | Kotoda |
| 7,972,330 B2 | 7/2011 | Alejandro et al. |
| 7,976,552 B2 | 7/2011 | Suzuki |
| 7,985,239 B2 | 7/2011 | Suzuki |
| 7,988,685 B2 | 8/2011 | Ziaie et al. |
| 8,021,362 B2 | 9/2011 | Deem et al. |
| 8,029,504 B2 | 10/2011 | Long |

(56) References Cited

U.S. PATENT DOCUMENTS

| | | | |
|---|---|---|---|
| 8,034,046 B2 | 10/2011 | Eidenschink | |
| 8,037,591 B2 | 10/2011 | Spivey et al. | |
| 8,048,067 B2 | 11/2011 | Davalos et al. | |
| 8,048,108 B2 | 11/2011 | Sibbitt et al. | |
| 8,052,699 B1 | 11/2011 | Sherwinter | |
| 8,057,510 B2 | 11/2011 | Ginn et al. | |
| 8,062,306 B2 | 11/2011 | Nobis et al. | |
| 8,062,311 B2 | 11/2011 | Litscher et al. | |
| 8,066,632 B2 | 11/2011 | Dario et al. | |
| 8,070,759 B2 | 12/2011 | Stefanchik et al. | |
| 8,070,804 B2 | 12/2011 | Hyde et al. | |
| 8,075,572 B2 | 12/2011 | Stefanchik et al. | |
| 8,075,587 B2 | 12/2011 | Ginn | |
| 8,088,062 B2 | 1/2012 | Zwolinski | |
| 8,096,459 B2 | 1/2012 | Ortiz et al. | |
| 8,096,941 B2 | 1/2012 | Fowler et al. | |
| 8,100,922 B2 | 1/2012 | Griffith | |
| 8,109,872 B2 | 2/2012 | Kennedy, II et al. | |
| 8,114,072 B2 | 2/2012 | Long et al. | |
| 8,114,119 B2 | 2/2012 | Spivey et al. | |
| 8,118,821 B2 | 2/2012 | Mouw | |
| 8,147,424 B2 | 4/2012 | Kassab et al. | |
| 8,157,813 B2 | 4/2012 | Ko et al. | |
| 8,157,834 B2 | 4/2012 | Conlon | |
| 8,172,772 B2 | 5/2012 | Zwolinski et al. | |
| 8,182,414 B2 | 5/2012 | Handa et al. | |
| 8,187,166 B2 | 5/2012 | Kuth et al. | |
| 8,206,295 B2 | 6/2012 | Kaul | |
| 8,211,125 B2 | 7/2012 | Spivey | |
| 8,221,310 B2 | 7/2012 | Saadat et al. | |
| 8,241,204 B2 | 8/2012 | Spivey | |
| 8,251,068 B2 | 8/2012 | Schnell | |
| 8,252,057 B2 | 8/2012 | Fox | |
| 8,262,563 B2 | 9/2012 | Bakos et al. | |
| 8,262,655 B2 | 9/2012 | Ghabrial et al. | |
| 8,262,680 B2 | 9/2012 | Swain et al. | |
| 8,303,581 B2 | 11/2012 | Arts et al. | |
| 8,308,738 B2 | 11/2012 | Nobis et al. | |
| 8,317,806 B2 | 11/2012 | Coe et al. | |
| 8,328,836 B2 | 12/2012 | Conlon et al. | |
| 8,337,394 B2 | 12/2012 | Vakharia | |
| 8,337,492 B2 | 12/2012 | Kunis et al. | |
| 8,343,041 B2 | 1/2013 | Byers et al. | |
| 8,353,487 B2 | 1/2013 | Trusty et al. | |
| 8,357,170 B2 | 1/2013 | Stefanchik | |
| 8,361,066 B2 | 1/2013 | Long et al. | |
| 8,361,112 B2 | 1/2013 | Carroll, II et al. | |
| 8,403,926 B2 | 3/2013 | Nobis et al. | |
| 8,408,108 B2 | 4/2013 | Redemann et al. | |
| 8,409,200 B2 | 4/2013 | Holcomb et al. | |
| 8,425,505 B2 | 4/2013 | Long | |
| 8,430,811 B2 | 4/2013 | Hess et al. | |
| 8,449,452 B2 | 5/2013 | Iddan et al. | |
| 8,449,538 B2 | 5/2013 | Long | |
| 8,480,657 B2 | 7/2013 | Bakos | |
| 8,480,689 B2 | 7/2013 | Spivey et al. | |
| 8,485,968 B2 | 7/2013 | Weimer et al. | |
| 8,496,574 B2 | 7/2013 | Trusty et al. | |
| 8,500,697 B2 | 8/2013 | Kurth et al. | |
| 8,506,564 B2 | 8/2013 | Long et al. | |
| 8,523,939 B1 | 9/2013 | Hausen | |
| 8,529,563 B2 | 9/2013 | Long et al. | |
| 8,545,396 B2 | 10/2013 | Cover et al. | |
| 8,568,410 B2 | 10/2013 | Vakharia et al. | |
| 8,579,897 B2 | 11/2013 | Vakharia et al. | |
| 8,608,652 B2 | 12/2013 | Voegele et al. | |
| 8,636,648 B2 | 1/2014 | Gazdzinski | |
| 8,640,940 B2 * | 2/2014 | Ohdaira | A61B 17/115 227/175.1 |
| 8,652,150 B2 | 2/2014 | Swain et al. | |
| 8,668,686 B2 | 3/2014 | Govari et al. | |
| 8,679,003 B2 | 3/2014 | Spivey | |
| 8,753,335 B2 | 6/2014 | Moshe et al. | |
| 8,771,260 B2 | 7/2014 | Conlon et al. | |
| 8,828,031 B2 | 9/2014 | Fox et al. | |
| 8,888,792 B2 | 11/2014 | Harris et al. | |
| 8,906,035 B2 | 12/2014 | Zwolinski et al. | |
| 8,911,452 B2 | 12/2014 | Skakoon et al. | |
| 2001/0023333 A1 | 9/2001 | Wise et al. | |
| 2002/0022771 A1 | 2/2002 | Diokno et al. | |
| 2002/0022857 A1 | 2/2002 | Goldsteen et al. | |
| 2002/0023353 A1 | 2/2002 | Ting-Kung | |
| 2002/0029055 A1 | 3/2002 | Bonutti | |
| 2002/0042562 A1 | 4/2002 | Meron et al. | |
| 2002/0049439 A1 | 4/2002 | Mulier et al. | |
| 2002/0052610 A1 * | 5/2002 | Skakoon | A61B 19/201 606/129 |
| 2002/0068945 A1 | 6/2002 | Sixto, Jr. et al. | |
| 2002/0078967 A1 | 6/2002 | Sixto, Jr. et al. | |
| 2002/0082516 A1 | 6/2002 | Stefanchik | |
| 2002/0095164 A1 | 7/2002 | Andreas et al. | |
| 2002/0107530 A1 | 8/2002 | Sauer et al. | |
| 2002/0111615 A1 * | 8/2002 | Cosman | A61B 18/1477 606/41 |
| 2002/0133115 A1 | 9/2002 | Gordon et al. | |
| 2002/0138086 A1 | 9/2002 | Sixto, Jr. et al. | |
| 2002/0147456 A1 | 10/2002 | Diduch et al. | |
| 2002/0156372 A1 * | 10/2002 | Skakoon | A61B 19/201 600/431 |
| 2002/0165592 A1 | 11/2002 | Glukhovsky et al. | |
| 2002/0173805 A1 | 11/2002 | Matsuno et al. | |
| 2002/0183591 A1 | 12/2002 | Matsuura et al. | |
| 2003/0014090 A1 | 1/2003 | Abrahamson | |
| 2003/0018373 A1 | 1/2003 | Eckhardt et al. | |
| 2003/0023255 A1 | 1/2003 | Miles et al. | |
| 2003/0036679 A1 | 2/2003 | Kortenbach et al. | |
| 2003/0069602 A1 | 4/2003 | Jacobs et al. | |
| 2003/0078471 A1 | 4/2003 | Foley et al. | |
| 2003/0083681 A1 | 5/2003 | Moutafis et al. | |
| 2003/0114731 A1 | 6/2003 | Cadeddu et al. | |
| 2003/0114732 A1 | 6/2003 | Webler et al. | |
| 2003/0120257 A1 | 6/2003 | Houston et al. | |
| 2003/0124009 A1 | 7/2003 | Ravi et al. | |
| 2003/0130564 A1 | 7/2003 | Martone et al. | |
| 2003/0130656 A1 | 7/2003 | Levin | |
| 2003/0139646 A1 | 7/2003 | Sharrow et al. | |
| 2003/0158521 A1 | 8/2003 | Ameri | |
| 2003/0167062 A1 | 9/2003 | Gambale et al. | |
| 2003/0171651 A1 | 9/2003 | Page et al. | |
| 2003/0176880 A1 | 9/2003 | Long et al. | |
| 2003/0187351 A1 * | 10/2003 | Franck et al. | 600/429 |
| 2003/0216611 A1 | 11/2003 | Vu | |
| 2003/0216615 A1 | 11/2003 | Ouchi | |
| 2003/0220545 A1 | 11/2003 | Ouchi | |
| 2003/0225312 A1 | 12/2003 | Suzuki et al. | |
| 2003/0225332 A1 | 12/2003 | Okada et al. | |
| 2003/0229269 A1 | 12/2003 | Humphrey | |
| 2003/0229371 A1 | 12/2003 | Whitworth | |
| 2003/0236549 A1 | 12/2003 | Bonadio et al. | |
| 2004/0002683 A1 | 1/2004 | Nicholson et al. | |
| 2004/0024414 A1 | 2/2004 | Downing | |
| 2004/0034369 A1 | 2/2004 | Sauer et al. | |
| 2004/0054322 A1 | 3/2004 | Vargas | |
| 2004/0098007 A1 | 5/2004 | Heiss | |
| 2004/0101456 A1 | 5/2004 | Kuroshima et al. | |
| 2004/0104999 A1 | 6/2004 | Okada | |
| 2004/0116948 A1 | 6/2004 | Sixto, Jr. et al. | |
| 2004/0127940 A1 | 7/2004 | Ginn et al. | |
| 2004/0133077 A1 | 7/2004 | Obenchain et al. | |
| 2004/0133089 A1 | 7/2004 | Kilcoyne et al. | |
| 2004/0136779 A1 | 7/2004 | Bhaskar | |
| 2004/0138525 A1 | 7/2004 | Saadat et al. | |
| 2004/0138529 A1 | 7/2004 | Wiltshire et al. | |
| 2004/0138587 A1 | 7/2004 | Lyons, IV | |
| 2004/0161451 A1 | 8/2004 | Pierce et al. | |
| 2004/0167545 A1 | 8/2004 | Sadler et al. | |
| 2004/0176689 A1 | 9/2004 | Walker et al. | |
| 2004/0186350 A1 | 9/2004 | Brenneman et al. | |
| 2004/0193009 A1 | 9/2004 | Jaffe et al. | |
| 2004/0193146 A1 | 9/2004 | Lee et al. | |
| 2004/0193186 A1 | 9/2004 | Kortenbach et al. | |
| 2004/0193188 A1 | 9/2004 | Francese | |
| 2004/0193189 A1 | 9/2004 | Kortenbach et al. | |
| 2004/0193200 A1 | 9/2004 | Dworschak et al. | |

(56) References Cited

U.S. PATENT DOCUMENTS

| | | |
|---|---|---|
| 2004/0199052 A1 | 10/2004 | Banik et al. |
| 2004/0199159 A1 | 10/2004 | Lee et al. |
| 2004/0206859 A1 | 10/2004 | Chong et al. |
| 2004/0210245 A1 | 10/2004 | Erickson et al. |
| 2004/0215058 A1 | 10/2004 | Zirps et al. |
| 2004/0223309 A1* | 11/2004 | Haemer ............ G01R 1/07314 361/767 |
| 2004/0225183 A1 | 11/2004 | Michlitsch et al. |
| 2004/0225186 A1 | 11/2004 | Horne, Jr. et al. |
| 2004/0225323 A1 | 11/2004 | Nagase et al. |
| 2004/0230095 A1 | 11/2004 | Stefanchik et al. |
| 2004/0230096 A1 | 11/2004 | Stefanchik et al. |
| 2004/0230161 A1 | 11/2004 | Zeiner |
| 2004/0243108 A1 | 12/2004 | Suzuki |
| 2004/0249246 A1 | 12/2004 | Campos |
| 2004/0249367 A1 | 12/2004 | Saadat et al. |
| 2004/0249394 A1 | 12/2004 | Morris et al. |
| 2004/0249443 A1 | 12/2004 | Shanley et al. |
| 2004/0254572 A1 | 12/2004 | McIntyre et al. |
| 2004/0260198 A1 | 12/2004 | Rothberg et al. |
| 2004/0260315 A1 | 12/2004 | Dell et al. |
| 2004/0260337 A1 | 12/2004 | Freed |
| 2005/0004515 A1 | 1/2005 | Hart et al. |
| 2005/0033265 A1 | 2/2005 | Engel et al. |
| 2005/0033277 A1 | 2/2005 | Clague et al. |
| 2005/0033319 A1 | 2/2005 | Gambale et al. |
| 2005/0033333 A1 | 2/2005 | Smith et al. |
| 2005/0043690 A1 | 2/2005 | Todd |
| 2005/0049616 A1 | 3/2005 | Rivera et al. |
| 2005/0059963 A1 | 3/2005 | Phan et al. |
| 2005/0059964 A1 | 3/2005 | Fitz |
| 2005/0065397 A1 | 3/2005 | Saadat et al. |
| 2005/0065509 A1 | 3/2005 | Coldwell et al. |
| 2005/0065517 A1 | 3/2005 | Chin |
| 2005/0070754 A1 | 3/2005 | Nobis et al. |
| 2005/0070763 A1 | 3/2005 | Nobis et al. |
| 2005/0070764 A1 | 3/2005 | Nobis et al. |
| 2005/0080413 A1 | 4/2005 | Canady |
| 2005/0080435 A1 | 4/2005 | Smith et al. |
| 2005/0085693 A1 | 4/2005 | Belson et al. |
| 2005/0085832 A1 | 4/2005 | Sancoff et al. |
| 2005/0090837 A1 | 4/2005 | Sixto, Jr. et al. |
| 2005/0090838 A1 | 4/2005 | Sixto, Jr. et al. |
| 2005/0096502 A1 | 5/2005 | Khalili |
| 2005/0101837 A1 | 5/2005 | Kalloo et al. |
| 2005/0101838 A1 | 5/2005 | Camillocci et al. |
| 2005/0101984 A1 | 5/2005 | Chanduszko et al. |
| 2005/0107663 A1 | 5/2005 | Saadat et al. |
| 2005/0107664 A1 | 5/2005 | Kalloo et al. |
| 2005/0110881 A1 | 5/2005 | Glukhovsky et al. |
| 2005/0113847 A1 | 5/2005 | Gadberry et al. |
| 2005/0119613 A1 | 6/2005 | Moenning et al. |
| 2005/0124855 A1 | 6/2005 | Jaffe et al. |
| 2005/0125010 A1 | 6/2005 | Smith et al. |
| 2005/0131279 A1 | 6/2005 | Boulais et al. |
| 2005/0131457 A1 | 6/2005 | Douglas et al. |
| 2005/0137454 A1 | 6/2005 | Saadat et al. |
| 2005/0143647 A1 | 6/2005 | Minai et al. |
| 2005/0143690 A1 | 6/2005 | High |
| 2005/0143774 A1 | 6/2005 | Polo |
| 2005/0143803 A1 | 6/2005 | Watson et al. |
| 2005/0149087 A1 | 7/2005 | Ahlberg et al. |
| 2005/0149096 A1 | 7/2005 | Hilal et al. |
| 2005/0159648 A1 | 7/2005 | Freed |
| 2005/0165272 A1 | 7/2005 | Okada et al. |
| 2005/0165378 A1 | 7/2005 | Heinrich et al. |
| 2005/0165411 A1 | 7/2005 | Orban, III |
| 2005/0165429 A1 | 7/2005 | Douglas et al. |
| 2005/0182429 A1 | 8/2005 | Yamanouchi |
| 2005/0192478 A1 | 9/2005 | Williams et al. |
| 2005/0192598 A1 | 9/2005 | Johnson et al. |
| 2005/0192602 A1 | 9/2005 | Manzo |
| 2005/0192654 A1 | 9/2005 | Chanduszko et al. |
| 2005/0209624 A1 | 9/2005 | Vijay |
| 2005/0215858 A1 | 9/2005 | Vail, III |
| 2005/0216036 A1 | 9/2005 | Nakao |
| 2005/0216050 A1 | 9/2005 | Sepetka et al. |
| 2005/0228224 A1 | 10/2005 | Okada et al. |
| 2005/0228406 A1 | 10/2005 | Bose |
| 2005/0234297 A1 | 10/2005 | Devierre et al. |
| 2005/0240249 A1 | 10/2005 | Tu et al. |
| 2005/0250983 A1 | 11/2005 | Tremaglio et al. |
| 2005/0250990 A1 | 11/2005 | Le et al. |
| 2005/0250993 A1 | 11/2005 | Jaeger |
| 2005/0251166 A1 | 11/2005 | Vaughan et al. |
| 2005/0251176 A1 | 11/2005 | Swanstrom et al. |
| 2005/0261674 A1 | 11/2005 | Nobis et al. |
| 2005/0267492 A1 | 12/2005 | Poncet et al. |
| 2005/0272975 A1 | 12/2005 | McWeeney et al. |
| 2005/0272977 A1 | 12/2005 | Saadat et al. |
| 2005/0273084 A1 | 12/2005 | Hinman et al. |
| 2005/0274935 A1 | 12/2005 | Nelson |
| 2005/0277945 A1 | 12/2005 | Saadat et al. |
| 2005/0277951 A1 | 12/2005 | Smith et al. |
| 2005/0277952 A1 | 12/2005 | Arp et al. |
| 2005/0277954 A1 | 12/2005 | Smith et al. |
| 2005/0277955 A1 | 12/2005 | Palmer et al. |
| 2005/0277956 A1 | 12/2005 | Francese et al. |
| 2005/0277957 A1 | 12/2005 | Kuhns et al. |
| 2005/0283118 A1 | 12/2005 | Uth et al. |
| 2005/0283119 A1 | 12/2005 | Uth et al. |
| 2005/0288555 A1 | 12/2005 | Binmoeller |
| 2006/0004406 A1 | 1/2006 | Wehrstein et al. |
| 2006/0004409 A1 | 1/2006 | Nobis et al. |
| 2006/0004410 A1 | 1/2006 | Nobis et al. |
| 2006/0015009 A1 | 1/2006 | Jaffe et al. |
| 2006/0015131 A1 | 1/2006 | Kierce et al. |
| 2006/0020167 A1 | 1/2006 | Sitzmann |
| 2006/0020247 A1 | 1/2006 | Kagan et al. |
| 2006/0025654 A1 | 2/2006 | Suzuki et al. |
| 2006/0025781 A1 | 2/2006 | Young et al. |
| 2006/0025812 A1 | 2/2006 | Shelton, IV |
| 2006/0025819 A1 | 2/2006 | Nobis et al. |
| 2006/0036267 A1 | 2/2006 | Saadat et al. |
| 2006/0041188 A1 | 2/2006 | Dirusso et al. |
| 2006/0058582 A1 | 3/2006 | Maahs et al. |
| 2006/0058776 A1 | 3/2006 | Bilsbury |
| 2006/0064083 A1 | 3/2006 | Khalaj et al. |
| 2006/0069396 A1 | 3/2006 | Meade et al. |
| 2006/0069424 A1 | 3/2006 | Acosta et al. |
| 2006/0069425 A1 | 3/2006 | Hillis et al. |
| 2006/0069429 A1 | 3/2006 | Spence et al. |
| 2006/0074413 A1 | 4/2006 | Behzadian |
| 2006/0079885 A1* | 4/2006 | Rick ................ A61B 18/1477 606/41 |
| 2006/0079890 A1 | 4/2006 | Guerra |
| 2006/0089528 A1 | 4/2006 | Tartaglia et al. |
| 2006/0095031 A1 | 5/2006 | Ormsby |
| 2006/0095060 A1 | 5/2006 | Mayenberger et al. |
| 2006/0100687 A1 | 5/2006 | Fahey et al. |
| 2006/0106423 A1 | 5/2006 | Weisel et al. |
| 2006/0111209 A1 | 5/2006 | Hinman et al. |
| 2006/0111210 A1 | 5/2006 | Hinman et al. |
| 2006/0111703 A1 | 5/2006 | Kunis et al. |
| 2006/0111704 A1 | 5/2006 | Brenneman et al. |
| 2006/0129166 A1 | 6/2006 | Lavelle |
| 2006/0135962 A1 | 6/2006 | Kick et al. |
| 2006/0135971 A1 | 6/2006 | Swanstrom et al. |
| 2006/0135984 A1 | 6/2006 | Kramer et al. |
| 2006/0142644 A1 | 6/2006 | Mulac et al. |
| 2006/0142652 A1 | 6/2006 | Keenan |
| 2006/0142790 A1 | 6/2006 | Gertner |
| 2006/0142798 A1 | 6/2006 | Holman et al. |
| 2006/0149129 A1 | 7/2006 | Watts et al. |
| 2006/0149131 A1 | 7/2006 | Or |
| 2006/0149132 A1 | 7/2006 | Iddan |
| 2006/0149135 A1 | 7/2006 | Paz |
| 2006/0161190 A1 | 7/2006 | Gadberry et al. |
| 2006/0167416 A1 | 7/2006 | Mathis et al. |
| 2006/0167482 A1 | 7/2006 | Swain et al. |
| 2006/0178560 A1 | 8/2006 | Saadat et al. |
| 2006/0183975 A1 | 8/2006 | Saadat et al. |
| 2006/0184161 A1 | 8/2006 | Maahs et al. |
| 2006/0189844 A1 | 8/2006 | Tien |

(56) References Cited

U.S. PATENT DOCUMENTS

| | | |
|---|---|---|
| 2006/0189845 A1 | 8/2006 | Maahs et al. |
| 2006/0190027 A1 | 8/2006 | Downey |
| 2006/0195084 A1 | 8/2006 | Slater |
| 2006/0200005 A1 | 9/2006 | Bjork et al. |
| 2006/0200121 A1 | 9/2006 | Mowery |
| 2006/0200169 A1 | 9/2006 | Sniffin |
| 2006/0200170 A1 | 9/2006 | Aranyi |
| 2006/0200199 A1 | 9/2006 | Bonutti et al. |
| 2006/0217665 A1 | 9/2006 | Prosek |
| 2006/0217697 A1 | 9/2006 | Lau et al. |
| 2006/0217742 A1 | 9/2006 | Messerly et al. |
| 2006/0217743 A1 | 9/2006 | Messerly et al. |
| 2006/0229639 A1 | 10/2006 | Whitfield |
| 2006/0229640 A1 | 10/2006 | Whitfield |
| 2006/0237022 A1 | 10/2006 | Chen et al. |
| 2006/0237023 A1 | 10/2006 | Cox et al. |
| 2006/0241570 A1 | 10/2006 | Wilk |
| 2006/0247500 A1 | 11/2006 | Voegele et al. |
| 2006/0247576 A1 | 11/2006 | Poncet |
| 2006/0247663 A1 | 11/2006 | Schwartz et al. |
| 2006/0247673 A1 | 11/2006 | Voegele et al. |
| 2006/0253004 A1 | 11/2006 | Frisch et al. |
| 2006/0253039 A1 | 11/2006 | McKenna et al. |
| 2006/0258907 A1 | 11/2006 | Stefanchik et al. |
| 2006/0258908 A1 | 11/2006 | Stefanchik et al. |
| 2006/0258910 A1 | 11/2006 | Stefanchik et al. |
| 2006/0258954 A1 | 11/2006 | Timberlake et al. |
| 2006/0258955 A1 | 11/2006 | Hoffman et al. |
| 2006/0259010 A1 | 11/2006 | Stefanchik et al. |
| 2006/0259073 A1 | 11/2006 | Miyamoto et al. |
| 2006/0264752 A1 | 11/2006 | Rubinsky et al. |
| 2006/0264904 A1 | 11/2006 | Kerby et al. |
| 2006/0264930 A1 | 11/2006 | Nishimura |
| 2006/0270902 A1 | 11/2006 | Igarashi et al. |
| 2006/0271042 A1 | 11/2006 | Latterell et al. |
| 2006/0271102 A1 | 11/2006 | Bosshard et al. |
| 2006/0276835 A1 | 12/2006 | Uchida |
| 2006/0281970 A1 | 12/2006 | Stokes et al. |
| 2006/0282106 A1 | 12/2006 | Cole et al. |
| 2006/0285732 A1 | 12/2006 | Horn et al. |
| 2006/0287644 A1 | 12/2006 | Inganas et al. |
| 2006/0287666 A1 | 12/2006 | Saadat et al. |
| 2006/0293626 A1 | 12/2006 | Byrum et al. |
| 2007/0000550 A1 | 1/2007 | Osinski |
| 2007/0002135 A1 | 1/2007 | Glukhovsky |
| 2007/0005019 A1 | 1/2007 | Okishige |
| 2007/0010801 A1 | 1/2007 | Chen et al. |
| 2007/0015965 A1 | 1/2007 | Cox et al. |
| 2007/0016225 A1 | 1/2007 | Nakao |
| 2007/0027469 A1 | 2/2007 | Smith et al. |
| 2007/0032700 A1 | 2/2007 | Fowler et al. |
| 2007/0032701 A1 | 2/2007 | Fowler et al. |
| 2007/0043261 A1 | 2/2007 | Watanabe et al. |
| 2007/0049800 A1 | 3/2007 | Boulais |
| 2007/0049902 A1 | 3/2007 | Griffin et al. |
| 2007/0049968 A1 | 3/2007 | Sibbitt et al. |
| 2007/0051375 A1 | 3/2007 | Milliman |
| 2007/0060880 A1 | 3/2007 | Gregorich et al. |
| 2007/0066869 A1 | 3/2007 | Hoffman |
| 2007/0067017 A1 | 3/2007 | Trapp |
| 2007/0073102 A1 | 3/2007 | Matsuno et al. |
| 2007/0073269 A1 | 3/2007 | Becker |
| 2007/0078439 A1 | 4/2007 | Grandt et al. |
| 2007/0079924 A1 | 4/2007 | Saadat et al. |
| 2007/0083195 A1 | 4/2007 | Werneth et al. |
| 2007/0088370 A1 | 4/2007 | Kahle et al. |
| 2007/0100375 A1 | 5/2007 | Mikkaichi et al. |
| 2007/0100376 A1 | 5/2007 | Mikkaichi et al. |
| 2007/0106113 A1 | 5/2007 | Ravo |
| 2007/0106118 A1 | 5/2007 | Moriyama |
| 2007/0106317 A1 | 5/2007 | Shelton, IV et al. |
| 2007/0112251 A1 | 5/2007 | Nakhuda |
| 2007/0112331 A1 | 5/2007 | Weber et al. |
| 2007/0112342 A1 | 5/2007 | Pearson et al. |
| 2007/0112383 A1 | 5/2007 | Conlon et al. |
| 2007/0112385 A1 | 5/2007 | Conlon |
| 2007/0112417 A1 | 5/2007 | Shanley et al. |
| 2007/0112425 A1 | 5/2007 | Schaller et al. |
| 2007/0118115 A1 | 5/2007 | Artale et al. |
| 2007/0123840 A1 | 5/2007 | Cox |
| 2007/0129605 A1 | 6/2007 | Schaaf |
| 2007/0129719 A1 | 6/2007 | Kendale et al. |
| 2007/0129760 A1 | 6/2007 | Demarais et al. |
| 2007/0135709 A1 | 6/2007 | Rioux et al. |
| 2007/0135803 A1 | 6/2007 | Belson |
| 2007/0142706 A1 | 6/2007 | Matsui et al. |
| 2007/0142710 A1 | 6/2007 | Yokoi et al. |
| 2007/0142779 A1 | 6/2007 | Duane et al. |
| 2007/0142780 A1 | 6/2007 | Van Lue |
| 2007/0154460 A1 | 7/2007 | Kraft et al. |
| 2007/0156028 A1 | 7/2007 | Van Lue et al. |
| 2007/0156116 A1 | 7/2007 | Gonzalez |
| 2007/0156127 A1 | 7/2007 | Rioux et al. |
| 2007/0161855 A1 | 7/2007 | Mikkaichi et al. |
| 2007/0162101 A1 | 7/2007 | Burgermeister et al. |
| 2007/0167901 A1 | 7/2007 | Herrig et al. |
| 2007/0173691 A1 | 7/2007 | Yokoi et al. |
| 2007/0173869 A1 | 7/2007 | Gannoe et al. |
| 2007/0173870 A2 | 7/2007 | Zacharias |
| 2007/0173872 A1 | 7/2007 | Neuenfeldt |
| 2007/0179525 A1 | 8/2007 | Frecker et al. |
| 2007/0179530 A1 | 8/2007 | Tieu et al. |
| 2007/0197865 A1 | 8/2007 | Miyake et al. |
| 2007/0198057 A1 | 8/2007 | Gelbart et al. |
| 2007/0203398 A1 | 8/2007 | Bonadio et al. |
| 2007/0203487 A1 | 8/2007 | Sugita |
| 2007/0208336 A1 | 9/2007 | Kim et al. |
| 2007/0208364 A1 | 9/2007 | Smith et al. |
| 2007/0208407 A1 | 9/2007 | Gerdts et al. |
| 2007/0213754 A1 | 9/2007 | Mikkaichi et al. |
| 2007/0225552 A1 | 9/2007 | Segawa et al. |
| 2007/0225554 A1 | 9/2007 | Maseda et al. |
| 2007/0233040 A1 | 10/2007 | Macnamara et al. |
| 2007/0244356 A1 | 10/2007 | Carrillo, Jr. et al. |
| 2007/0244358 A1 | 10/2007 | Lee |
| 2007/0250038 A1 | 10/2007 | Boulais |
| 2007/0250057 A1 | 10/2007 | Nobis et al. |
| 2007/0250075 A1* | 10/2007 | Skakoon ............... A61B 19/201 606/130 |
| 2007/0250076 A1* | 10/2007 | Skakoon ............... A61B 19/201 606/130 |
| 2007/0250077 A1* | 10/2007 | Skakoon ............... A61B 19/201 606/130 |
| 2007/0255096 A1 | 11/2007 | Stefanchik et al. |
| 2007/0255100 A1 | 11/2007 | Barlow et al. |
| 2007/0255273 A1 | 11/2007 | Fernandez et al. |
| 2007/0255275 A1* | 11/2007 | Skakoon ............... A61B 19/201 606/41 |
| 2007/0255303 A1 | 11/2007 | Bakos et al. |
| 2007/0255306 A1 | 11/2007 | Conlon et al. |
| 2007/0260112 A1 | 11/2007 | Rahmani |
| 2007/0260117 A1 | 11/2007 | Zwolinski et al. |
| 2007/0260121 A1 | 11/2007 | Bakos et al. |
| 2007/0260242 A1 | 11/2007 | Dycus et al. |
| 2007/0260273 A1 | 11/2007 | Cropper et al. |
| 2007/0260302 A1 | 11/2007 | Igaki |
| 2007/0270629 A1 | 11/2007 | Charles |
| 2007/0270889 A1 | 11/2007 | Conlon et al. |
| 2007/0270895 A1 | 11/2007 | Nobis et al. |
| 2007/0270907 A1 | 11/2007 | Stokes et al. |
| 2007/0282165 A1 | 12/2007 | Hopkins et al. |
| 2007/0282371 A1 | 12/2007 | Lee et al. |
| 2007/0293727 A1 | 12/2007 | Goldfarb et al. |
| 2007/0299387 A1 | 12/2007 | Williams et al. |
| 2008/0004650 A1 | 1/2008 | George |
| 2008/0015409 A1 | 1/2008 | Barlow et al. |
| 2008/0015413 A1 | 1/2008 | Barlow et al. |
| 2008/0015552 A1 | 1/2008 | Doyle et al. |
| 2008/0021416 A1 | 1/2008 | Arai et al. |
| 2008/0022927 A1 | 1/2008 | Zhang et al. |
| 2008/0027387 A1 | 1/2008 | Grabinsky |
| 2008/0033244 A1 | 2/2008 | Matsui et al. |
| 2008/0033451 A1 | 2/2008 | Rieber et al. |
| 2008/0051629 A1 | 2/2008 | Sugiyama et al. |

(56) References Cited

U.S. PATENT DOCUMENTS

| | | |
|---|---|---|
| 2008/0051735 A1 | 2/2008 | Measamer et al. |
| 2008/0058586 A1 | 3/2008 | Karpiel |
| 2008/0058854 A1 | 3/2008 | Kieturakis et al. |
| 2008/0065169 A1 | 3/2008 | Colliou et al. |
| 2008/0071264 A1 | 3/2008 | Azure |
| 2008/0082108 A1* | 4/2008 | Skakoon ............... A61B 19/201 606/130 |
| 2008/0086172 A1 | 4/2008 | Martin et al. |
| 2008/0097159 A1 | 4/2008 | Ishiguro |
| 2008/0097472 A1 | 4/2008 | Agmon et al. |
| 2008/0097483 A1 | 4/2008 | Ortiz et al. |
| 2008/0103527 A1 | 5/2008 | Martin et al. |
| 2008/0114384 A1 | 5/2008 | Chang et al. |
| 2008/0119870 A1 | 5/2008 | Williams |
| 2008/0119891 A1 | 5/2008 | Miles et al. |
| 2008/0125774 A1 | 5/2008 | Palanker et al. |
| 2008/0125796 A1 | 5/2008 | Graham |
| 2008/0132892 A1 | 6/2008 | Lunsford et al. |
| 2008/0139882 A1 | 6/2008 | Fujimori |
| 2008/0140069 A1 | 6/2008 | Filloux et al. |
| 2008/0140071 A1 | 6/2008 | Vegesna |
| 2008/0150754 A1 | 6/2008 | Quendt |
| 2008/0171907 A1 | 7/2008 | Long et al. |
| 2008/0177135 A1 | 7/2008 | Muyari et al. |
| 2008/0188710 A1 | 8/2008 | Segawa et al. |
| 2008/0188868 A1 | 8/2008 | Weitzner et al. |
| 2008/0200755 A1 | 8/2008 | Bakos |
| 2008/0200762 A1 | 8/2008 | Stokes et al. |
| 2008/0200911 A1 | 8/2008 | Long |
| 2008/0200933 A1 | 8/2008 | Bakos et al. |
| 2008/0200934 A1 | 8/2008 | Fox |
| 2008/0208213 A1 | 8/2008 | Benjamin et al. |
| 2008/0208280 A1 | 8/2008 | Lindenthaler et al. |
| 2008/0221587 A1 | 9/2008 | Schwartz |
| 2008/0228213 A1 | 9/2008 | Blakeney et al. |
| 2008/0230972 A1 | 9/2008 | Ganley |
| 2008/0234696 A1 | 9/2008 | Taylor et al. |
| 2008/0243106 A1 | 10/2008 | Coe et al. |
| 2008/0243148 A1 | 10/2008 | Mikkaichi et al. |
| 2008/0243176 A1 | 10/2008 | Weitzner et al. |
| 2008/0249567 A1 | 10/2008 | Kaplan |
| 2008/0262513 A1 | 10/2008 | Stahler et al. |
| 2008/0262524 A1 | 10/2008 | Bangera et al. |
| 2008/0262540 A1 | 10/2008 | Bangera et al. |
| 2008/0275474 A1 | 11/2008 | Martin et al. |
| 2008/0275475 A1 | 11/2008 | Schwemberger et al. |
| 2008/0287737 A1 | 11/2008 | Dejima |
| 2008/0287983 A1 | 11/2008 | Smith et al. |
| 2008/0300461 A1 | 12/2008 | Shaw et al. |
| 2008/0300547 A1 | 12/2008 | Bakos |
| 2008/0300571 A1 | 12/2008 | LePivert |
| 2008/0306493 A1 | 12/2008 | Shibata et al. |
| 2008/0309758 A1 | 12/2008 | Karasawa et al. |
| 2008/0312496 A1 | 12/2008 | Zwolinski |
| 2008/0312499 A1 | 12/2008 | Handa et al. |
| 2008/0312500 A1 | 12/2008 | Asada et al. |
| 2008/0312506 A1 | 12/2008 | Spivey et al. |
| 2008/0319436 A1 | 12/2008 | Daniel et al. |
| 2008/0319439 A1 | 12/2008 | Ootsubu |
| 2009/0005636 A1 | 1/2009 | Pang et al. |
| 2009/0030278 A1 | 1/2009 | Minakuchi |
| 2009/0053003 A1* | 2/2009 | Clark ................... B23B 47/287 408/103 |
| 2009/0054728 A1 | 2/2009 | Trusty |
| 2009/0062788 A1 | 3/2009 | Long et al. |
| 2009/0062795 A1 | 3/2009 | Vakharia et al. |
| 2009/0069634 A1 | 3/2009 | Larkin |
| 2009/0076499 A1 | 3/2009 | Azure |
| 2009/0078736 A1 | 3/2009 | Van Lue |
| 2009/0082776 A1 | 3/2009 | Cresina |
| 2009/0082779 A1 | 3/2009 | Nakao |
| 2009/0093690 A1 | 4/2009 | Yoshizawa |
| 2009/0112059 A1 | 4/2009 | Nobis |
| 2009/0112063 A1 | 4/2009 | Bakos et al. |
| 2009/0125042 A1 | 5/2009 | Mouw |
| 2009/0131751 A1 | 5/2009 | Spivey et al. |
| 2009/0143639 A1 | 6/2009 | Stark |
| 2009/0143649 A1 | 6/2009 | Rossi |
| 2009/0143794 A1 | 6/2009 | Conlon et al. |
| 2009/0143818 A1 | 6/2009 | Faller et al. |
| 2009/0149710 A1 | 6/2009 | Stefanchik et al. |
| 2009/0177031 A1 | 7/2009 | Surti et al. |
| 2009/0177219 A1 | 7/2009 | Conlon |
| 2009/0182325 A1 | 7/2009 | Werneth et al. |
| 2009/0182332 A1 | 7/2009 | Long et al. |
| 2009/0192344 A1 | 7/2009 | Bakos et al. |
| 2009/0192534 A1 | 7/2009 | Ortiz et al. |
| 2009/0198212 A1 | 8/2009 | Timberlake et al. |
| 2009/0198231 A1 | 8/2009 | Esser et al. |
| 2009/0198253 A1 | 8/2009 | Omori |
| 2009/0209990 A1 | 8/2009 | Yates et al. |
| 2009/0210000 A1 | 8/2009 | Sullivan et al. |
| 2009/0216248 A1 | 8/2009 | Uenohara et al. |
| 2009/0221873 A1 | 9/2009 | McGrath |
| 2009/0227999 A1 | 9/2009 | Willis et al. |
| 2009/0228001 A1 | 9/2009 | Pacey |
| 2009/0248055 A1 | 10/2009 | Spivey et al. |
| 2009/0259105 A1 | 10/2009 | Miyano et al. |
| 2009/0269317 A1 | 10/2009 | Davalos |
| 2009/0281559 A1 | 11/2009 | Swain et al. |
| 2009/0287206 A1 | 11/2009 | Jun |
| 2009/0287236 A1 | 11/2009 | Bakos et al. |
| 2009/0292164 A1 | 11/2009 | Yamatani |
| 2009/0292167 A1 | 11/2009 | Kimoto |
| 2009/0306652 A1* | 12/2009 | Buysse ................ A61B 19/201 606/41 |
| 2009/0322864 A1 | 12/2009 | Karasawa et al. |
| 2009/0326332 A1 | 12/2009 | Carter |
| 2010/0010294 A1 | 1/2010 | Conlon et al. |
| 2010/0010298 A1 | 1/2010 | Bakos et al. |
| 2010/0010303 A1 | 1/2010 | Bakos |
| 2010/0023032 A1 | 1/2010 | Granja Filho |
| 2010/0030211 A1 | 2/2010 | Davalos et al. |
| 2010/0036198 A1 | 2/2010 | Tacchino et al. |
| 2010/0042045 A1 | 2/2010 | Spivey |
| 2010/0048990 A1 | 2/2010 | Bakos |
| 2010/0049223 A1 | 2/2010 | Granja Filho |
| 2010/0056862 A1 | 3/2010 | Bakos |
| 2010/0056864 A1 | 3/2010 | Lee |
| 2010/0076451 A1 | 3/2010 | Zwolinski et al. |
| 2010/0076460 A1 | 3/2010 | Taylor et al. |
| 2010/0081875 A1 | 4/2010 | Fowler et al. |
| 2010/0091128 A1 | 4/2010 | Ogasawara et al. |
| 2010/0113872 A1 | 5/2010 | Asada et al. |
| 2010/0121362 A1 | 5/2010 | Clague et al. |
| 2010/0130817 A1 | 5/2010 | Conlon |
| 2010/0152539 A1 | 6/2010 | Ghabrial et al. |
| 2010/0152762 A1 | 6/2010 | Ceniccola et al. |
| 2010/0179530 A1* | 7/2010 | Long et al. ...................... 606/33 |
| 2010/0191050 A1 | 7/2010 | Zwolinski |
| 2010/0191267 A1 | 7/2010 | Fox |
| 2010/0198149 A1 | 8/2010 | Fox |
| 2010/0198248 A1 | 8/2010 | Vakharia |
| 2010/0198254 A1 | 8/2010 | Schaeffer |
| 2010/0210906 A1 | 8/2010 | Wendlandt |
| 2010/0217367 A1 | 8/2010 | Belson |
| 2010/0249700 A1 | 9/2010 | Spivey |
| 2010/0256628 A1 | 10/2010 | Pearson et al. |
| 2010/0261994 A1 | 10/2010 | Davalos et al. |
| 2010/0268025 A1 | 10/2010 | Belson |
| 2010/0286791 A1 | 11/2010 | Goldsmith |
| 2010/0292686 A1* | 11/2010 | Rick .................. A61B 18/1477 606/33 |
| 2010/0298642 A1 | 11/2010 | Trusty et al. |
| 2010/0312056 A1 | 12/2010 | Galperin et al. |
| 2010/0331622 A2 | 12/2010 | Conlon |
| 2010/0331758 A1 | 12/2010 | Davalos et al. |
| 2011/0022058 A1* | 1/2011 | Skakoon ............... A61B 19/201 606/129 |
| 2011/0022059 A1* | 1/2011 | Skakoon ............... A61B 19/201 606/129 |
| 2011/0077476 A1 | 3/2011 | Rofougaran |
| 2011/0093009 A1 | 4/2011 | Fox |
| 2011/0098694 A1 | 4/2011 | Long |

(56) References Cited

U.S. PATENT DOCUMENTS

| | | | |
|---|---|---|---|
| 2011/0098704 A1 | 4/2011 | Long et al. |
| 2011/0106221 A1 | 5/2011 | Neal, II et al. |
| 2011/0112434 A1 | 5/2011 | Ghabrial et al. |
| 2011/0115891 A1 | 5/2011 | Trusty |
| 2011/0124964 A1 | 5/2011 | Nobis |
| 2011/0152610 A1 | 6/2011 | Trusty et al. |
| 2011/0152859 A1 | 6/2011 | Long et al. |
| 2011/0152878 A1 | 6/2011 | Trusty et al. |
| 2011/0152888 A1 | 6/2011 | Ho et al. |
| 2011/0152923 A1 | 6/2011 | Fox |
| 2011/0160514 A1 | 6/2011 | Long et al. |
| 2011/0190659 A1 | 8/2011 | Long et al. |
| 2011/0190764 A1 | 8/2011 | Long et al. |
| 2011/0193948 A1 | 8/2011 | Amling et al. |
| 2011/0245619 A1 | 10/2011 | Holcomb |
| 2011/0285488 A1 | 11/2011 | Scott et al. |
| 2012/0004502 A1 | 1/2012 | Weitzner et al. |
| 2012/0029335 A1 | 2/2012 | Sudam et al. |
| 2012/0078266 A1* | 3/2012 | Tyson, Jr. ............... 606/129 |
| 2012/0088965 A1 | 4/2012 | Stokes et al. |
| 2012/0089089 A1 | 4/2012 | Swain et al. |
| 2012/0089093 A1 | 4/2012 | Trusty |
| 2012/0101413 A1 | 4/2012 | Beetel et al. |
| 2012/0116155 A1 | 5/2012 | Trusty |
| 2012/0149981 A1 | 6/2012 | Khait et al. |
| 2012/0149982 A1* | 6/2012 | Fonger et al. .......... 600/114 |
| 2012/0179148 A1 | 7/2012 | Conlon |
| 2012/0191075 A1 | 7/2012 | Trusty |
| 2012/0191076 A1 | 7/2012 | Voegele et al. |
| 2012/0220998 A1 | 8/2012 | Long et al. |
| 2012/0220999 A1 | 8/2012 | Long |
| 2012/0221002 A1 | 8/2012 | Long et al. |
| 2012/0238796 A1 | 9/2012 | Conlon |
| 2012/0289857 A1 | 11/2012 | Toth et al. |
| 2012/0330306 A1 | 12/2012 | Long et al. |
| 2013/0030430 A1 | 1/2013 | Stewart et al. |
| 2013/0090666 A1 | 4/2013 | Hess et al. |
| 2013/0138091 A1 | 5/2013 | Coe et al. |
| 2013/0158348 A1 | 6/2013 | Nobis et al. |
| 2013/0172672 A1 | 7/2013 | Iddan et al. |
| 2013/0217970 A1 | 8/2013 | Weisenburgh, II et al. |
| 2013/0231530 A1 | 9/2013 | Lien et al. |
| 2013/0245356 A1 | 9/2013 | Fernandez et al. |
| 2013/0261389 A1 | 10/2013 | Long |
| 2013/0267834 A1* | 10/2013 | McGee ............... A61M 5/46 600/424 |
| 2013/0331649 A1 | 12/2013 | Khait et al. |
| 2014/0012247 A1 | 1/2014 | Bakos et al. |
| 2014/0039491 A1 | 2/2014 | Bakos et al. |
| 2014/0039492 A1 | 2/2014 | Long |
| 2014/0052126 A1 | 2/2014 | Long et al. |
| 2014/0052216 A1 | 2/2014 | Long et al. |
| 2014/0121678 A1 | 5/2014 | Trusty et al. |
| 2014/0243597 A1 | 8/2014 | Weisenburgh, II et al. |
| 2015/0100064 A1* | 4/2015 | Skakoon ............ A61B 19/201 606/129 |

FOREIGN PATENT DOCUMENTS

| | | |
|---|---|---|
| DE | 4323585 A1 | 1/1995 |
| DE | 19713797 A1 | 10/1997 |
| DE | 19757056 B4 | 8/2008 |
| DE | 102006027873 B4 | 10/2009 |
| EP | 0086338 A1 | 8/1983 |
| EP | 0286415 A2 | 10/1988 |
| EP | 0499491 A2 | 8/1992 |
| EP | 0589454 A2 | 3/1994 |
| EP | 0464479 B1 | 3/1995 |
| EP | 0529675 B1 | 2/1996 |
| EP | 0621009 B1 | 7/1997 |
| EP | 0724863 B1 | 7/1999 |
| EP | 0760629 B1 | 11/1999 |
| EP | 0818974 B1 | 7/2001 |
| EP | 1281356 A2 | 2/2003 |
| EP | 0947166 B1 | 5/2003 |
| EP | 0836832 B1 | 12/2003 |
| EP | 1402837 A1 | 3/2004 |
| EP | 0744918 B1 | 4/2004 |
| EP | 0931515 B1 | 8/2004 |
| EP | 0941128 B1 | 10/2004 |
| EP | 1411843 B1 | 10/2004 |
| EP | 1150614 B1 | 11/2004 |
| EP | 1477104 A1 | 11/2004 |
| EP | 1481642 A1 | 12/2004 |
| EP | 1493391 A1 | 1/2005 |
| EP | 0848598 B1 | 2/2005 |
| EP | 1281360 131 | 3/2005 |
| EP | 1568330 A1 | 8/2005 |
| EP | 1452143 B1 | 9/2005 |
| EP | 1616527 A2 | 1/2006 |
| EP | 1006888 81 | 3/2006 |
| EP | 1629764 A1 | 3/2006 |
| EP | 1013229 B1 | 6/2006 |
| EP | 1721561 A1 | 11/2006 |
| EP | 1153578 B1 | 3/2007 |
| EP | 1334696 B1 | 3/2007 |
| EP | 1769766 A1 | 4/2007 |
| EP | 1836971 A2 | 9/2007 |
| EP | 1836980 A1 | 9/2007 |
| EP | 1854421 A2 | 11/2007 |
| EP | 1857061 A1 | 11/2007 |
| EP | 1875876 A1 | 1/2008 |
| EP | 1891881 A1 | 2/2008 |
| EP | 1902663 A1 | 3/2008 |
| EP | 1477106 B1 | 6/2008 |
| EP | 1949844 A1 | 7/2008 |
| EP | 1518499 B1 | 8/2008 |
| EP | 1582138 B1 | 9/2008 |
| EP | 1709918 B1 | 10/2008 |
| EP | 1985226 A2 | 10/2008 |
| EP | 1994904 A1 | 11/2008 |
| EP | 1707130 B1 | 12/2008 |
| EP | 0723462 B1 | 3/2009 |
| EP | 1769749 B1 | 11/2009 |
| EP | 2135545 A2 | 12/2009 |
| EP | 1493397 B1 | 9/2011 |
| FR | 2731610 A1 | 9/1996 |
| GB | 330629 A | 6/1930 |
| GB | 2335860 A | 10/1999 |
| GB | 2403909 A | 1/2005 |
| GB | 2421190 A | 6/2006 |
| GB | 2443261 A | 4/2008 |
| JP | 56-46674 | 4/1981 |
| JP | 63309252 | 12/1988 |
| JP | 4038960 | 2/1992 |
| JP | 8-29699 | 2/1996 |
| JP | H9-75365 | 3/1997 |
| JP | H10-24049 | 1/1998 |
| JP | 2000/107197 | 4/2000 |
| JP | 2000245683 | 9/2000 |
| JP | 2002-369791 | 12/2002 |
| JP | 2003-088494 | 3/2003 |
| JP | 2003-235852 A | 8/2003 |
| JP | 2004-33525 | 2/2004 |
| JP | 2004-065745 | 3/2004 |
| JP | 2005-121947 | 5/2005 |
| JP | 2005-261514 | 9/2005 |
| JP | 2005-296063 | 10/2005 |
| JP | 2006297005 | 11/2006 |
| JP | 2006-343510 | 12/2006 |
| JP | 2007-20806 | 2/2007 |
| JP | 2007-125264 | 5/2007 |
| JP | 2007-516792 A | 6/2007 |
| JP | 2010/503496 A | 2/2010 |
| NL | 1021295 C2 | 2/2004 |
| SU | 194230 | 5/1967 |
| SU | 980703 | 12/1982 |
| WO | WO 84/01707 A1 | 5/1984 |
| WO | WO 86/07543 A1 | 12/1986 |
| WO | WO 92/13494 A1 | 8/1992 |
| WO | WO 93/10850 A1 | 6/1993 |
| WO | WO 93/20760 A1 | 10/1993 |
| WO | WO 93/20765 A1 | 10/1993 |

(56) References Cited

FOREIGN PATENT DOCUMENTS

| | | |
|---|---|---|
| WO | WO 95/09666 A1 | 4/1995 |
| WO | WO 96/22056 A1 | 7/1996 |
| WO | WO 96/27331 A1 | 9/1996 |
| WO | WO 96/39946 A1 | 12/1996 |
| WO | WO 97/12557 A1 | 4/1997 |
| WO | WO 98/01080 A1 | 1/1998 |
| WO | WO 99/00060 A1 | 1/1999 |
| WO | WO 99/09919 A1 | 3/1999 |
| WO | WO 99/17661 A1 | 4/1999 |
| WO | WO 99/30622 A2 | 6/1999 |
| WO | WO 00/35358 A1 | 6/2000 |
| WO | WO 00/68665 A1 | 11/2000 |
| WO | WO 01/10319 A1 | 2/2001 |
| WO | WO 01/26708 A1 | 4/2001 |
| WO | WO 01/41627 A2 | 6/2001 |
| WO | WO 01/58360 A2 | 8/2001 |
| WO | WO 02/11621 A2 | 2/2002 |
| WO | WO 02/34122 A2 | 5/2002 |
| WO | WO 02/094082 A2 | 11/2002 |
| WO | WO 03/045260 A1 | 6/2003 |
| WO | WO 03/047684 A2 | 6/2003 |
| WO | WO 03/059412 A2 | 7/2003 |
| WO | WO 03/078721 A2 | 9/2003 |
| WO | WO 03/081761 A2 | 10/2003 |
| WO | WO 03/082129 A2 | 10/2003 |
| WO | WO 2004/006789 A1 | 1/2004 |
| WO | WO 2004/028613 A2 | 4/2004 |
| WO | WO 2004/037123 A1 | 5/2004 |
| WO | WO 2004/037149 A1 | 5/2004 |
| WO | WO 2004/052221 A1 | 6/2004 |
| WO | WO 2004/086984 A1 | 10/2004 |
| WO | WO 2005/009211 A2 | 2/2005 |
| WO | WO 2005/018467 A2 | 3/2005 |
| WO | WO 2005/037088 A2 | 4/2005 |
| WO | WO 2005/048827 A1 | 6/2005 |
| WO | WO 2005/065284 A2 | 7/2005 |
| WO | WO 2005/097019 A2 | 10/2005 |
| WO | WO 2005/097234 A2 | 10/2005 |
| WO | WO 2005/112810 A2 | 12/2005 |
| WO | WO 2005/120363 A1 | 12/2005 |
| WO | WO 2005/122866 A1 | 12/2005 |
| WO | WO 2006/007399 A1 | 1/2006 |
| WO | WO 2006/012630 A2 | 2/2006 |
| WO | WO 2006/040109 A1 | 4/2006 |
| WO | WO 2006/041881 A2 | 4/2006 |
| WO | WO 2006/060405 A2 | 6/2006 |
| WO | WO 2006/110733 A2 | 10/2006 |
| WO | WO 2006/113216 A2 | 10/2006 |
| WO | WO 2007/013059 A2 | 2/2007 |
| WO | WO 2007/014063 A2 | 2/2007 |
| WO | WO 2007/035537 A2 | 3/2007 |
| WO | WO 2007/048085 A2 | 4/2007 |
| WO | WO 2007/063550 A2 | 6/2007 |
| WO | WO 2007/100067 A1 | 9/2007 |
| WO | WO 2007/109171 A2 | 9/2007 |
| WO | WO 2007/135577 A2 | 11/2007 |
| WO | WO 2007/143200 A2 | 12/2007 |
| WO | WO 2007/144004 A1 | 12/2007 |
| WO | WO 2008/005433 A1 | 1/2008 |
| WO | WO 2008/033356 A2 | 3/2008 |
| WO | WO 2008/034103 A2 | 3/2008 |
| WO | WO 2008/041225 A2 | 4/2008 |
| WO | WO 2008/076337 A1 | 6/2008 |
| WO | WO 2008/076800 A2 | 6/2008 |
| WO | WO 2008/079440 A2 | 7/2008 |
| WO | WO 2008/080062 A2 | 7/2008 |
| WO | WO 2008/101075 A2 | 8/2008 |
| WO | WO 2008/101086 A2 | 8/2008 |
| WO | WO 2008/102154 A2 | 8/2008 |
| WO | WO 2008/108863 A2 | 9/2008 |
| WO | WO 2008/151237 A1 | 12/2008 |
| WO | WO 2009/021030 A1 | 2/2009 |
| WO | WO 2009/027065 A1 | 3/2009 |
| WO | WO 2009/029065 A1 | 3/2009 |
| WO | WO 2009/032623 A2 | 3/2009 |
| WO | WO 2009/036457 A1 | 3/2009 |
| WO | WO 2009/121017 A1 | 10/2009 |
| WO | WO 2010/027688 A1 | 3/2010 |
| WO | WO 2010/056716 A2 | 5/2010 |
| WO | WO 2010/080974 A1 | 7/2010 |
| WO | WO 2010/088481 A1 | 8/2010 |
| WO | WO 2012/031204 A2 | 3/2012 |
| WO | WO 2012/071526 A2 | 5/2012 |

OTHER PUBLICATIONS

Ethicon, Inc., "Wound Closure Manual; Chapter 3 (The Surgical Needle)," 15 pages, (1994).

Guido M. Sclabas, M.D., et al., "Endoluminal Methods for Gastrotomy Closure in Natural Orifice TransEnteric Surgery (NOTES)," Surgical Innovation, vol. 13, No. 1, pp. 23-30, Mar. 2006.

Fritscher-Ravens, et al., "Transgastric Gastropexy and Hiatal Hernia Repair for GERD Under EUS Control: a Porcine Model," Gastrointestinal Endoscopy, vol. 59, No. 1, pp. 89-95, 2004.

Ogando, "Prototype Tools That Go With the Flow," Design News, 2 pages, Jul. 17, 2006.

Edd, et al., "In Vivo Results of a New Focal Tissue Ablation Technique: Irreversible Electroporation," IEEE Trans Biomed Eng, vol. 53, pp. 1409-1415, 2006.

Kennedy, et al., "High-Burst-Strength, Feedback-Controlled Bipolar Vessel Sealing," Surgical Endoscopy, vol. 12, pp. 876-878 (1998).

Collins et al., "Local Gene Therapy of Solid Tumors with GM-CSF and B7-1 Eradicates Both Treated and Distal Tumors," Cancer Gene Therapy, vol. 13, pp. 1061-1071 (2006).

K. Sumiyama et al., "Transesophageal Mediastinoscopy by Submucosal Endoscopy With Mucosal Flap Safety Value Technique," Gastrointest Endosc., Apr. 2007, vol. 65(4), pp. 679-683 (Abstract).

K. Sumiyama et al., "Submucosal Endoscopy with Mucosal Flap Safety Valve," Gastrointest Endosc. Apr. 2007, vol. 65(4) pp. 694-695 (Abstract).

K. Sumiyama et al., "Transgastric Cholecystectomy: Transgastric Accessibility to the Gallbladder Improved with the SEMF Method and a Novel Multibending Therapeutic Endoscope," Gastrointest Endosc., Jun. 2007, vol. 65(7), pp. 1028-1034 (Abstract).

K. Sumiyama et al., "Endoscopic Caps," Tech. Gastrointest. Endosc., vol. 8, pp. 28-32, 2006.

"Z-Offset Technique Used in the Introduction of Trocar During Laparoscopic Surgery," M.S. Hershey NOTES Presentation to EES NOTES Development Team, Sep. 27, 2007.

F.N. Denans, Nouveau Procede Pour La Guerison Des Plaies Des Intestines. Extrait Des Seances De La Societe Royale De Medecine De Marseille, Pendant Le Mois De Decembre 1825, et le Premier Tremestre De 1826, Séance Du 24 Fevrier 1826. Recueil De La Societe Royale De Medecin De Marseille. Marseille: Impr. D'Achard, 1826; 1:127-31. (with English translation).

I. Fraser, "An Historical Perspective on Mechanical Aids in Intestinal Anastamosis," Surg. Gynecol. Obstet. (Oct. 1982), vol. 155, pp. 566-574.

M.E. Ryan et al., "Endoscopic Intervention for Biliary Leaks After Laparoscopic Cholecystectomy: A Multicenter Review," Gastrointest. Endosc., vol. 47(3), 1998, pp. 261-266.

C. Cope, "Creation of Compression Gastroenterostomy by Means of the Oral, Percutaneous, or Surgical Introduction of Magnets: Feasibility Study in Swine," J. Vase Interv Radiol, (1995), vol. 6(4), pp. 539-545.

J.W. Hazey et al., "Natural Orifice Transgastric Endoscopic Peritoneoscopy in Humans: Initial Clinical Trial," Surg Endosc, (Jan. 2008), vol. 22(1), pp. 16-20.

N. Chopita et al., "Endoscopic Gastroenteric Anastamosis Using Magnets," Endoscopy, (2005), vol. 37(4), pp. 313-317.

C. Cope et al., "Long Term Patency of Experimental Magnetic Compression Gastroenteric Anastomoses Achieved with Covered Stents," Gastrointest Endosc, (2001), vol. 53, pp. 780-784.

(56) References Cited

OTHER PUBLICATIONS

H. Okajima et al., "Magnet Compression Anastamosis for Bile Duct Stenosis After Duct to Duct Biliary Reconstruction in Living Donor Liver Transplantation," Liver Transplantation (2005), pp. 473-475.
A. Fritscher-Ravens et al., "Transluminal Endosurgery: Single Lumen Access Anastamotic Device for Flexible Endoscopy," Gastrointestinal Endosc, (2003), vol. 58(4), pp. 585-591.
G.A. Hallenbeck, M.D. et al., "An Instrument for Colorectal Anastomosis Without Sutrues," Dis Col Rectum, (1963), vol. 5, pp. 98-101.
T. Hardy, Jr., M.D. et al., "A Biofragmentable Ring for Sutureless Bowel Anastomosis. An Experimental Study," Dis Col Rectum, (1985), vol. 28, pp. 484-490.
P. O'Neill, M.D. et al., "Nonsuture Intestinal Anastomosis," Am J. Surg, (1962), vol. 104, pp. 761-767.
C.P. Swain, M.D. et al., "Anastomosis at Flexible Endoscopy: An Experimental Study of Compression Button Gastrojejunostomy," Gastrointest Endosc, (1991), vol. 37, pp. 628-632.
J.B. Murphy, M.D., "Cholecysto-Intestinal, Gastro-Intestinal, Entero-Intestinal Anastomosis, and Approximation Without Sutures (original research)," Med Rec, (Dec. 10, 1892), vol. 42(24), pp. 665-676.
USGI® EndoSurgical Operating System—g-Prox® Tissue Grasper/Approximation Device; [online] URL: http://www.usgimedical.com/eos/components-gprox.htm—accessed May 30, 2008 (2 pages).
Printout of web page—http://www.vacumed.com/zcom/product/Product.do?compid=27&prodid=852, #51XX Low-Cost Permanent Tubes 2MM ID, Smooth Interior Walls, VacuMed, Ventura, California, Accessed Jul. 24, 2007.
Endoscopic Retrograde Cholangiopancreatogram (ERCP); [online] URL: http://www.webmd.com/digestive-disorders/endoscopic-retrograde-cholangiopancreatogram-ercp.htm; last updated: Apr. 30, 2007; accessed: Feb. 21, 2008 (6 pages).
ERCP; Jackson Siegelbaum Gastroenterology; [online] URL: http://www.gicare.com/pated/epdgs20.htm; accessed Feb. 21, 2008 (3 pages).
D.G. Fong et al., "Transcolonic Ventral Wall Hernia Mesh Fixation in a Porcine Model," Endoscopy 2007; 39: 865-869.
B. Rubinsky, Ph.D., "Irreversible Electroporation in Medicine," Technology in Cancer Research and Treatment, vol. 6, No. 4, Aug. (2007), pp. 255-259.
D.B. Nelson, MD et al., "Endoscopic Hemostatic Devices," Gastrointestinal Endoscopy, vol. 54, No. 6, 2001, pp. 833-840.
CRE™ Pulmonary Balloon Dilator; [online] URL: http://www.bostonscientific.com/Device.bsci?page=HCP_Overview&navRelId=1000.1003&method=D . . . , accessed Jul. 18, 2008 (4 pages).
J.D. Paulson, M.D., et al., "Development of Flexible Culdoscopy," The Journal of the American Association of Gynecologic Laparoscopists, Nov. 1999, vol. 6, No. 4, pp. 487-490.
H. Seifert, et al., "Retroperitoneal Endoscopic Debridement for Infected Peripancreatic Necrosis," The Lancet, Research Letters, vol. 356, Aug. 19, 2000, pp. 653-655.
K.E. Mönkemüller, M.D., et al., "Transmural Drainage of Pancreatic Fluid Collections Without Electrocautery Using the Seldinger Technique," Gastrointestinal Endoscopy, vol. 48, No. 2, 1998, pp. 195-200, (Received Oct. 3, 1997; Accepted Mar. 31, 1998).
D. Wilhelm et al., "An Innovative, Safe and Sterile Sigmoid Access (ISSA) for NOTES," Endoscopy 2007, vol. 39, pp. 401-406.
Nakazawa et al., "Radiofrequency Ablation of Hepatocellular Carcinoma: Correlation Between Local Tumor Progression After Ablation and Ablative Margin," AJR, 188, pp. 480-488 (Feb. 2007).
Miklavčič et al., "A validated model of in vivo electric field distribution in tissues for electrochemotherapy and for DNA electrotransfer for gene therapy," Biochimica et Biophysica Acta, 1523, pp. 73-83 (2000).
Evans, "Ablative and catether-delivered therapies for colorectal liver metastases (CRLM)," EJSO, 33, pp. S64-S75 (2007).
Wong et al., "Combined Percutaneous Radiofrequency Ablation and Ethanol Injection for Hepatocellular Carcinoma in High-Risk Locations," AJR, 190, pp. W187-W195 (2008).
Heller et al., "Electrically mediated plasmid DNA delivery to hepatocellular carcinomas in vivo," Gene Therapy, 7, pp. 826-829 (2000).
Widera et al., "Increased DNA Vaccine Delivery and Immunogenicity by Electroporation in Vivo," The Journal of Immunology, 164, pp. 4635-4640 (2000).
Weaver et al., "Theory of electroporation: A review," Bioelectrochemistry and Bioenergetics, 41, pp. 135-160 (1996).
Mulier et al., "Radiofrequency Ablation Versus Resection for Resectable Colorectal Liver Metastases: Time for a Randomized Trial?" Annals of Surgical Oncology, 15(1), pp. 144-157 (2008).
Link et al., "Regional Chemotherapy of Nonresectable Colorectal Liver Metastases with Mitoxanthrone, 5-Fluorouracil, Folinic Acid, and Mitomycin C May Prolong Survival," Cancer, 92, pp. 2746-2753 (2001).
Guyton et al., "Membrane Potentials and Action Potentials," W.B. Sanders, ed, Textbook of Medical Physiology, p. 56 (2000).
Guyton et al., "Contraction of Skeletal Muscle," Textbook of Medical Physiology, pp. 82-84 (2000).
"Ethicon Endo-Surgery Novel Investigational Notes and SSL Devices Featured in 15 Presentations at Sages," Apr. 22, 2009 Press Release; URL http://www.jnj.com/connect/news/all/20090422_152000; accessed Aug. 28, 2009 (3 pages).
"Ethicon Endo-Surgery Studies Presented At DDW Demonstrate Potential of Pure NOTES Surgery With Company's Toolbox," Jun. 3, 2009 Press Release; URL http://www.jnj.com/connect/news/product/20090603_120000; accessed Aug. 28, 2009 (3 pages).
Castellvi et al., "Hybrid Transvaginal NOTES Sleeve Gastrectomy in a Porcine Model Using a Magnetically Anchored Camera and Novel Instrumentation," Abstract submitted along with Poster at Sages Annual Meeting in Phoenix, AZ, Apr. 22, 2009 (1 page).
Castellvi et al., "Hybrid Transvaginal NOTES Sleeve Gastrectomy in a Porcine Model Using a Magnetically Anchored Camera and Novel Instrumentation," Poster submitted along with Abstract at Sages Annual Meeting in Phoenix, AZ, Apr. 22, 2009 (1 page).
OCTO Port Modular Laparoscopy System for Single Incision Access, Jan. 4, 2010; URL http://www.medgadget.com/archives/2010/01/octo_port_modular_laparo . . . ; accessed Jan. 5, 2010 (4 pages).
Hakko Retractors, obtained Aug. 25, 2009 (5 pages).
Zadno et al., "Linear Superelasticity in Cold-Worked NI-TI," Engineering Aspects of Shape Memory Alloys, pp. 414-419 (1990).
How Stuff Works "How Smart Structures Will Work," http://science.howstuffworks.com/engineering/structural/smart-structure1.htm; accessed online Nov. 1, 2011 (3 pages).
Instant Armor: Science Videos—Science News—ScienCentral; http://www.sciencentral.com/articlesiview.php3?article_id=218392121; accessed online Nov. 1, 2011 (2 pages).
Stanway, Smart Fluids: Current and Future Developments. Material Science and Technology, 20, pp. 931-939, 2004; accessed online Nov. 1, 2011 at http://www.dynamics.group.shef.ac.uk/smart/smart.htm (7 pages).
Jolly et al., Properties and Applications of Commercial Magnetorheological Fluids. SPIE 5th Annual Int. Symposium on Smart Structures and Materials, 1998 (18 pages).
Rutala et al. "Guideline for Disinfection and Sterilization in Healthcare Facilities, 2008" (available at http://www.cdc.gov/hicpac/Disinfection_Sterilization/13_11sterilizingPractices.html).
Bewlay et al., "Spinning" in ASM Handbook, vol. 14B, Metalworking: Sheet Forming (2006).
Schoenbach et al. "Bacterial Decontamination of Liquids with Pulsed Electric Fields" IEEE Transactions on Dielectrics and Electrical Insulation. vol. 7 No. 5. Oct. 2000, pp. 637-645.

\* cited by examiner

NEEDLE PROBE GUIDE

FIELD OF TECHNOLOGY

The present invention generally relates to surgical devices and methods.

BACKGROUND

Electrical ablation therapy has been employed in medicine for the treatment of undesirable tissue such as diseased tissue, cancer, malignant and benign tumors, masses, lesions, and other abnormal tissue growths. While conventional apparatuses, systems, and methods for the electrical ablation of undesirable tissue are effective, one drawback with conventional electrical ablation treatment is the resulting permanent damage that may occur to the healthy tissue surrounding the abnormal tissue due primarily to the detrimental thermal effects resulting from exposing the tissue to thermal energy generated by the electrical ablation device. This may be particularly true when exposing the tissue to electric potentials sufficient to cause cell necrosis using high temperature thermal therapies including focused ultrasound ablation, radiofrequency (RF) ablation, or interstitial laser coagulation. Other techniques for tissue ablation include chemical ablation, in which chemical agents are injected into the undesirable tissue to cause ablation as well as surgical excision, cryotherapy, radiation, photodynamic therapy, Moh's micrographic surgery, topical treatments with 5-fluorouracil, laser ablation. Other drawbacks of conventional thermal, chemical, and other ablation therapy are cost, length of recovery, and the extraordinary pain inflicted on the patient.

Conventional thermal, chemical, and other ablation techniques have been employed for the treatment of a variety of undesirable tissue. Thermal and chemical ablation techniques have been used for the treatment of varicose veins resulting from reflux disease of the greater saphenous vein (GSV), in which the varicose vein is stripped and then is exposed to either chemical or thermal ablation. Other techniques for the treatment of undesirable tissue are more radical. Prostate cancer, for example, may be removed using a prostatectomy, in which the entire or part of prostate gland and surrounding lymph nodes are surgically removed. Like most other forms of cancer, radiation therapy may be used in conjunction with or as an alternate method for the treatment of prostate cancer. Another thermal ablation technique for the treatment of prostate cancer is RF interstitial tumor ablation (RITA) via trans-rectal ultrasound guidance. While these conventional methods for the treatment of prostate cancer are effective, they are not preferred by many surgeons and may result in detrimental thermal effects to healthy tissue surrounding the prostate. Similar thermal ablation techniques may be used for the treatment of basal cell carcinoma (BCC) tissue, a slowly growing cutaneous malignancy derived from the rapidly proliferating basal layer of the epidermis. BCC tissue in tumors ranging in size from about 5 mm to about 40 mm may be thermally ablated with a pulsed carbon dioxide laser. Nevertheless, carbon dioxide laser ablation is a thermal treatment method and may cause permanent damage to healthy tissue surrounding the BCC tissue. Furthermore, this technique requires costly capital investment in carbon dioxide laser equipment.

Undesirable tissue growing inside a body lumen such as the esophagus, large bowel, or in cavities formed in solid tissue such as the breast, for example, can be difficult to destroy using conventional ablation techniques. Surgical removal of undesirable tissue, such as a malignant or benign tumor, from the breast is likely to leave a cavity. Surgical resection of residual intralumenal tissue may remove only a portion of the undesirable tissue cells within a certain margin of healthy tissue. Accordingly, some undesirable tissue is likely to remain within the wall of the cavity due to the limitation of conventional ablation instrument configurations, which may be effective for treating line-of-sight regions of tissue, but may be less effective for treating the residual undesirable tissue.

Accordingly, there remains a need for improved electrical ablation apparatuses, systems, and methods for the treatment of undesirable tissue found in diseased tissue, cancer, malignant and benign tumors, masses, lesions, and other abnormal tissue growths. There remains a need for minimally invasive treatment of undesirable tissue through the use of irreversible electroporation (IRE) ablation techniques without causing the detrimental thermal effects of conventional thermal ablation techniques.

SUMMARY

An aspect of the present disclosure is directed to a device for guiding electrodes relative to a tissue treatment region. The device comprises a body comprising a first passage through the body, wherein the first passage is structured to axially restrain a first electrode, and wherein the first electrode comprises a proximal end and a distal end. The body also comprises a second passage through the body, wherein the second passage is substantially parallel to the first passage, wherein the second passage is structured to axially restrain a second electrode, and wherein the second electrode comprises a proximal end and a distal end. Further, the distal end of the first electrode is spaced a predetermined distance from the distal end of the second electrode when the first electrode is restrained in the first passage and the second electrode is restrained in the second passage. The predetermined distance corresponds to a treatment distance in the tissue treatment region. Additionally, the distal ends of the first and second electrodes are operably structured to conduct current.

FIGURES

The novel features of the various described embodiments are set forth with particularity in the appended claims. The various embodiments, however, both as to organization and methods of operation, together with advantages thereof, may be understood in accordance with the following description taken in conjunction with the accompanying drawings as follows.

FIG. 1 is a schematic of an electrical ablation system and a flexible endoscope according to various embodiments of the present disclosure;

FIGS. 2A-D depict one embodiment of the electrical ablation device of the electrical ablation system of FIG. 1 in various phases of deployment;

DESCRIPTION

Figure 1:
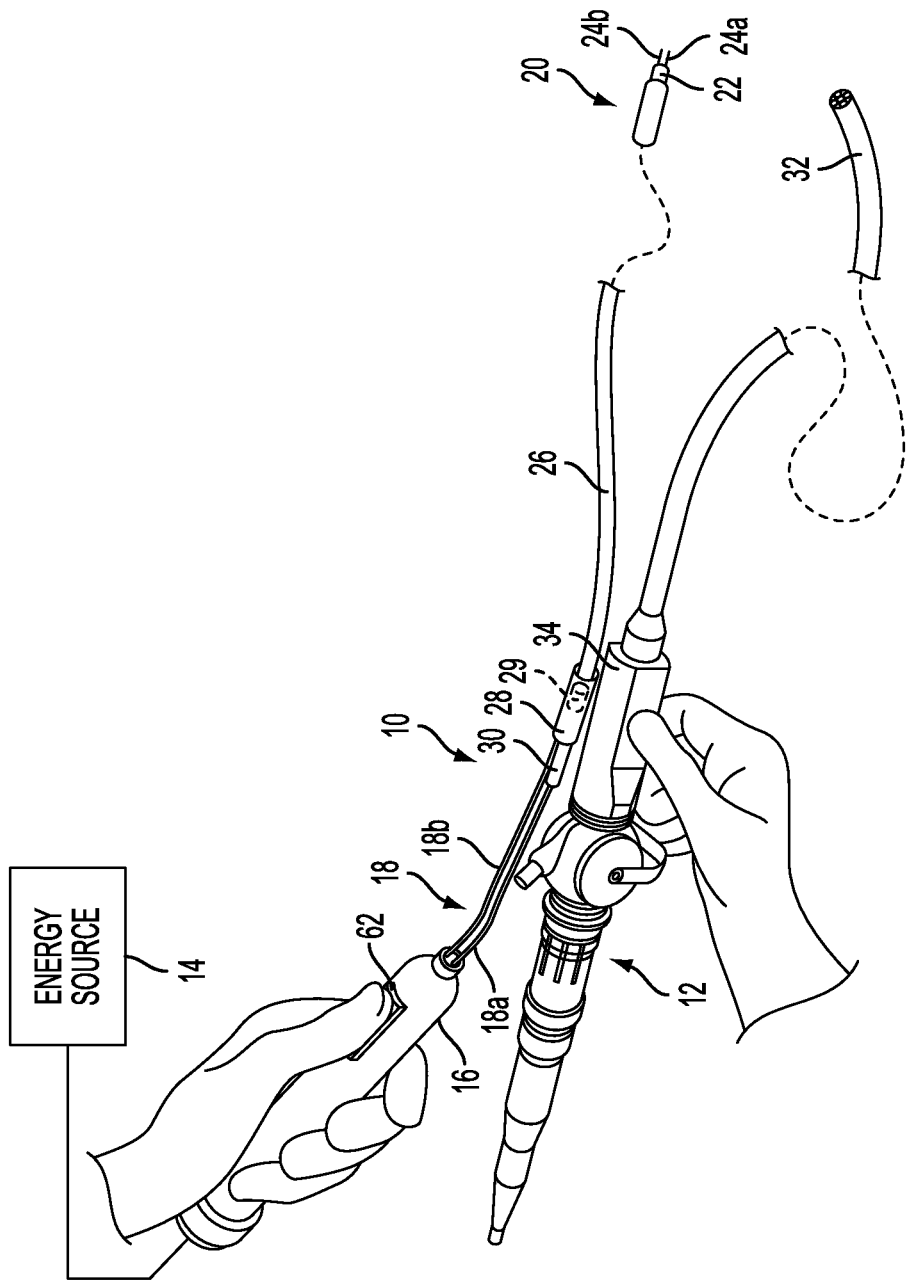

Various embodiments are directed to apparatuses, systems, and methods for the electrical ablation treatment of undesirable tissue such as diseased tissue, cancer, malignant and benign tumors, masses, lesions, and other abnormal tissue growths. Numerous specific details are set forth to provide a thorough understanding of the overall structure, function, manufacture, and use of the embodiments as described in the specification and illustrated in the accompanying drawings. It will be understood, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "operator", "surgeon" and "clinician" may be used interchangeably throughout the specification with reference to a person, multiple persons, a robotic device, multiple robotic devices, or a combination thereof that may use a surgical instrument described herein and/or perform a step of a method described herein. These terms are not intended to be limiting and absolute.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Electrical ablation devices in accordance with the described embodiments may comprise one or more electrodes configured to be positioned into or proximal to undesirable tissue in a tissue treatment region (e.g., target site, worksite) where there is evidence of abnormal tissue growth, for example. In general, the electrodes comprise an electrically conductive portion (e.g., medical grade stainless steel) and are configured to electrically couple to an energy source. Once the electrodes are positioned into or proximal to the undesirable tissue, an energizing potential is applied to the electrodes to create an electric field to which the undesirable tissue is exposed. The energizing potential (and the resulting electric field) may be characterized by multiple parameters such as frequency, amplitude, pulse width (duration of a pulse or pulse length), and/or polarity. Depending on the diagnostic or therapeutic treatment to be rendered, a particular electrode may be configured either as an anode (+) or a cathode (−) or may comprise a plurality of electrodes with at least one configured as an anode and at least one other configured as a cathode. Regardless of the initial polar configuration, the polarity of the electrodes may be reversed by reversing the polarity of the output of the energy source.

In various embodiments, a suitable energy source may comprise an electrical waveform generator, which may be configured to create an electric field that is suitable to create irreversible electroporation in undesirable tissue at various electric field amplitudes and durations. The energy source may be configured to deliver irreversible electroporation pulses in the form of direct-current (DC) and/or alternating-current (AC) voltage potentials (e.g., time-varying voltage potentials) to the electrodes. The irreversible electroporation pulses may be characterized by various parameters such as frequency, amplitude, pulse length, and/or polarity. The undesirable tissue may be ablated by exposure to the electric potential difference across the electrodes.

In one embodiment, the energy source may comprise a wireless transmitter to deliver energy to the electrodes using wireless energy transfer techniques via one or more remotely positioned antennas. Wireless energy transfer or wireless power transmission is the process of transmitting electrical energy from an energy source to an electrical load without interconnecting wires. An electrical transformer is the simplest instance of wireless energy transfer. The primary and secondary circuits of a transformer are not directly connected and the transfer of energy takes place by electromagnetic coupling through a process known as mutual induction. Power also may be transferred wirelessly using RF energy. Wireless power transfer technology using RF energy is produced by Powercast, Inc. and can achieve an output of 6 volts for a little over one meter. Other low-power wireless power technology has been proposed such as described in U.S. Pat. No. 6,967,462, the entire disclosure of which is incorporated by reference herein.

The apparatuses, systems, and methods in accordance with certain described embodiments may be configured for minimally invasive ablation treatment of undesirable tissue through the use of irreversible electroporation to be able to ablate undesirable tissue in a controlled and focused manner without inducing thermally damaging effects to the surrounding healthy tissue. The apparatuses, systems, and methods in accordance with the described embodiments may be configured to ablate undesirable tissue through the use of electroporation or electropermeabilization. More specifically, in various embodiments, the apparatuses, systems, and methods in accordance with the described embodiments may be configured to ablate undesirable tissue through the use of irreversible electroporation. Electroporation increases the permeabilization of a cell membrane by exposing the cell to electric pulses. The external electric field (electric potential/per unit length) to which the cell membrane is exposed to significantly increases the electrical conductivity and permeability of the plasma in the cell membrane. The primary parameter affecting the transmembrane potential is the potential difference across the cell membrane. Irreversible electroporation is the application of an electric field of a specific magnitude and duration to a cell membrane such that the permeabilization of the cell membrane cannot be reversed, leading to cell death without inducing a significant amount of heat in the cell membrane. The destabilizing potential forms pores in the cell membrane when the potential across the cell membrane exceeds its dielectric strength causing the cell to die under a process known as apoptosis and/or necrosis. The application of irreversible electroporation pulses to cells is an effective way to ablate large volumes of undesirable tissue without deleterious thermal effects to the surrounding healthy tissue associated with thermal-inducing ablation treatments. This is because irreversible electroporation destroys cells without heat and thus does not destroy the cellular support structure or regional vasculature. A destabilizing irreversible electroporation pulse, suitable to cause cell death without inducing a significant amount of thermal damage to the surrounding healthy tissue, may have amplitude in the range of about several hundred to about several thousand volts and is generally applied across biological membranes over a distance of about several millimeters, for example, for a relatively long duration. Thus, the undesirable tissue may be ablated in-vivo through the delivery of destabilizing electric fields by quickly creating cell necrosis.

The apparatuses, systems, and methods for electrical ablation therapy in accordance with the described embodiments may be adapted for use in minimally invasive surgical procedures to access the tissue treatment region in various anatomic locations such as the brain, lungs, breast, liver, gall bladder, pancreas, prostate gland, and various internal body lumen defined by the esophagus, stomach, intestine, colon, arteries, veins, anus, vagina, cervix, fallopian tubes, and the peritoneal cavity, for example, without limitation. Minimally invasive electrical ablation devices may be introduced to the tissue treatment region using a trocar inserted though a small opening formed in the patient's body or through a natural body orifice such as the mouth, anus, or vagina using translumenal access techniques known as Natural Orifice Translumenal Endoscopic Surgery (NOTES)™. Once the electrical ablation devices (e.g., electrodes) are located into or proximal to the undesirable tissue in the treatment region, electric field potentials can be applied to the undesirable tissue by the energy source. The electrical ablation devices can comprise portions that may be inserted into the tissue treatment region percutaneously (e.g., where access to inner organs or other tissue is done via needle-puncture of the skin). Other portions of the electrical ablation devices may be introduced into the tissue treatment region endoscopically (e.g., laparoscopically and/or thoracoscopically) through trocars or working channels of the endoscope, through small incisions, or transcutaneously (e.g., where electric pulses are delivered to the tissue treatment region through the skin).

FIG. 1 illustrates one embodiment of an electrical ablation system 10. The electrical ablation system 10 may be employed to ablate undesirable tissue such as diseased tissues, cancers, tumors, masses, lesions, abnormal tissue growths inside a patient using electrical energy. The electrical ablation system 10 may be used in conjunction with endoscopic, laparoscopic, thoracoscopic, open surgical procedures via small incisions or keyholes, percutaneous techniques, transcutaneous techniques, and/or external non-invasive techniques, or any combinations thereof without limitation. The electrical ablation system 10 may be configured to be positioned within a natural body orifice of the patient such as the mouth, anus, or vagina and advanced through internal body lumen or cavities such as the esophagus, colon, cervix, urethra, for example, to reach the tissue treatment region. The electrical ablation system 10 also may be configured to be positioned and passed through a small incision or keyhole formed through the skin or abdominal wall of the patient to reach the tissue treatment region using a trocar. The tissue treatment region may be located in the brain, lungs, breast, liver, gall bladder, pancreas, prostate gland, various internal body lumen defined by the esophagus, stomach, intestine, colon, arteries, veins, anus, vagina, cervix, fallopian tubes, and the peritoneal cavity, for example, without limitation. The electrical ablation system 10 can be configured to treat a number of lesions and ostepathologies comprising metastatic lesions, tumors, fractures, infected sites, and/or inflamed sites. Once positioned into or proximate the tissue treatment region, the electrical ablation system 10 can be actuated (e.g., energized) to ablate the undesirable tissue. In one embodiment, the electrical ablation system 10 may be configured to treat diseased tissue in the gastrointestinal (GI) tract, esophagus, lung, or stomach that may be accessed orally. In another embodiment, the electrical ablation system 10 may be adapted to treat undesirable tissue in the liver or other organs that may be accessible using translumenal access techniques such as, without limitation, NOTES™ techniques, where the electrical ablation devices may be initially introduced through a natural orifice such as the mouth, anus, or vagina and then advanced to the tissue treatment site by puncturing the walls of internal body lumen such as the stomach, intestines, colon, cervix. In various embodiments, the electrical ablation system 10 may be adapted to treat undesirable tissue in the brain, liver, breast, gall bladder, pancreas, or prostate gland, using one or more electrodes positioned percutaneously, transcutaneously, translumenally, minimally invasively, and/or through open surgical techniques, or any combination thereof.

In one embodiment, the electrical ablation system 10 may be employed in conjunction with a flexible endoscope 12, as well as a rigid endoscope, laparoscope, or thoracoscope, such as the GIF-H180 model available from Olympus Corporation. In one embodiment, the endoscope 12 may be introduced to the tissue treatment region trans-anally through the colon, trans-orally through the esophagus and stomach, trans-vaginally through the cervix, transcutaneously, or via an external incision or keyhole formed in the abdomen in conjunction with a trocar. The electrical ablation system 10 may be inserted and guided into or proximate the tissue treatment region using the endoscope 12.

In the embodiment illustrated in FIG. 1, the endoscope 12 comprises an endoscope handle 34 and an elongate relatively flexible shaft 32. The distal end of the flexible shaft 32 may comprise a light source and a viewing port. Optionally, the flexible shaft 32 may define one or more working channels for receiving various instruments, such as electrical ablation devices, for example, therethrough. Images within the field of view of the viewing port are received by an optical device, such as a camera comprising a charge coupled device (CCD) usually located within the endoscope 12, and are transmitted to a display monitor (not shown) outside the patient.

In one embodiment, the electrical ablation system 10 may comprise an electrical ablation device 20, a plurality of electrical conductors 18, a handpiece 16 comprising an activation switch 62, and an energy source 14, such as an electrical waveform generator, electrically coupled to the activation switch 62 and the electrical ablation device 20. The electrical ablation device 20 comprises a relatively flexible member or shaft 22 that may be introduced to the tissue treatment region using a variety of known techniques such as an open incision and a trocar, through one of more of the working channels of the endoscope 12, percutaneously, or transcutaneously, for example.

In one embodiment, one or more electrodes (e.g., needle electrodes, balloon electrodes), such as first and second electrodes 24a, 24b, extend out from the distal end of the electrical ablation device 20. In one embodiment, the first electrode 24a may be configured as the positive electrode and the second electrode 24b may be configured as the negative electrode. The first electrode 24a is electrically connected to a first electrical conductor 18a, or similar electrically conductive lead or wire, which is coupled to the positive terminal of the energy source 14 through the activation switch 62. The second electrode 24b is electrically connected to a second electrical conductor 18b, or similar electrically conductive lead or wire, which is coupled to the negative terminal of the energy source 14 through the activation switch 62. The electrical conductors 18a, 18b are electrically insulated from each other and surrounding structures, except for the electrical connections to the respective electrodes 24a, 24b. In various embodiments, the electrical ablation device 20 may be configured to be introduced into or proximate the tissue treatment region using the endoscope 12 (laparoscope or thoracoscope), open surgical procedures, or external and non-invasive medical procedures. The electrodes 24a, 24b may be referred to herein as endoscopic or laparoscopic electrodes, although variations thereof may be inserted transcutaneously or percutaneously. As described herein, either one or both electrodes 24a, 24b may be adapted and configured to slideably move in and out of a cannula, lumen, or channel defined within the flexible shaft 22.

Once the electrodes 24a, 24b are positioned at the desired location into or proximate the tissue treatment region, the electrodes 24a, 24b may be connected to or disconnected from the energy source 14 by actuating or de-actuating the switch 62 on the handpiece 16. The switch 62 may be operated manually or may be mounted on a foot switch (not shown), for example. The electrodes 24a, 24b deliver electric field pulses to the undesirable tissue. The electric field pulses may be characterized based on various parameters such as pulse shape, amplitude, frequency, and duration. The electric field pulses may be sufficient to induce irreversible electroporation in the undesirable tissue. The induced potential depends on a variety of conditions such as tissue type, cell size, and electrical pulse parameters. The primary electrical pulse parameter affecting the transmembrane potential for a specific tissue type is the amplitude of the electric field and pulse length that the tissue is exposed to.

In one embodiment, a protective sleeve or sheath 26 may be slideably disposed over the flexible shaft 22 and within a handle 28. In another embodiment, the sheath 26 may be slideably disposed within the flexible shaft 22 and the handle 28, without limitation. The sheath 26 is slideable and may be located over the electrodes 24a, 24b to protect the trocar and prevent accidental piercing when the electrical ablation device 20 is advanced therethrough. Either one or both of the electrodes 24a, 24b of the electrical ablation device 20 may be adapted and configured to slideably move in and out of a cannula, lumen, or channel formed within the flexible shaft 22. As described herein, the second electrode 24b may be fixed in place. The second electrode 24b may provide a pivot about which the first electrode 24a can be moved in an arc to other points in the tissue treatment region to treat larger portions of the diseased tissue that cannot be treated by fixing the electrodes 24a, 24b in one location. In one embodiment, either one or both of the electrodes 24a, 24b may be adapted and configured to slideably move in and out of a working channel formed within a flexible shaft 32 of the flexible endoscope 12 or may be located independently of the flexible endoscope 12. Various features of the first and second electrodes 24a, 24b are described in more detail in FIGS. 2A-D.

In one embodiment, the first and second electrical conductors 18a, 18b may be provided through the handle 28. In the illustrated embodiment, the first electrode 24a can be slideably moved in and out of the distal end of the flexible shaft 22 using a slide member 30 to retract and/or advance the first electrode 24a. In various embodiments either or both electrodes 24a, 24b may be coupled to the slide member 30, or additional slide members, to advance and retract the electrodes 24a, 24b, e.g., position the electrodes 24a, 24b. In the illustrated embodiment, the first electrical conductor 18a coupled to the first electrode 24a is coupled to the slide member 30. In this manner, the first electrode 24a, which is slideably movable within the cannula, lumen, or channel defined by the flexible shaft 22, can advanced and retracted with the slide member 30.

In various other embodiments, transducers or sensors 29 may be located in the handle 28 of the electrical ablation device 20 to sense the force with which the electrodes 24a, 24b penetrate the tissue in the tissue treatment zone. This feedback information may be useful to determine whether either one or both of the electrodes 24a, 24b have been properly inserted in the tissue treatment region. As is particularly well known, cancerous tumor tissue tends to be denser than healthy tissue and thus greater force is required to insert the electrodes 24a, 24b therein. The transducers or sensors 29 can provide feedback to the operator, surgeon, or clinician to physically sense when the electrodes 24a, 24b are placed within the cancerous tumor. The feedback information provided by the transducers or sensors 29 may be processed and displayed by circuits located either internally or externally to the energy source 14. The sensor 29 readings may be employed to determine whether the electrodes 24a, 24b have been properly located within the cancerous tumor thereby assuring that a suitable margin of error has been achieved in locating the electrodes 24a, 24b.

In one embodiment, the input to the energy source 14 may be connected to a commercial power supply by way of a plug (not shown). The output of the energy source 14 is coupled to the electrodes 24a, 24b, which may be energized using the activation switch 62 on the handpiece 16, or in one embodiment, an activation switch mounted on a foot activated pedal (not shown). The energy source 14 may be configured to produce electrical energy suitable for electrical ablation, as described in more detail herein.

In one embodiment, the electrodes 24a, 24b are adapted and configured to electrically couple to the energy source 14 (e.g., generator, waveform generator). Once electrical energy is coupled to the electrodes 24a, 24b, an electric field is formed at a distal end of the electrodes 24a, 24b. The energy source 14 may be configured to generate electric pulses at a predetermined frequency, amplitude, pulse length, and/or polarity that are suitable to induce irreversible electroporation to ablate substantial volumes of undesirable tissue in the treatment region. For example, the energy source 14 may be configured to deliver DC electric pulses having a predetermined frequency, amplitude, pulse length, and/or polarity suitable to induce irreversible electroporation to ablate substantial volumes of undesirable tissue in the treatment region. The DC pulses may be positive or negative relative to a particular reference polarity. The polarity of the DC pulses may be reversed or inverted from positive-to-negative or negative-to-positive a predetermined number of times to induce irreversible electroporation to ablate substantial volumes of undesirable tissue in the treatment region.

In one embodiment, a timing circuit may be coupled to the output of the energy source 14 to generate electric pulses. The timing circuit may comprise one or more suitable switching elements to produce the electric pulses. For example, the energy source 14 may produce a series of n electric pulses (where n is any positive integer) of sufficient amplitude and duration to induce irreversible electroporation suitable for tissue ablation when the n electric pulses are applied to the electrodes 24a, 24b. In one embodiment, the electric pulses may have a fixed or variable pulse length, amplitude, and/or frequency.

The electrical ablation device 20 may be operated either in bipolar or monopolar mode. In bipolar mode, the first electrode 24a is electrically connected to a first polarity and the second electrode 24b is electrically connected to the opposite polarity. For example, in monopolar mode, the first electrode 24a is coupled to a prescribed voltage and the second electrode 24b is set to ground. In the illustrated embodiment, the energy source 14 may be configured to operate in either the bipolar or monopolar modes with the electrical ablation system 10. In bipolar mode, the first electrode 24a is electrically connected to a prescribed voltage of one polarity and the second electrode 24b is electrically connected to a prescribed voltage of the opposite polarity. When more than two electrodes are used, the polarity of the electrodes may be alternated so that any two adjacent electrodes may have either the same or opposite polarities, for example.

In one embodiment, the energy source 14 may be configured to produce RF waveforms at predetermined frequencies, amplitudes, pulse widths or durations, and/or polarities suitable for electrical ablation of cells in the tissue treatment region. One example of a suitable RF energy source is a commercially available conventional, bipolar/monopolar electrosurgical RF generator such as Model Number ICC 350, available from Erbe, GmbH.

In one embodiment, the energy source 14 may be configured to produce destabilizing electrical potentials (e.g., fields) suitable to induce irreversible electroporation. The destabilizing electrical potentials may be in the form of bipolar/monopolar DC electric pulses suitable for inducing irreversible electroporation to ablate tissue undesirable tissue with the electrical ablation device 20. A commercially available energy source suitable for generating irreversible electroporation electric field pulses in bipolar or monopolar mode is a pulsed DC generator such as Model Number ECM 830, available from BTX Molecular Delivery Systems. In bipolar mode, the first electrode 24a may be electrically coupled to a first polarity and the second electrode 24b may be electrically coupled to a second (e.g., opposite) polarity of the energy source 14. Bipolar/monopolar DC electric pulses may be produced at a variety of frequencies, amplitudes, pulse lengths, and/or polarities. Unlike RF ablation systems, however, which require high power and energy levels delivered into the tissue to heat and thermally destroy the tissue, irreversible electroporation requires very little energy input into the tissue to kill the undesirable tissue without the detrimental thermal effects because with irreversible electroporation the cells are destroyed by electric field potentials rather than heat.

In one embodiment, the energy source 14 may be coupled to the first and second electrodes 24a, 24b by either a wired or a wireless connection. In a wired connection, the energy source 14 is coupled to the electrodes 24a, 24b by way of the electrical conductors 18a, 18b, as shown. In a wireless connection, the electrical conductors 18a, 18b may be replaced with a first antenna (not shown) coupled the energy source 14 and a second antenna (not shown) coupled to the electrodes 24a, 24b, wherein the second antenna is remotely located from the first antenna. In one embodiment, the energy source may comprise a wireless transmitter to deliver energy to the electrodes using wireless energy transfer techniques via one or more remotely positioned antennas.

In at least one embodiment, the energy source 14 can be configured to produce DC electric pulses at frequencies in the range of approximately 1 Hz to approximately 10000 Hz, amplitudes in the range of approximately ±100 to approximately ±8000 VDC, and pulse lengths (e.g., pulse width, pulse duration) in the range of approximately 1 µs to approximately 100 ms. In at least one embodiment, the energy source can be configured to produce biphasic waveforms and/or monophasic waveforms that alternate around approximately 0V. In various embodiments, for example, the polarity of the electric potentials coupled to the electrodes 24a, 24b can be reversed during the electrical ablation therapy. For example, initially, the DC electric pulses can have a positive polarity and an amplitude in the range of approximately +100 to approximately +3000 VDC. Subsequently, the polarity of the DC electric pulses can be reversed such that the amplitude is in the range of approximately −100 to approximately −3000 VDC. In another embodiment, the DC electric pulses can have an initial positive polarity and amplitude in the range of approximately +100 to +6000 VDC and a subsequently reversed polarity and amplitude in the range of approximately −100 to approximately −6000 VDC.

In at least one embodiment, the undesirable cells in the tissue treatment region can be electrically ablated with DC pulses suitable to induce irreversible electroporation at frequencies of approximately 10 Hz to approximately 100 Hz, amplitudes in the range of approximately +700 to approximately +1500 VDC, and pulse lengths of approximately 10 µs to approximately 50 µs. In another embodiment, the abnormal cells in the tissue treatment region can be electrically ablated with an electrical waveform having an amplitude of approximately +500 VDC and pulse duration of approximately 20 ms delivered at a pulse period T or repetition rate, frequency f=1/T, of approximately 10 Hz. In another embodiment, the undesirable cells in the tissue treatment region can be electrically ablated with DC pulses suitable to induce irreversible electroporation at frequencies of approximately 200 Hz, amplitudes in the range of approximately +3000 VDC, and pulse lengths of approximately 10 ms. It has been determined that an electric field strength of 1,000V/cm can be suitable for destroying living tissue by inducing irreversible electroporation by DC electric pulses.

In various embodiments, the energy source 14 can be configured to produce AC electric pulses at frequencies in the range of approximately 1 Hz to approximately 10000 Hz, amplitudes in the range of approximately ±8000 to approximately ±8000 VAC, and pulse lengths (e.g., pulse width, pulse duration) in the range of approximately 1 µs to approximately 100 ms. In one embodiment, the undesirable cells in the tissue treatment region can be electrically ablated with AC pulses suitable to induce irreversible electroporation at pulse frequencies of approximately 4 Hz, amplitudes of approximately ±6000 VAC, and pulse lengths of approximately 20 ms. It has been determined that an electric field strength of 1,500V/cm can be suitable for destroying living tissue by inducing irreversible electroporation by AC electric pulses.

Figure 2A:
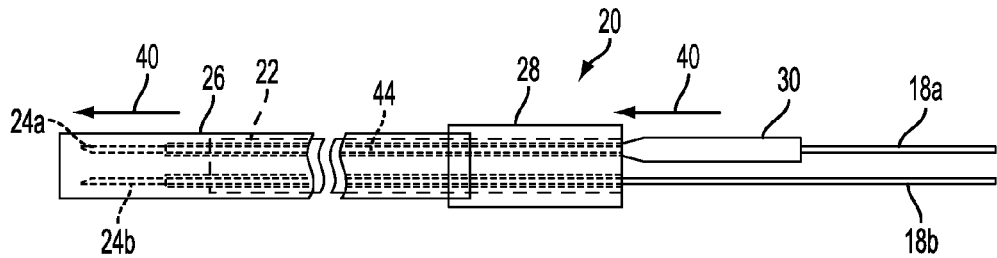
Figure 2B:
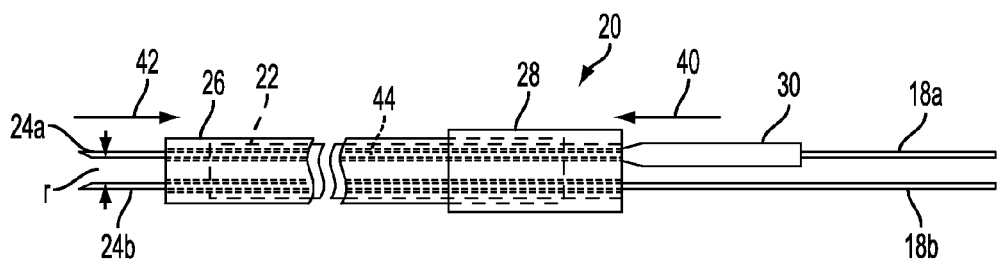
Figure 2C:
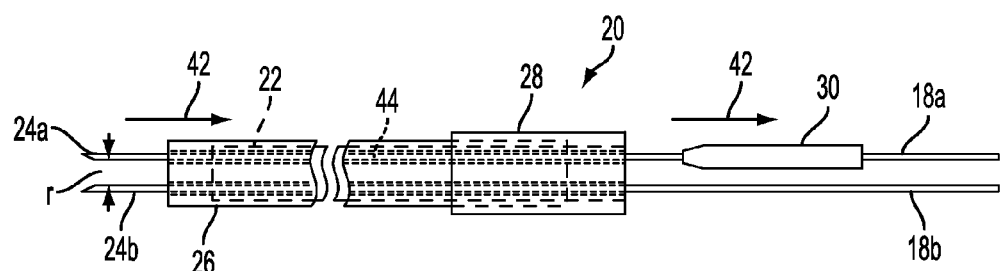
Figure 2D:
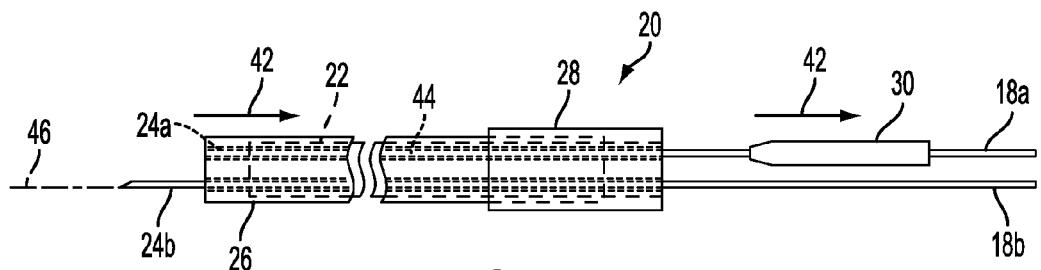
Figure 4:
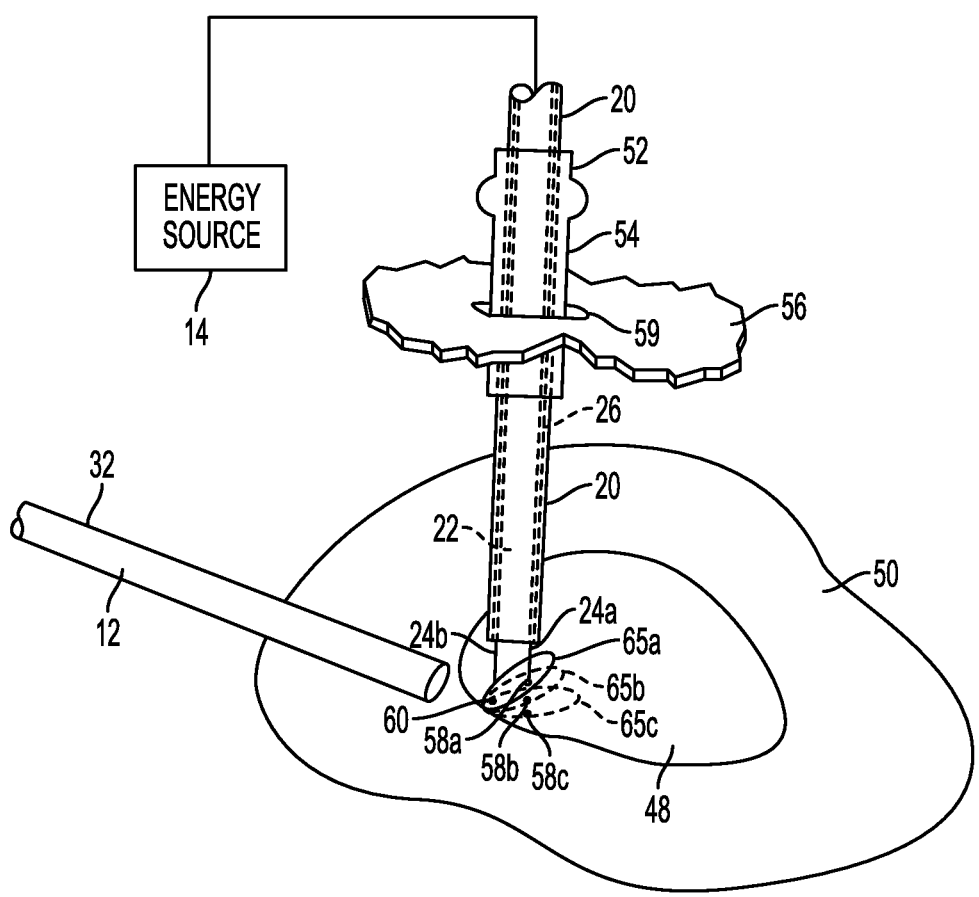
FIG. 4 is a schematic illustrating the electrical ablation system shown in FIGS. 1 and 2A-D in use to treat undesirable tissue located in the liver according to various embodiments of the present disclosure.

FIGS. 2A-D illustrate one embodiment of the electrical ablation device 20 in various phases of deployment. In the embodiment illustrated in FIGS. 2A-D, the sheath 26 is disposed over the flexible shaft 22, however, the sheath 26 may be disposed within the flexible shaft 22. The electrical ablation device 20 may be used in conjunction with the electrical ablation system 10 shown in FIG. 1. It will be appreciated that other devices and electrode configurations may be employed without limitation, such as, for example, the electrical ablation device 800 having electrodes 824a, 824b, 824c, 824d, as described herein. FIG. 2A illustrates an initial phase of deployment wherein the sheath 26 is extended in the direction indicated by arrow 40 to cover the electrodes 24a, 24b. The electrodes 24a, 24b may have dimensions of about 0.5 mm, about 1 mm, or about 1.5 mm in diameter. It will be appreciated that the dimensions of the electrodes 24a, 24b may be anywhere from about 0.5 mm to about 1.5 mm in diameter. The electrical ablation device 20 may be introduced into the tissue treatment region through a trocar, as illustrated in FIG. 4, for example. FIG. 2B illustrates another phase of deployment wherein the sheath 26 is retracted within the handle 28 in the direction indicated by arrow 42. In this phase of deployment, the first and second electrodes 24a, 24b extend through the distal end of the flexible shaft 22 and are ready to be inserted into or proximate the tissue treatment region. The first electrode 24a may be retracted in direction 42 through a lumen 44 formed in the flexible shaft 22 by holding the handle 28 and pulling on the slide member 30. FIG. 2C illustrates a transition phase wherein the first electrode 24a is the process of being retracted in direction 42 by pulling on the slide member 30 handle, for example, in the same direction. FIG. 2D illustrates another phase of deployment wherein the first electrode 24a is in a fully retracted position. In this phase of deployment the electrical ablation device 20 can be pivotally rotated about an axis 46 defined by the second electrode 24b. The electrodes 24a, 24b are spaced apart by a treatment distance "r." The treatment distance "r" between the electrodes 24a, 24b may be 5.0 mm, about 7.5 mm, or about 10 mm. The treatment distance "r" between the electrodes 24a, 24b may be 1.0 cm, about 1.5 cm, or about 2 cm. Thus, the electrical ablation device 20 may be rotated in an arc about the pivot formed by the second electrode 24b, the first electrode 24a may be placed in a new location in the tissue treatment region within the treatment radius "r." Retracting the first electrode 24a and pivoting about the second electrode 24b enables the surgeon or clinician to target and treat a larger tissue treatment region essentially comprising a circular region having a treatment radius "r," which is the distance between the electrodes 24a, 24b. Thus, the electrodes 24a, 24b may be located in a plurality of positions in and around the tissue treatment region in order to treat much larger regions of tissue. Increasing the electrode 24a, 24b diameter and spacing the electrodes 24a, 24b further apart enables the generation of an electric field over a much larger tissue regions and thus the ablation of larger volumes of undesirable tissue. In this manner, the operator can treat a larger tissue treatment region comprising cancerous lesions, polyps, or tumors, for example.

Although the electrical ablation electrodes according to the described embodiments have been described in terms of the particular needle type electrodes 24a, 24b as shown in the embodiments illustrated in FIGS. 1 and 2A-D, other configurations of electrical ablation electrodes may be employed for the ablation of undesirable tissue, without limitation. In one embodiment, the electrical ablation device 20 may comprise two or more fixed electrodes that are non-retractable. In another embodiment, the electrical ablation device 20 may comprise two or more retractable electrodes, one embodiment of which is described below with reference to FIG. 3. In another embodiment, the electrical ablation device 20 may comprise at least one slidable electrode disposed within at least one working channel of the flexible shaft 32 of the endoscope 12. In another embodiment, the electrical ablation device 20 may comprise at least one electrode may be configured to be inserted into the tissue treatment region transcutaneously or percutaneously. Still in various other embodiments, the electrical ablation device 20 may comprise at least one electrode configured to be introduced to the tissue treatment region transcutaneously or percutaneously and at least one other electrode may be configured to be introduced to the tissue treatment region through at least one working channel of the flexible shaft 32 of the endoscope 12. The embodiments, however, are not limited in this context.

Various electrical ablation devices are disclosed in commonly-owned U.S. patent application Ser. No. 11/897,676 titled "ELECTRICAL ABLATION SURGICAL INSTRUMENTS," filed Aug. 31, 2007, now U.S. Patent Application Publication No. 2009/0062788, the entire disclosure of which is incorporated herein by reference in its entirety. Various other devices are disclosed in commonly-owned U.S. patent application Ser. No. 12/352,375, titled "ELECTRICAL ABLATION DEVICES", filed on Jan. 12, 2009, now U.S. Patent Application Publication No. 2010/0179530, the entire disclosure of which is incorporated herein by reference in its entirety.

Figure 3:
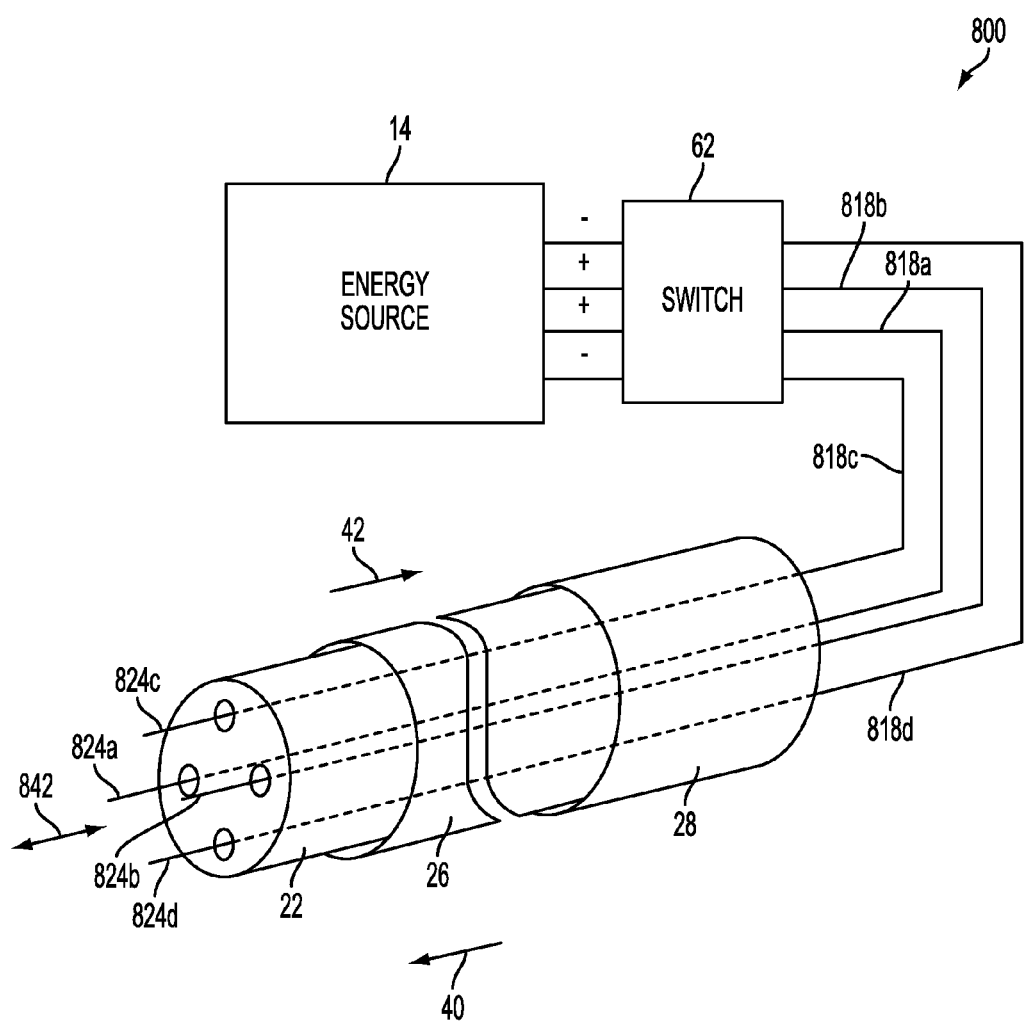
FIG. 3 is a perspective view of one embodiment of an electrical ablation device comprising multiple electrode probes according to various embodiments of the present disclosure.

As previously described with reference to the embodiments illustrated in FIGS. 2A-D, as shown in FIG. 3, in one embodiment, the protective sleeve or sheath 26 may be slidably disposed over the flexible shaft 22 and within the handle 28. In an initial phase of deployment, the sheath 26 is extended in direction 40 to cover the electrodes 824a, 824b, 824c, 824d to protect the trocar and prevent accidental piercing when the electrical ablation device 800 is advanced therethrough. Once the electrodes 824a, 824b, 824c, 824d are located into or proximate the tissue treatment region, the sheath 26 is retracted in direction 42 to expose the electrodes 824a, 824b, 824c, 824d. One or more of the electrodes 824a, 824b, 824c, 824d of the electrical ablation device 800 may be adapted and configured to slideably move in and out of a cannula, lumen, or channel formed within the flexible shaft 22. In one embodiment all of the electrodes 824a, 824b, 824c, 824d are configured to slideably move in and out channels formed within lumens formed within the flexible shaft 22, referred to for example as the lumen 44 in the embodiments illustrated in FIGS. 2A-D, to advance and retract the electrodes 824a, 824b, 824c, 824d as may be desired by the operator. Nevertheless, in other embodiments, it may be desired to fix all or certain ones of the one or more electrodes 824a, 824b, 824c, 824d in place.

The various embodiments of electrodes described in the present specification, e.g., the electrodes 24a, 24b, or 824a-

*m*, may be configured for use with an electrical ablation device (not shown) comprising an elongated flexible shaft to house the needle electrodes 24*a*, 24*b*, or 824*a-m*, for example. The needle electrodes 24*a*, 24*b*, or 824*a-m*, are free to extend past a distal end of the electrical ablation device. The flexible shaft comprises multiple lumen formed therein to slidably receive the needle electrodes 24*a*, 24*b*, or 824*a-m*. A flexible sheath extends longitudinally from a handle portion to the distal end. The handle portion comprises multiple slide members received in respective slots defining respective walls. The slide members are coupled to the respective needle electrodes 24*a*, 24*b*, or 824*a-m*. The slide members are movable to advance and retract the electrode 24*a*, 24*b*, or 824*a-m*. The needle electrodes 24*a*, 24*b*, or 824*a-m*, may be independently movable by way of the respective slide members. The needle electrodes 24*a*, 24*b*, or 824*a-m*, may be deployed independently or simultaneously. An electrical ablation device (not shown) comprising an elongated flexible shaft to house multiple needle electrodes and a suitable handle is described in commonly owned U.S. patent application Ser. No. 11/897,676 titled "ELECTRICAL ABLATION SURGICAL INSTRUMENTS," filed Aug. 31, 2007, now U.S. Patent Application Publication No. 2009/0062788, the entire disclosure of which is incorporated herein by reference in its entirety.

It will be appreciated that the embodiments of the electrical ablation devices 20, 800 described with referenced to FIGS. 2A-D and 3, may be introduced inside a patient endoscopically, transcutaneously, percutaneously, through an open incision, through a trocar (as shown in FIG. 4), through a natural orifice, or any combination thereof. In one embodiment, the outside diameter of the electrical ablation devices 20, 800 may be sized to fit within a working channel of an endoscope and in other embodiments the outside diameter of the electrical ablation devices 20, 800 may be sized to fit within a hollow outer sleeve 620, or trocar, as shown in FIG. 4, for example. The hollow outer sleeve 620 or trocar is inserted into the upper gastrointestinal tract of a patient and may be sized to also receive a flexible endoscopic portion of an endoscope 622 (e.g., gastroscope), similar to the endoscope 12 described in FIG. 1.

FIG. 4 illustrates one embodiment of the electrical ablation system 10 shown in FIG. 1 in use to treat undesirable tissue 48 located in the liver 50. The undesirable tissue 48 may be representative of a variety of diseased tissues, cancers, tumors, masses, lesions, abnormal tissue growths, for example. In use, the electrical ablation device 20 may be introduced into or proximate the tissue treatment region through a port 52 of a trocar 54. The trocar 54 is introduced into the patient via a small incision 59 formed in the skin 56. The endoscope 12 may be introduced into the patient trans-anally through the colon, trans-vaginally, trans-orally down the esophagus and through the stomach using translumenal techniques, or through a small incision or keyhole formed through the patient's abdominal wall (e.g., the peritoneal wall). The endoscope 12 may be employed to guide and locate the distal end of the electrical ablation device 20 into or proximate the undesirable tissue 48. Prior to introducing the flexible shaft 22 through the trocar 54, the sheath 26 is slid over the flexible shaft 22 in a direction towards the distal end thereof to cover the electrodes 24*a*, 24*b* (as shown in FIG. 2A) until the distal end of the electrical ablation device 20 reaches the undesirable tissue 48.

Once the electrical ablation device 20 has been suitably introduced into or proximate the undesirable tissue 48, the sheath 26 is retracted to expose the electrodes 24*a*, 24*b* (as shown in FIG. 2B) to treat the undesirable tissue 48. To ablate the undesirable tissue 48, the operator initially may locate the first electrode 24*a* at a first position 58*a* and the second electrode 24*b* at a second position 60 using endoscopic visualization and maintaining the undesirable tissue 48 within the field of view of the flexible endoscope 12. In various embodiments, the operator may place the first and/or second electrodes 24*a*, 24*b* with the aid of pre-operative and/or intra-operative images such as, for example, images acquired by magnetic resonance imaging (MRI), X-ray fluorescence (XRF) imaging, ultrasound imaging and/or computed tomography (CT) imaging, for example. The pre-operative and intra-operative images can comprise a three-dimensional image of the patient's body, for example, and can aid the operator in placing the electrodes 24*a*, 24*b* in or proximal to the undesired tissue 48 in the tissue treatment region while maintaining a safe distance from critical structures within the body, for example. In various embodiments, the pre-operative and intra-operative images can be recorded and registered into a common coordinate system mapped to the patient's body, for example. In some embodiments, registration points can be attached to the patient's body during a pre-operative scan, for example, and can be left in place during the surgical procedure, for example. Further, in such embodiments, the electrical ablation device 20 can comprise registration points, such as registration points on the handpiece 16 (FIG. 1) and/or on the electrodes 24*a*, 24*b*, for example, such that the position of the electrodes 24*a*, 24*b* relative to registration points within the patient's body can be determined.

The first position 58*a* may be near a perimeter edge of the undesirable tissue 48. Once the electrodes 24*a*, 24*b* are located into or proximate the undesirable tissue 48, the electrodes 24*a*, 24*b* are energized with irreversible electroporation pulses to create a first necrotic zone 65*a*. For example, once the first and second electrodes 24*a*, 24*b* are located in the desired positions 60 and 58*a*, the undesirable tissue 48 may be exposed to an electric field generated by energizing the first and second electrodes 24*a*, 24*b* with the energy source 14. The electric field may have a magnitude, frequency, and pulse length suitable to induce irreversible electroporation in the undesirable tissue 48 within the first necrotic zone 65*a*. The size of the necrotic zone is substantially dependent on the size and separation of the electrodes 24*a*, 24*b*, as previously described. The treatment time is defined as the time that the electrodes 24*a*, 24*b* are activated or energized to generate the electric pulses suitable for inducing irreversible electroporation in the undesirable tissue 48.

This procedure may be repeated to destroy relatively larger portions of the undesirable tissue 48. The position 60 may be taken as a pivot point about which the first electrode 24*a* may be rotated in an arc of radius "r," the distance between the first and second electrodes 24*a*, 24*b*. Prior to rotating about the second electrode 24*b*, the first electrode 24*a* is retracted by pulling on the slide member 30 (FIGS. 1 and 2A-D) in a direction towards the proximal end and rotating the electrical ablation device 20 about the pivot point formed at position 60 by the second electrode 24*b*. Once the first electrode 24*a* is rotated to a second position 58*b*, it is advanced to engage the undesirable tissue 48 at point 58*b* by pushing on the slide member 30 in a direction towards the distal end. A second necrotic zone 65*b* is formed upon energizing the first and second electrodes 24*a*, 24*b*. A third necrotic zone 65*c* is formed by retracting the first electrode 24*a*, pivoting about pivot point 60 and rotating the first electrode 24*a* to a new location, advancing the first electrode 24a into the undesirable tissue 48 and energizing the first and second electrodes 24a, 24b. This process may be repeated as often as necessary to create any number of necrotic zones 65p, where p is any positive integer, within multiple circular areas of radius "r," for example, that is suitable to ablate the entire undesirable tissue 48 region. At anytime, the surgeon or clinician can reposition the first and second electrodes 24a, 24b and begin the process anew. Similar techniques may be employed to ablate any other undesirable tissues that may be accessible trans-anally through the colon, and/or orally through the esophagus and the stomach using translumenal access techniques. Therefore, the embodiments are not limited in this context.

Figure 5:
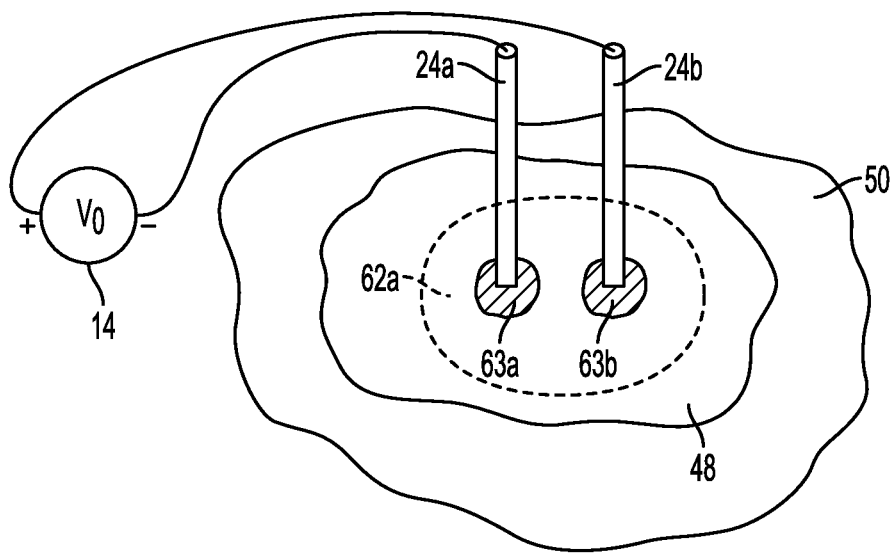
FIG. 5 is a detailed schematic illustrating the electrical ablation system shown in FIG. 4 in use to treat undesirable tissue located in the liver according to various embodiments of the present disclosure.

FIG. 5 illustrates a detailed view of one embodiment of the electrical ablation system 10 shown in FIG. 4 in use to treat undesirable tissue 48 located in the liver 50. The first and second electrodes 24a, 24b are embedded into or proximate the undesirable tissue 48 on the liver 50. The first and second electrodes 24a, 24b are energized to deliver one or more electrical pulses of amplitude and length sufficient to induce irreversible electroporation in the undesirable tissue 48 and create the first necrotic zone 65a. Additional electric pulses may be applied to the tissue immediately surrounding the respective electrodes 24a, 24b to form second, thermal, necrotic zones 63a,b near the electrode-tissue-interface. The duration of an irreversible electroporation energy pulse determines whether the temperature of the tissue 63a,b immediately surrounding the respective electrodes 24a, 24b raises to a level sufficient to create thermal necrosis. As previously described, varying the electrode 24a, 24b size and spacing can control the size and shape of irreversible electroporation induced necrotic zone 65a. Electric pulse amplitude and length can be varied to control the size and shape of the thermally induced necrotic zones near the tissue-electrode-interface.

Figure 6:
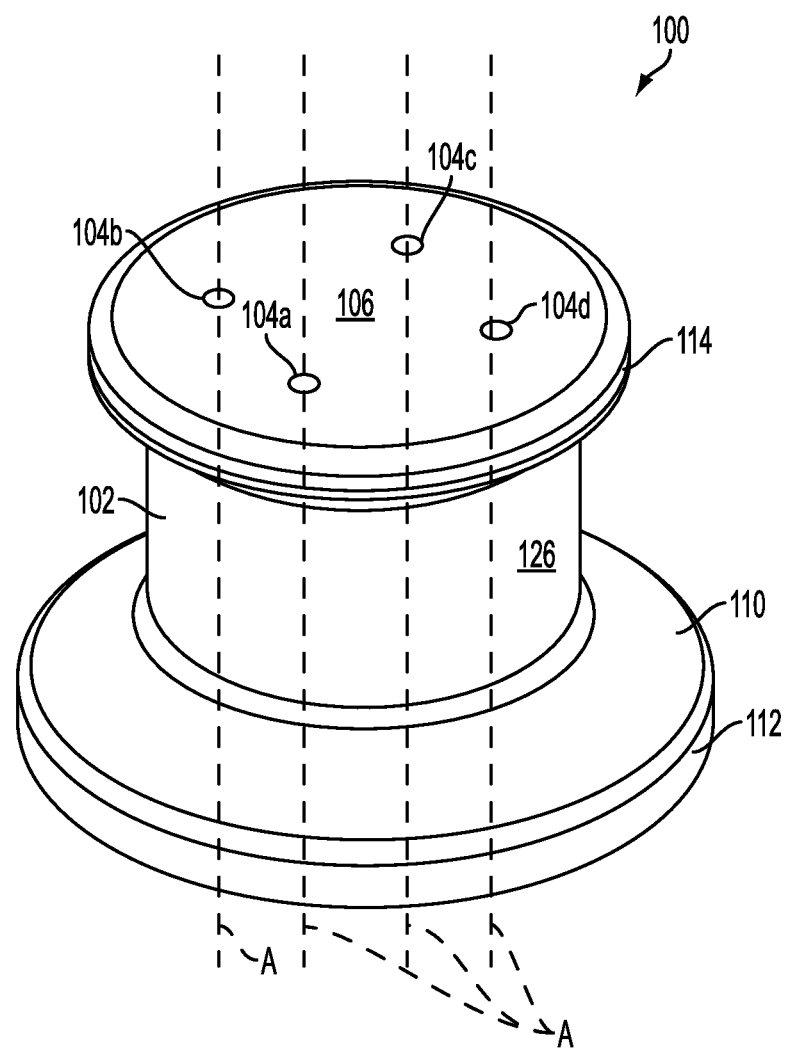
FIG. 6 is a perspective view of a probe guide according to various embodiments of the present disclosure.
Figure 7:
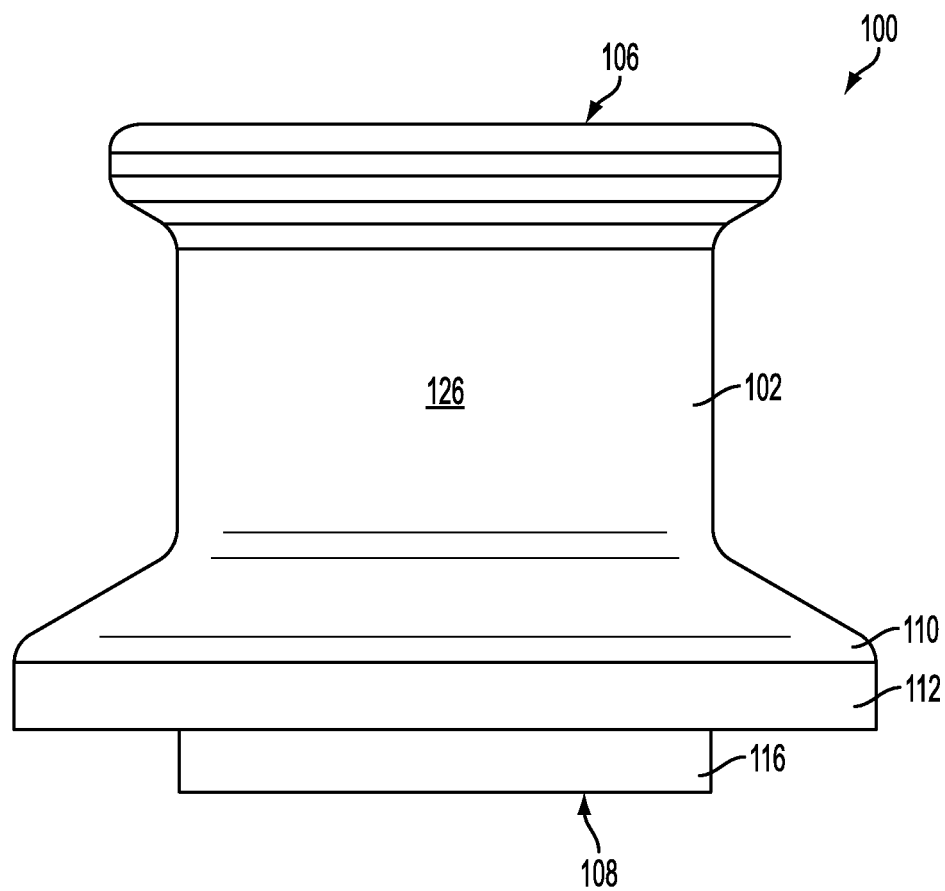
FIG. 7 is an elevational view of one embodiment of the probe guide of FIG. 6.
Figure 8:
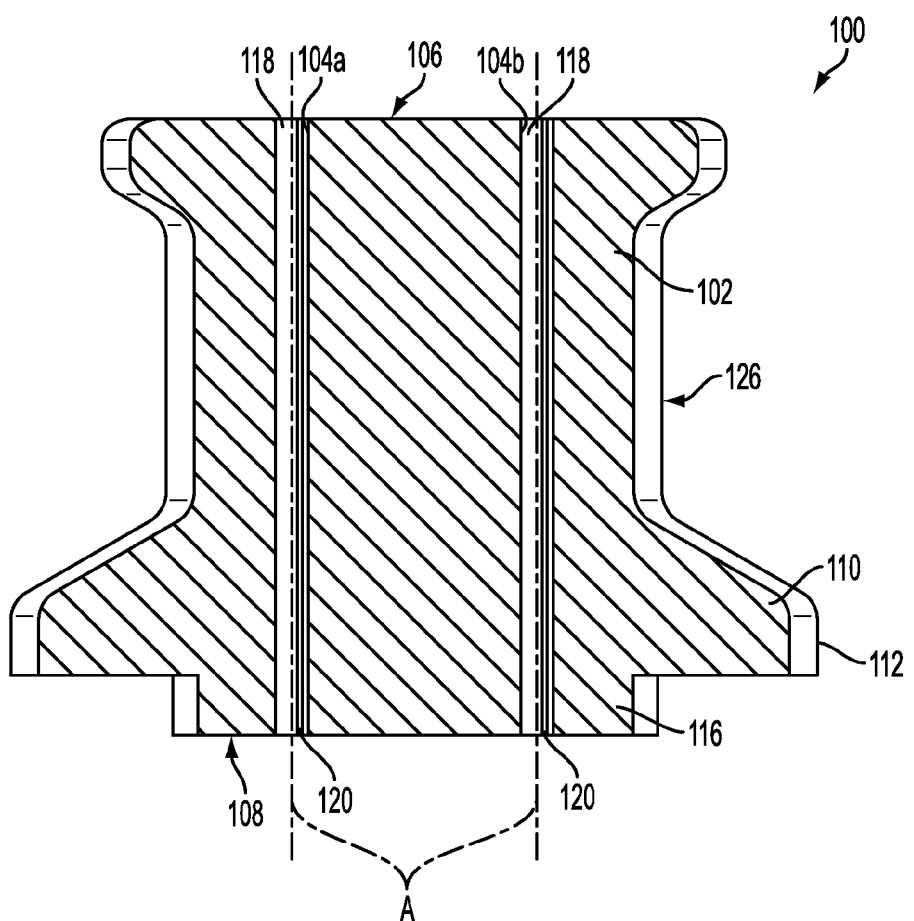
FIG. 8 is an elevational, cross-sectional view of one embodiment of the probe guide of FIG. 6.

Referring to FIGS. 6-8, in one embodiment, a probe guide 100 can be structured to guide electrodes, such as electrodes 824a, 824b, 824c, 824d (FIG. 3), in or proximal to a tissue treatment region. In various embodiments, the probe guide 100 can maintain the parallel alignment of the electrodes 824a, 824b, 824c, 824d, for example, and/or maintain a predetermined distance or gap between the electrodes 824a, 824b, 824c, 824d, for example. In some embodiments, the probe guide 100 can comprise a body portion 102 and, in various embodiments, the body portion 102 can comprise at least two passages, such as first passage 104a and second passage 104b, which can extend through the body portion 102. The passages 104a, 104b can extend through the body portion 102 from a first or proximal surface 106 to a second or tissue contacting surface 108, for example. The first passage 104a can be structured to axially restrain the first electrode 824a, for example, and the second passage 104b can be structured to axially restrain the second electrode 824b, for example. Furthermore, in various embodiments, the first passage 104a can be parallel or substantially parallel to the second passage 104b. Referring primarily to FIG. 8, an axis A can pass through each passage 104a, 104b, for example. In various embodiments, the axis A can define the central axis of each passage 104a, 104b. The axes A defining the first and second passages 104a, 104b can be separated by a predetermined distance or gap of approximately 1.0 cm to approximately 2.5 cm, for example. In some embodiments, the axes defining the first and second passages 104a, 104b can be separated by approximately 1.5 cm, for example.

In various embodiments the first passage 104a can be structured to axially restrain the first electrode 824a and the second passage 104b can be structured to axially restrain the second electrode 824b, for example. In some embodiments, the first and second electrodes 824a, 824b can comprise a proximal end and a distal end. In at least one embodiment, the distal end of the first electrode 824a can be spaced a predetermined distance from the distal end of the second electrode 824b when the first electrode 824a is restrained in the first passage 104a and the second electrode 824b is axially restrained in the second passage 104b, for example. The predetermined distance between the distal ends of the first and second electrodes 824a, 824b can correspond to a treatment distance in the tissue treatment region. In various embodiments, as described herein, the distal ends of the first and second electrodes 824a, 824b can be operably structured to conduct current therebetween when at least one of the first and second electrodes 824a, 824b is energized by an energy source 14 (FIG. 3). In various embodiments, the energy source 14 can comprise a radio frequency energy source, a pulsed radio frequency energy source, an irreversible electroporation energy source and/or a pulsed irreversible electroporation energy source, for example. In some embodiments, the current conducted between the distal ends of the first and second electrodes 824a, 824b can be selected to generate an electric field of approximately 1500 volts per centimeter, for example.

In at least one embodiment, the body portion 102 can comprise at least four passages, such as the first passage 104a, the second passage 104b, a third passage 104b and a fourth passage 104d; the passages 104a, 104b, 104c, 104d can extend through the body portion 102 from the first surface 106 to the second surface 108, for example. The first passage 104a can be structured to axially restrain the first electrode 824a, for example, the second passage 104b can be structured to axially restrain the second electrode 824b, for example, the third passage 104c can be structured to axially restrain the third electrode 824c, for example, and the fourth passage 104d can be structured to axially restrain the fourth electrode 824d, for example. In various embodiments the passages 104a, 104b, 104c, 104d through the body portion 102 of the probe guide 100 can be parallel and/or substantially parallel. Furthermore, as described herein, an energy source 14 (FIG. 3) can be structured to operably energize at least one of the electrodes 824a, 824b, 824c, 824d such that the electrodes 824a, 824b, 824c, 824d conduct current therebetween.

Referring primarily to the embodiment illustrated in FIG. 6, an axis A can pass through each passage 104a, 104b, 104c, 104d, for example. In various embodiments, an axis A can define the central axis of each passage 104a, 104b. The axes A defining the passages 104a, 104b, 104c, 104d can be separated by predetermined distance or gap of approximately 1.0 cm to approximately 2.5 cm, for example. In at least one embodiment, the axes defining the first and second passages 104a, 104b can be separated by approximately 1.5 cm, for example, the axes defining the second and third passages 104b, 104c can be separated by approximately 1.5 cm, for example, the axes defining the third and fourth passages 104c, 104 can be separated by approximately 1.5 cm, for example, and the axes defining the fourth and first passages 104d, 104a can be separated by approximately 1.5 cm, for example. In at least one embodiment, the axes defining the first and third passages 104a, 104c can be separated by approximately 2.5 cm, for example. In various embodiments, the predetermined distances between the passages 104a, 104b, 104c, 104d may be equidistant or substantially equidistant. In other embodiments, the at least two predetermined distances between the passages 104a, 104b, 104c, 104d can be different. In various embodiments, the axes defining the passages 104a, 104b, 104c, 104d can correspond with the edges of a parallelogram in the body portion 102 of the probe guide 100, for example. In various embodiments, the parallelogram can be substantially cubic and/or rectangular, for example. Referring primarily to FIG. 8, the passages 104a, 104b can comprise an inner surface 118 that define the bores through the body portion 102 of the probe guide 100. In various embodiments, referring to FIG. 8, for example, the inner surface can comprise a radiopaque material such as, for example, a metallic sleeve or a metallic surface coating. In various embodiments, the inner surface 118 can comprise a longitudinal track 120 that comprises the radiopaque material, for example, an embedded metal wire or rod, or a metal sleeve filled with plastic.

In some embodiments, the probe guide 100 can comprise a rim 114 at and/or near the first surface 106 of the probe guide 100. In various embodiments, the probe guide 100 can also comprise a base 110 at and/or near the second surface 108 of the probe guide 100. In some embodiments, the base 110 and/or the rim 114 can comprise a substantially circular, elliptical or polygonal perimeter. For example, the base 110 can comprise a circular perimeter 112. The base 110 and/or the rim 114 can comprise a wider cross-sectional area than the body portion 102 of the probe guide 100, for example. Furthermore, the base 110 and/or the rim 114 can extend peripherally from an outer surface 126 of the body portion 102 of the probe guide 100, for example. In various embodiments, the probe guide 100 can also comprise an extension 116 extending from the body portion 102. In various embodiments, the extension 116 can comprise the second or tissue contacting surface 108 of the probe guide 100. The extension 116 can comprise a cross-sectional area that is smaller than, larger than, or approximately equal to the cross-sectional area of the base 110 and/or the body portion 102, for example.

During use, an operator may desire to position multiple electrodes, such as the first electrode 824a, the second electrode 824b, the third electrode 824c, and/or the fourth electrode 824d in or proximal to a tissue treatment region. Further, the operator may desire that the electrodes 824a, 824b, 824c, and/or 824d are separated by a predetermined distance or distances when positioned in or proximal to the tissue treatment region, for example. In some embodiments, the probe guide 100 can comprise a predetermined distance or distances between the passages 104a, 104b, 104c, and/or 104d, for example, which can correspond with a preferred treatment distance or distances between the electrodes 824a, 824b, 824c, and/or 824d, for example. In various embodiments, the operator can position the probe guide 100 relative to the tissue treatment region. In at least one embodiment, the second surface 108 and/or the base 110 of the probe guide 100 can be positioned adjacent to, abutting and/or against tissue in or proximal to the tissue treatment region. The first electrode 824a can be axially advanced through the first passage 104a of the probe guide 100, for example. In various embodiments, the first electrode 824a can pierce or puncture tissue to arrive at a preferred first position in the tissue treatment region. In some embodiments, the first electrode 824a can be positioned relative to the tissue treatment region and, subsequently, the first electrode 824a can be positioned within the first passage 104a of the probe guide 100, In at least one embodiment, the probe guide 100 can then be axially moved along the first electrode 824a towards a distal position on the first electrode 824a, in which the probe guide 100 is positioned adjacent to, against, and/or abutting tissue in or proximal to the tissue treatment region.

When the first electrode 824a and the probe guide 100 are appropriately positioned relative to tissue in the tissue treatment region, the distal end of the second electrode 824b can be axially advanced through the second passage 104b of the probe guide 100, for example. As the distal end of the second electrode 824b is advanced through the second passage 104b, the second passage 1804b can guide the second electrode 824b a predetermined distance from the distal end of the first electrode 824a, for example, and/or along a path parallel or substantially parallel to the first electrode 824a, for example. In various embodiments, the distal end of the third electrode 824c can be similarly advanced through the third passage 104c of the probe guide 100 and/or the distal end of the fourth electrode 824d can be similarly advanced through the fourth passage 104d of the probe guide. The second electrode 824b, the third electrode 824c, and the fourth electrode 824d can be advanced simultaneously, consecutively, or a combination thereof. As the distal end of the third electrode 824c is advanced through the third passage 104c, the third passage 104c can guide the third electrode 824c a predetermined distance from the distal end of the first electrode 824a and/or the second electrode 824b, for example, and/or along a path parallel or substantially parallel to the first electrode 824a and/or the second electrode 824b, for example. Similarly, as the distal end of the fourth electrode 824d is advanced through the fourth passage 104d, the fourth passage 104d can guide the fourth electrode 824d a predetermined distance from the distal end of the first electrode 824a, the second electrode 824b and/or the third electrode 824c, for example, and/or along a path parallel or substantially parallel to the first electrode 824a, the second electrode 824b and/or the third electrode 824c, for example. Once the electrodes 824a, 824b, 824c, 824d are positioned in the tissue treatment region, the electrodes 824a, 824b, 824c, 824d can define a first target treatment zone or necrotic zone 65a (FIG. 4) in the tissue treatment region.

As described herein, in particular with the embodiments of the electrodes illustrated in FIG. 3, at least one electrode 824a, 824b, 824c, 824d can be energized by an energy source 14 such that the electrodes 824a, 824b, 824c, 824d conduct current therebetween. In various embodiments, the current can non-thermally ablate tissue in the first target treatment zone in the tissue treatment region, for example. In some embodiments, the electrodes 824a, 824b, 824c, 824d can be withdrawn from the probe guide 100, which can then be repositioned relative to the tissue treatment region, for example. The probe guide 100 can be pivoted and/or translated, for example. In various embodiments, the electrodes 824a, 824b, 824c, 824d can then be re-advanced through the passages 104a, 104b, 104c, 104d to treat tissue in a second target treatment zone in the tissue treatment region, for example. The process can be repeated for a multiple target treatment zones until all tissue in the tissue treatment region has been treated by the electrical ablation device 800 (FIG. 3), for example.

Figure 56:
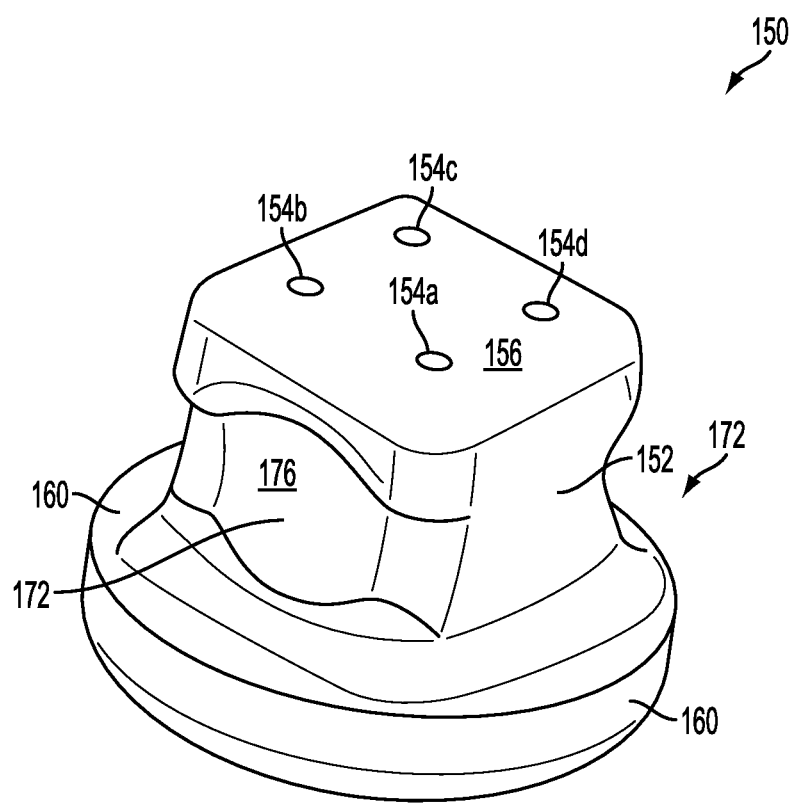
FIG. 56 is a perspective view of a probe guide according to various embodiments of the present disclosure.

Referring now to FIG. 56, in one embodiment, a probe guide 150 can comprise a body portion 152 having a plurality of passages, such as first passage 154a, second passage 154b, third passage 154c, and fourth passage 154d; the passages 154a, 154b, 154c, 154d can extend through the body portion 152 from a first surface 156 to a second or tissue contacting surface, for example. In various embodiments, the body portion 152 can be substantially rectangular and may comprise rounded corners, for example. The first passage 154a can be structured to axially restrain the first electrode 824a, for example, the second passage 154b can be structured to axially restrain the second electrode 824b, for example, the third passage 154c can be structured to axially restrain the third electrode 824c, for example, and the fourth passage 154d can be structured to axially restrain the fourth electrode 824d, for example. Similar to embodiments described herein, the passages 154a, 154b, 154c, 154d through the body portion 152 of the probe guide 150 can be parallel and/or substantially parallel and can be separated by a predetermined distance or distances of approximately 1.0 cm to 2.5 cm, for example. Furthermore, as described herein, an energy source 14 (FIG. 3) can be structured to operably energize at least one of the electrodes 824a, 824b, 824c, 824d such that the electrodes 824a, 824b, 824c, 824d conduct current therebetween.

In the embodiment illustrated in FIG. 56, the body portion 152 can comprise an outer surface 176. In at least one embodiment, the outer surface 176 can comprise a contour 172 directed into the body portion 152, for example. In various embodiments, the outer surface 176 can comprise a plurality of contours 172. The body portion 152 can comprise a first contour 172 on a first side of the body portion 152, for example, and a second contour 172 on a second side of the body portion 152, for example. In various embodiments, the contour 172 on the first side of the body 152 can extend into the body 152 towards the contour 172 on the second side of the body portion 152, for example. The contour(s) 172 can provide a gripping surface for the operator to grasp, position, and/or hold the probe guide 150 relative to tissue in the tissue treatment region. In some embodiments, the probe guide 150 can also comprise a rim and/or a base 162, which can be similar to rim 114 and base 110, described in herein.

Figure 9:
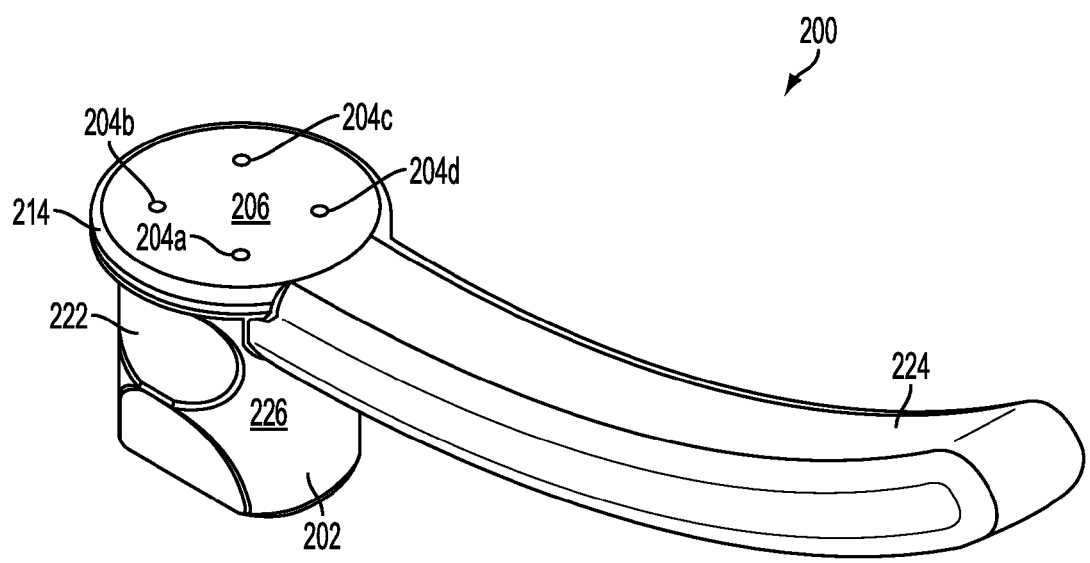
FIG. 9 is a perspective view of a probe guide having a handle according to various embodiments of the present disclosure.
Figure 10:
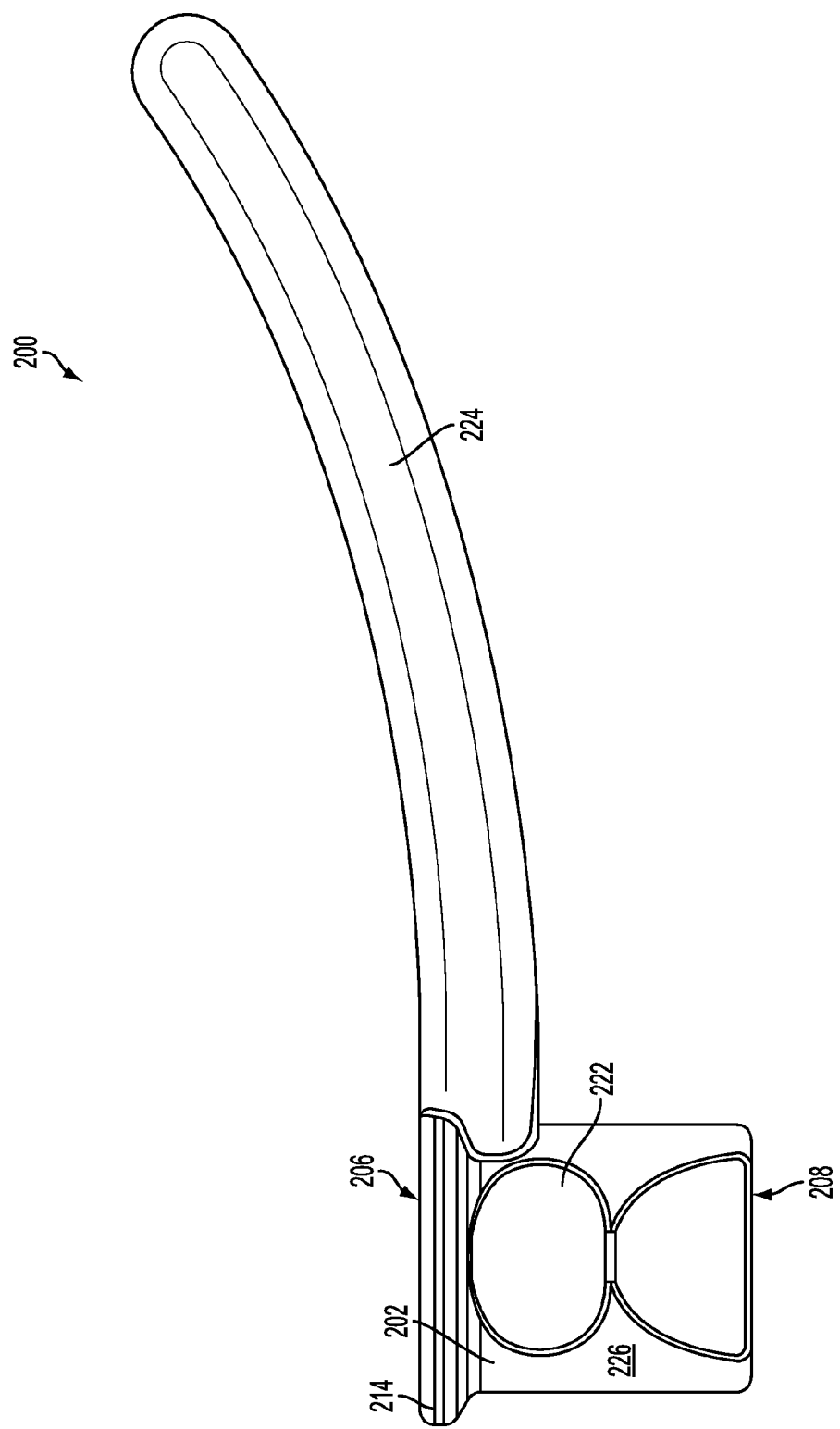
FIG. 10 is an elevational view of one embodiment of the probe guide of FIG. 9.

Referring now to FIGS. 9 and 10, in one embodiment, a probe guide 200 can comprise a body portion 202 and a handle 224, for example. In various embodiments, the body portion 202 can comprise a plurality of passages, such as first passage 204a, second passage 204b, third passage 204b and fourth passage 204d; the passages 204a, 204b, 204c, 204d can extend through the body portion 202 from a first surface 206 to a second or tissue contacting surface 208, for example. The first passage 204a can be structured to axially restrain the first electrode 824a, for example, the second passage 204b can be structured to axially restrain the second electrode 824b, for example, the third passage 204c can be structured to axially restrain the third electrode 824c, for example, and the fourth passage 204d can be structured to axially restrain the fourth electrode 824d, for example. Similar to embodiments described herein, the passages 204a, 204b, 204c, 204d through the body portion 102 of the probe guide 100 can be parallel and/or substantially parallel and can be separated by a predetermined distance or distances of approximately 1.0 cm to 2.5 cm, for example. Furthermore, as described herein, an energy source 14 (FIG. 3) can be structured to operably energize at least one of the electrodes 824a, 824b, 824c, 824d such that the electrodes 824a, 824b, 824c, 824d conduct current therebetween.

In the embodiments illustrated in FIGS. 9 and 10, the body portion 202 can comprise an outer surface 226. In at least one embodiment, the outer surface 226 can comprise a contour 222 directed into the body portion 202, for example. In various embodiments, the outer surface 226 can comprise a plurality of contours 222. The body portion 202 can comprise a first contour 222 on a first side of the body portion 202, for example, and a second contour 222 on a second side of the body portion 202, for example. In various embodiments, the contour 222 on the first side of the body 202 can extend into the body 202 towards the contour 222 on the second side of the body portion 202, for example. In some embodiments, the probe guide 200 can also comprise a rim 214 and/or a base, such as rim 114 and base 110, described in herein. In various embodiments, the probe guide 200 can comprise a handle 224 extending from the body portion 202 of the probe guide 200. The handle 224 can comprise a substantially accurate profile, for example, a substantially flat profile, for example, or a combination thereof. In various embodiments, the handle 224 can comprise an ergonomic shape or grip.

Similar to other embodiments described herein, the probe guide 200, illustrated in FIGS. 9 and 10, for example, can be positioned in or proximal to the tissue treatment region. In various embodiments, the tissue contacting surface 208 can be positioned adjacent to, against, and/or abutting tissue in the tissue treatment region, for example. In various embodiments, the handle 224 and/or the contours 222 can facilitate accurate positioning of the body portion 202 of the probe guide 200 relative to a target treatment zone in the tissue treatment region. Similar to other embodiments, once the probe guide 200 is positioned relative to the tissue treatment region, the first electrode 824a can be advanced through the first passage 204a, for example, the second electrode 824b can be advanced through the second passage 204b, for example, the third electrode 824c can be advanced through the third passage 204c, for example, and/or the fourth electrode 824d can be advanced though the fourth passage 204d, for example. In various embodiments, the handle 224 and/or contours 222 can facilitate steadiness of the body portion 202 of the probe guide 200 relative to the tissue treatment region as the electrodes 824a, 824b, 824c and/or 824d are advanced through the passages 204a, 204b, 204c and/or 204d of the body portion 202.

Figure 11:
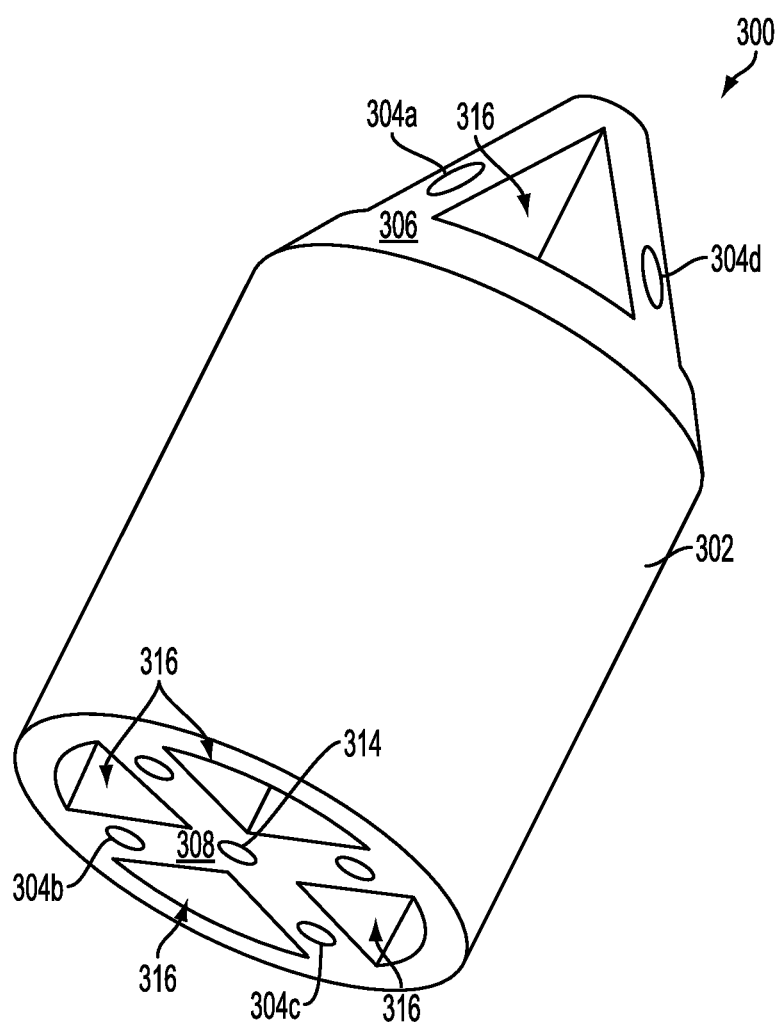
FIG. 11 is a perspective view of a probe guide according to various embodiments of the present disclosure.

In various embodiments, referring primarily to FIG. 11, in one embodiment, a probe guide 300 can comprise a substantially cylindrical body 302 having a first or top surface 306 and a second or bottom surface 308. In various embodiments, at least one surface 306, 308 can comprise a substantially conical shape. Referring to FIG. 11, the first surface 306 can comprise a substantially conical shape, for example. The probe guide 300 can also comprise a plurality of passages 304a, 304b, 304c, 304d configured to axially restrain the electrodes 824a, 824b, 824c, 824d, similar to other embodiments described herein. In various embodiments, the cylindrical body 302 can comprise a plurality of openings or channels 316 therethrough. For example, four openings 316 can extend from the first, conical surface 306 through the body 302 to the second surface 308, for example. The openings 316 can provide a channel for heat and/steam to escape or vent from the tissue treatment region, for example, when current is conducted between the electrodes 824a, 824b, 824c, 824d, as described herein. In various embodiments, the guide 300 can also comprise a central bore 314. In some embodiments, the central bore 314 can provide the clinician with a central reference point for positioning the probe guide 300 and the electrode probes 824a, 824b, 824c and/or 824d relative to a target treatment zone in a tissue treatment region. For example, the central bore 314 can be positioned at or near a central position in the target treatment zone. The electrodes 824a, 824b, 824c, and/or 824d can be positioned within the passages 204a, 204b, 204c, and/or 204d of the probe guide 400 such that the electrodes 824a, 824b, 824c, and/or 824d surround the central position in the target treatment zone, for example.

Figure 12:
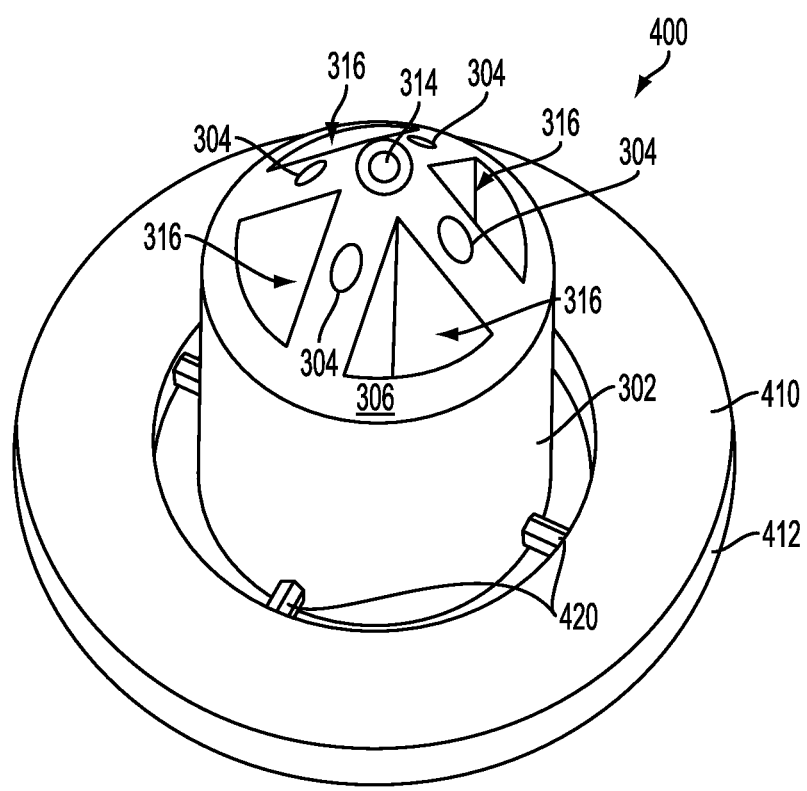
FIG. 12 is a perspective view of a probe guide having a base according to various embodiments of the present disclosure.
Figure 13:
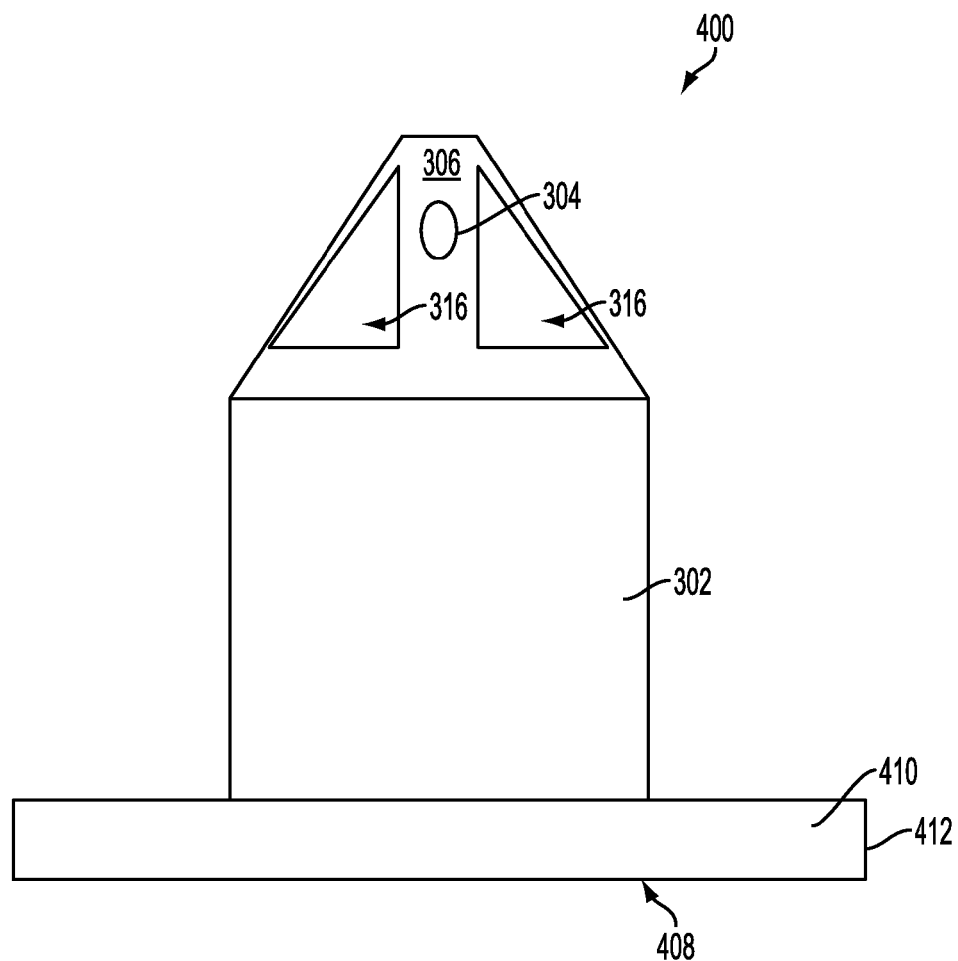
FIG. 13 is an elevational view of one embodiment of the probe guide of FIG. 12.
Figure 14:
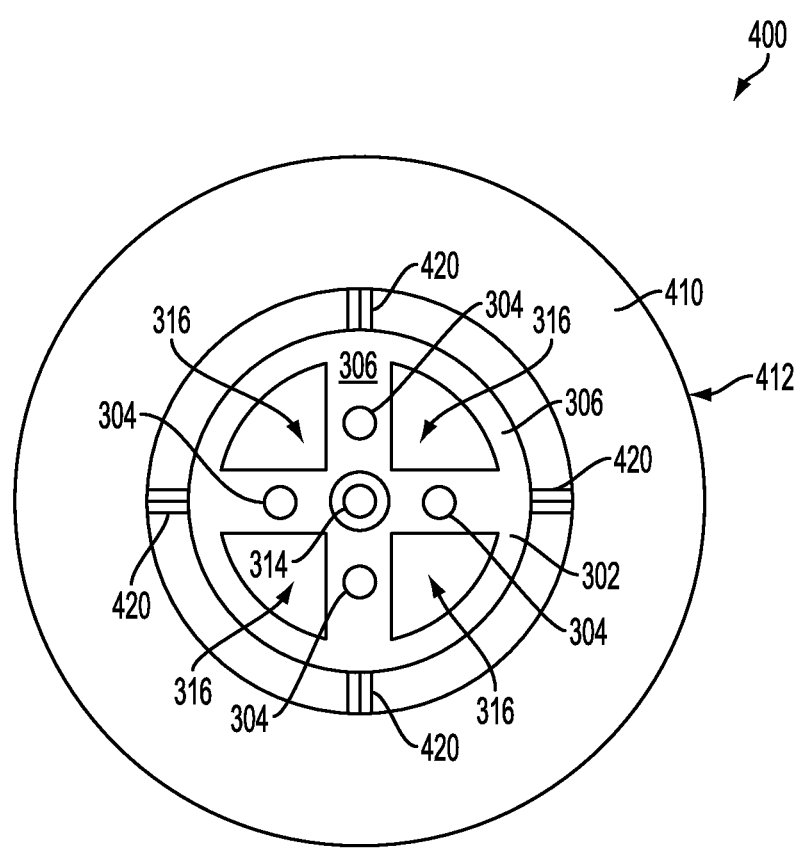
FIG. 14 is a plan view of one embodiment of the probe guide of FIG. 12.

Referring now to FIGS. 12-14, in one embodiment, a probe guide 400 can comprise the cylindrical body 302 described herein. In various embodiments, the probe guide 400 can also comprise a base 410. The base 410 can extend from the second or bottom surface 308 of the cylindrical body 302, for example. In some embodiments, the base 410 can be connected to the body portion 302 by flanges or ribs 420. In various embodiments, at least two ribs 420 can extend from the cylindrical body 302 to the base 410, for example. In other embodiments, at least four ribs 420 can extend between the base 410 and the cylindrical body 302. In such embodiments, a space or gap can be positioned between portions of the cylindrical body 302 and portions of the base 410, for example. In other embodiments, the base 410 can peripherally extend from the cylindrical body 302 such that no spaces or gaps are positioned between the cylindrical body 302 and the base 410. In various embodiments, the base 410 can comprise a tissue contacting surface 408 (FIG. 13) that is structured to operably abut tissue when the electrodes 824a, 824b, 824c, 824d are positioned relative to a tissue treatment region, as described herein. In at least one embodiment, the tissue contacting surface 408 of the base 410 can help to steady the cylindrical body 302 relative to the tissue treatment region.

Figure 15:
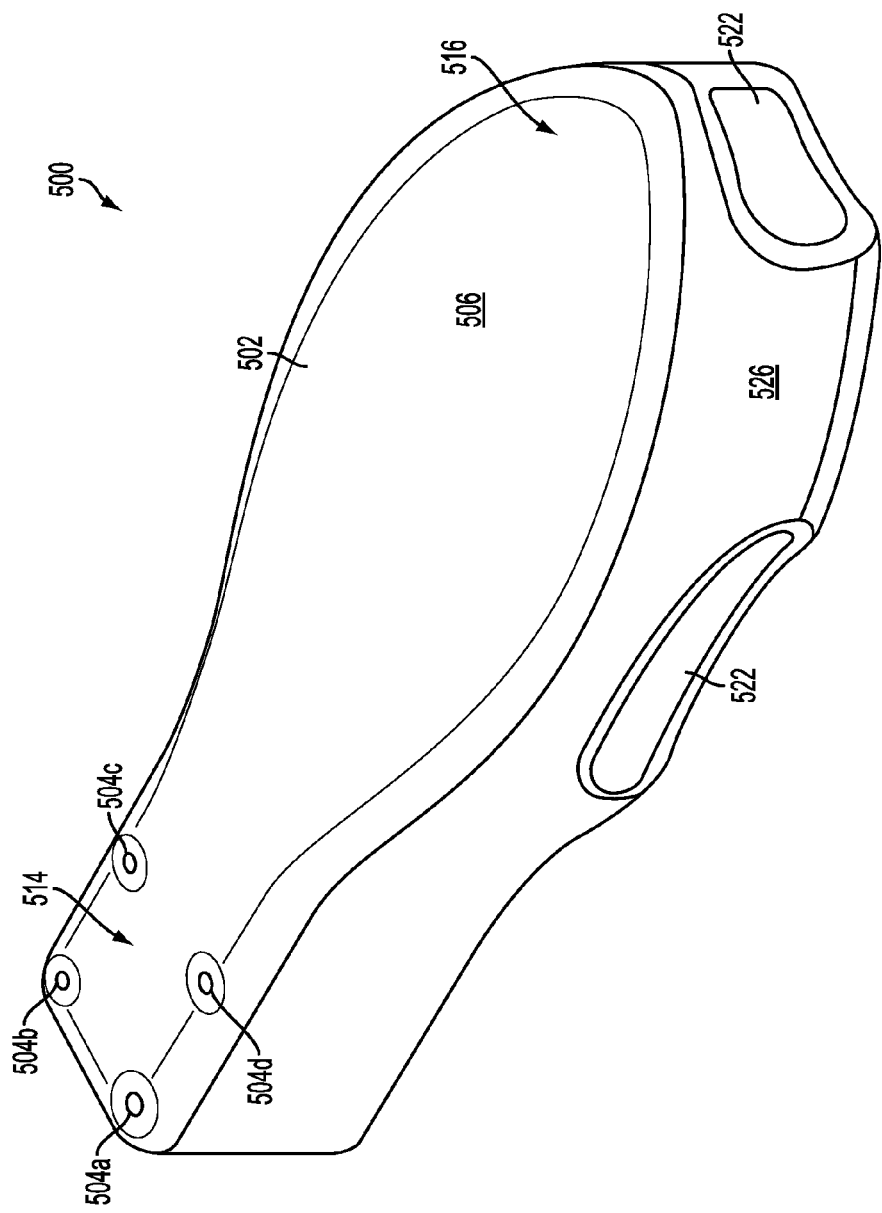
FIG. 15 is a perspective view of a probe guide according to various embodiments of the present disclosure.

Referring to FIG. 15, in one embodiment, a probe guide 500 can comprise a body portion 502 and, in various embodiments, a plurality of passages can extend through the body portion 502. The passages can extend from a first or top surface 506 to a second or tissue contacting surface (not shown), for example. In some embodiments, two passages, such as a first passage 504a and a second passage 504b, can extend through the body portion 502. In other embodiments, at least four passages, such as passages 504a, 504b, 504c, 504d, can extend through the body portion 502 from the first surface 506 to the second surface. The passages 504a, 504b, 504c, 504d can be configured to axially restrain the electrodes 824a, 824b, 824c, 824d, for example, and/or guide the electrodes 824a, 824b, 824c, 824d in parallel or substantially parallel alignment, for example, similar to other embodiments described herein.

In various embodiments, the body portion 502 can comprise an outer surface 526. In some embodiments, at least one contour 522 can extend into the body portion 502 from the outer surface 526, for example. The contour 522 can be structured to provide a grip and holding means for the clinician to engage when positioning and/or steadying the probe guide 500 relative to the tissue treatment region. In various embodiments, a contour 522 can be positioned on a first side of the body 502 and another contour 522 can be positioned on a second side of the body portion 502, for example. Referring still to FIG. 15, in various embodiments, the passages 504a, 504b, 504c, 504d through the body portion 502 can be clustered together at or near a first end 514 of the body portion 502. In such embodiments, a section of the body portion 502 can extend away from the passages 504a, 504b, 504c, 504d and towards a second end 516 of the body portion 502. In some embodiments, a significant section of the body 502 can extend away from the passages 504a, 504b, 504c, 504d and towards the second end 516. In various embodiments, the body portion 502 at the second end 516 can provide a significant tissue contacting surface (not shown) to position against tissue in the tissue treatment region, for example. In at least one embodiment, at least one contour 522 in the outer surface 526 of the body portion 502 can be position at or near the second end 516 and around the tissue contacting surface of the body 502. The extended tissue contacting surface and/or contours 522 can help the operator position and/or steady the probe guide 500 relative to the tissue treatment region.

Figure 16:
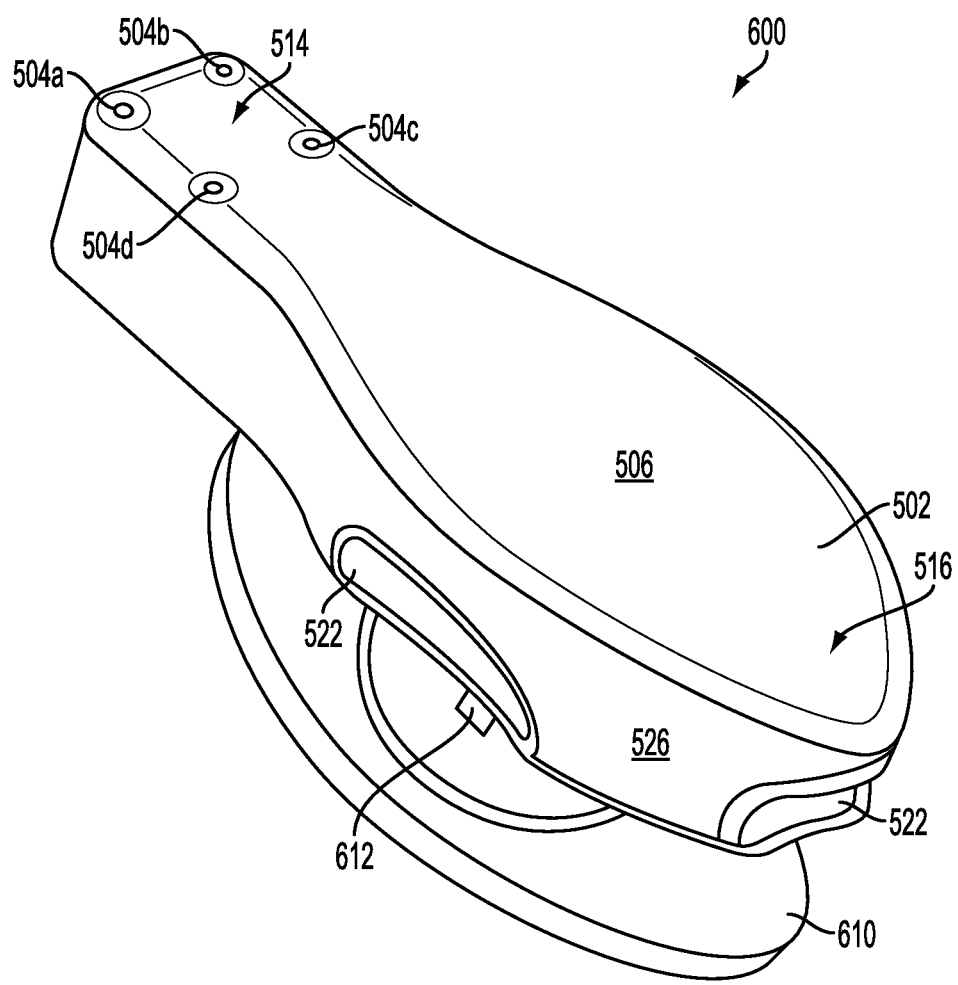
FIG. 16 is a perspective view of a probe guide having a base according to various embodiments of the present disclosure.

Referring now to FIG. 16, in one embodiment, a probe guide 600 can comprise the body portion 502 as described herein. In the embodiments illustrated in FIG. 16, the probe guide 600 can also comprise a base 610 that extends from the body portion 502, for example. In various embodiments, the base 610 can be pivotally connected to the body portion 502. The base 610 can be pivotally connected to the body portion 502 by a pivot joint, pivot pin, and/or pivot shaft, for example. In various embodiments, a pivot shaft such as pivot shaft 612 can extend between the base 610 and the body portion 502 to enable pivoting of the body portion 502 relative to the base 610. In such embodiments, a tissue contacting surface (not shown) on the base 610 can be positioned adjacent to, abutting and/or against tissue in the tissue treatment region; furthermore, the body portion 502, including the passages 504a, 504b, 504c, 504d therethrough, can pivot relative to the base 610.

Similar to other embodiments described herein, the probe guide 600 can be positioned relative to the tissue treatment region and the first electrode 824a can be axially advanced through the first passage 504a, for example. In various embodiments, the contours 522 can help the operator engage or grip the body portion 602 of the probe guide 600 and position the body portion 602 relative to the first target treatment zone in the tissue treatment region. As described herein, once the probe guide 600 and the first electrode 824a are positioned relative to the tissue treatment region, the second electrode 824b can be advanced through the second passage 504b, for example, the third electrode 824c can be advanced through the third passage 504c, for example, and/or the fourth electrode 824d can be advanced though the fourth passage 504d, for example. The electrodes 824a, 824b, 824c, 824d can be positioned relative to the tissue treatment region such that a current conducted therebetween treats tissue in a first target zone.

In various embodiments, the electrodes 824a, 824b, 824c, 824d can be withdrawn from the body portion 502 of the probe guide 600 and from the first target treatment zone. The body portion 502 of the probe guide 600 and the passages 504a, 504b, 504c, 504d therethrough can pivot on the pivot shaft 612 relative to the base 610. In such embodiments, the tissue contacting surface on the base 610 can remain stationary or significantly stationary relative to the tissue treatment region. In other embodiments, referring again to the embodiment illustrated in FIG. 15, the tissue contacting surface on the body portion 502 can be lifted and/or pivoted relative to the tissue treatment region, for example. In various embodiments, once the body portion 502 of the probe guide 600 has pivoted to a new position, the electrodes 824a, 824b, 824c, 824d can be axially advanced through the passages 504a, 504b, 504c, 504d, respectively, as described herein. In various embodiments, the electrodes 824a, 824b, 824c, 824d can be positioned relative to the tissue treatment region such that a current conducted therebetween treats tissue in a second target treatment zone. In at least one embodiment, the electrodes 824a, 824b, 824c, 824d can be re-withdrawn, the body portion 502 can pivot, and the electrodes 824a, 824b, 824c, 824d can be re-advanced to treat tissue in another target treatment zone. In some embodiments, the process can be repeated until tissue throughout the tissue treatment region has been treated by the electrical ablation device 800 (FIG. 3), for example.

Figure 17:
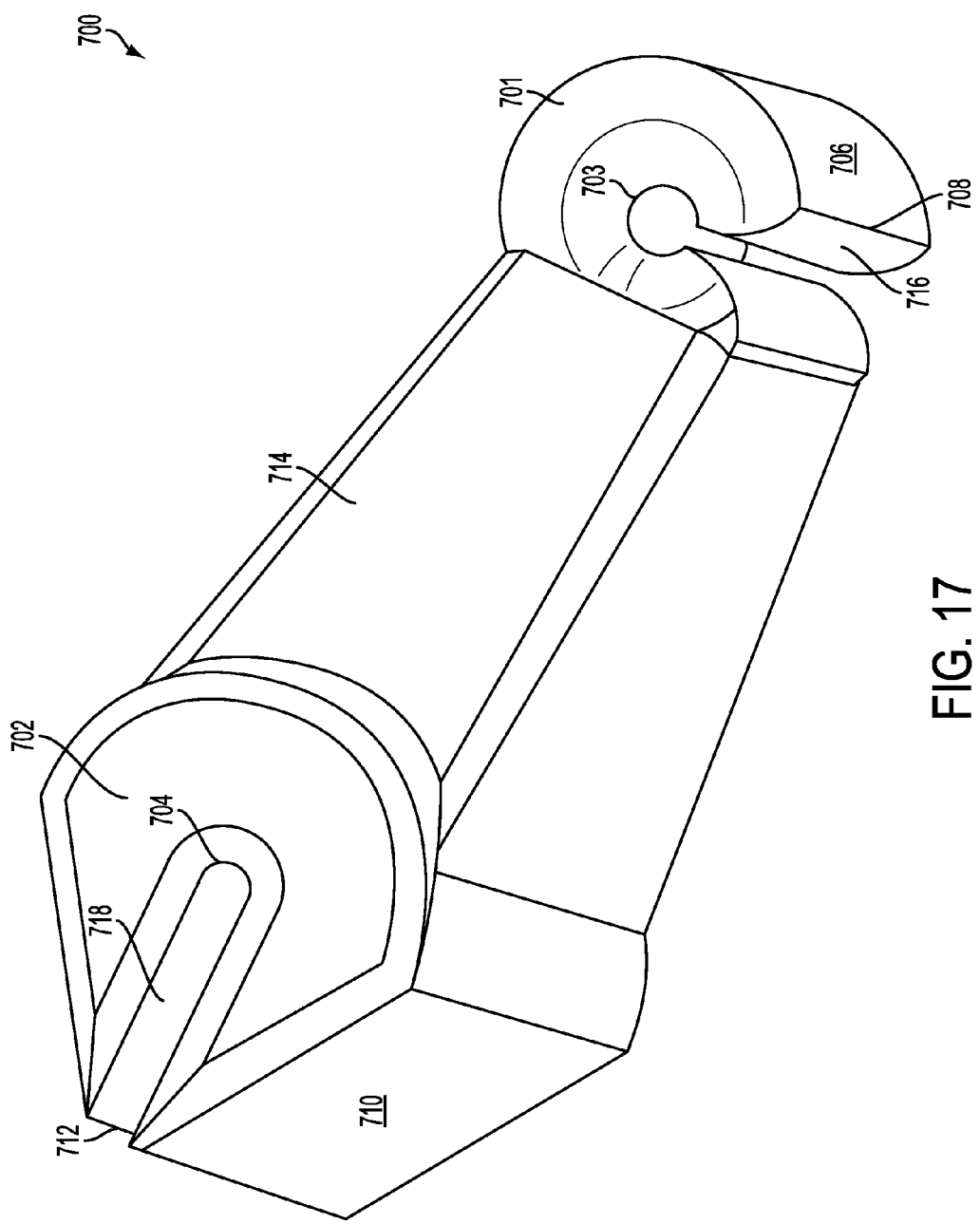
FIG. 17 is a perspective view of a probe guide having orthogonal outlets according to various embodiments of the present disclosure.

Referring to FIG. 17, in one embodiment, a probe guide 700 can comprise a first body portion 701 and a second body portion 702. In various embodiments, a first passage 703 can extend through the first body portion, for example, and a second passage 704 can extend through the second body portion 702, for example. In various embodiments, the first passage 703 can be structured to axially restrain the first electrode 24a (FIG. 1), for example, and the second passage 704 can be structured to axially restrain the second electrode 24b, for example. In some embodiments, the distal end of the first electrode 24a can be spaced a predetermined distance from the distal end of the second electrode 24b when the first electrode 24a is axially restrained in the first passage 703 and the second electrode 24b is axially restrained in the second passage 704. Further, the predetermined distance between the distal ends of the first and second electrodes 24a, 24b can correspond to a treatment distance in the tissue treatment region. The distal ends of the first and second electrodes 24a, 24b can be operatively structured to conduct currents therebetween when at least one of the first and second electrodes 24a, 24b is energized by an energy source 14 (FIG. 1), for example.

In the embodiments illustrated in FIG. 17, a connecting portion or flange 714 can connect the first body portion 701 and the second body portion 702. The length of the connecting portion 714 can affect the predetermined distance between the first and second passages 703, 704, for example. In various embodiments, the first and/or second body portions 701, 702 can comprise as substantially cylindrical shape. In at least one embodiment, the first body portion 701 can comprise a semi-cylindrical shape and a triangular shape, for example. The height of the first body portion 701 can be greater than, less than, or substantially equal to the height of the second body portion 702. In various embodiments, the connecting portion 714 can comprise a sloped or angled surface that connects the first and second body portions 701, 702.

In various embodiments, the first body portion 701 can comprise a first slot 716 extending from the first passage 703 to an outer surface 706 of the first body portion 701. The first slot 716 can reach the outer surface 706 at a first outlet 708, for example. In various embodiments, the first electrode 24a (FIG. 1) can be axially restrained in the first passage 703. Further, the first electrode 24a can be removed from the first passage 703 through the first slot 716 in the first body portion 701. In various embodiments, the first passage 703 can comprise a first width and the first slot 716 can comprise a minimum width. In various embodiments, the minimum width of the first slot 716 can substantially equal the first width of the first passage 703. In such embodiments, the first electrode 24a can easily and smoothly move in and out of the first passage 703 through the first slot 716. In other embodiments, the minimum width of the first slot 716 can be less than or greater than the first width of the first passage 703. In embodiments where the minimum width of the first slot 716 is less than the first width of the first passage 703, the first slot 716 can restrict movement of the first electrode 24a in and/or out of the first passage 703. In various embodiments, the first electrode 24a must be aligned with the first slot 716 and pulled through the first slot 716 to move the first electrode 24a into and/or out of first passage 703 of the first body portion 701. In some embodiments, a force must be applied to move the first electrode 24a in and/or out of the first passage 703.

Similarly, in various embodiments, the second body portion 702 can comprise a second slot 718 extending from the second passage 704 to an outer surface 710 of the second body portion 702. The second slot 718 can reach the outer surface 710 at a second outlet 712, for example. In various embodiments, the second electrode 24b (FIG. 1) can be axially restrained in the second passage 704. Further, the second electrode 24b can be removed from the second passage 704 through the second slot 718 in the second body portion 702. In various embodiments, the second passage 704 can comprise a second width and the second slot 718 can comprise a minimum width. In various embodiments, the minimum width of the second slot 718 can substantially equal the second width of the second passage 704. In such embodiments, the second electrode 24b can easily and smoothly move in and out of the second passage 704 through the second slot 718. In other embodiments, the minimum width of the second slot 718 can be less than or greater than the second width of the second passage 704. In embodiments where the minimum width of the second slot 718 is less than the second width of the second passage 707, the second slot 718 can restrict movement of the second electrode 24b in and/or out of the second passage 704. In various embodiments, the second electrode 24b must be aligned with the second slot 718 and pulled through the second slot 718 to move the second electrode 24b into and/or out of second passage 704 of the second body portion 702. In some embodiments, a force must be applied to move the second electrode 24b in and/or out of the second passage 704.

In various embodiments, the first slot 716 can be substantially orthogonal to the second slot 718, for example. In other embodiments, the slots 716, 718 can be substantially aligned and/or angularly offset from each other by less than or more than approximately 90 degrees, for example. In various embodiments, at least one of the first and second slots 716, 718 can be substantially flared. The first slot 716 can be flared such that the first slot 716 widens as the first slot 716 extends from the first passage 703 to the outer surface 706, for example. Additionally or alternatively, the second slot 718 can be flared such that the second slot 718 widens as the second slot 718 extends from the second passage 704 to the outer surface 710, for example. In various embodiments, an orthogonal or angled arrangement of the entry outlets 708, 712 can facilitate entry and/or repositioning of the electrodes 24a, 24b, relative to the tissue treatment region.

Similar to the embodiments described herein in connection with FIGS. 6-16, for example, the probe guide 700 can be positioned relative to this tissue treatment region and the first and second electrodes 24a, 24b can be axially advanced through the first and second passages 703, 704, respectively. The first and second electrodes 24a, 24b can be positioned in the tissue treatment region and the first and second passages 703, 704 can maintain parallel alignment of the first and second electrodes 24a, 24b, for example, and/or maintain a predetermined treatment distance. As described herein, current can be conducted between the first and second electrodes 24a, 24b to treat tissue in the target treatment zone positioned therebetween. In various embodiments, at least one of the first and second electrodes 24a, 24b can be withdrawn from its respective passage 703, 704 and moved to another position. For example, the second electrode 24b can be removed from the second passage 704 through the second slot 718, for example. The second body portion 702 can then be pivoted relative to the first body portion 701 before the second electrode 24b is axially advanced through the second passage 704 and into the tissue treatment region, for example. In various embodiments, the minimum width of the first slot 716 can prevent the first electrode 24a from moving out of the first passage 703 as the second body portion 702 pivots relative thereto.

In various embodiments, the first and second body portions 701, 702 of the probe guide 700 can be positioned relative to the tissue treatment region before the first and/or second electrodes 24a, 24b are positioned relative to the tissue treatment region. For example, when the probe guide 700 is positioned relative to a tissue treatment region, the first electrode 24a can be axially advanced through the first passage 703 or moved through the first slot 706 into the first passage 703, for example. In various embodiments, the flanged shape of the first slot 716 and facilitate entry of the first electrode through the minimum width of the first slot 716 and into the first passage 703, for example. The second electrode 24b can then be drawn through the second slot 718 and into the second passage 704, for example.

Figure 18:
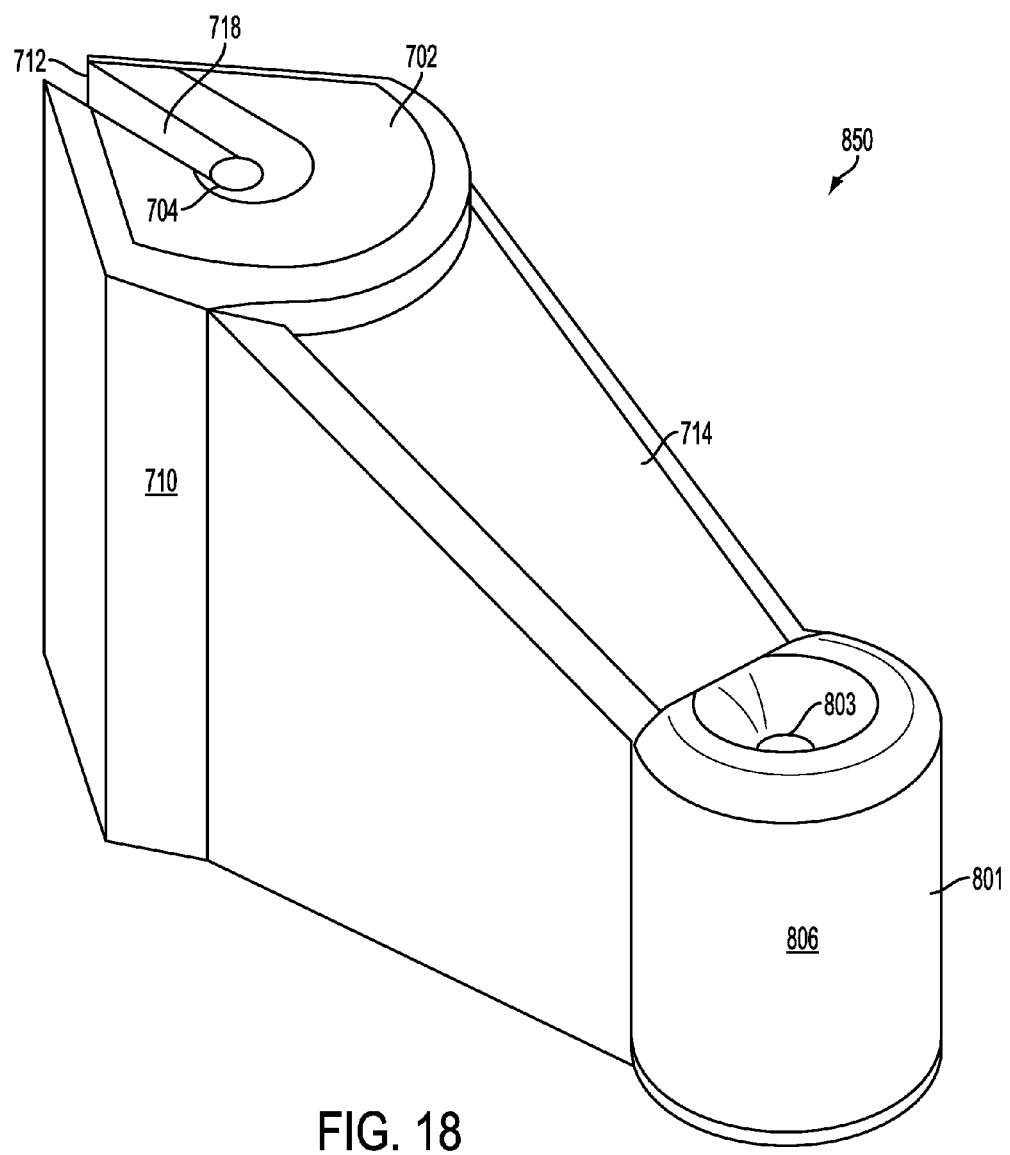
FIG. 18 is a perspective view of a probe guide having an outlet according to various embodiments of the present disclosure.

Referring to FIG. 18, a probe guide 850 can comprise the second body portion 702 and connecting flange 714 as described herein. Further, in various embodiments, the probe guide 850 can comprise a first body portion 801. The first body portion 801 can comprise a first passage 803 structured to axially restrain a first electrode, for example. The first passage 803 need not comprise a slot and/or outlet to an outer surface 806 of the first body portion 800, for example. In such embodiments, similar to the embodiments described herein, once the first electrode 24a and the first body portion 801 are positioned relative to the tissue treatment region, the second body portion 702 can be pivoted relative to the first body portion 801 such that the passages 803, 704 are appropriately positioned relative to the tissue treatment region. In various embodiments, the second electrode can be axially advanced through the second passage 704 and/or laterally advanced through the second slot 718 and current can be conducted through the distal ends of the first and second electrodes 24a, 24b to treat tissue therebetween. In various embodiments, the second electrode can then be axially withdrawn through the second passage 704 and/or laterally withdrawn through the second slot 718, for example. In some embodiments, the second body portion 702 can then be pivoted relative to the first body portion 801 before the second electrode 24b is re-advanced through the second body portion 702 to treat another tissue zone in the tissue treatment region.

Figure 19:
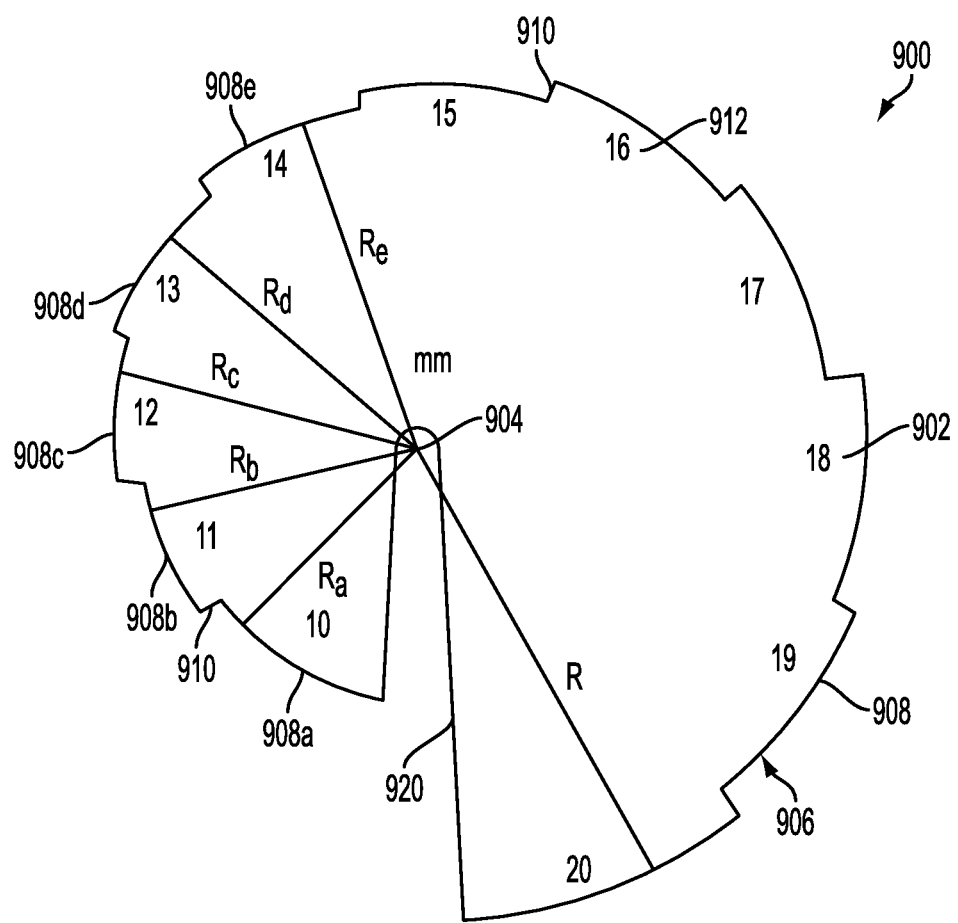
FIG. 19 is a plan view of a probe guide having indicia of measurement according to various embodiments of the present disclosure.

Referring to FIG. 19, in one embodiment, a probe guide 900 can comprise a body 902 having an outer perimeter 906. The probe guide 900 can comprise a substantially flat disc and/or may comprise a substantial height. In various embodiments, the outer perimeter 906 can comprise a plurality of contours 908. The perimeter 906 can comprise a first contour 908a, a second contour 908b, a third contour 908c, a fourth contour 908d, and a fifth contour 908e, for example. In various embodiments, the body 902 can comprise a passage 904 structured to axially restrain the first electrode 24a. A groove 920 can extend between the passage 904 and the outer perimeter 906 of the body 902, for example. In various embodiments, the groove 920 can be structured to permit movement of the first electrode 24a therethrough. In various embodiments, a radius R can extend from the passage 904 to the outer perimeter 906 of the body 902. In some embodiments, the radius R can vary at each contour 908 around the outer perimeter 906 of the body 902. For example, a first radius $R_a$ can extend between the passage 904 and the first contour 908a, for example, a second radius $R_b$ can extend from the passage 904 to the second contour 908b, for example, and a third radius $R_b$ can extend from the passage 904 to the third contour 908c, for example.

In various embodiments, as described herein, a second electrode 24b can be positioned along a contour 908 of the perimeter 906. Furthermore, in various embodiments, a distal end of the first electrode 24a can be spaced from a distal end of the second electrode 24b by the variable radius R when the first electrode 24a is axially restrained in the passage 904 and the second electrode 24b is positioned along a contour 908 of the outer perimeter 906, for example. In various embodiments, the probe guide 900 can hold the electrodes 24a, 24b in axial alignment with each other when the first electrode 24a is axially restrained in the passage 904 and the second electrode 24b is positioned along a contour 908. Further, in various embodiments, the radius R can correspond to a treatment distance in the tissue treatment region. Furthermore, as described herein, the distal ends of the first and second electrodes 24a, 24b can be operatively structured to conduct current therebetween when at least one of the first and second electrodes 24a, 24b is energized by an energy source 14 (FIG. 1).

In various embodiments, the body 902 can also comprise a plurality of traversing edges 910. In various embodiments, a traversing edge 910 can be positioned between two adjacent contours 908 around the perimeter 906 of the body 902. A traversing edge 910 can be positioned between the first and second contours 908a, 908b, for example. In various embodiments, the traversing edge 910 can comprise a substantially straight edge. In other embodiments, the traversing edge 910 can comprise a curve or contour. In some embodiments, a curved traversing edge can correspond with the perimeter of the second electrode 24b such that the curved traversing edge can receive and hold the second electrode 24b in position along a contour 908 of the outer perimeter 906. Furthermore referring still to FIG. 19, the probe guide 900 can comprise indicia of measurements 612 that enable the operator to determine the treatment distance between the first electrode and the second electrode. For example, the electrode probe guide 900 can comprise length measurement such as centimeters, millimeters and/or inches to indicate the length of the radius around the perimeter 906 of the body 902. The first radius $R_a$ can correspond to 10 mm, for example, the second radius $R_b$ can correspond to 11 mm, for example, the third radius $R_c$ can correspond to 12 mm, for example, the fourth radius $R_d$ can correspond to 13 mm, for example, and the fifth radius $R_e$ can correspond to 14 mm, for example.

Similar to other embodiments described herein, the first electrode 24a can be positioned within the passage 904 of the probe guide 900. The first electrode 24a can laterally traverse the groove 920, for example, and/or axially translate through the passage 904, for example, when the probe guide 900 is positioned relative to the tissue treatment region. In various embodiments, once the probe guide 900 and the first electrode 24a are positioned relative to the tissue treatment region, the second electrode 24b can be positioned along a contour 908 such that the radius R corresponds with the preferred tissue treatment distance. In various embodiments, the electrical ablation device 800 can be used with the probe guide 900. In such embodiments, the passage 804 can axially restrain the first electrode 824a and the second, third and/or fourth electrodes 824b, 824c, 824d can be positioned along a contour of the probe guide 900, for example. The electrodes 824a, 824b, 824c, 824d can be positioned relative to the tissue treatment region such that a current conducted therebetween treats tissue in the target treatment zone of the tissue treatment region.

Figure 20:
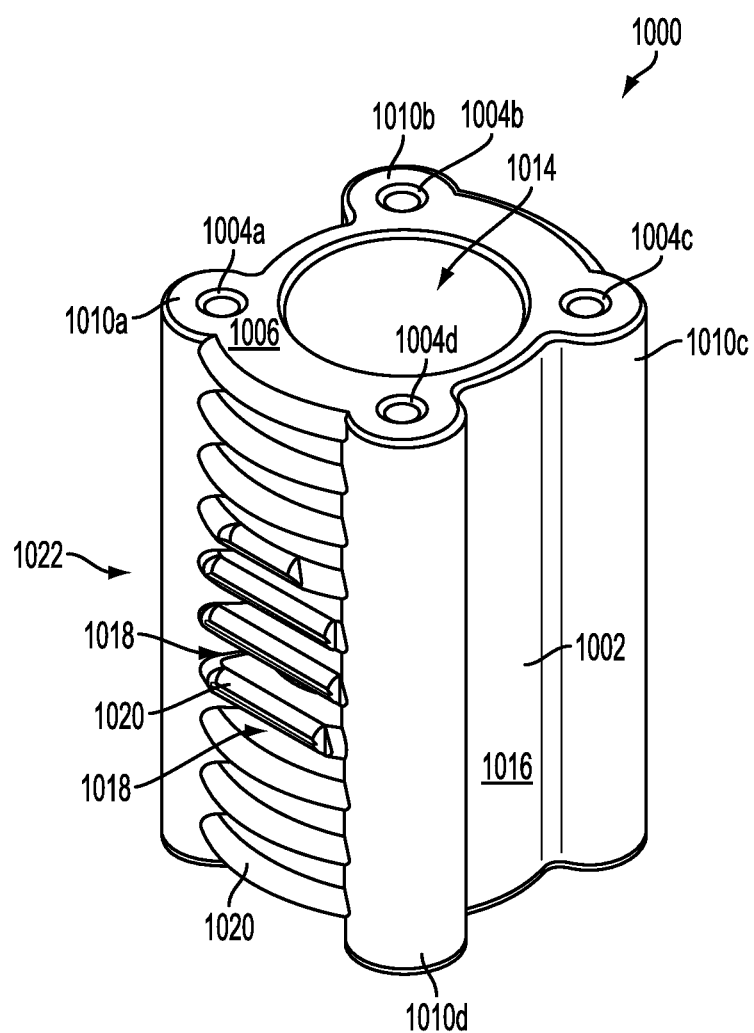
FIG. 20 is a perspective view of a probe guide comprising a bore, and a plurality of ribs and vents according to various embodiments of the present disclosure.
Figure 21:
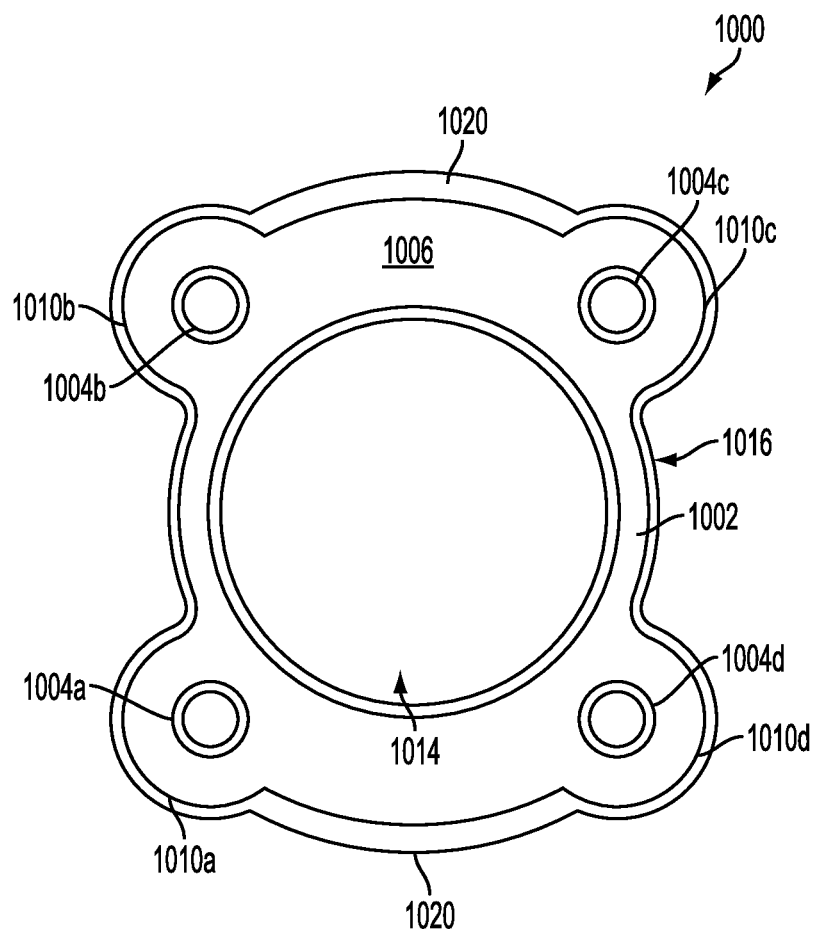
FIG. 21 is a plan view of one embodiment of the probe guide of FIG. 20.

Referring now to FIGS. 20 and 21, a probe guide 1000 can comprise a body portion 1002 and a bore 1014 extending therethrough. In various embodiments, the body portion 1002 can comprise a top surface 1006 and a bottom surface (not shown). The bore 1014 can extend from the top surface 1006 to the bottom surface, for example. In various embodiments, the body 1002 can comprise a plurality of enclosures. The body 1002 can have two enclosures 1010a, 1010c, for example, or four enclosures 1010a, 1010b, 1010c, 1010d, for example. The body portion 1002 can comprise a number of enclosures 1010 that equals the number of electrodes that the probe guide 1000 is structured to axially restrain, for example. In various embodiments, a passage 1004a, 1004b, 1004c, 1004d can extend through each enclosure 1010a, 1010b, 1010c, 1010d from the top surface 1006 to the bottom surface of the body portion 1002, for example. Similar to the other embodiments described herein, each passage 1004a, 1004b, 1004c, 1004d can be structured to axially restrain an electrode positioned therein. Further, the passages 1004a, 1004b, 1004c, 1004d can be substantially parallel such that the electrodes 824a, 824b, 824c, 824d (FIG. 3) are held in a parallel or substantially parallel arrangement by the probe guide 1000, for example. The enclosures 1010a, 1010b, 1010c, 1010d can be spaced equidistance or non-equidistance around the perimeter of the body portion 1002. In some embodiments, the enclosures 1010a, 1010b, 1010c, 1010d can be positioned around the perimeter of the body portion 1002 such that the passages 1004a, 1004b, 1004c, 1004d through the enclosures 1010a, 1010b, 1010c, 1010d, respectively, are positioned a predetermined distance or distances from each other.

In various embodiments, the probe guide 1000 can also comprise a plurality of ribs 1020. The ribs 1020 can extend between adjacent enclosures 1010 of the body 1002. In various embodiments, the ribs can laterally traverse between the first enclosure 1010a and the fourth enclosure 1010d, for example. The probe guide 1000 can also comprise an outer surface 1016. A plurality of vents 1018 can extend from the outer surface 1016 to the bore 1014 through the body portion 1002, for example. In various embodiments, the vents 1018 can be positioned between two adjacent ribs 1020 of the body portion 1002. In various embodiments, the probe guide 1000 can comprise four enclosures 1010 positioned around the perimeter of the body portion 1002, for example. In various embodiments, a first plurality of ribs and/or vents 1018 can be positioned between the first and fourth enclosures 1010a, 1010d of the body portion 1002. Furthermore, a second plurality of ribs 1020 and/or vents 1018 can be positioned between the second and third enclosures 1010b, 1010c of the body portion 1002, for example. Referring to FIG. 20, the body portion 1002 can also comprise a contour or grip 1022. In various embodiments, the body portion 1002 can comprise a plurality of contours or grips 1022 therein. In some embodiments, a first grip 1022 can be positioned on a first side of the body portion 1002 between the first and fourth enclosures 1010a, 1010d, for example, and a second grip 1022 can be positioned on a second side of the body portion 1002 between the second and third enclosures 1010b, 1010c, for example. In various embodiments, the contours 1022 can provide a grip for the operator to engage or hold when placing the probe guide 1000 relative to the tissue treatment region, for example.

Figure 22:
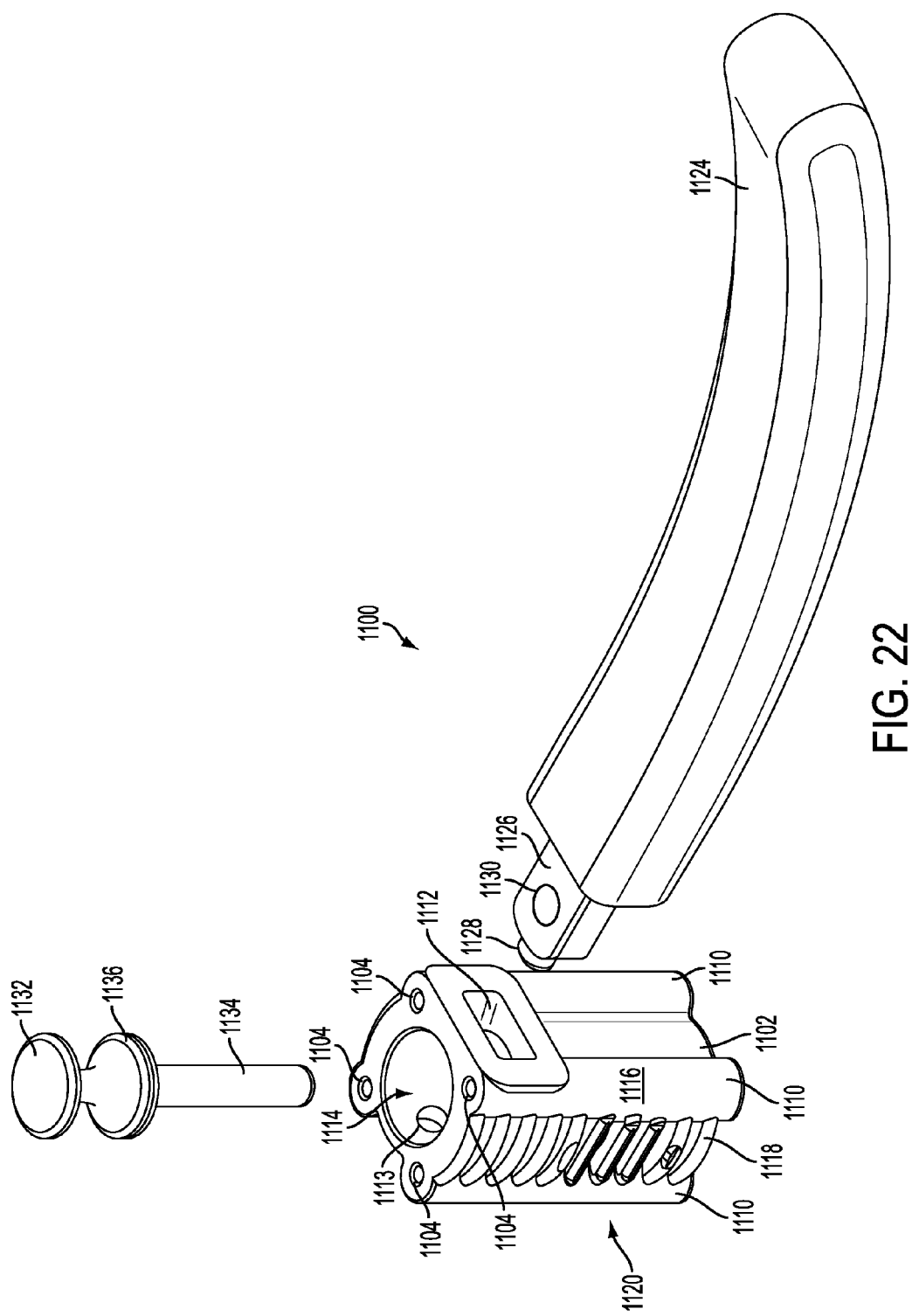
FIG. 22 is a perspective, exploded view of a probe guide having a removable handle according to various embodiments of the present disclosure.
Figure 23:
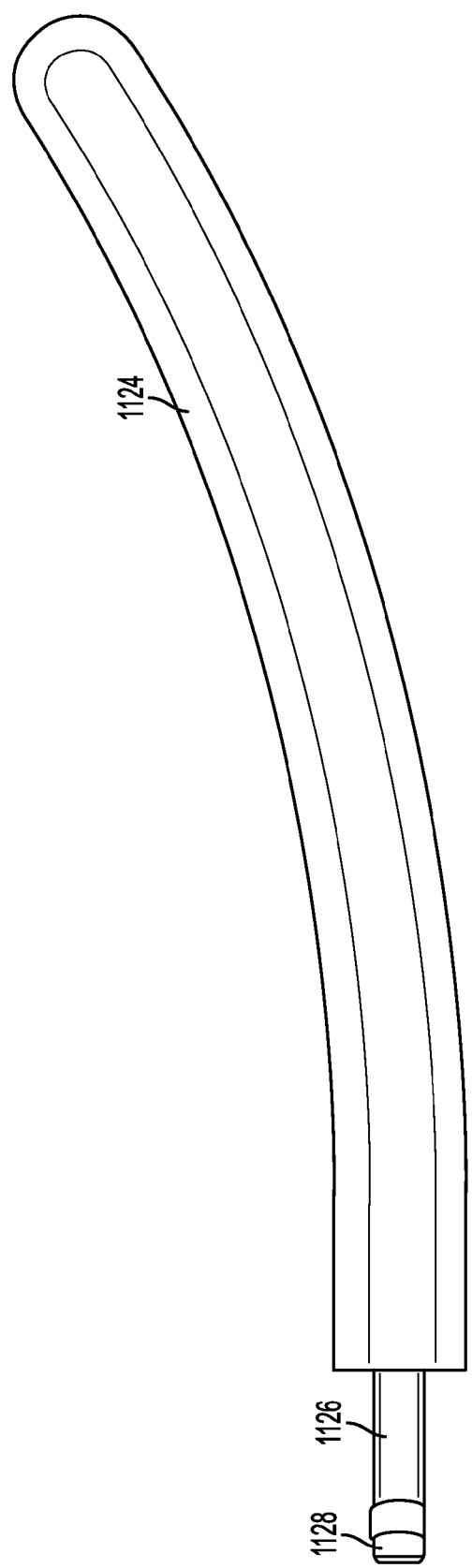
FIG. 23 is an elevational view of the removeable handle of one embodiment of the probe guide of FIG. 22.
Figure 24:
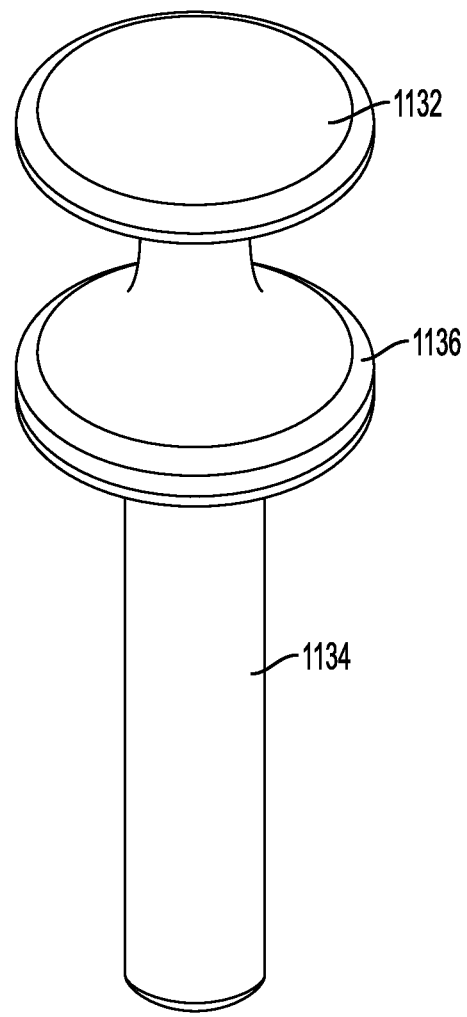
FIG. 24 is a perspective view of a locking element of one embodiment of the probe guide of FIG. 22.
Figure 25:
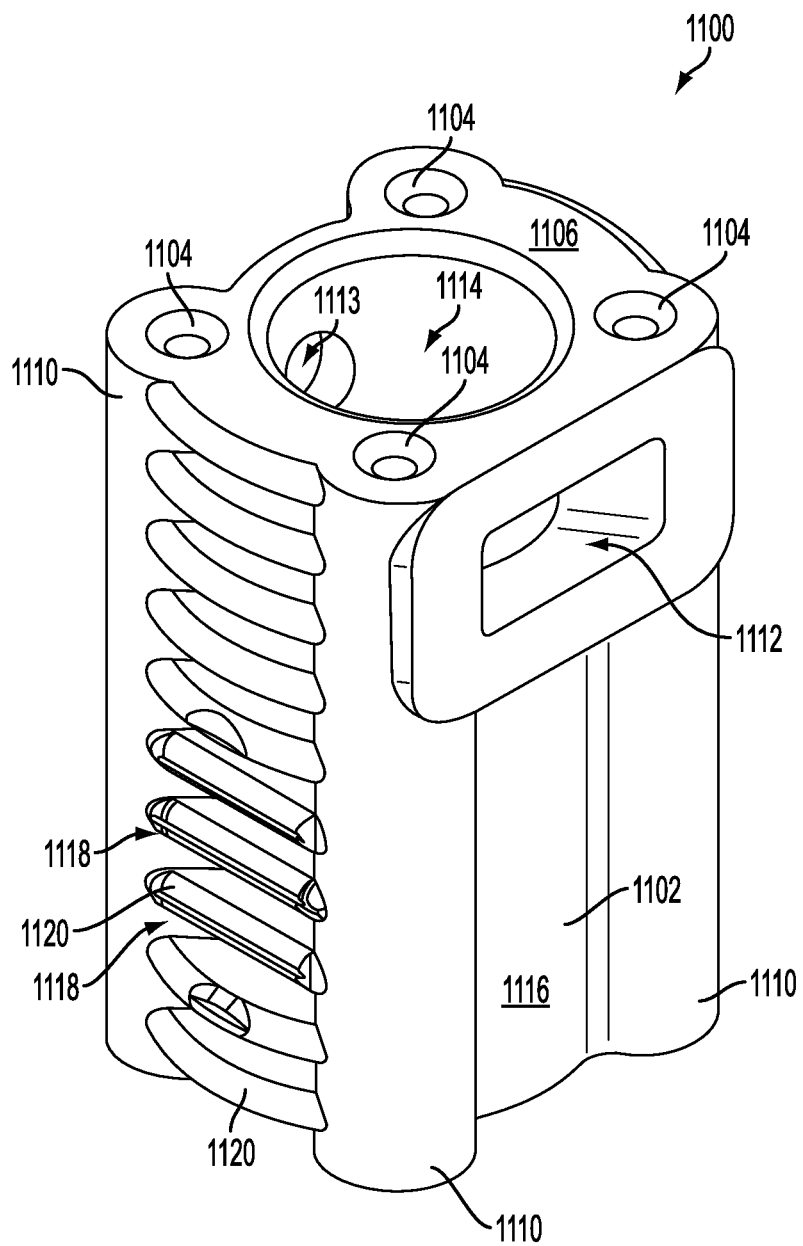
FIG. 25 is a perspective view of the body portion of one embodiment of the probe guide of FIG. 22.
Figure 26:
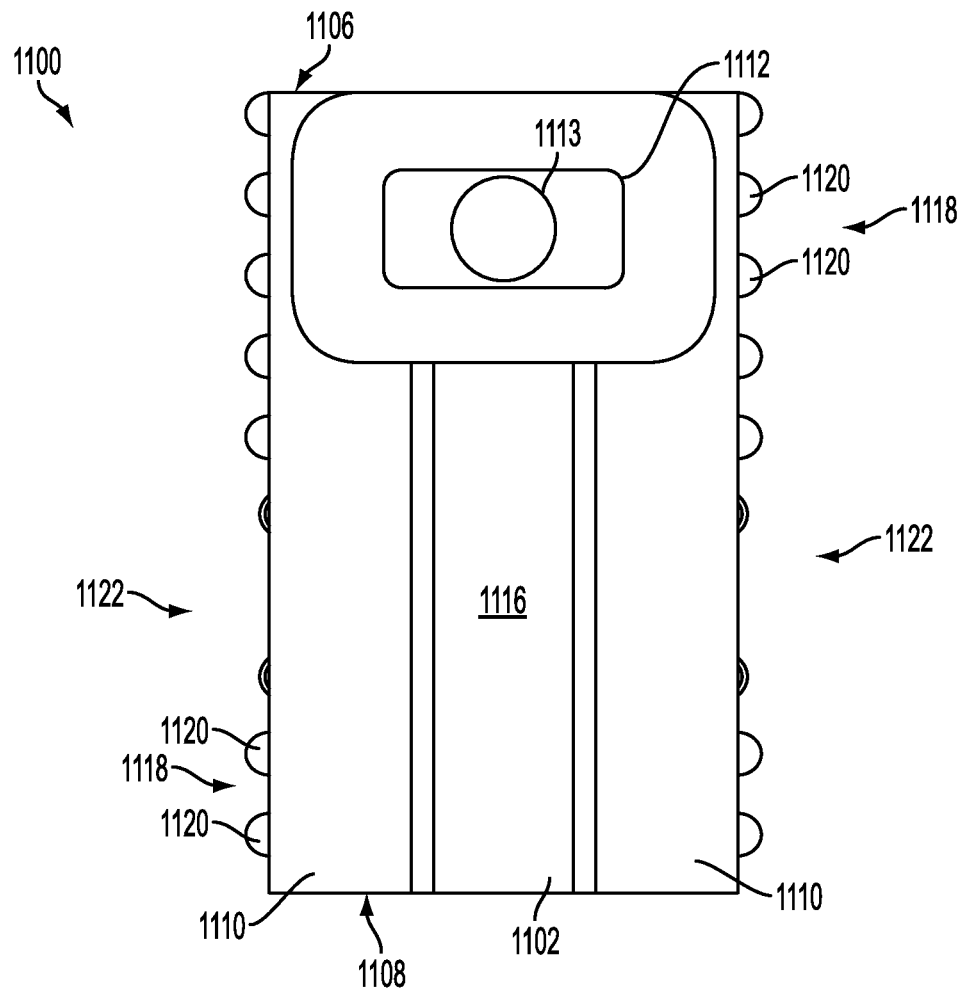
FIG. 26 is an elevational view of the body portion of one embodiment of the probe guide of FIG. 22.
Figure 27:
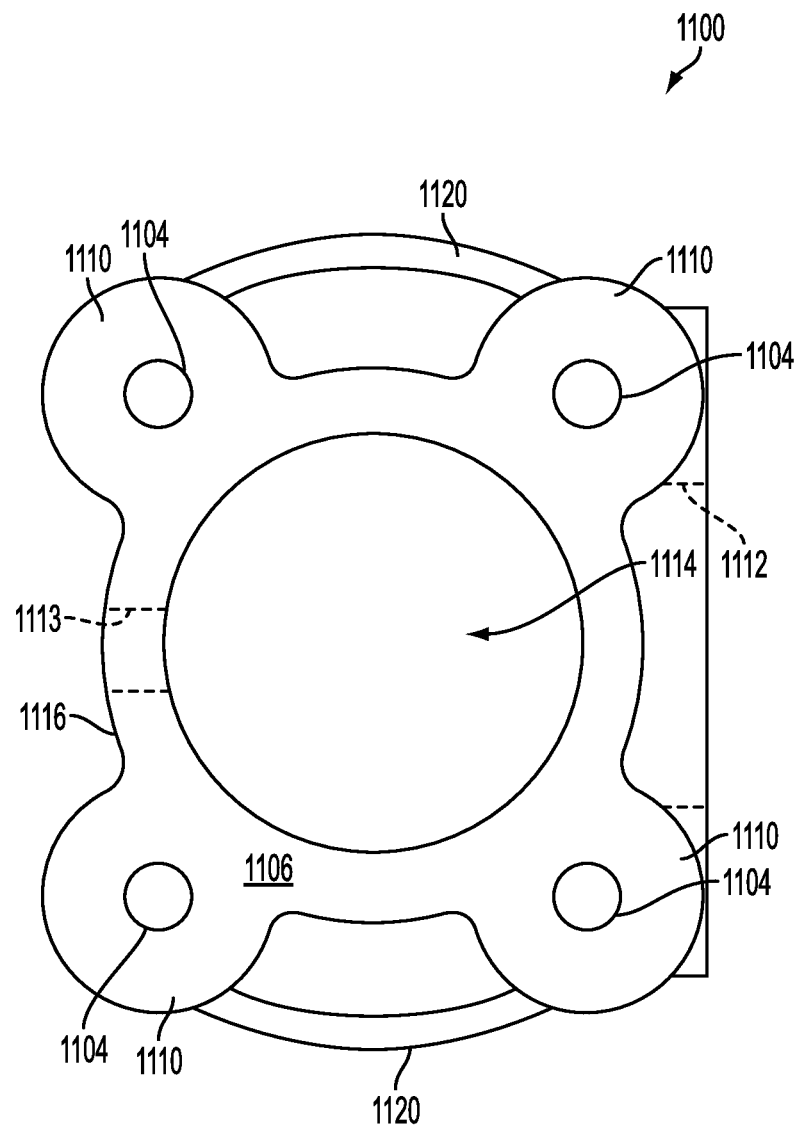
FIG. 27 is a plan view of the body portion of one embodiment of the probe guide of FIG. 22.
Figure 28:
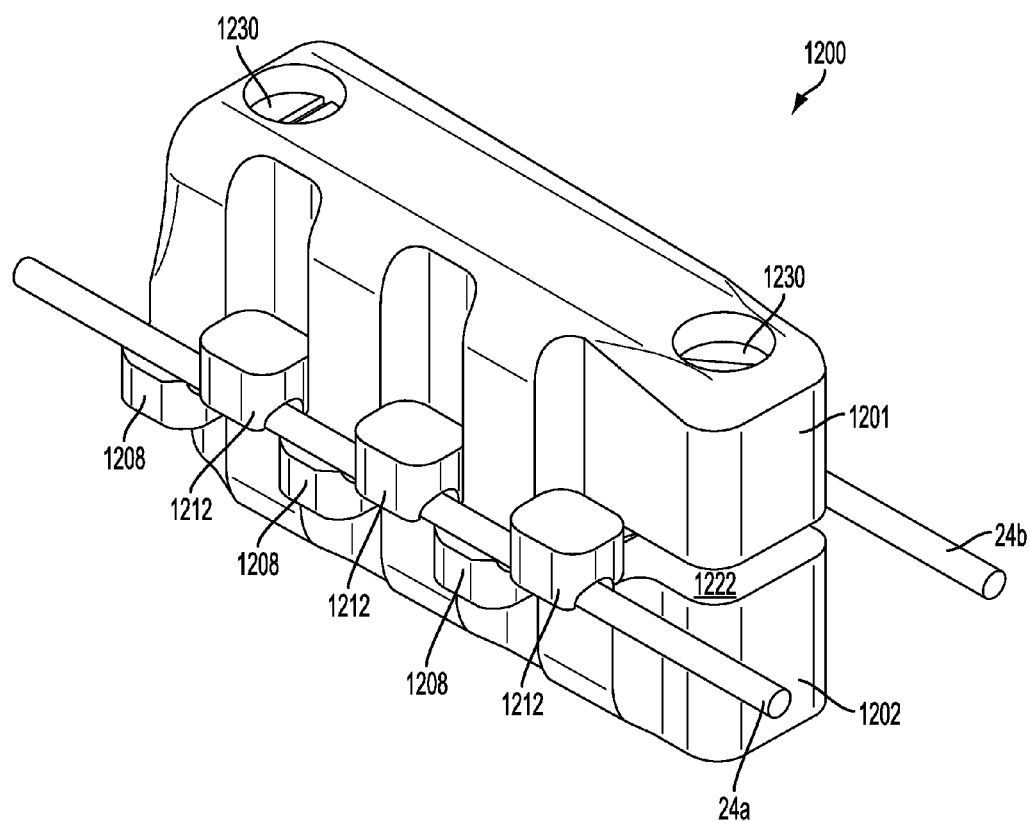
FIG. 28 is a perspective view of a spring loaded probe guide according to various embodiments of the present disclosure.

Referring now to FIGS. 22-27, a probe guide 1100 can comprise a body portion 1102, similar to the body portion 1002 described herein. The body portion 1102 can comprise first, second, third and fourth enclosures 1110a, 1110b, 1110c, 1110d similar to enclosures 1010a, 1010b, 1010c, 1010, for example, and/or first, second, third, and fourth passages 1104a, 1104b, 1104c, 1104d similar to passages 1004a, 1004b, 1004c, 1004d. The probe guide 1100 can also comprise a handle 1124 and/or a locking element 1132, for example. In various embodiments, the handle 1124 can be removable. In other embodiments, the handle 1124 can be fixedly secured to the body portion 1102. Referring primarily to FIG. 23, the handle 1124 can comprise an extension 1126 that extends from the handle 1124 to a distal portion 1128 thereof. In various embodiments, an orifice 1130 can extend through at least a portion of the extension 1126, for example. Referring primarily to FIG. 22, the extension 1126 can be positioned within the body portion 1102 of the probe guide 1100. In such embodiments, the extension 1126 can be positioned through at least a portion of a proximal opening 1112 (FIG. 26) in the body portion 1102, for example. Furthermore, in various embodiments the distal portion 1028 of the handle 1124 can extend through a bore 1114 of the body portion and into a distal opening 1113 (FIG. 25) in the body portion 1102, for example. In such embodiments, the orifice 1130 on the extension 1126 of the handle 1124 can be aligned with the bore 1114 of the body portion 1102. In various embodiments, referring primarily to FIG. 24, a locking element 1132 can comprise a plunger or shaft 1134 and a rib 1136. In various embodiments, at least a portion of the locking element 1132 can be positioned within the bore 1114 of the body 1102. When a portion of the locking element 1132 is positioned within the bore 1114, the locking element 1132 can secure or lock the handle 1124 to the body portion 1202, for example. In some embodiments, the plunger 1134 can extend through the orifice 1130 of the handle 1124 to lock the handle 1124 in place.

Similar to embodiments described herein, the probe guide 1100 can be positioned relative to the tissue treatment region and the first electrode 824a can be axially advanced through the first passage 1104a of the probe guide 1100, for example. In various embodiments, the handle 1124 and/or contours 1120 can facilitate accurate positioning of the body portion 1102 of the probe guide 1100 relative to the first electrode 824a and/or the target zone in the tissue treatment region. As described herein, once the probe guide 1100 and the first electrode 824a are positioned relative to the tissue treatment region, the second electrode 824b, the third electrode 824c, and/or the fourth electrode 824d can be advanced though passages 1104b, 1104c, 1104d, respectively, of the probe guide 1100. In various embodiments, the handle 1124 and/or contours 1120 can facilitate steadiness of the body portion 1102 of the probe guide 1100 as electrodes 824b, 824c and/or 824d are advanced through the passages 1104 of the body portion 1102.

Referring now to FIGS. 28-34, a probe guide 1200 can comprise a first body portion 1201 and a second body portion 1202. In some embodiments, the probe guide 1200 can also comprise at least one spring element 1240 positioned between the first body portion 1201 and the second body portion 1202, for example. The probe guide can comprise two spring elements 1240, for example, and the spring elements 1240 can comprise coil springs, for example. In various embodiments, the spring elements 1240 can be movable from an initial configuration to at least one deformed configuration.

Figure 29:
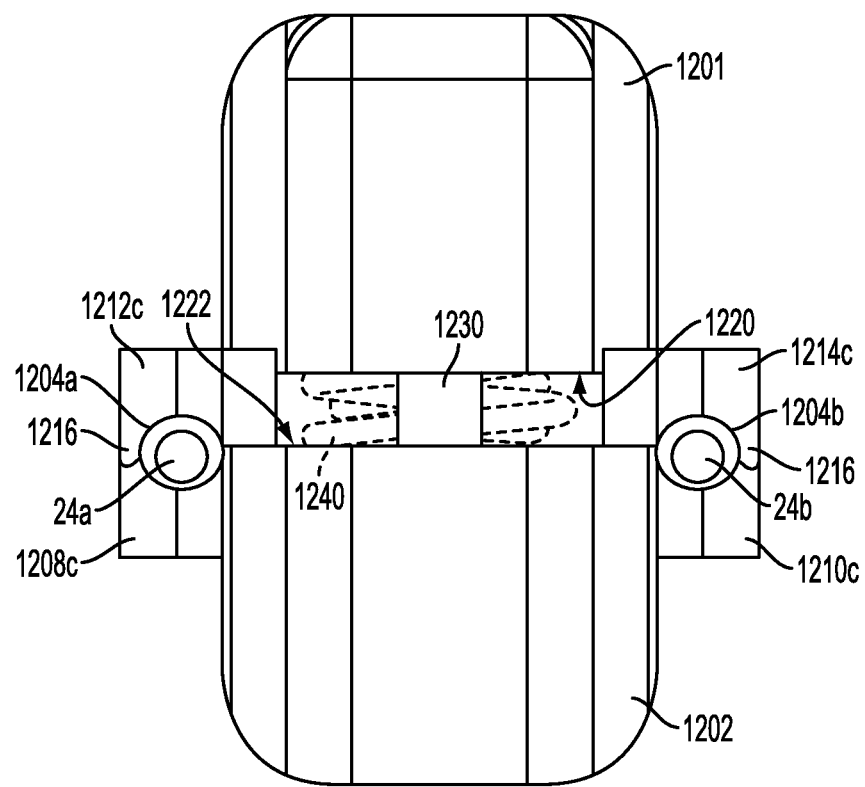
FIG. 29 is an elevational view of one embodiment of the spring loaded probe guide of FIG. 28.
Figure 30:
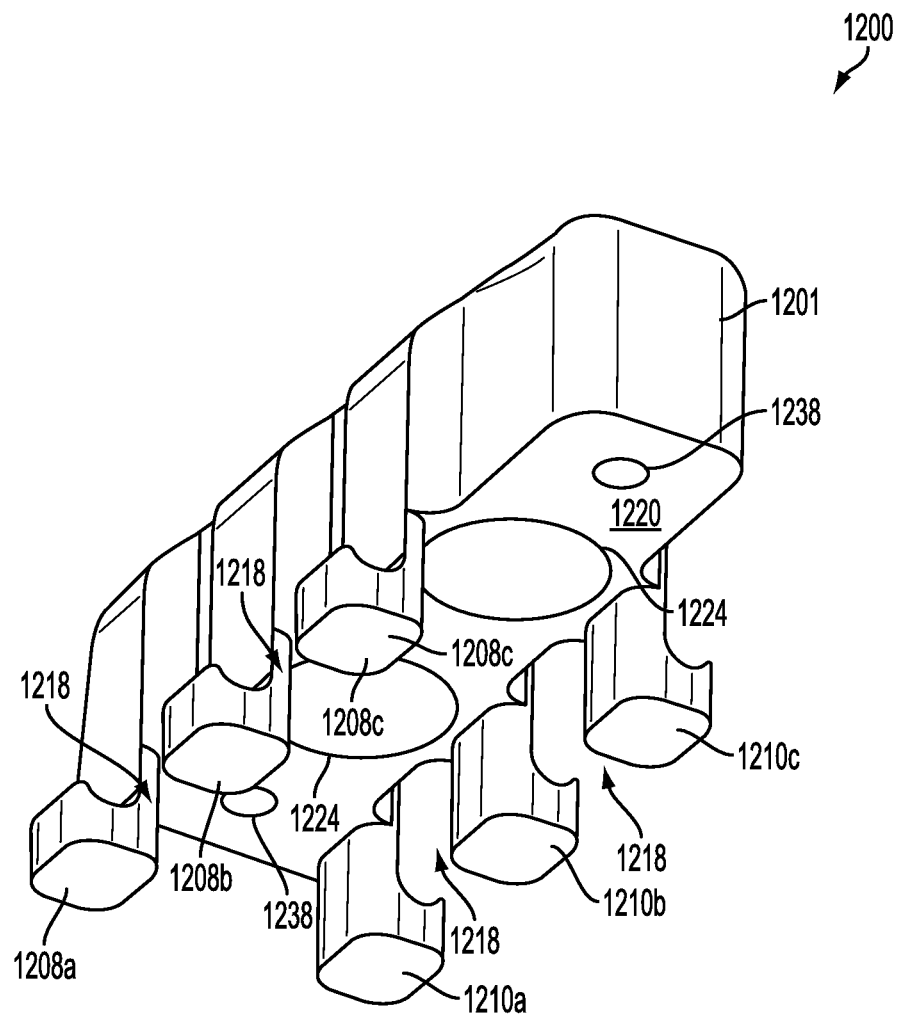
FIG. 30 is a perspective view of the first body portion of one embodiment of the spring loaded probe guide of FIG. 28.
Figure 31:
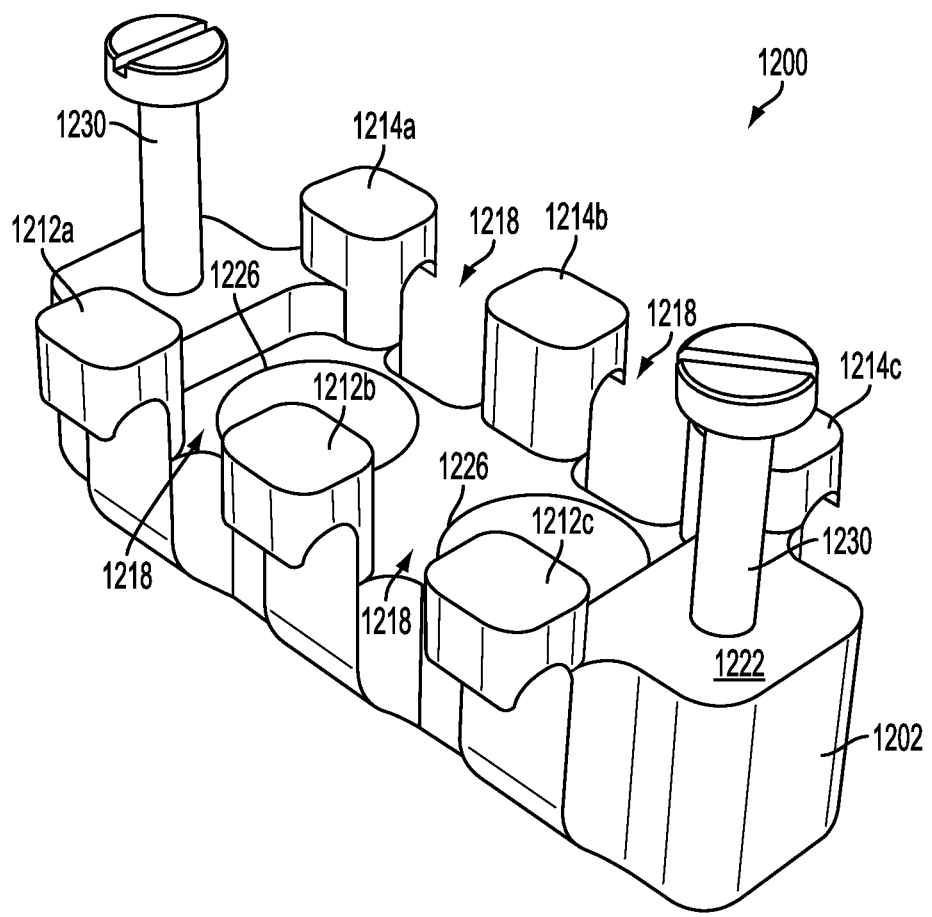
FIG. 31 is a perspective view of the second body portion and the fasteners of one embodiment of the spring loaded probe guide of FIG. 28.

Referring primarily to FIG. 30, the first body portion 1201 can comprise a plurality of first catches 1208, 1210. In various embodiments, the plurality of first catches 1208, 1210 can extend from the first side and/or the second side of the first body portion 1201. In some embodiments, at least one first side first catch 1208 can be positioned on a first side of the first body portion 1201, for example, and at least one second side first catch 1210 can be positioned on a second side of the first body portion 1201, for example. Referring still to FIG. 30, the first body portion 1201 can comprise an inner surface 1220. In some embodiments, when the first body portion 1201 is positioned relative to the second body portion 1202 (FIGS. 28 and 29), the inner surface 1220 can be positioned adjacent to the second body portion 1202. In some embodiments, the inner surface 1220 can be positioned adjacent to an inner surface 1222 on the second body portion 1202 (FIG. 31). When the first body portion 1201 is positioned relative to the second body portion 1202, the plurality of first catches 1208, 1210 can extend from the inner surface 1220 of the first body portion 1201 towards the second body portion 1202, for example. As described herein, the first catches 1208, 1210 can each comprise a hooked extension (FIG. 29). The first catches 1208, 1210 and/or the hook(s) 1216 can form channels 1204a, 1204b (FIG. 29) configured to restrain the electrodes 24a, 24b (FIG. 1), as described herein. Referring again to FIG. 30, the inner surface 1220 of the first body portion 1201 can also comprise an orifice 1238 and/or at least one opening or depression 1224. As described herein, the orifice 1238 can be configured to receive the shaft of a screw 1230, for example, and the depression 1224 can be configured to receive a spring element 1240, for example.

Referring still to FIG. 30, the plurality of first catches 1208, 1210, can comprise a plurality of first side first catches 1208 and/or a plurality of second side first catches 1210, for example. The first side first catches 1208 can comprise an "A" first side first catch 1208a, a "B" first side first catch 1208b, and/or a "C" first side first catch 1208c, for example. In other embodiments, the plurality of first side first catches 1208 can comprise additional and/or fewer first side first catches 1208. Furthermore, the first side first catches 1208a, 1208b, 1208c can be positioned along the first side of the first body portion 1201 and can be separated by a gap 1218 between each first side first catch 1208a, 1208b, 1208c. For example, a gap 1218 can be positioned between the "A" first side first catch 1208a and the "B" first side first catch 1208b, for example. Similarly, the second side of the first body portion 1201 can comprise a plurality of second side first catches 1210. The plurality of second side first catches 1210 can comprise an "A" second side first catch 1210a, a "B" second side first catch 1210b, and/or a "C" second side first catch 1210c, for example. Similar to the description above, the plurality of second side first catches 1210 can comprise additional and/or fewer second side first catches 1210, for example. Additionally, in various embodiments, gaps 1218 can be positioned between adjacent second side first catches 1210a, 1210b, 1210c. For example, a gap 1218 can be positioned between the "B" second side first catch 1210b and the "C" second side first catch 1210c.

Figure 33:
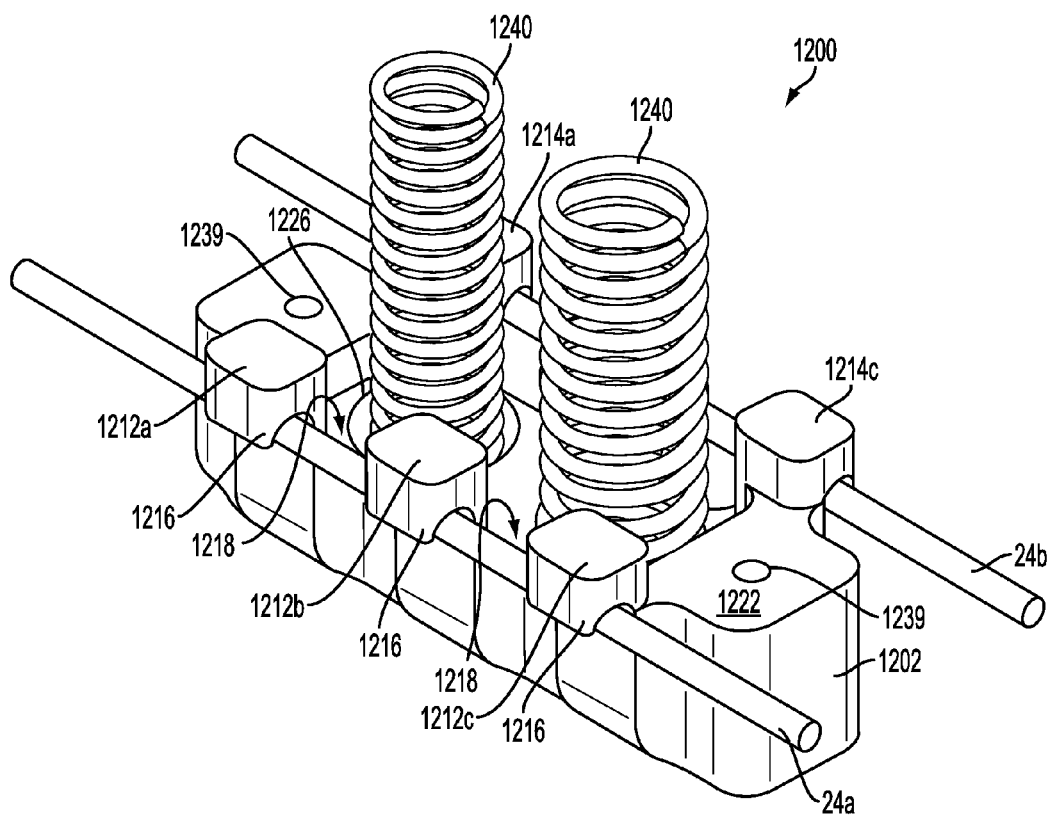
FIG. 33 is a perspective view of one embodiment of the spring loaded probe guide of FIG. 28 with the first body portion removed therefrom.
Figure 34:
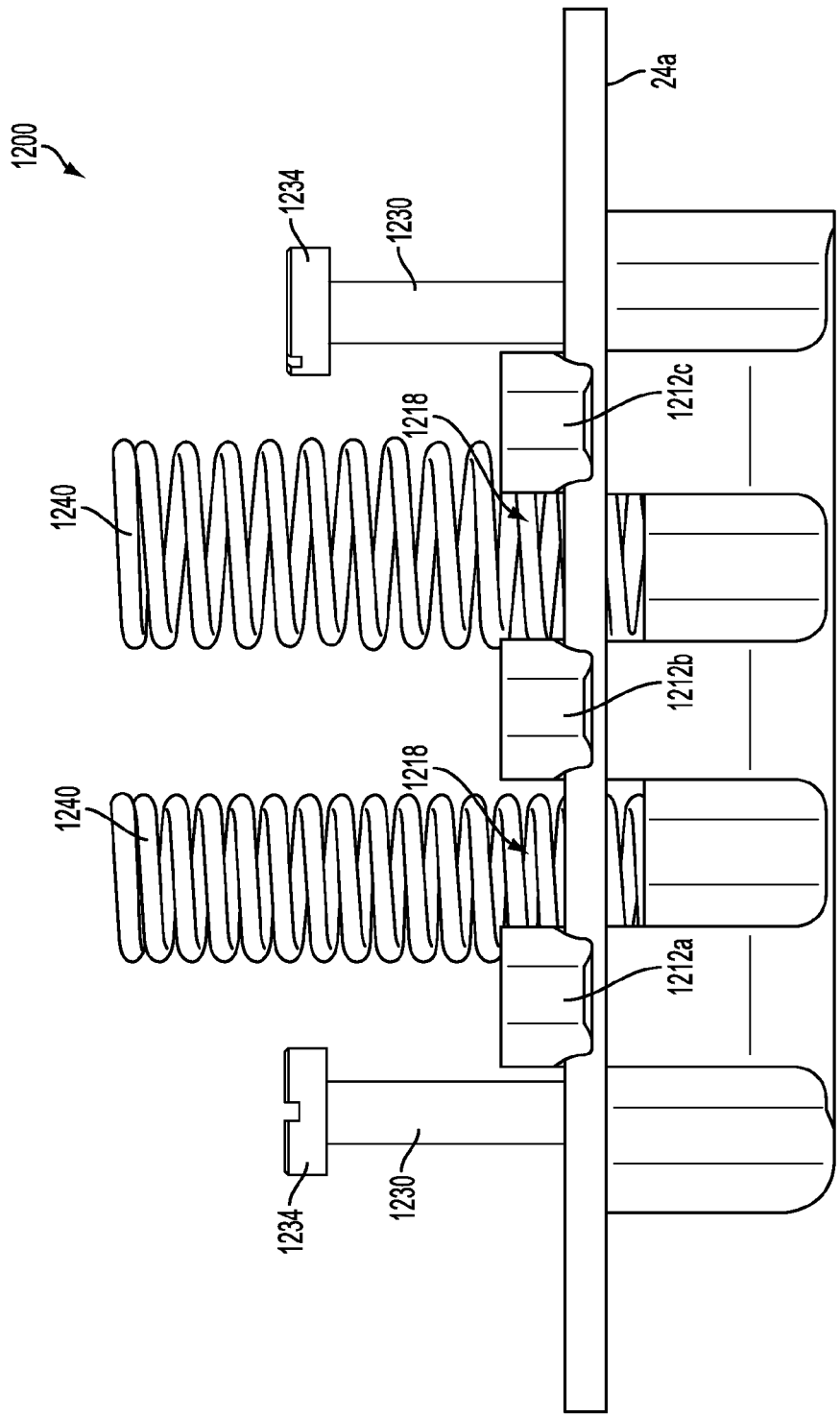
FIG. 34 is an elevational view of one embodiment of the spring loaded probe guide of FIG. 28 with the first body portion removed therefrom.

Referring primarily to FIG. 31, the second body portion 1202 can comprise a plurality of second catches 1212, 1214. In various embodiments, the plurality of second catches 1212, 1214 can extend from the first side and/or the second side of the second body portion 1202. In some embodiments, at least one first side second catch 1212 can be positioned on a first side of the second body portion 1202, for example, and at least one second side second catch 1214 can be positioned on a second side of the second body portion 1202, for example. Referring still to FIG. 31, the second body portion 1202 can comprise an inner surface 1222. In some embodiments, when the second body portion 1202 is positioned relative to the first body portion 1201 (FIGS. 28 and 29), the inner surface 1222 can be positioned adjacent to the first body portion 1201. In some embodiments, the inner surface 1222 can be positioned adjacent to the inner surface 1220 on the first body portion 1201 (FIG. 30). When the second body portion 1202 is positioned relative to the first body portion 1201, the plurality of second catches 1212, 1214 can extend from the inner surface 1222 of the second body portion 1202 towards the first body portion 1201, for example. As described herein, the second catches 1212, 1214 can each comprise a hooked extension (FIG. 29). The second catches 1212, 1214 and/or the hook(s) 1216 can form channels 1204a, 1204b (FIG. 29) configured to restrain electrodes 24a, 24b (FIG. 1), as described herein. Referring primarily to FIG. 33, the inner surface 1222 of the second body portion 1202 can also comprise an orifice 1239 and/or at least one depression or opening 1226. As described herein, the orifice 1239 can be configured to receive the shaft of a screw 1230, for example, and the depression 1226 can be configured to receive a spring element 1240, for example.

Referring to FIG. 31, the plurality of second catches 1212, 1214, can comprise a plurality of first side second catches 1212 and/or a plurality of second side second catches 1214, for example. The first side second catches 1212 can comprise an "A" first side second catch 1212a, a "B" first side second catch 1212b, and/or a "C" first side second catch 1212c, for example. In other embodiments, the plurality of first side second catches 1212 can comprise additional and/or fewer first side second catches 1212. Furthermore, the first side second catches 1208a, 1208b, 1208c can be positioned along the first side of the second body portion 1202 and can be separated by a gap 1218 between each first side second catch 1212a, 1212b, 1212c. For example, a gap 1218 can be positioned between the "A" first side second catch 1212a and the "B" first side second catch 1212b, for example. Similarly, the second side of the second body portion 1202 can comprise a plurality of second side second catches 1214. The plurality of second side second catches 1214 can comprise an "A" second side second catch 1214a, a "B" second side second catch 1214b, and/or a "C" second side second catch 1214c, for example. Similar to the description above, the plurality of second side second catches 1214 can comprise additional and/or fewer second side first catches 1214, for example. Additionally, in various embodiments, gaps 1218 can be positioned between adjacent second side second catches 1214a, 1214b, 1214c, for example. For example, a gap 1218 can be positioned between the "B" second side second catch 1214b and the "C" second side second catch 1214c.

Figure 32:
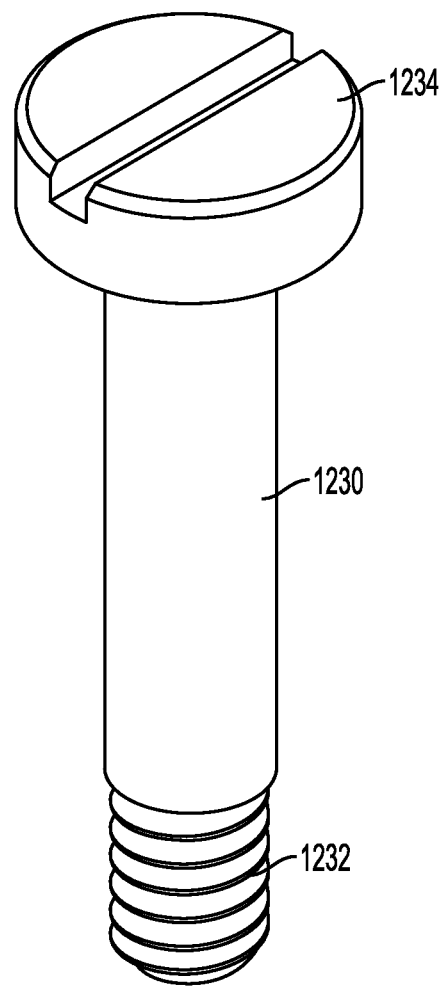
FIG. 32 is a perspective view of a fastener of one embodiment of the spring loaded probe guide of FIG. 28.

Referring now to FIG. 32, the fastener 1230 can comprise threads 1232 and/or a head 1234, for example. In some embodiments, referring again to FIGS. 28 and 29, the fastener 1230 can attach the first body portion 1201 to the second body portion 1202. As described herein, the fastener 1230 can extend through an orifice 1238 in the first body portion 1201 and an orifice 1239 in the second body portion 1202, for example. The inner surface 1220 of the first body portion 1201 and the inner surface 1222 of the second body portion 1202 can be defined by the amount the screw and/or screws 1230 are threadably engaged with the first and/or second body portions 1201, 1202. For example, the fastener(s) 1230 can be tightened such that the gap between the inner surface 1220 of the first body portion 1201 and the inner surface 1222 of the second body portion 1202 is reduced. In other embodiments, the fastener(s) 1230 can be loosened such that the gap between the inner surface 1220 of the first body portion 1201 and the inner surface 1222 of the second body portion 1202 is increased. In other embodiments, the first and second body portions 1201, 1202 can be secured together by non-threaded fasteners.

Referring primarily to FIGS. 29 and 33, the probe guide 1200 can comprise the spring element 1240, which can be positioned in the depression 1226 in the inner surface 1224 of the second body portion 1202. In various embodiments, the spring element 1240 can extend towards the first body portion 1201, for example. When the fastener(s) 1230 secure the first body portion to the second body portion, the spring element or elements 1240 can be restrained therebetween. In various embodiments, the spring element(s) can be compressed between the first and second body portions 1201, 1202. The amount that the spring element(s) 1240 are compressed can depend on the fasteners 1230 and the gap between the first and second body portions 1201, 1202, for example. In at least one embodiment, the threaded fasteners 1240 can be tightened to reduce the gap between the body portions 1201, 1202, for example, and to compress the spring elements 1240 more, for example. The threaded fasteners 1240 can be loosened to increase the gap between the body portions 1201, 1202, for example, and to decompress the spring elements 1240, for example. The clamping force on the electrodes can be changed by adjusting the spring. For example, a heavier gauge wire for the spring can be used to increase the forces on the spring element.

Referring primarily to FIG. 29, in various embodiments, the plurality of first and second catches 1208, 1210, 1212, and 1214 can form the first and second channels 1204a, 1204b. The first channel 1204a can be structured to restrain the first electrode 24a when the spring 1240 is in the initial configuration, for example, and the second channel 1204b can be structured to restrain the second electrode 24b when the spring 1240 is in the initial configuration, for example. In some embodiments, the first side first catches 1208a, 1208b, 1208c and the first side second catches 1212a, 1212b, 1212c can form the first channel 1204a that is configured to restrain the first electrode 24A. Similarly, the second side first catches 1210a, 1210b, 1210c and the second side second catches 1214a, 1214b, 1214c can form the second channel 1204b that is configured to restrain the second electrode 24B, for example. In such embodiments, the first channel 1204a can be positioned on the first side of the first body portion 1201, for example, and the second channel 1204b can be positioned on the second side of the first body portion 1201. Furthermore, as described herein, the distal end of the first electrode 24a can be spaced from the distal end of the second electrode 24b by a predetermined distance when the first electrode 24a is axially restrained in the first channel 104a and the second electrode 24b is axially restrained in the second channel 104b. The pre-determined distance can correspond to a treatment distance in the tissue treatment region. Furthermore, the distal ends of the first and second electrodes 24a, 24b can be operatively structured to conduct current therebetween when at least one of the first and second electrodes 24a, 24b is energized by an energy source 14 (FIG. 1).

In various embodiments, the first electrode 24a can be positioned relative to the tissue treatment region. As described herein, pre-operative and intra-operative three-dimensional imaging can aid the operator in placing the first electrode 24a in the target treatment zone of the tissue treatment region, for example. In various embodiments, once the first electrode 24a is positioned relative to the tissue treatment region, the probe guide 1200 can be positioned around at least a portion of the first electrode 24a. In some embodiments, to position the probe guide 1200 around at least a portion of the first electrode 24a, the spring element 1240 can be deformed or compressed from an initial configuration to a deformed configuration such that the first channel 1204a defined by the plurality of first side first catches 1208 and the plurality of first side second catches 1212 opens to receive the first electrode 24a. The probe guide 1200 can be squeezed or compressed, for example, to open the channel 1204a to receive the first electrode 24a. In various embodiments, once the probe guide 1200 is in position relative to the first electrode 24a, e.g., the first electrode 24a is axially retained in the first channel 1204a, the second electrode 24b can be axially advanced through the second channel 1204b defined by the plurality of second side first catches 1210 and the plurality of second side second catches 1214, for example. In other embodiments, to position the probe guide 1200 around at least a portion of the second electrode 24b, the spring element 1240 can be deformed or compressed from an initial configuration to a deformed configuration such that the second channel 1204b defined by the plurality of second side first catches 1210 and the plurality of second side second catches 1214 opens to receive the second electrode 24b. In various embodiments, an actuator (not shown) can compress the spring elements 1240 to open the first and/or second channels 1204a, 1204b, for example. Further, in some embodiments, the actuator can decompress the spring elements 1240 to close the first and/or second channels 1204a, 1204b, for example. In various embodiments, when the spring element 1240 is in the initial configuration, the probe guide 1200 can exert a clamping force on the electrode 24a, 24b restrained therein.

Figure 35:
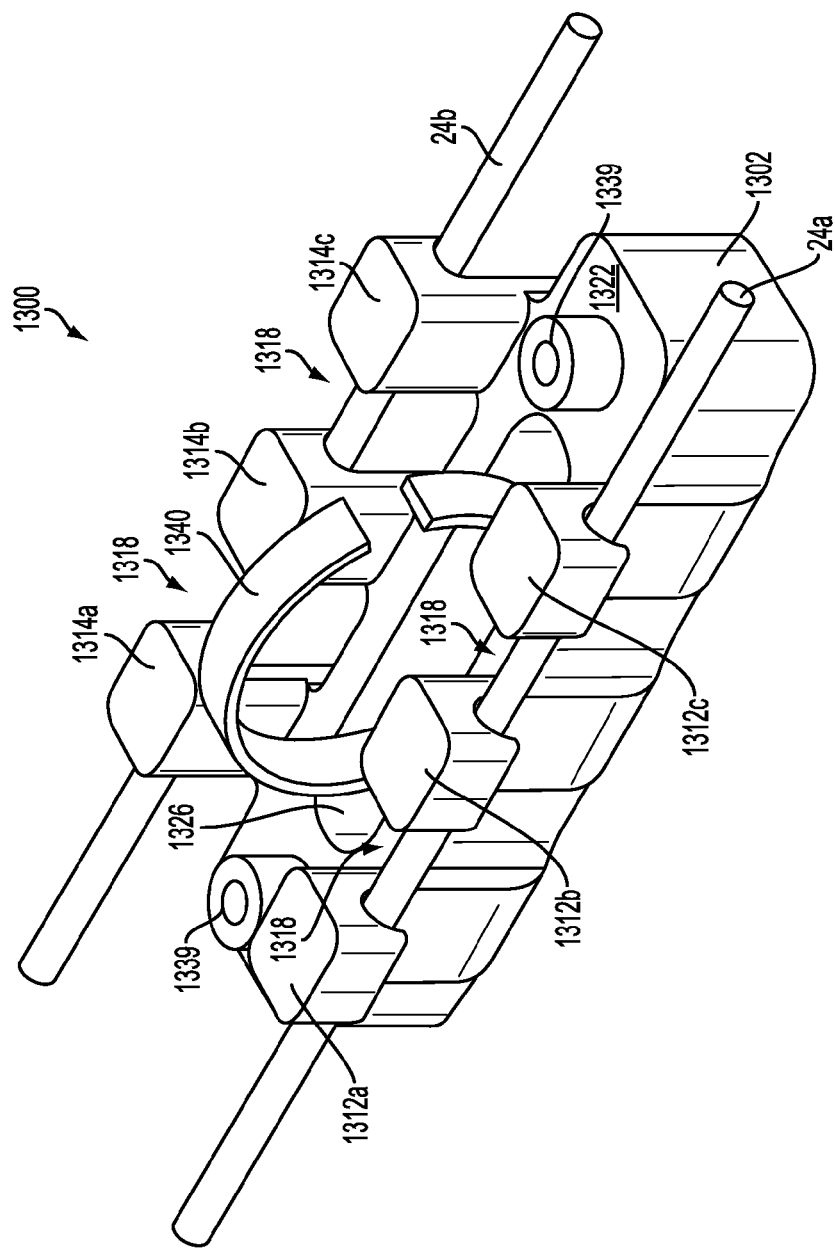
FIG. 35 is a perspective view of a spring loaded probe guide having a leaf spring and with the second body portion removed therefrom according to various embodiments of the present disclosure.
Figure 36:
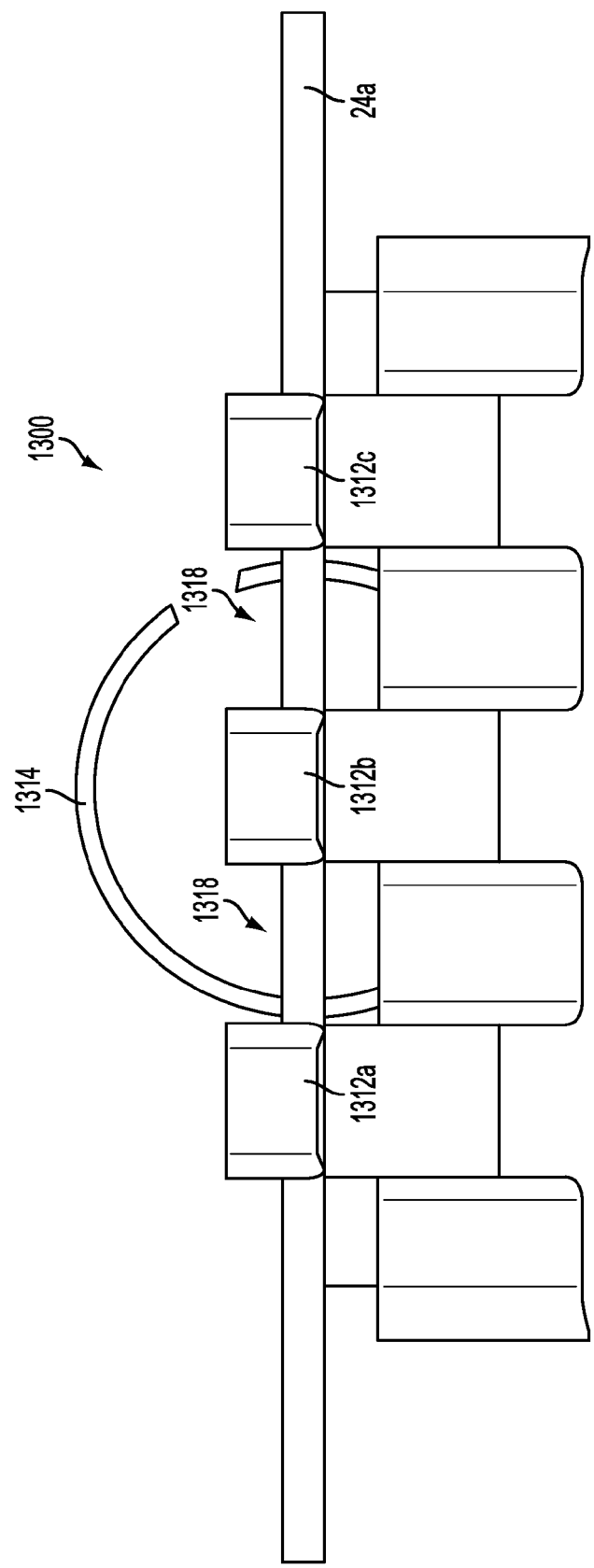
FIG. 36 is an elevational view of one embodiment of the spring loaded probe guide of FIG. 35 with the first body portion removed therefrom.

In various embodiments, referring to FIGS. 35 and 36, a probe guide 1300 can comprise first and second body portions 1301, 1302 similar to the first and second body portions 1201, 1202 of probe guide 1200 described herein. Referring primarily to FIG. 35, the second body portion 1302 can comprise an opening or depression 1326 in an inner surface 1322 that is configured to receive a spring element 1340. In various embodiments, the spring element 1340 can comprise a leaf spring. Similar to other embodiments described herein, the spring element 1340 can be deformed from an initial configuration to a deformed configuration such that channel(s) defined by catches on the first and second body portions 1301, 1302, including first side second catches 1312a, 1312b, 1312c, for example, and second side second catches 1314a, 1314b, 1314c, for example, can open to receive the first and/or second electrodes 24a, 24b for example. Further, when the spring element 1340 returns to the initial configuration, the catches can close such that the channel(s) can axially restrain the first and/or second electrodes 24a, 24b for example.

Figure 37:
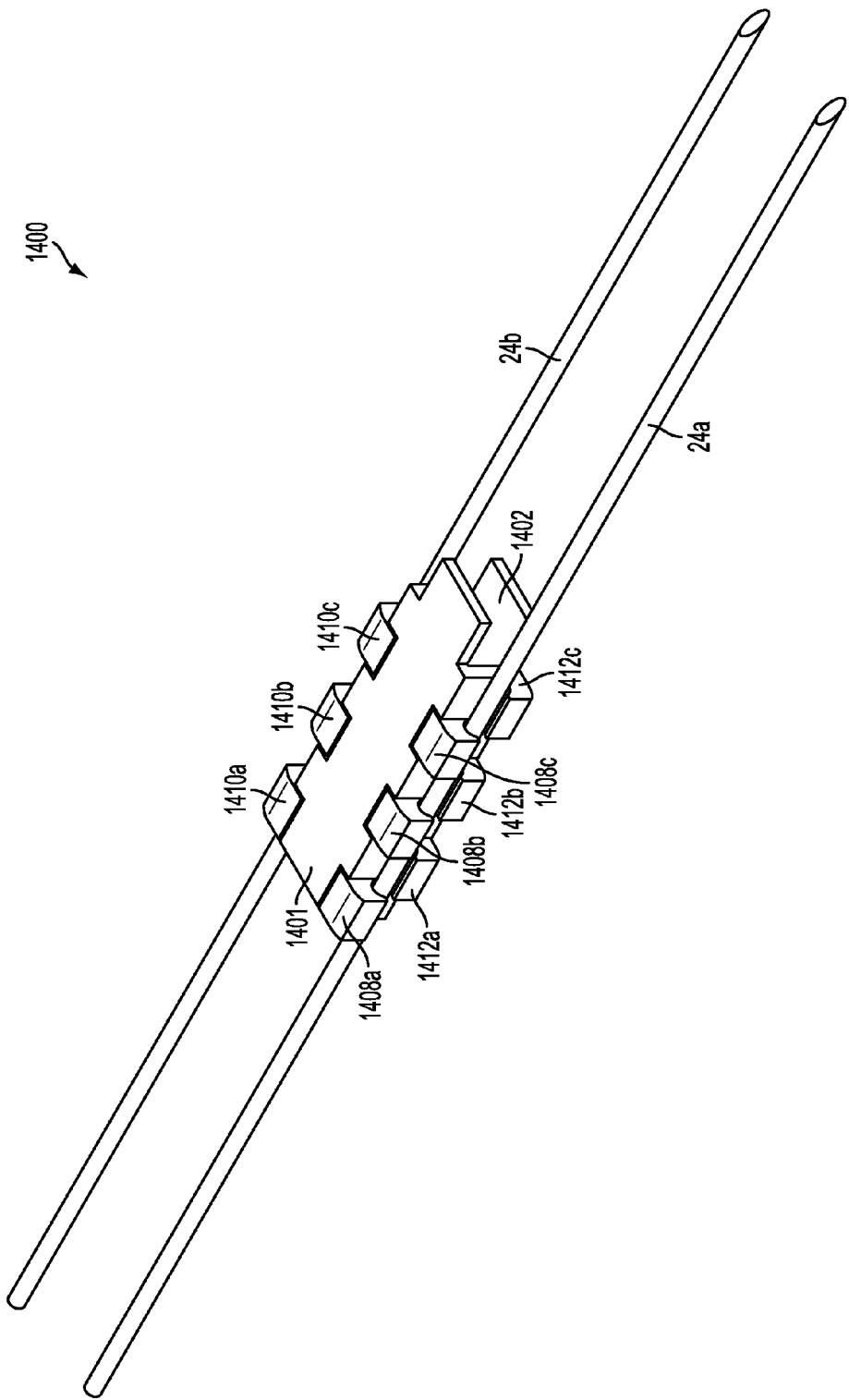
FIG. 37 is a perspective view of a spring loaded probe guide according to various embodiments of the present disclosure.
Figure 38:
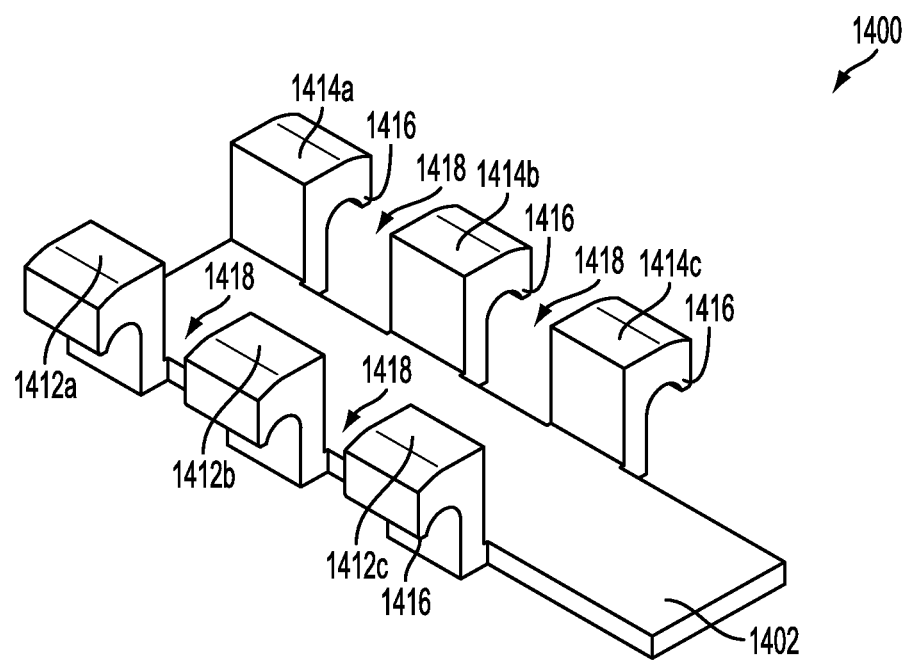
FIG. 38 is a perspective view of the second body portion of one embodiment of the spring loaded probe guide of FIG. 37.
Figure 39:
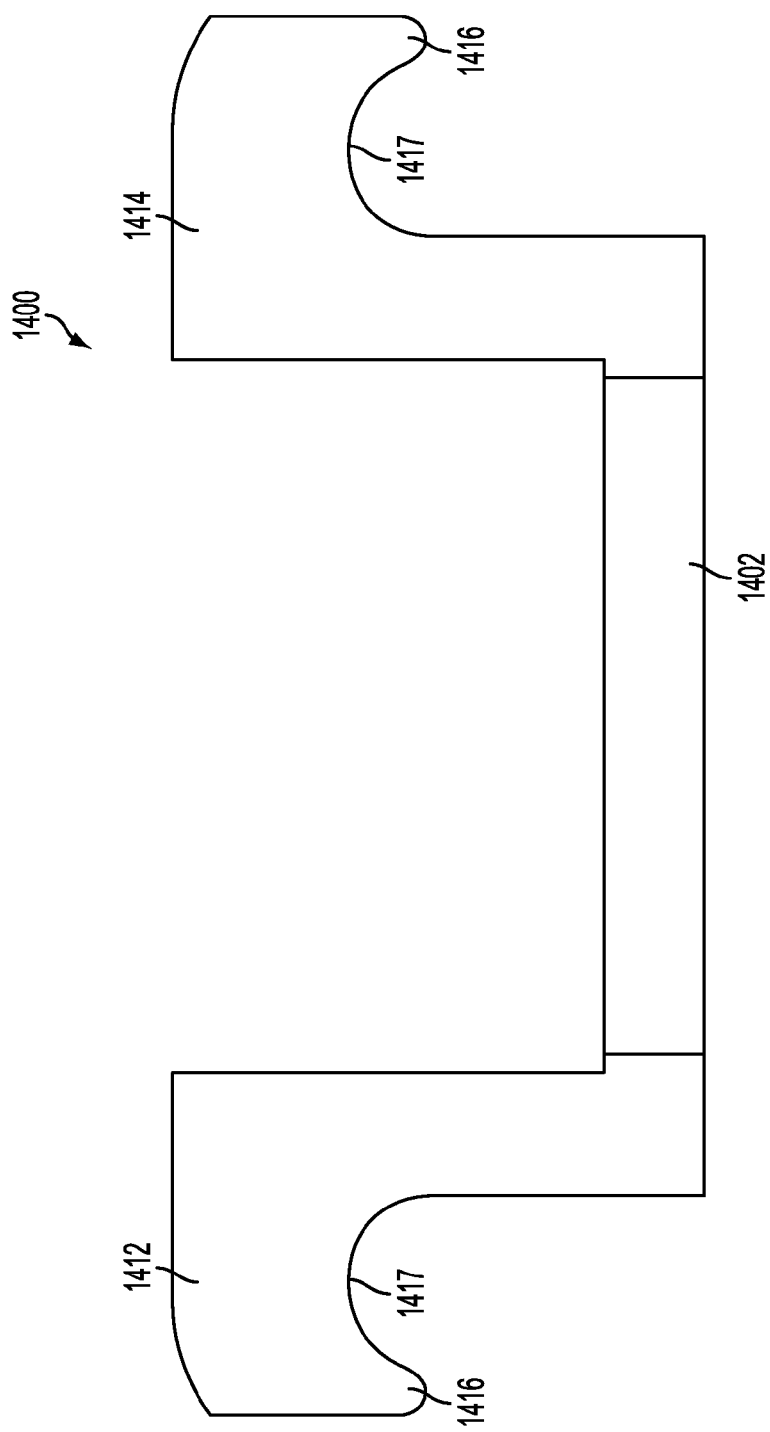
FIG. 39 is an elevational view of the second body portion of one embodiment of the spring loaded probe guide of FIG. 37.

In various embodiments, referring now to FIGS. 37-39, a probe guide 1400 can comprise a first body portion 1401 and a second body portion 1402, similar to first and second body portions 1201, 1202 of probe guide 1200 described herein. In various embodiments, a spring element (not shown) can be positioned between the first body portion 14010 and the second body portion 1402. The spring element can be a leaf spring, coil spring, or collapsible foam, for example. Similar to other embodiments described herein, the spring element can be movable from an initial configuration to deformed configurations. In various embodiments, referring primarily to FIG. 38, the first body portion can comprise a substantially flat surface with a plurality of first side second catches 1412 and a plurality of second side second catches 1414 extending therefrom. Similar to other embodiments described herein, a gap 1418 can be positioned between adjacent catches 1412, 1414. Referring primarily to FIG. 39, the plurality of first side second catches 1412 and the plurality of second side second catches 1414 can each comprise a hook or hooked extension 1416. In various embodiments, the first side second catch 1412 can extend substantially away from the second body portion 1402. However, in various embodiments, the hooked extension 1416 can extend back towards the second body portion 1402. A contour 1417 can curve around a portion of the first side second catch 1412 and/or the second side second catch 1414, for example. In various embodiments, when the first and second body portions 1401, 1402 are positioned relative to each other to form a first and second channel to receive the electrodes 24a, 24b, the contours 1417 can be positioned adjacent to the electrodes 24a, 24b, for example.

Referring now to FIGS. 40-44, a probe guide 1500 can comprise a first body portion 1501 and a second body portion 1502. In various embodiments, a spring element (not shown) can be positioned between the first and second body portions 1501, 1502. In various embodiments, referring primarily to FIGS. 41-43, the first body portion 1501 can comprise a substantially rectangular shape having a slot 1504 therethrough. In some embodiments, the slot 1504 can be rectangular or substantially rectangular. In other embodiments, the slot 1504 can be tapered, for example. Further, a flange 1508 can extend along a portion of the first body portion 1501 to a catch 1510, for example. In some embodiments, the catch 1510 can be positioned at a distal end of the first body portion 1501. In various embodiments, the catch 1510 can comprise at least one hook or hooked extension 1516 extending therefrom. Further, in at least one embodiment, the catch 1510 can comprise an angled projection 1518 extending towards the slot 1504, for example.

Figure 44:
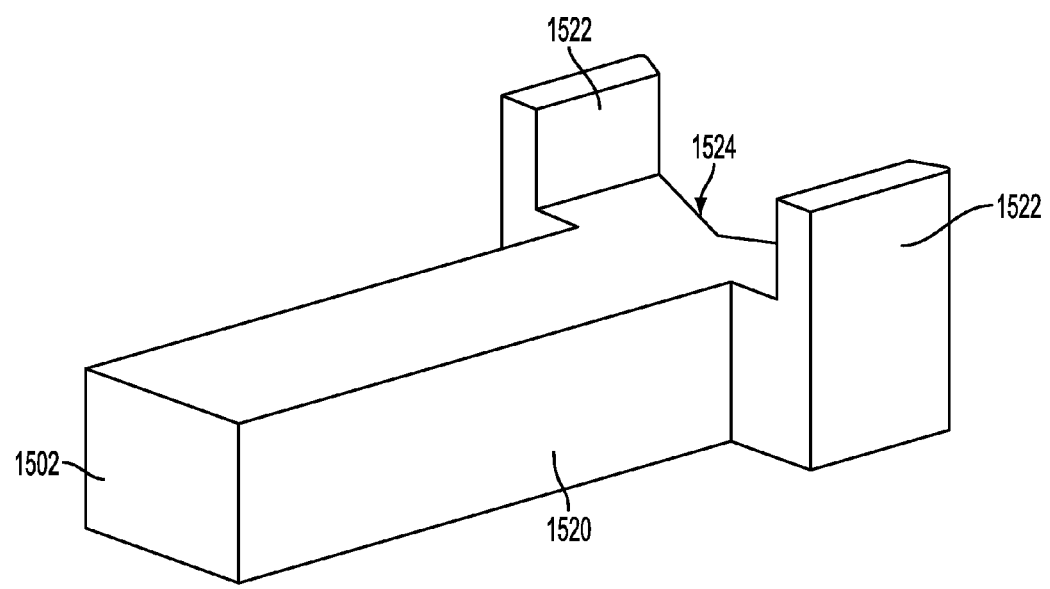
FIG. 44 is a perspective view of the second body portion of one embodiment of the spring loaded probe guide of FIG. 40.

Referring now to FIG. 44, the second body portion 1502 can comprise a longitudinal extension 1520 and at least one leg 1522. In some embodiments, the second body portion 1502 can comprise a first leg 1522 on a first side, for example, and a second leg 1522 on a second side, for example. Further, in at least one embodiment, an end of the second body portion can comprise a taper 1524. In various embodiments, referring again to FIG. 40, the first body portion 1501 can be positioned relative to the second body portion 1502 such that the longitudinal extension 1520 fits within the slot 1504. Further, the legs 1522 of the second body portion 1502 can fit along the flange 1508 of the first body portion 1501 when the first body portion 1501 is positioned relative to the second body portion 1502, for example. In such embodiments, the second body portion 1502 can fit within the substantially T-shaped cut-out in the first body portion 1501 between the slot 1504 and the catch 1510. Further, the taper 1524 of the second body portion 1501 can be structured to receive the angled projection 1518 of the first body portion, for example.

Figure 40:
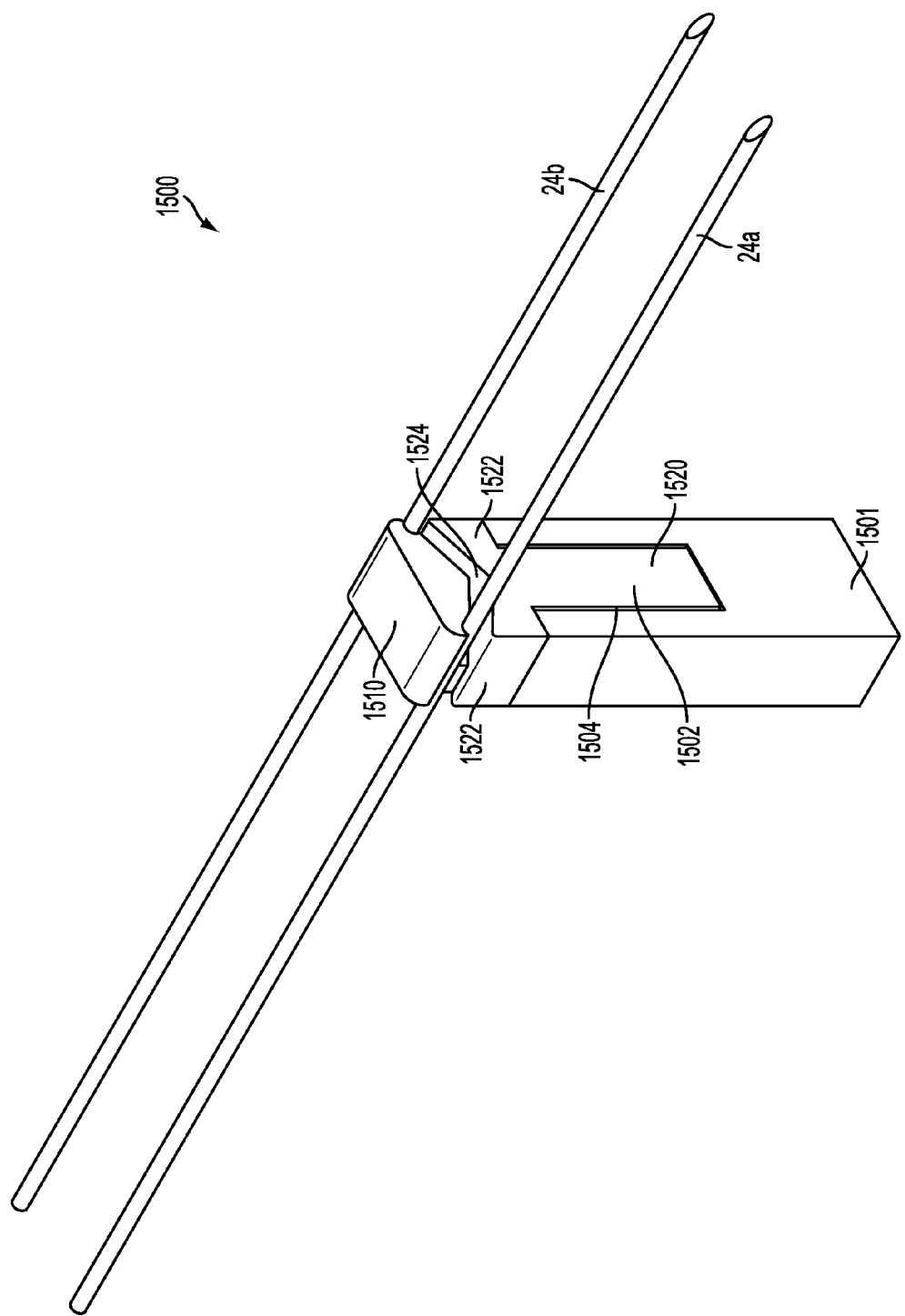
FIG. 40 is a perspective view of a spring loaded probe guide according to various embodiments of the present disclosure.
Figure 41:
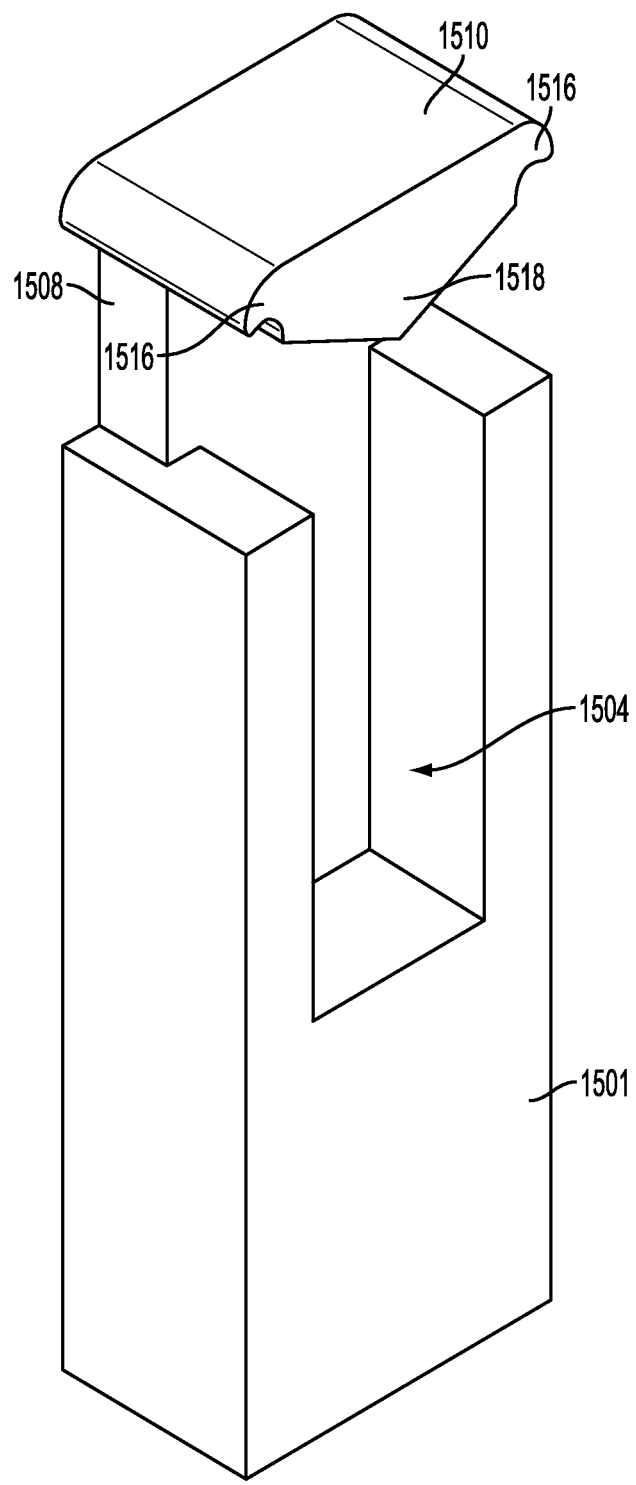
FIG. 41 is a perspective view of the first body portion of one embodiment of the spring loaded probe guide of FIG. 40.
Figure 42:
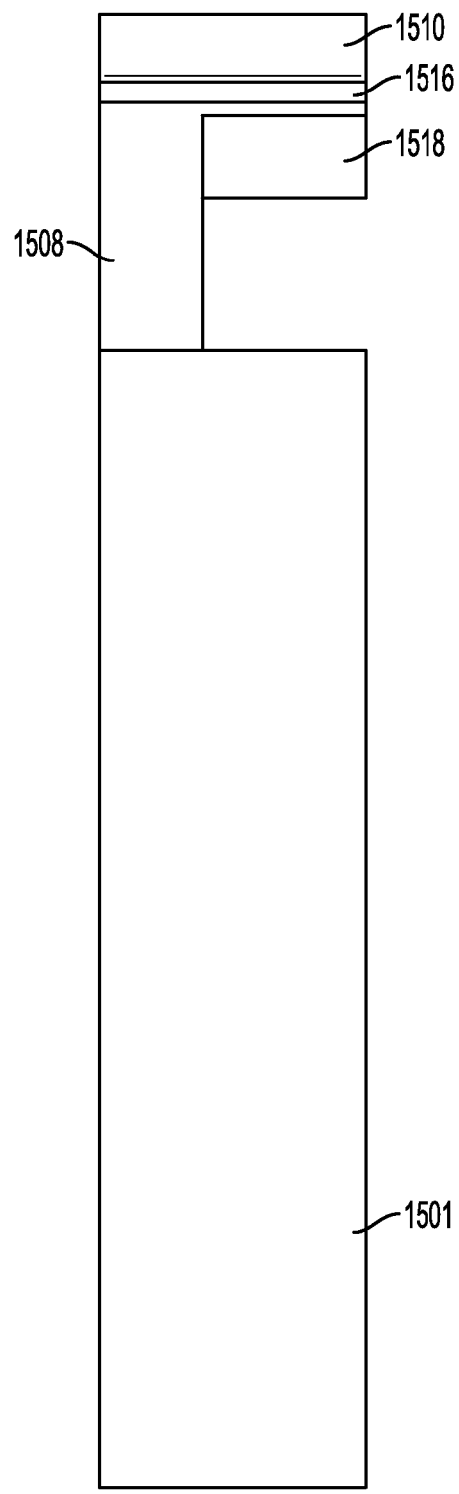
FIG. 42 is an elevational view of the first body portion of one embodiment of the spring loaded probe guide of FIG. 40.
Figure 43:
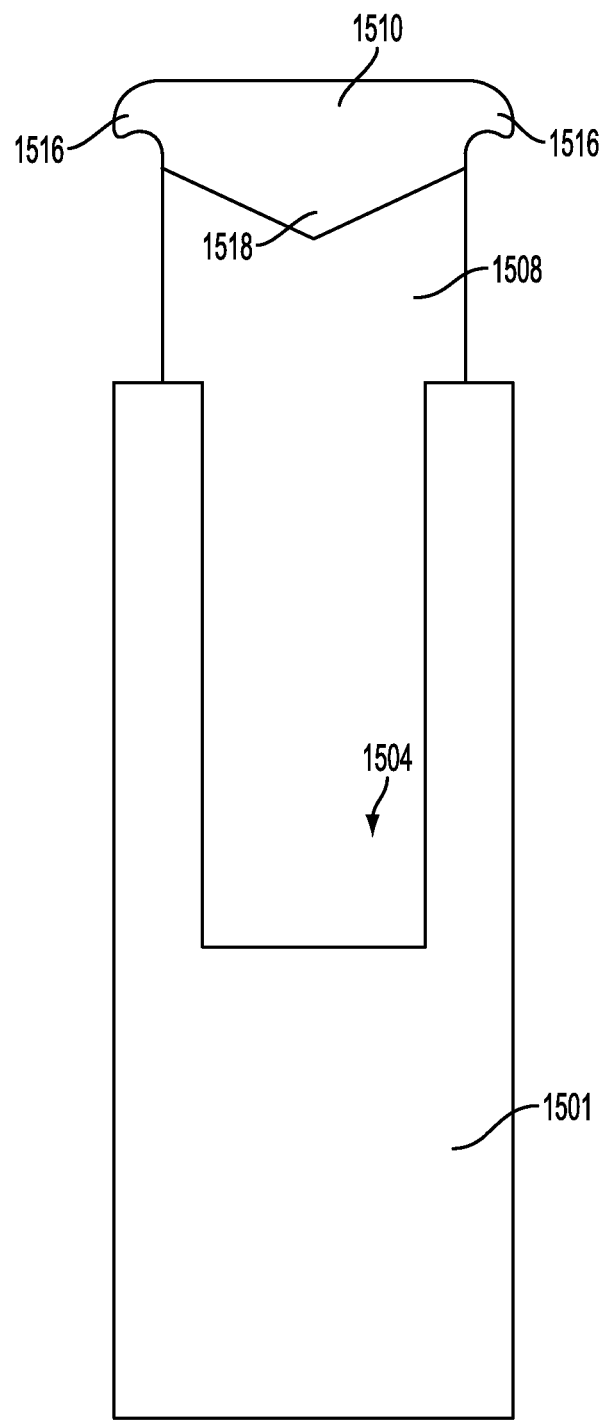
FIG. 43 is a plan view of the first body portion of one embodiment of the spring loaded probe guide of FIG. 40.

In various embodiments, referring primarily to FIG. 40, a spring (not shown) can be positioned between at least a portion of the first body portion 1501 and a portion of the second body portion 1502. Similar to embodiments described herein, the first channel can be configured to receive the first electrode 24a and the second channel can be configured to receive the second electrode 24b. In various embodiments, when the spring is compressed, the channels can widen or open such that the first electrode 24a and/or the second electrode 24b can move into and/or out of their respective channels, for example. In such embodiments, the first electrode 24a can be positioned relative to the tissue treatment region in a patient. Subsequently, the probe guide 1500 can be positioned around at least a portion of the first electrode 24a, for example, by compressing the spring element and moving the second body portion 1502 relative to the first body portion 1501 such that the first channel opens to receive the first electrode 24a, for example. Subsequently, the second electrode 24b can be axially advanced through the second channel formed between the first body portion 1501 and the second body portion 1502. When the spring returns or seeks to return to its pre-compressed configuration, the probe guide 1500 can exert a clamping force on the first and second electrodes 24a, 24b restrained therein.

Figure 45:
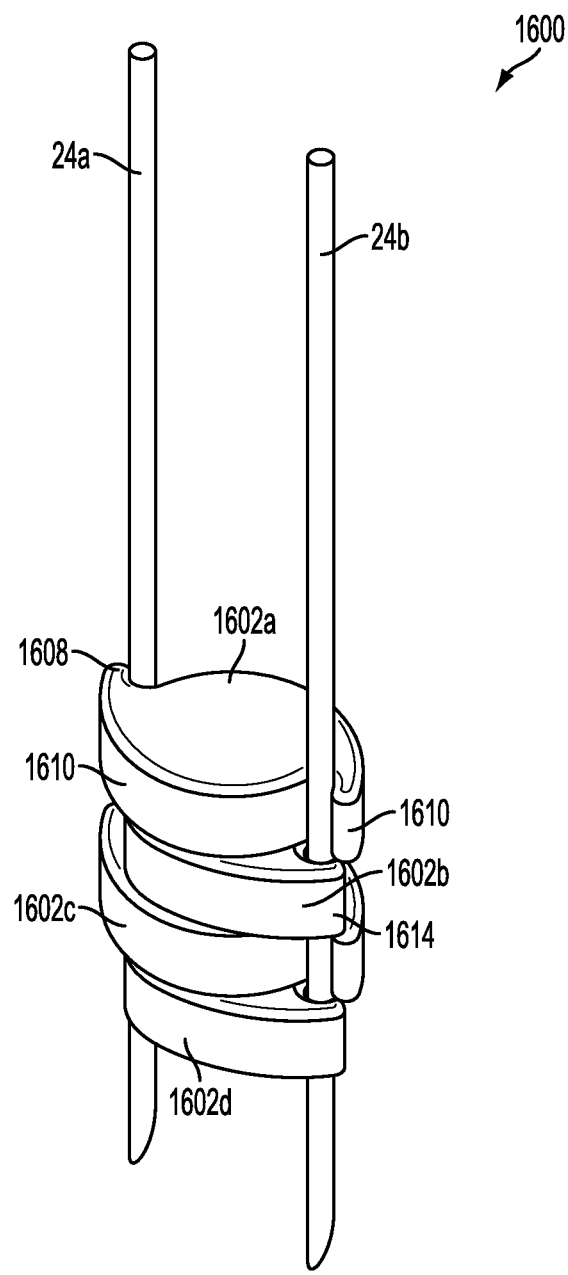
FIG. 45 is an elevational view of a probe guide according to various embodiments of the present disclosure.
Figure 46:
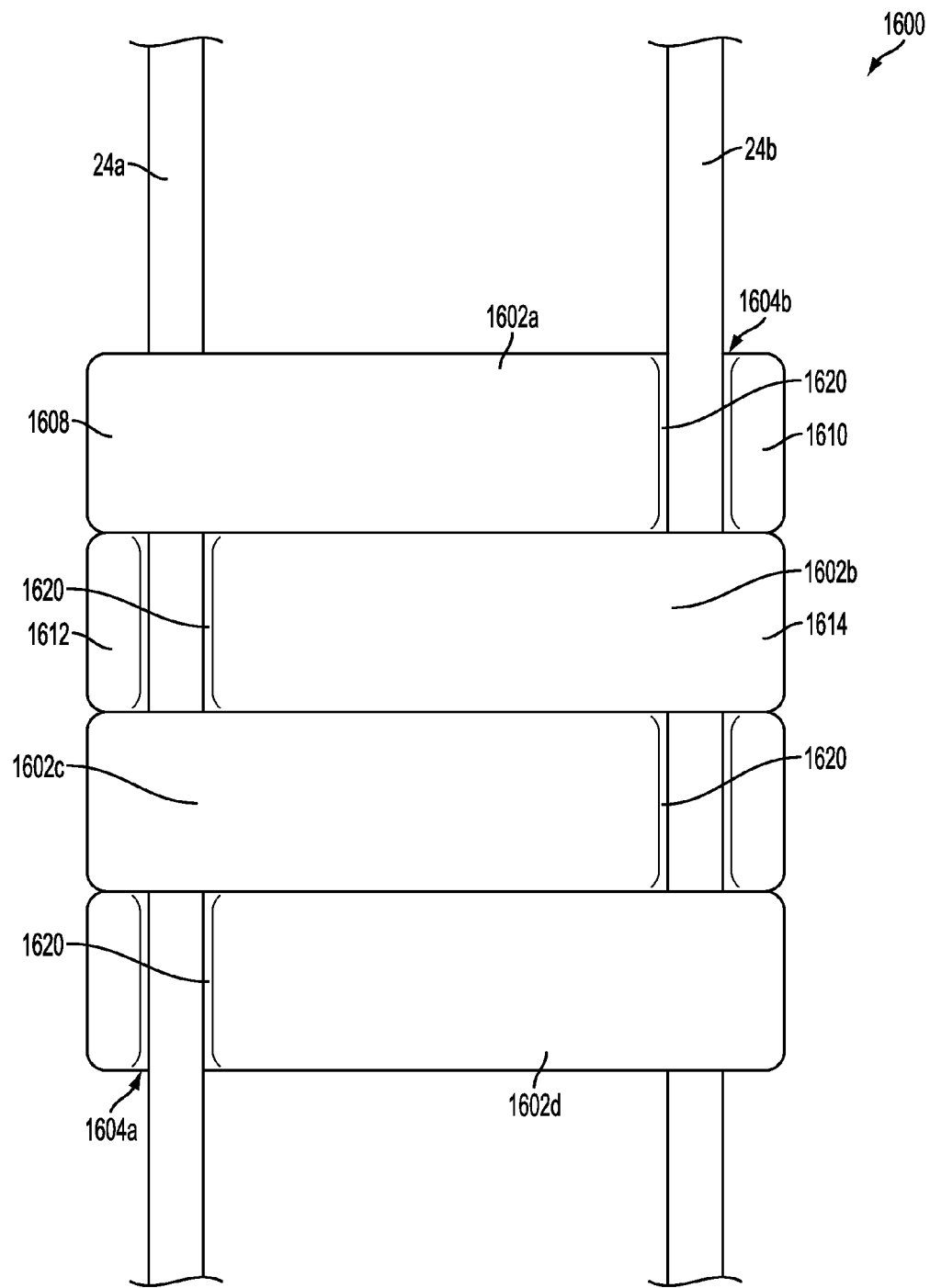
FIG. 46 is an elevational view of one embodiment of the probe guide of FIG. 45.
Figure 47:
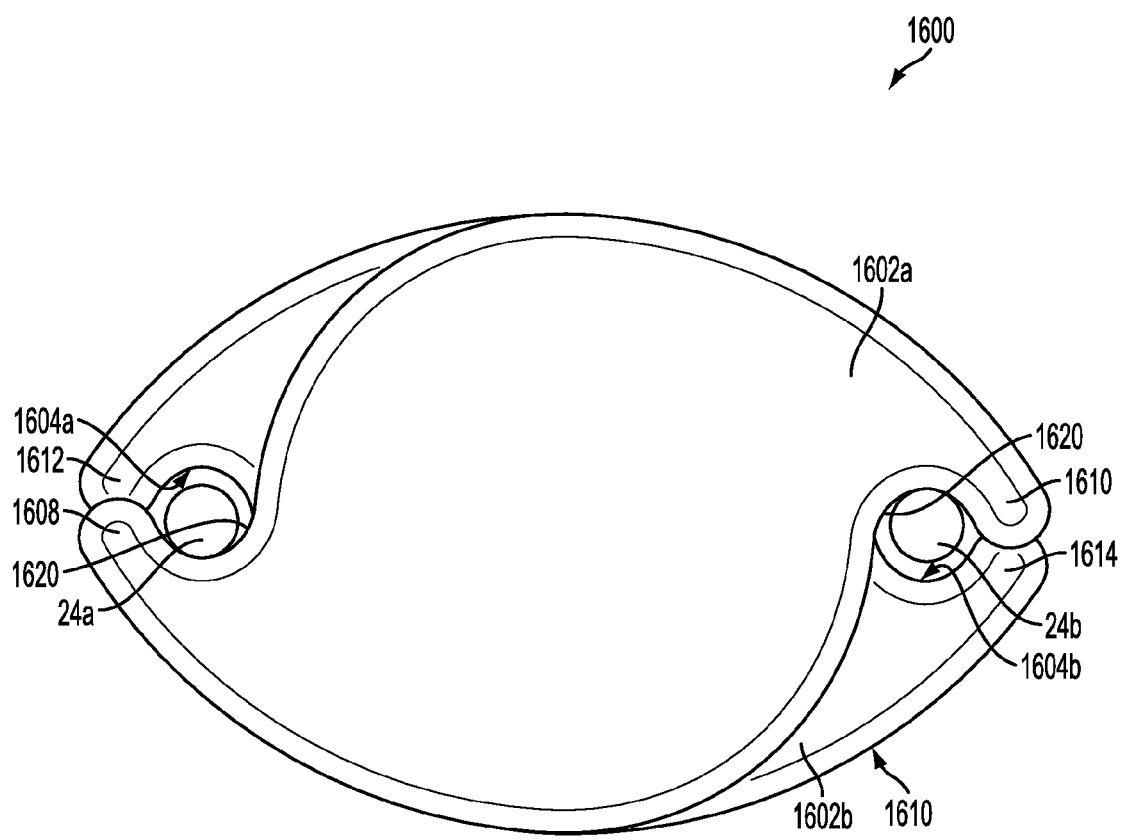
FIG. 47 is a plan view of one embodiment of the probe guide of FIG. 45.
Figure 48:
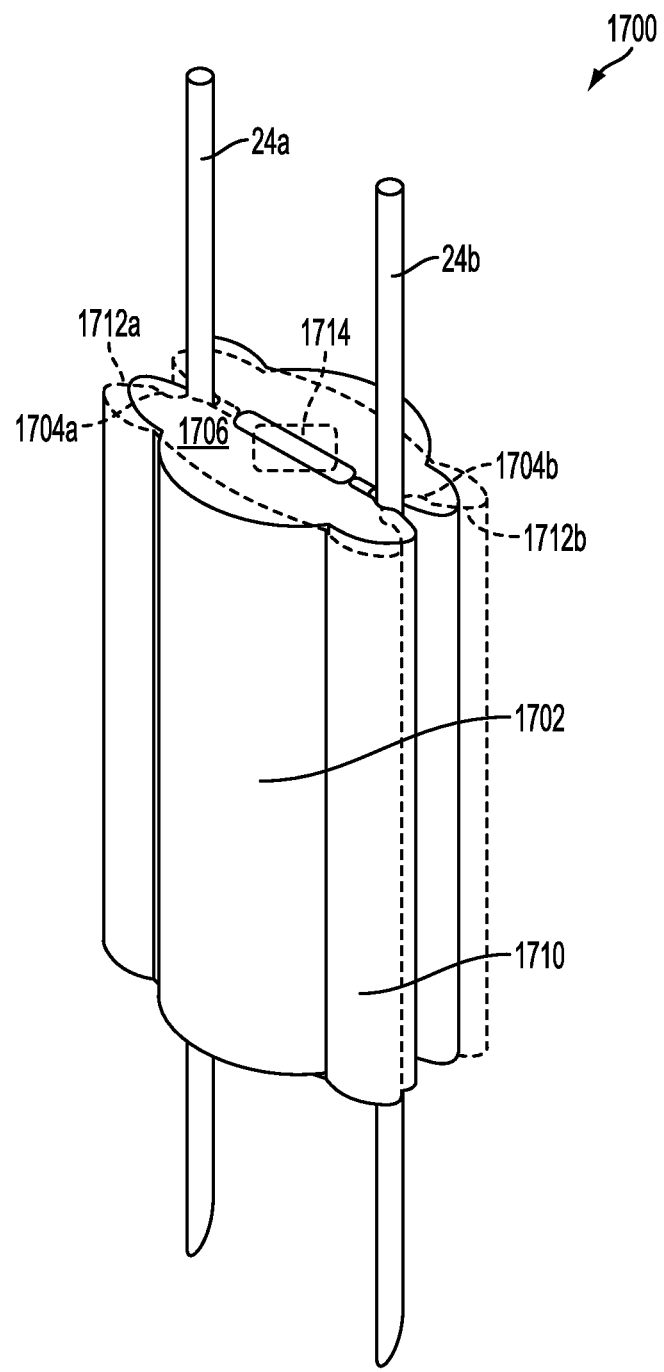
FIG. 48 is a perspective view an elastomeric probe guide showing the outline of the elastomeric probe guide in an initial, undeformed configuration and in a second, deformed configuration according to various embodiments of the present disclosure.

Referring to FIGS. 45-47, a probe guide 1600 can comprise a first body portion 1602a and a second body portion 1602b. In various embodiments, referring primarily to FIG. 47, the first body portion 1602a can comprise a first end first catch 1608 and a second end first catch 1610. The first end first catch 1608 can be positioned at or near a first distal end of the first body portion 1602a, for example, and the second end first catch 1610 can be positioned at or near a second distal end of the first body portion 1602a, for example. In various embodiments, the first end first catch 1608 and the second end first catch 1610 can each comprise an arcuate contour 1620 such that the first body portion 1602a turns or bends in a first direction at the first distal end and in a second direction at the second distal end. In some embodiments, the first direction can be an opposite or substantially opposite direction to the second direction. Further, in various embodiments, the second body portion 1602b can comprise a first end second catch 1612 and a second end second catch 1614. The first end second catch 1612 can be positioned at or near a first distal end of the second body portion 1602b, for example, and the second end second catch 1614 can be positioned at or near a second distal end of the second body portion 1602b, for example. In various embodiments, the first end second catch 1612 and the second end second catch 1614 can each comprise an arcuate contour 1620 such that the second body portion 1602b bends in a first direction at the first distal end and in a second direction at the second distal end. In some embodiments, the first direction can be an opposite or substantially opposite direction to the second direction.

In various embodiments, the first and second body portions 1602a, 1602b can be symmetrical or substantially symmetrical. Further, the first and second body portions 1602a, 1602b can be positioned relative to each other such that the first catches 1608, 1610 of the first body portion 1602a and the second catches 1612, 1614 of the second body portion 1602b can form passages through the probe guide 1600. For example, the second body portion 1602b can be positioned relative to the first body portion 1602a such that the first end first catch 1608 of the first body portion and the first end second catch 1612 of the second body portion 1602b form a first passage 1604a. Similarly, the second body portion 1602b can be positioned relative to the first body portion 1602a such that the second end first catch 1610 of the first body portion and the second end second catch 1614 of the second body portion 1602b form a second passage 1604b. Similar to embodiments described herein, the first passage 1604a can be structured to axially restrain the first electrode 24a, for example, and the second passage 1604b can be structured to axially restrain the second electrode 24b, for example.

In various embodiments, at least one of the first body portion 1602a and the second body portion 1602b can be pivotable. In various embodiments, the first body portion 1602a can pivot relative to the second body portion 1602b. In some embodiments, the first and second body portions 1602a, 1602b can be structured to pivot. The first body portion 1602a can pivot from an open guide position to a closed guide position, for example. In some embodiments, the first and second body portions 1602a, 1602b can pivot from the open guide position to the closed guide position. In various embodiments, when the first body portion 1602a is pivoted to the open guide position, a first outlet or opening (not shown) can open or expand. The first opening can extend from the first passage 1604a to an outer surface 1610 of the probe guide 1600, for example. In various embodiments, the first opening can be structured to receive the first electrode 24a (FIG. 1) when the first body portion 1602a is pivoted to the open position. Further, the first opening can permit movement of the first electrode 24a out of the first passage 1604a. In various embodiments, when the first body portion 1602a is pivoted to the closed position, the first opening can narrow or close such that the first opening cannot receive the first electrode 24a therethrough and the first electrode 24a cannot move in or out of the first passage 1604a.

In various embodiments, when the first body portion 1602a is pivoted to the open position, a second opening (not shown) can open or expand. The second opening can extend from the second passage 1604b to an outer surface 1610 of the probe guide 1600. In various embodiments, the second opening can be structured to receive the second electrode 24b (FIG. 1) when the first body portion 1602a is pivoted to the open position. Further, the second opening can permit movement of the second electrode 24b out of the second passage 1604b. In various embodiments, when the first body portion 1602a is pivoted to the closed position, the second opening can narrow or close such that the second opening cannot receive the second electrode 24b therethrough and the second electrode 24b cannot move in or out of the second passage 1604b.

In various embodiments, the probe guide 1600 can comprise an actuator (not shown). The actuator can pivot the first body portion between the open guide and closed guide positions. Further, in some embodiments, the actuator can be positioned in the hand piece 16 of the electrical ablation device 20 (FIG. 1). In some embodiments, the probe guide 1600 can also comprise a shell (not shown) structured to hold the first body portion 1602a relative to the second body portion 1602b. Furthermore, the probe guide 1600 can comprise additional body portions. For example, the probe guide can comprise a third body portion 1602c and a fourth body portion 1602d. In various embodiments, at least one of the first, second, third, and fourth body portions 1602a, 1602b, 1602c, 1602d can be symmetrical with another body portion 1602a, 1602b, 1602c, 1602d, for example.

Similar to embodiments described herein, the distal end of the first electrode 24a (FIG. 1) can be spaced from the distal end of the second electrode 24b (FIG. 1) by a predetermined distance when the first electrode 24a is axially restrained in the first passage 1604a and the second electrode 24b is axially restrained in the second passage 1604b, for example. Further, the predetermined distance can correspond to a treatment distance in a tissue treatment region. In at least one embodiment, the distal ends of the first and second electrodes 24a, 24b can be operably structured to conduct current therebetween when at least one of the first and second electrodes 24a, 24b is energized by an energy source 14 (FIG. 1), as described herein. During use, an operator can position the first electrode 24a relative to the tissue treatment region. As described herein, pre-operative and intra-operative three-dimensional imaging can aid the operator in placing the first electrode 24a in the target treatment zone of the tissue treatment region, for example. In various embodiments, the operator can puncture diseased tissue with the distal end of the first electrode 24a, for example, and insert at least a portion of the first electrode 24a therethrough. The distal end of the first electrode 24a can be inserted into the diseased tissue a predetermined depth, for example. Once the first electrode 24a is in place relative to the tissue treatment region, the operator may desire to position the second electrode 24b at a second position relative to the tissue treatment region such that a treatment distance is defined between the distal ends of the first and second electrodes 24a, 24b. A probe guide, such as probe guide 1600, for example, can be selected. In various embodiments, the selected probe guide 1600 can comprise a predetermined distance between the first and second passages 1604a, 1604b, which can correspond with a preferred treatment distance. The operator may pivot at least one of the first body portion 1602a and second body portion such that the first opening opens the first passage 1604a to the outer surface 1610 of the probe guide 1600. In at least one embodiment, the operator may engage an actuator to open or enlarge the first passage 1604a to the outer surface 1610. Upon opening or enlarging the first passage 1604a to the outer surface 1610 of the probe guide 1600, the first electrode 24a can pass through the first opening to the first passage 1604a. Once the first electrode 24a is positioned in the first passage 1604a, the operator can pivot at least one of the first body portion 1602a and the second body portion 1602b such that the first opening narrows or closes the first passage 1604a to the outer surface 1610 of the probe guide 1600. The narrowed or closed first passage 1604a can axially restrain the first electrode 24a therein.

In various embodiments, the second passage 1604b can be defined through at least a portion of the probe guide 1600 when at least one of the first body portion 1602a and second body portion 1602b is pivoted to the closed position. In such embodiments, the second opening may be closed or narrowed such that the second electrode 24b can be axially restrained in the second passage 1604b. In various embodiments, when the first and/or second body portions 1602a, 1602b are pivoted to the closed position, the distal end of the second electrode 24b can be axially advanced through the second passage 1604b to the tissue treatment region. As the distal end of the second electrode 24b is advanced through the second passage 1604b, the second passage 1604b can guide the second electrode 24b a predetermined distance from the distal end of the first electrode 24a, for example, and/or along a path parallel or substantially parallel to the first electrode 24a, for example.

Figure 49:
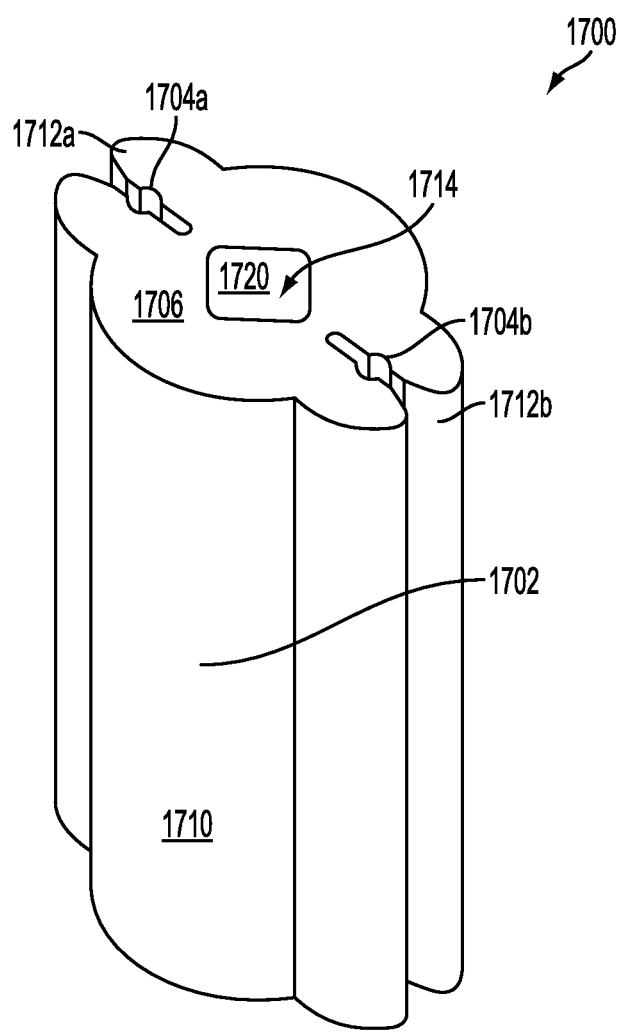
FIG. 49 is a perspective view of one embodiment of the elastomeric probe guide of FIG. 48 depicting the body portion in the initial, undeformed configuration.
Figure 50:
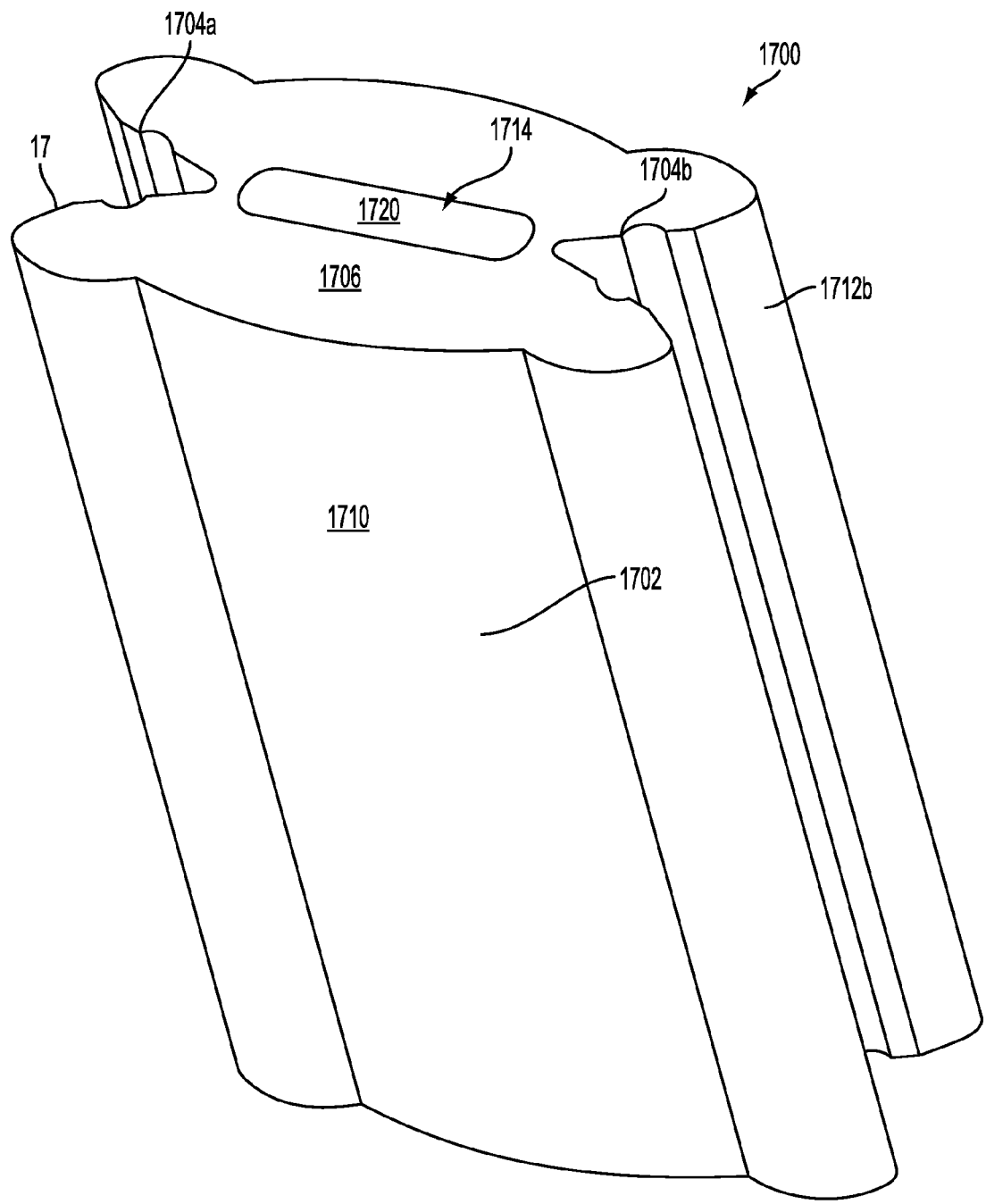
FIG. 50 is a perspective view of one embodiment of the elastomeric probe guide of FIG. 48 depicting the body portion in the second, deformed configuration.
Figure 51:
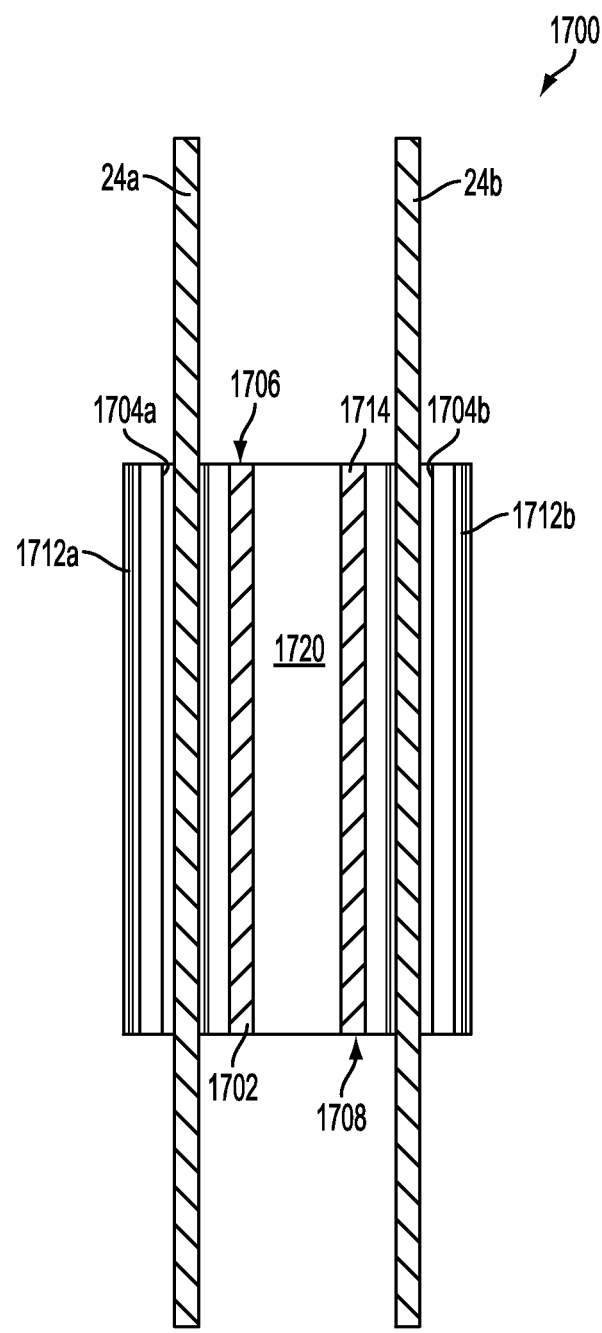
FIG. 51 is an elevational, cross-sectional view of one embodiment of the elastomeric probe guide of FIG. 48 depicting the body portion in an initial, undeformed configuration.

Referring to FIGS. 48-51, a probe guide 1700 can comprise a body 1702. In various embodiments, the body 1702 can comprise a resilient and/or elastomeric material such that the body 1702 seeks to return to an initial configuration when the body 1702 is deformed from the initial configuration to a deformed configuration. The body 1702 can comprise Pellethane® TPE, Santoprene™ thermoplastic vulcanizate (TPV), and/or silicone, for example. In various embodiments, the body 1702 can comprise silicone, for example, having a durometer Shore A hardness of 40-90. In at least one embodiment, referring primarily to FIG. 51, the probe guide 1700 can comprise a bore 1714 at least partially therethrough. The bore can extend from a top or proximal surface 1706 to a bottom or distal surface 1708, for example. In various embodiments, the bore 1714 can define an inner surface 1720 through the body 1702. In some embodiments, the inner surface 1720 of the bore 1714 can be deformable from an initial configuration to at least one deformed configuration. In various embodiments, the probe guide 1700 can also comprise a first passage 1704a through the body 1702 and/or a second passage 1704b though the body 1702. The first passage 1704a can be positioned on a first side of the bore 1714, for example, and the second passage 1704b can be positioned on a second side of the bore 1714, for example. In at least one embodiment, the first passage 1704a can be structured to axially restrain the first electrode 24a when the body 1702 and/or the inner surface 1720 of the bore 1714 is in the initial configuration (FIG. 49). Further, in at least one embodiment, the second passage 1704b can be structured to axially restrain the second electrode 24*b* when the body 1702 and/or the inner surface 1720 of the bore is in the initial configuration (FIG. 49). In various embodiments, the first electrode 24*a* can be releasable from the first passage 1704*a* when the body 1702 and/or the inner surface 1720 of the bore 1714 is moved from the initial configuration to a deformed configuration (FIG. 50). Further, in various embodiments, the second electrode 24*b* can be releasable from the second passage 1704*b* when the body 1702 and/or the inner surface 1720 of the bore 1714 is moved from the initial configuration to a deformed configuration (FIG. 50). As described herein, the first and second electrodes 24*a*, 24*b* can be released from the first and second passages 1704*a*, 1704*b* through outlets 1712*a*, 1712*b*, respectively.

In various embodiments, the bore 1714 can comprise a maximum diameter or width across the bore 1714. In some embodiments, the bore 1714 can comprise a substantially cubic, rhombic, or rectangular cross-sectional geometry when the body 1702 is in the initial, undeformed configuration. In other embodiments, the cross-sectional geometry of the bore 1714 can comprise a circular, elliptical, or polygonal shape. When the body 1702 and/or the inner surface 1720 of the bore 1714 is moved to a deformed configuration, the maximum width of the bore 1714 can be reduced, the maximum length across the bore 1714 can be increased, and/or the cross-sectional geometry of the bore 1714 can be altered. In various embodiments, the maximum width across the bore 1714 can be reduced, the maximum length across the bore can be increased, and the cross-sectional geometry of the bore 1714 can be changed from a substantially rhombic geometry to a substantially elongated oval geometry.

In various embodiments, the body 1702 can also comprise at least one outlet or slot 1712*a*, 1712*b*. In at least one embodiment, a first outlet 1712*a* can extend from the outer surface 1710 of the body 1702 to at least the first passage 1704*a*, for example, and a second outlet 1712*b* can extend from the outer surface 1710 to at least the second passage 1704*b*, for example. The first outlet 1712*a* can extend from a first side of the body 1702 towards the bore 1714, for example, and the second outlet 1712*b* can extend from a second side of the body towards the bore 1714, for example. In various embodiments, the geometry of the outlets 1712*a*, 1712*b* can be altered when the body 1702 and/or the inner surface 1720 of the bore 1714 is moved from an initial configuration to a deformed configuration. The outlets 1712*a*, 1712*b* can comprise an outward flare, for example, when the body 1702 and/or the inner surface of the bore 1714 is moved to a deformed configuration (FIG. 50). As described herein, altering the geometry of the outlets 1712*a*, 1712*b* can permit the release of the first and/or second electrodes 24*a*, 24*b* from the first and/or second passages 1704*a*, 1704*b*, respectively.

In various embodiments, the first outlet 1712*a* can comprise a first minimum diameter when the body 1702 and/or the inner surface 1720 of the bore 1714 is in an initial configuration and the first outlet 1712*a* can comprise a second minimum diameter when the body 1702 and/or the inner surface 1720 of the bore 1714 is in a deformed configuration. In at least one embodiment, the first minimum diameter can be less than the second minimum diameter. Further, in various embodiments, the first minimum diameter can be less than the diameter of the first electrode 24*a*, for example, and the second minimum diameter can be greater than the diameter of the first electrode 24*a*, for example. In such embodiments, the first electrode 24*a* can move through the first outlet 1712*a* when the body 1702 and/or the inner surface 1720 of the bore 1714 is in a deformed configuration, for example. Further, the first electrode 24*a* can be restrained in the first passage 1704*a* when the body 1702 and/or the inner surface 1720 of the bore 1714 is in the initial configuration, i.e., the first electrode 24*a* cannot move or fit through the first outlet 1712*a*, for example. In some embodiments, the first minimum diameter of the first outlet 1712*a* can substantially match the diameter of the first electrode 24*a* and, in various embodiments, the first outlet 1712*a* can apply a clamping force to the first electrode 24*a* to hold the first electrode 24*a* in position when the body 1702 and/or the inner surface 1720 of the bore 1714 is in the initial configuration.

Similarly, in various embodiments, the second outlet 1712*b* can comprise a first minimum diameter when the body 1702 and/or the inner surface 1720 of the bore 1714 is in an initial configuration and the second outlet 1712*b* can comprise a second minimum diameter when the body 1702 and/or the inner surface 1720 of the bore 1714 is in a deformed configuration. In at least one embodiment, the first minimum diameter can be less than the second minimum diameter. Further, in various embodiments, the first minimum diameter can be less than the diameter of the second electrode 24*b*, for example, and the second minimum diameter can be greater than the diameter of the second electrode 24*b*, for example. In such embodiments, the second electrode 24*b* can move through the second outlet 1712*b* when the body 1702 and/or the inner surface 1720 of the bore 1714 is in a deformed configuration, for example. Further, the second electrode 24*b* can be restrained in the second passage 1704*b* when the body 1702 and/or the inner surface 1720 of the bore 1714 is in the initial configuration, i.e., the second electrode 24*b* cannot move or fit through the second outlet 1712*b*, for example. In some embodiments, the first minimum diameter of the second outlet 1712*b* can substantially match the diameter of the second electrode 24*b* and, in various embodiments, the second outlet 1712*b* can apply a clamping force to the second electrode 24*b* to hold the second electrode 24*b* in position when the body 1702 and/or the inner surface 1720 of the bore 1714 is in the initial configuration.

Similar to embodiments described herein, the distal end of the first electrode 24*a* can be spaced from a distal end of the second electrode 24*b* by a predetermined distance when the first electrode 24*a* is axially restrained in the first passage 1704*a* and the second electrode 24*b* is axially restrained in the second passage 1704*b*, for example. Further, the predetermined distance can correspond to a treatment distance in a tissue treatment region. In at least one embodiment, the distal ends of the first and second electrodes 24*a*, 24*b* can be operably structured to conduct current therebetween when at least one of the first and second electrodes 24*a*, 24*b* is energized by an energy source 14 (FIG. 1), as described herein. During use, an operator can position the first electrode 24*a* relative to the tissue treatment region. As described herein, pre-operative and intra-operative three-dimensional imaging can aid the operator in placing the first electrode 24*a* in the target treatment zone of the tissue treatment region, for example. Once the first electrode 24*a* is in place relative to the tissue treatment region, the operator may desire to position the second electrode 24*b* at a second position relative to the tissue treatment region such that a treatment distance is defined between the distal ends of the first and second electrodes 24*a*, 24*b*, for example. A probe guide, such as probe guide 1700, for example, can be selected by the operator. In various embodiments, the selected probe guide 1700 can comprise a predetermined distance between the first and second passages 1704a, 1704b, which can correspond with a preferred treatment distance between electrodes 24a, 24b. The operator may deform the body 1702 and/or the inner surface 1720 of the bore 1714 from the initial configuration to a deformed configuration such that the geometry of the first outlet 1712a changes to accommodate the first electrode 24a therethrough (FIG. 50). Upon deforming the probe guide 1700, the first electrode 24a can pass through the first outlet 1712a to the first passage 1704a. Once the first electrode 24a is positioned in the first passage 1704a, the operator can release the body 1702 of the probe guide 1700. In at least one embodiment, the body 1702 can seek to return to the initial, undeformed configuration when released by the operator, for example (FIG. 49). Further, the probe guide 1700 can substantially return to the initial, undeformed configuration such that the first and second passages 1704a, 1704b are structured to axially restrain the first and second electrodes 24a, 24b, respectively.

In various embodiments, the second passage 1704b can be defined through at least a portion of the probe guide 1700 when the body 1702 and/or the inner surface 1720 of the bore 1714 returns or substantially returns to the initial, undeformed configuration (FIG. 49). In such embodiments, the second outlet 1712b may be closed or narrowed such that the second electrode 24b can be axially restrained in the second passage 1704b, i.e., the second electrode 24b cannot move through the second outlet 1712b out of the second passage 1704b. In various embodiments, when the body 1702 has substantially returned in the initial configuration, the distal end of the second electrode 24b can be axially advanced through the second passage 1704b to the tissue treatment region. As the distal end of the second electrode 24b is advanced through the second passage 1704b, the second passage 1704b can guide the second electrode 24b a predetermined distance from the distal end of the first electrode 24a, for example, and/or along a path parallel or substantially parallel to the first electrode 24a, for example.

Figure 52:
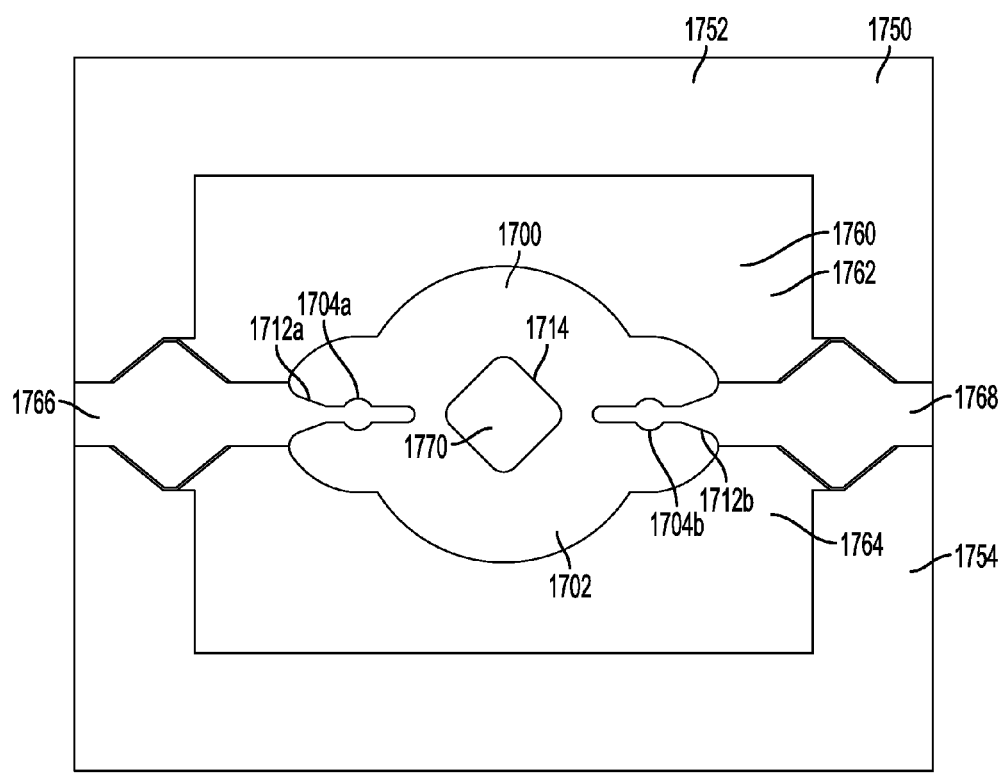
FIG. 52 is a plan view of a frame for molding the elastomeric probe guide of FIG. 48 according to various embodiments of the present disclosure.

Referring primarily to FIG. 52, the probe guide 1700 can be manufactured by a molding technique, for example. In various embodiments, a frame 1750 can comprise a top 1752 and a bottom 1754. In some embodiments, a mold 1760 can comprise an upper portion 1762, a lower portion 1764, a first side portion 1766, a second side portion 1768 and/or a central portion 1770, for example. In at least one embodiment, the lower portion 1764 of the mold 1760 can be removably positioned in the bottom 1754 of the frame 1750, for example, and/or the upper portion 1762 of the mold 1760 can be removably positioned in the top 1752 of the frame 1750, for example. The upper portion 1762 of the mold 1760 can comprise a surface that corresponds to the outer surface 1710 of the body 1702 of the probe guide 1700, for example. Further, the lower portion 1764 of the mold 1760 can comprise a surface that corresponds to the outer surface 1710 of the body 1702 of the probe guide 1700, for example. In at least one embodiment, at least a portion of the second side portion 1766 can comprise a geometry that corresponds to the geometry of the second outlet 1712b and/or the second passage 1704b, for example. Further, at least a portion of the first side portion 1768 can comprise a geometry that at least substantially corresponds to the geometry of the first outlet 1712a and/or the first passage 1704a, for example.

In various embodiments, the upper portion 1762, the lower portion 1764, the first side portion 1766, and the second side portion 1768 can be positioned between the top 1752 and the bottom 1754 of the frame 1750. Further, the central portion 1770 can be positioned between the upper portion 1762, the lower portion 1764, the first side portion 1766 and the second side portion 1768. The central portion 1770 can be held or retained in place by a pin or bracket in an end wall (not shown) of the frame 1750, for example. In at least one embodiment, once the mold 1760 is positioned in the frame 1750, the material forming the body 1702 of the probe guide 1700 can be added to the frame 1750. The body material 1702 can be fluidic when added to the frame 1750. In various embodiments, the body material can be poured into the frame 1750 and can flow around the first and second side portions 1766, 1768 and the central portion 1770, for example. In various embodiments, after the body material cures, or at least sufficiently cures, the body 1702 of the probe guide 1700 can be removed from the frame 1750.

Figure 53:
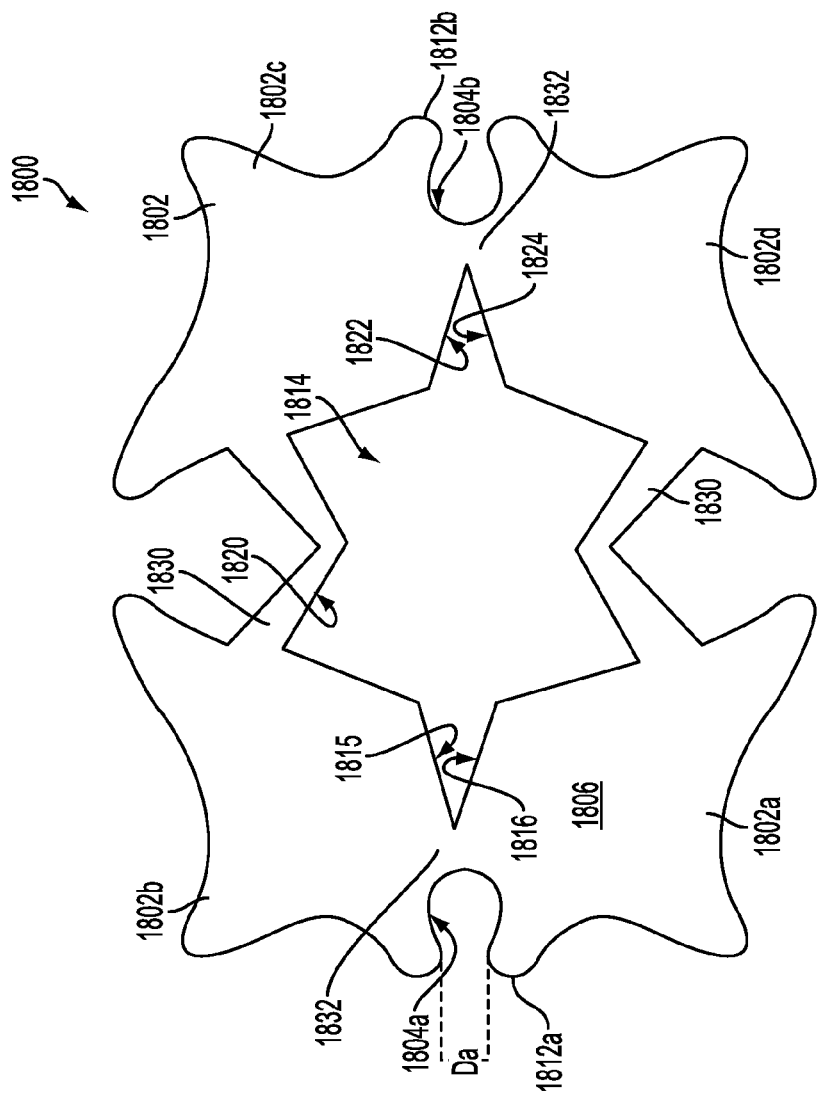
FIG. 53 is an elevational view of an elastomeric probe guide depicting the probe guide in an initial, undeformed configuration according to various embodiments of the present disclosure.
Figure 54:
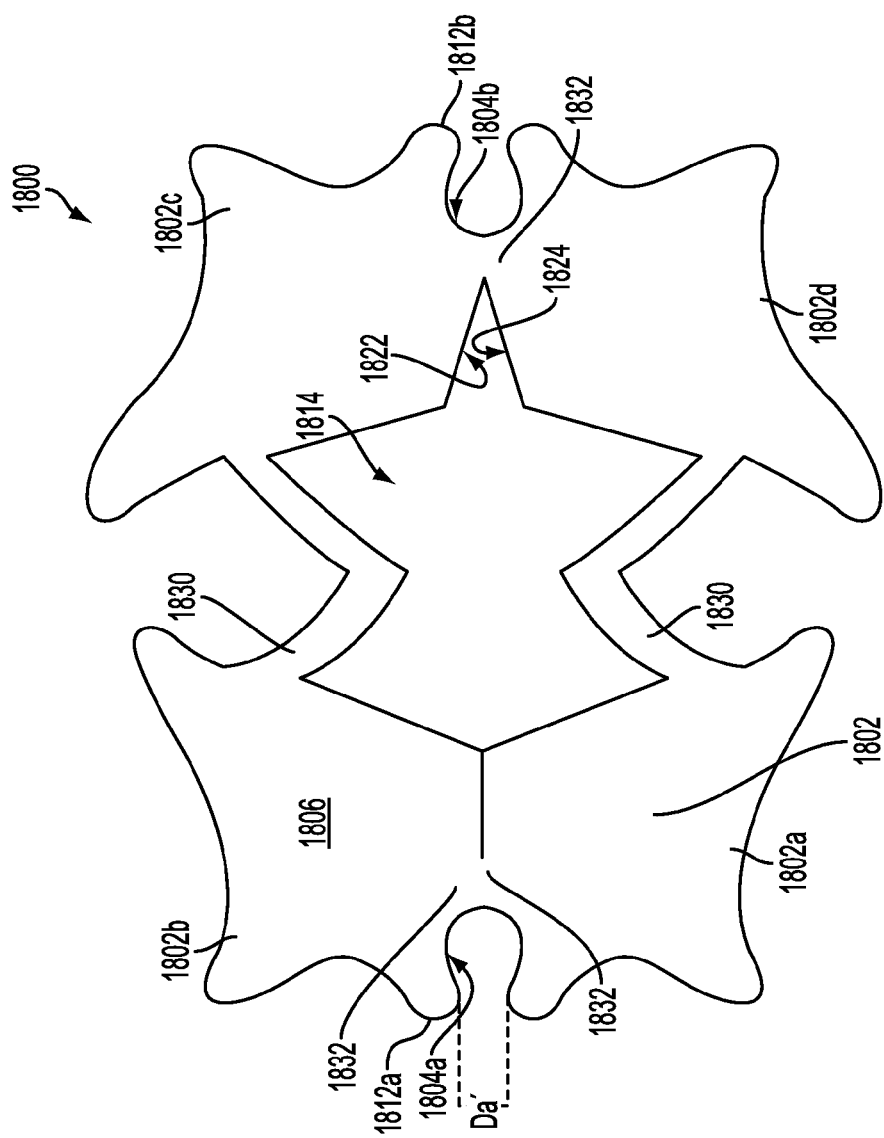
FIG. 54 is an elevational view of one embodiment of the elastomeric probe guide of FIG. 43 depicting the probe guide in a deformed configuration.

Referring to FIGS. 53 and 54, a probe guide 1800 can comprise a body 1802. In various embodiments, the body 1802 can comprise a resilient and/or elastomeric material such that the body 1802 seeks to return to an initial configuration when the body is deformed from the initial configuration to a deformed configuration. The body 1802 can comprise Pellethane® TPE, Santoprene™ thermoplastic vulcanizate (TPV), and/or silicone, for example. In various embodiments, the body 1702 can comprise silicone, for example, having a durometer Shore A hardness of 40-90. In at least one embodiment, the probe guide 1800 can comprise a bore 1814 at least partially therethrough. The bore 1814 can extend from a top or proximal surface 1806 to a bottom or distal surface (not shown), for example. In various embodiments, the bore 1814 can define an inner surface 1820 through the body 1802. In some embodiments, the inner surface 1820 of the bore 1814 can be deformable from an initial configuration to at least one deformed configuration. In various embodiments, the probe guide 1800 can also comprise a first passage 1804a through the body 1802 and/or a second passage 1804b though the body 1802. The first passage 1804a can be positioned on a first side of the bore 1814, for example, and the second passage 1804b can be positioned on a second side of the bore 1814, for example. In at least one embodiment, the first passage 1804a can be structured to axially restrain the first electrode 24a (FIG. 1) when the body 1802 and/or the inner surface 1820 of the bore 1814 is in the initial configuration (FIG. 53). Further, in at least one embodiment, the second passage 1804b can be structured to axially restrain the second electrode 24b (FIG. 1) when the body 1802 and/or the inner surface 1820 of the bore 1814 is in the initial configuration (FIG. 53). In various embodiments, the first electrode 24a can be releasable from the first passage 1804a when the body 1802 and/or the inner surface 1820 of the bore 1814 is moved from the initial configuration to a deformed configuration (FIG. 54). Further, in various embodiments, the second electrode 24b can be releasable from the second passage 1804b when the body 1802 and/or the inner surface 1820 of the bore 1814 is moved from the initial configuration to a deformed configuration (FIG. 54). As described herein, the first and second electrodes 24a, 24b can be released from the first and second passages 1804a, 1804b through outlets 1812a, 1812b, respectively. Deformation of the body 1802 and/or the inner surface 1820 of the bore 1814 can open the first passage 1804a, the second passage 1804b or both passages 1804a, 1804b, for example, to permit the release of the first electrode 24a, the second electrode 24b and/or both electrodes 24a, 24b, respectively.

In various embodiments, the inner surface 1820 of the bore 1814 can comprise a first edge 1815 and a second edge 1816. The first edge 1815 can be angularly offset from the second edge 1816 when the inner surface 1820 is in the initial configuration, for example. Further, the first edge 1815 can substantial abut or be substantially flush with the second edge 1816 when the inner surface 1820 is in a first deformed configuration, for example. Similarly, in various embodiments, the inner surface 1820 of the bore 1814 can comprise a third edge 1822 and a fourth edge 1824. The third edge 1822 can be angularly offset from the fourth edge 1824 when the inner surface in the initial configuration, for example. Further, the third edge 1822 can substantially abut or be substantially flush with the fourth edge 1824 when the inner surface 1820 is in a second deformed configuration. In various embodiments, the first deformed configuration can match or substantially match the second deformed configuration. In such embodiments, the first edge 1815 can be angularly offset from the second edge 1816 when the third edge 1822 is angularly offset from the fourth edge 1824, for example. Furthermore, in such embodiments, the first edge 1815 can substantially abut the second edge 1816 when the third edge 1822 substantially abuts the fourth edge 1824, for example. In various other embodiments, the first deformed configuration may not match the second deformed configuration. In such embodiments, the first edge 1815 can substantially abut the second edge 1816 even when the third edge 1822 does not substantially abut the fourth edge 1824, for example. In various embodiments, for example, the inner surface 1820 or the bore 1814 can be deformed such that the first edge 1815 substantially abuts the second edge 1816, however, despite such deformation of the inner surface 1820, the third and fourth edges 1822, 1824 can remain angularly offset, and thus, the initial minimum diameter of the second outlet 1812b can restrain the second electrode 24b (FIG. 1) such that the second electrode 24b is held in the second passage 1804b while the first electrode 24a can move through the first outlet 1812a. Furthermore, in various embodiments, when the first and second edges 1815, 1816 substantially abut and the third and fourth edges 1822, 824 remain angularly offset, the distance between the passages 1804a, 1804b can remain substantially the same.

Figure 55:
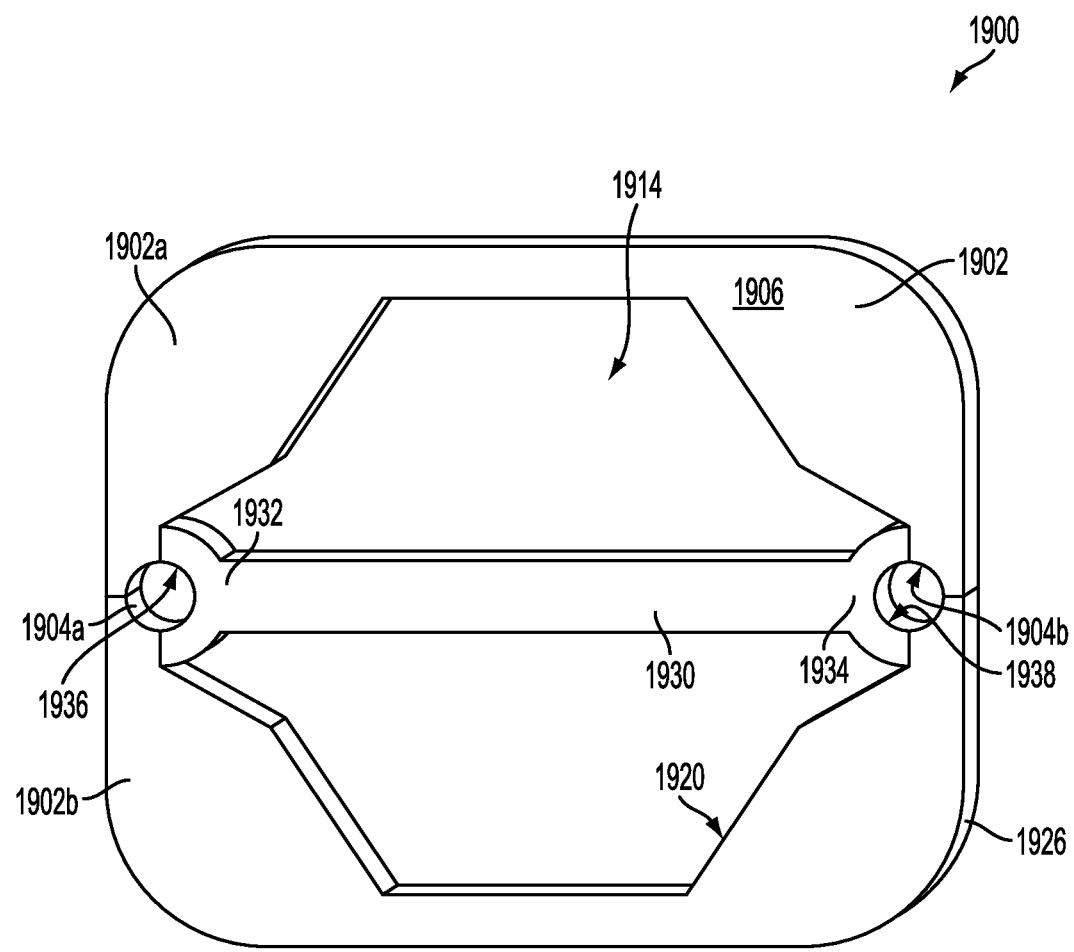
FIG. 55 is an elevational view of a probe guide having an elastomeric body and a substantially rigid beam according to various embodiments of the present disclosure.

Referring still to FIGS. 53 and 55, the body 1802 of the probe guide 1800 can comprise a plurality of body portions. The probe guide 1800 can comprise first, second, third and fourth body portions 1802a, 1802b, 1802c, 1802d, for example. In various embodiments, flanges 1830 can extend between at least two adjacent body portions. A flange 1830 can extend between the second and the third body portions 1802b, 1802c, for example, and another flange 1830 can extend between the fourth and the first body portions 1802d, 1802a, for example. In various embodiments, at least one of the flanges 1830 and/or the body portions 1802 comprises a resilient and/or elastomeric material. In various embodiments, at least two adjacent body portions can be attached at a flexible joint 1832. For example, the first and second body portions 1802a, 1802b can be attached at a flexible joint 1832 and the third and fourth body portions 1802c, 1802d can be attached at a flexible joint 1832, for example. In various embodiments, the flexible joints 1832 can permit the attached body portions to hinge relative to each other.

Referring primarily to FIG. 53, in at least one embodiment, the first passage 1804a and/or the first outlet 1812a can be formed between the first and second body portions 1802a, 1802b. The first outlet 1812a can comprise an initial minimum diameter $D_a$ when the inner surface 1820 of the bore 1814 is in the initial configuration, for example. In at least one embodiment, the initial minimum diameter $D_a$ of the first outlet 1812a can restrain the first electrode 24a (FIG. 1) such that the first electrode 24a is held in the first passage 1804a. Referring now to FIG. 54, when the inner surface 1820 of the bore 1814 is moved to a first deformed configuration, the first outlet 1812a can comprise a deformed minimum diameter $D_a'$, for example. The deformed minimum diameter $D_a'$ be larger than the initial minimum diameter $D_a$ such that the first outlet 1812a can permit movement of the first electrode 24a in or out of the first passage 1804a, for example.

Additionally or alternatively, the second passage 1804c and/or the second outlet 1812b can be formed between the third and fourth body portions 1802c, 1802d. The second outlet 1812a can comprise an initial minimum diameter when the inner surface 1820 of the bore 1814 is in the initial configuration, for example. In at least one embodiment, the initial minimum diameter of the second outlet 1812b can restrain the second electrode 24b such that the second electrode 24b is held in the second passage 1804b. When the inner surface 1820 is moved to a second deformed configuration, the second outlet 1812b can comprise a deformed minimum diameter, which can be larger than the initial minimum diameter such that the second outlet 1812b can permit movement of the second electrode 24b in or out of the second passage 1804b, for example.

Similar to embodiments described herein, the distal end of the first electrode 24a (FIG. 1) can be spaced from a distal end of the second electrode 24b (FIG. 1) by a predetermined distance when the first electrode 24a is axially restrained in the first passage 1804a and the second electrode 24b is axially restrained in the second passage 1804b, for example. Further, the predetermined distance can correspond to a treatment distance in a tissue treatment region. In at least one embodiment, the distal ends of the first and second electrodes 24a, 24b can be operably structured to conduct current therebetween when at least one of the first and second electrodes 24a, 24b is energized by an energy source 14 (FIG. 1), as described herein. During use, an operator can position the first electrode 24a relative to the tissue treatment region. As described herein, pre-operative and intra-operative three-dimensional imaging can aid the operator in placing the first electrode 24a in the target treatment zone of the tissue treatment region, for example. Once the first electrode 24a is in place relative to the tissue treatment region, the operator may desire to position the second electrode 24b at a second position relative to the tissue treatment region such that a treatment distance is defined between the distal ends of the first and second electrodes 24a, 24b, for example. A probe guide, such as probe guide 1800, for example, can be selected by the operator. In various embodiments, the selected probe guide 1800 can comprise a predetermined distance between the first and second passages 1804a, 1804b, which can correspond with a preferred treatment distance between electrodes 24a, 24b. The operator may deform the body 1802 and/or the inner surface 1820 of the bore 1814 from the initial configuration (FIG. 53) to a deformed configuration (FIG. 54) wherein the geometry of the first outlet 1812a changes to accommodate the first electrode 24a therethrough. Upon deforming the probe guide 1800, the first electrode 24a can pass through the first outlet 1812a to the first passage 1804a. Once the first electrode 24a is positioned in the first passage 1804a, the operator can release the body 1802 of the probe guide 1800. In various embodiments, the body 1802 can seek to return to the initial, undeformed configuration (FIG. 53) when released by the operator, for example. Further, the probe guide 1800 can return or substantially return to the initial, undeformed configuration such that the first and second passages 1804*a*, 1804*b* are structured to axially restrain the first and second electrodes 24*a*, 24*b*, respectively.

In various embodiments, the second passage 1804*b* can be defined through at least a portion of the probe guide 1800 when the body 1802 and/or the inner surface 1820 of the bore 1814 returns or substantially returns to the initial, undeformed configuration (FIG. 53). In such embodiments, the second outlet 1812*b* may be closed or narrowed such that the second electrode 24*b* can be axially restrained in the second passage 1804*b*, i.e., the second electrode 24*b* cannot move through the second outlet 1812*b* in or out of the second passage 1804*b*. In various embodiments, when the body 1802 has returned or substantially returned in the initial configuration, the distal end of the second electrode 24*b* can be axially advanced through the second passage 1804*b* to the tissue treatment region. As the distal end of the second electrode 24*b* is advanced through the second passage 1804*b*, the second passage 1804*b* can guide the second electrode 24*b* a predetermined distance from the distal end of the first electrode 24*a*, for example, and/or along a path substantially parallel to the first electrode 24*a*, for example. In other embodiments, the body 1802 and/or the inner surface 1820 of the bore 1814 can be deformed such that the second outlet 1812*b* opens or enlarges to permit lateral movement of the second electrode 24*b* therethrough to the second passage 1804*b*. Subsequently, the body 1802 can be released and the body 1802 can return or substantially return to the initial, undeformed configuration (FIG. 53), wherein the first and second electrodes 24*a*, 24*b* are axially restrained in the first and second passages 1804*a*, 1804*b*, respectively.

Referring to FIG. 55, a probe guide 1900 can comprise a body 1902. In various embodiments, the body 1902 can comprise a resilient and/or elastomeric material such that the body 1902 seeks to return to an initial configuration when the body is deformed from the initial configuration to a deformed configuration. The body 1902 can comprise Pellethane® TPE, Santoprene™ thermoplastic vulcanizate (TPV), and/or silicone, for example. In various embodiments, the body 1702 can comprise silicone, for example, having a durometer Shore A hardness of 40-90. In at least one embodiment, the probe guide 1900 can comprise a bore 1914 at least partially extending through the body 1902. The bore 1914 can extend from a top or proximal surface 1906 to a bottom or distal surface (not shown), for example. In various embodiments, the bore 1914 can define an inner surface 1920 through the body 1902. In some embodiments, the inner surface 1920 of the bore 1914 can be deformable from an initial configuration to at least one deformed configuration. In various embodiments, the probe guide 1900 can also comprise a first passage 1904*a* through the body 1902 and/or a second passage 1904*b* though the body 1902. The first passage 1904*a* can be positioned on a first side of the bore 1914, for example, and the second passage 1904*b* can be positioned on a second side of the bore 1914, for example. In at least one embodiment, the first passage 1904*a* can be structured to axially restrain the first electrode 24*a* when the body 1902 and/or the inner surface 1920 of the bore 1914 is in the initial configuration (FIG. 55). Further, in at least one embodiment, the second passage 1904*b* can be structured to axially restrain the second electrode 24*b* when the body 1902 and/or the inner surface 1920 of the bore is in the initial configuration. In various embodiments, the first electrode 24*a* can be releasable from the first passage 1904*a* when the body 1902 and/or the inner surface 1920 of the bore 1914 is moved from the initial configuration to a deformed configuration (not shown). Further, in various embodiments, the second electrode 24*b* can be releasable from the second passage 1904*b* when the body 1902 and/or the inner surface 1920 of the bore 1914 is moved from the initial configuration to a deformed configuration. As described herein, the first and second electrodes 24*a*, 24*b* can be released from the first and second passages 1904*a*, 1904*b* through outlets (not shown).

In various embodiments, the body 1902 of the probe guide 1900 can comprise a first body portion 1902*a* and a second body portion 1902*b*. In at least one embodiment, the first body portion 1902*a* can comprise an upper portion of the probe guide 1900, for example, and the second body portion 1902*b* can comprise a lower portion of the probe guide 1900, for example. Further, in various embodiments, at least one passage 1904*a*, 1904*b* can be positioned between and/or adjacent to the first and second body portions 1902*b*. For example, the first passage 1904*a* can be positioned between the first and second body portions 1902*a*, 1902*b* on a first side of the bore 1914 and the second passage 1904*b* can be positioned between the first and second body portions 1902*a*, 1902*b* on a second side of the bore 1914.

In at least one embodiment, the probe guide 1900 can also comprise a beam 1930. The beam 1903 can laterally traverse the bore 1914 from the first side to the second side of the probe guide 1900, for example. In various embodiments, the beam 1930 can comprise a substantially rigid or inflexible material such as polystyrene or a thermoplastic polymer, for example, polyethylene or polycarbonate, such as, for example, Lexan®, Makrolon®, Makroclear®. The beam 1930 can comprise a first end 1932 and a second end 1934, for example. In some embodiments, the first end 1932 can be positioned adjacent to the first passage 1904*a*, for example, and the second end 1934 can be positioned adjacent to the second passage 1904*b*, for example. In at least one embodiment, the first end 1932 can comprise a first groove 1936 and/or the second end 1934 can comprise a second groove 1938. The grooves 1936, 1938 can comprise an arcuate contour and/or semi-circle, for example. In various embodiments, the first groove 1936 can form a portion of the first passage 1904*a* and the second groove 1938 can for a portion of the second passage 1904*b*.

Referring still to FIG. 55, the beam 1930 can resist deformation when the inner surface 1920 of the bore 1914 is moved from an initial configuration to a deformed configuration. In at least one embodiment, when at least one of the body portions 1902*a*, 1902*b* and the inner surface 1920 of the probe guide 1900 is moved to a deformed configuration, the first and/or second passages 1904*a*, 1904*b* can open such that an electrode 24*a*, 24*b* can move into and/or out of the passages 1904*a*, 1904*b*, for example. In various embodiments, the first body portion 1902*a* can move away from the second body portion 1902 at the first passage 1904*a*, the second passage 1904*b* or both passages 1904*a*, 1904*b* to open the passage(s) 1904*a*, 1904*b* to an outer surface 1926 of the probe guide 1900. As the body portions 1902*a*, 1902*b* and/or the inner surface 1920 of the bore 1914 are deformed, the beam 1940 can resist deformation and remain stationary in the bore 1914, for example. In various embodiments, edges and or corners on the first and/or second body portions 1902*a*, 1902*b* can be structured to hold the beam 1930 relative to the body portions 1902*a*, 1902*b* and/or the passages 1904*a*, 1904*b*, for example. In other embodiments, fasteners and/or adhesive may secure the beam 1930 relative to the body portions 1902*a*, 1902*b* and/or the passages 1904*a*, 1904*b*, for example.

Similar to embodiments described herein, the distal end of the first electrode 24*a* (FIG. 1) can be spaced from a distal end of the second electrode 24b (FIG. 1) by a predetermined distance when the first electrode 24a is axially restrained in the first passage 1904a, for example, and the second electrode 24b is axially restrained in the second passage 1904b, for example. Further, the predetermined distance can correspond to a treatment distance in a tissue treatment region. In at least one embodiment, the distal ends of the first and second electrodes 24a, 24b can be operably structured to conduct current therebetween when at least one of the first and second electrodes 24a, 24b is energized by an energy source 14 (FIG. 1), as described herein. During use, an operator can position the first electrode 24a relative to the tissue treatment region. As described herein, pre-operative and intra-operative three-dimensional imaging can aid the operator in placing the first electrode 24a in the target treatment zone of the tissue treatment region, for example. Once the first electrode 24a is in place relative to the tissue treatment region, the operator may desire to position the second electrode 24b at a second position relative to the tissue treatment region such that a treatment distance is defined between the distal ends of the first and second electrodes 24a, 24b, for example. A probe guide, such as probe guide 1900, for example, can be selected by the operator. In various embodiments, the selected probe guide 1900 can comprise a predetermined distance between the first and second passages 1904a, 1904b, which can correspond with a preferred treatment distance between electrodes 24a, 24b. The operator may deform the body 1902 and/or the inner surface 1920 of the bore 1914 from the initial configuration to a deformed configuration such that an electrode 24a, 24b can pass into at least one of the first and second passages 1904a, 1904b. Upon deforming the probe guide 1900, the first electrode 24a can pass into the first passage 1904a, for example. Once the first electrode 24a is positioned in the first passage 1904a, the operator can release the body 1902 of the probe guide 1900. In at least one embodiment, the body 1902 can seek to return to the initial, undeformed configuration when released by the operator. Further, the probe guide 1900 can substantially return to the initial, undeformed configuration such that the first and second passages 1904a, 1904b are structured to axially restrain the first and second electrodes 24a, 24b, respectively.

In various embodiments, the second passage 1904b can be defined through at least a portion of the probe guide 1900 when the body 1902 and/or the inner surface 1920 of the bore 1914 returns or substantially returns to the initial, undeformed configuration (FIG. 55). In such embodiments, the second passage 1904b may be closed or narrowed such that the second electrode 24b can be axially restrained therein, i.e., the second electrode 24b cannot move laterally into or out of the second passage 1904b. In various embodiments, when the body 1902 has substantially returned to the initial configuration, the distal end of the second electrode 24b can be axially advanced through the second passage 1904b to the tissue treatment region. As the distal end of the second electrode 24b is advanced through the second passage 1904b, the second passage 1904b can guide the second electrode 24b a predetermined distance from the distal end of the first electrode 24a, for example, and/or along a path substantially parallel to the first electrode 24a, for example.

What is claimed is:

1. A laparoscopic system comprising:
an electrical ablation device comprising a first electrode and a second electrode;
an energy source electrically coupled to the first and second electrodes; and
an electrode guide for guiding the first and second electrodes relative to a tissue treatment region, wherein the electrode guide is dimensioned and shaped for placement internal to a patient body and is positionable within the patient body between the electrical ablation device and the tissue treatment region, and wherein the electrode guide comprises a body comprising:
a proximal surface;
a tissue-abutment surface configured to abut tissue in the tissue treatment region;
a first passage through the body from the proximal surface to the tissue-abutment surface, wherein the first passage is configured to receive the first electrode protruding from the electrical ablation device, and wherein the first passage is configured to axially restrain the first electrode when the electrode guide is positioned against the tissue; and
a second passage through the body from the proximal surface to the tissue-abutment surface, wherein the second passage is substantially parallel to the first passage, wherein the second passage is configured to receive the second electrode protruding from the electrical ablation device, and wherein the second passage is configured to axially restrain the second electrode when the electrode guide is positioned against the tissue;
wherein the first passage is spaced a predetermined distance from the second passage, and wherein the predetermined distance corresponds to a treatment distance in the tissue treatment region;
wherein the body comprises an elastomeric material, and wherein at least a portion of the body is moveable between a first configuration and a second configuration, wherein the body comprises an outer surface, and wherein the first passage comprises an outlet that operably closes the first passage to the outer surface when the body is in the first configuration.

2. The laparoscopic system of claim 1, wherein the energy source comprises a Radio Frequency (RF) energy source.

3. The laparoscopic system of claim 1, wherein the energy source comprises a pulsed energy source.

4. The laparoscopic system of claim 1, wherein the energy source comprises an irreversible electroporation energy source.

5. The laparoscopic system of claim 4, wherein the energy source comprises a pulsed energy source.

6. The laparoscopic system of claim 1, wherein a current supplied by the energy source is selected to generate an electric field of approximately 1500 Volts per centimeter.

7. A device for laparoscopic procedures, comprising:
an electrode guide for guiding electrodes relative to a tissue treatment region, wherein the electrode guide is dimensioned and shaped for placement internal to a patient body and is positionable within the patient body between an electrical ablation device and the tissue treatment region, wherein the electrode guide is separate and distinct from the electrical ablation device, and wherein the electrode guide comprises a body comprising:
a proximal surface;
a tissue-abutment surface configured to abut tissue in the tissue treatment region;
a first passage through the body from the proximal surface to the tissue-abutment surface, wherein the first passage is configured to receive a first electrode protruding from the electrical ablation device, and wherein the first passage is configured to axially restrain the first electrode when the electrode guide is positioned within the patient body against tissue in the tissue treatment region; and a second passage through the body from the proximal surface to the tissue-abutment surface, wherein the second passage is substantially parallel to the first passage, wherein the second passage is configured to receive a second electrode protruding from the electrical ablation device, and wherein the second passage is configured to axially restrain the second electrode when the electrode guide is positioned within the patient body against tissue in the tissue treatment region;

wherein the first passage is spaced a predetermined distance from the second passage, and wherein the predetermined distance corresponds to a treatment distance in the tissue treatment region;

wherein the body comprises an elastomeric material, and wherein at least a portion of the body is moveable between a first configuration and a second configuration, wherein the body comprises an outer surface, and wherein the first passage comprises an outlet that operably closes the first passage to the outer surface when the body is in the first configuration.

8. The device of claim 7, wherein the predetermined distance ranges from 1.0 centimeter to 2.0 centimeters.

9. The device of claim 7, wherein the outlet operably opens the first passage to the outer surface when the body is moved to the second configuration such that the outlet permits passage of the first electrode therethrough.

10. The device of claim 7, wherein the body generates a restoring force when moved from the first configuration to the second configuration such that the body seeks to return to the first configuration.

11. The device of claim 7, further comprising:
a third passage through the body, wherein the third passage is configured to axially restrain a third electrode; and
a fourth passage through the body, wherein the fourth passage is configured to axially restrain a fourth electrode;
wherein the third and fourth passages are substantially parallel to the first and second passages.

* * * * *